US012775013B2

(12) United States Patent
Gustafson et al.

(10) Patent No.: US 12,775,013 B2
(45) Date of Patent: Oct. 27, 2026

(54) IMMUNOMODULATORY CLINICAL BIOMARKER PROFILES AND USES THEREOF

(71) Applicants: Seattle Children's Hospital, Seattle, WA (US); Battelle Memorial Institute, Richland, WA (US)

(72) Inventors: Heather Gustafson, Seattle, WA (US); Rebecca Gardner, Seattle, WA (US); Bobbie-Jo M. Webb-Robertson, Seattle, WA (US); Katelyn Burleigh, Seattle, WA (US)

(73) Assignees: Seattle Children's Hospital, Seattle, WA (US); Battelle Memorial Institute, Richland, WA (US)

( * ) Notice: Subject to any disclaimer, the term of this patent is extended or adjusted under 35 U.S.C. 154(b) by 653 days.

(21) Appl. No.: 18/253,556

(22) PCT Filed: Nov. 19, 2021

(86) PCT No.: PCT/US2021/060198
§ 371 (c)(1),
(2) Date: May 18, 2023

(87) PCT Pub. No.: WO2022/109340
PCT Pub. Date: May 27, 2022

(65) Prior Publication Data

US 2024/0027460 A1 Jan. 25, 2024

Related U.S. Application Data

(60) Provisional application No. 63/166,952, filed on Mar. 26, 2021, provisional application No. 63/116,750, filed on Nov. 20, 2020.

(51) Int. Cl.
*G01N 33/575* (2026.01)
*A61K 40/11* (2025.01)
(Continued)

(52) U.S. Cl.
CPC ........ *G01N 33/57585* (2026.01); *A61K 40/11* (2025.01); *A61K 40/31* (2025.01);
(Continued)

(58) Field of Classification Search
CPC .... A61K 2239/48; A61K 40/11; A61K 40/31; A61K 40/4211; C12N 2501/2302;
(Continued)

(56) References Cited

U.S. PATENT DOCUMENTS

2011/0059012 A1 3/2011 Turtle et al.
2015/0212090 A1 7/2015 Kamat et al.
(Continued)

FOREIGN PATENT DOCUMENTS

WO WO-2008065694 A1 * 6/2008 ....... G01N 33/56972

OTHER PUBLICATIONS

Boudousquie, et al., "Polyfunctional response by ImmTAC (IMCgp100) redirected CD8+ and CD4+ T cells," Immunology, vol. 152, No. 3, 2017, pp. 425-438.
(Continued)

*Primary Examiner* — Jennifer Wecker
(74) *Attorney, Agent, or Firm* — Lee & Hayes, P.C.

(57) ABSTRACT

The present disclosure relates to biomarker profiles and their use to predict a subject's response to an immunomodulatory treatment. Biomarkers in these profiles include cytokines and other proteins associated with the interleukin 1 family and the type 1 interferon family. Particular biomarkers include interleukin (IL)-2, soluble IL-2 receptor alpha (sIL-2RA), IL-5, IL-6, IL-9, IL-10, IL-18, IL-18 binding protein (IL-18BP), IL-18 receptor 1 (IL-18R1), IL-18 receptor accessory protein (IL-18RAP), IL-22, C-type lectin-like receptor (CD161), CD56, interferon gamma (IFNγ), granulocyte macrophage colony stimulating factor (GM-CSF), serum amyloid A (SAA), and C-reactive protein (CRP).
(Continued)

Particular biomarkers also include populations of cells including CD161+ cells and CD56+dim cells. The biomarker profiles can be used to predict a subject's responsiveness to an immunomodulatory treatment (e.g., immunotherapy) before or after an immunomodulatory treatment has initiated and to direct treatment to yield responsive and non-toxic outcomes to the immunomodulatory treatment.

11 Claims, 109 Drawing Sheets

Specification includes a Sequence Listing.

(51) Int. Cl.

| | |
|---|---|
| ***A61K 40/31*** | (2025.01) |
| ***A61K 40/42*** | (2025.01) |
| ***C12N 5/0783*** | (2010.01) |
| ***G01N 33/68*** | (2006.01) |

(52) U.S. Cl.

CPC ........ *A61K 40/4211* (2025.01); *C12N 5/0636* (2013.01); *G01N 33/6863* (2013.01); *A61K 2239/48* (2023.05); *G01N 2333/54* (2013.01); *G01N 2333/555* (2013.01); *G01N 2800/52* (2013.01)

(58) Field of Classification Search

CPC ...... C12N 2501/2318; C12N 2501/515; C12N 5/0636; G01N 2333/54; G01N 2333/555; G01N 2333/57; G01N 2800/24; G01N 2800/52; G01N 33/574; G01N 33/57488; G01N 33/6863

See application file for complete search history.

(56) References Cited

U.S. PATENT DOCUMENTS

| | | | | |
|---|---|---|---|---|
| 2016/0215048 | A1* | 7/2016 | Pfeifer | A61P 9/10 |
| 2019/0277858 | A1 | 9/2019 | Li et al. | |
| 2022/0088070 | A1* | 3/2022 | Albertson | A61K 39/3955 |

OTHER PUBLICATIONS

Buscher, et al., "Natural variation of macrophage activation as disease-relevant phenotype predictive of inflammation and cancer survival," Nat. Commun., vol. 8, 2017, 10 pages.
Finney, et al., "CD19 CAR T cell product and disease attributes predict leukemia remission durability," J. Clin. Invest., vol. 129, No. 5, 2019, pp. 2123-2132.
Gardner, et al., "Intent-to-treat leukemia remission by CD19 CAR T cells of defined formulation and dose in children and young adults," Blood, vol. 129, vol. 25, 2017, pp. 3322-3331.
Hay, et al., "Kinetics and biomarkers of severe cytokine release syndrome after CD19 chimeric antigen receptor-modified T-cell therapy," Blood, vol. 130, No. 21, 2017, pp. 2295-2306.
Invitation to Pay Additional Fees Dated Jan. 21, 2022 for International Application No. PCT/US21/60198, 3 pages.
Lee, et al., "ASTCT Consensus Grading for Cytokine Release Syndrome and Neurologic Toxicity Associated with Immune Effector Cells," Biol. Blood Marrow Transplant, vol. 25, No. 4, 2019, pp. 625-638.
Lee, et al., "Current concepts in the diagnosis and management of cytokine release syndrome," Blood, vol. 124, No. 2, 2014, pp. 188-195.
Li, et al., "Type I Interferons: Distinct Biological Activities and Current Applications for Viral Infection," Cell Physiol. Biochem., vol. 51, No. 5, 2018, pp. 2377-2396.
Maude, et al., "Chimeric antigen receptor T cells for sustained remissions in leukemia," N. Engl. J. Med., vol. 371, No. 16, 2014, pp. 1507-1517.
Maude, et al., "Managing Cytokine Release Syndrome Associated With Novel T Cell-Engaging Therapies," Cancer J., vol. 20, No. 2, 2014, pp. 119-122.
Murray & Wynn, "Protective and pathogenic functions of macrophage subsets," Nat. Rev. Immunol., vol. 11, No. 11, 2011, pp. 723-737.
Nakahira, et al., "Synergy of IL-12 and IL-18 for IFN-gamma gene expression: IL-12-induced STAT4 contributes to IFN-gamma promoter activation by up-regulating the binding activity of IL-18-induced activator protein 1," J. Immunol., vol. 168, No. 3, 2002, pp. 1146-1153.
GenBank Accession No. NCT02028455 "A Pediatric and Young Adult Trial of Genetically Modified T Cells Directed Against CD19 for Relapsed/Refractory CD19+ Leukemia," Mar. 14, 2023; Accessed online May 4, 2023 at https://clinicaltrials.gov/ct2/show/NCT02028455?term=NCT02028455&draw=2&rank=1.
GenBank Accession No. NCT03330691 "A Feasibility and Safety Study of Dual Specificity CD19 and CD22 CAR-T Cell Immunotherapy for CD19+CD22+ Leukemia," Apr. 11, 2023; Accessed online May 4, 2023 at https://clinicaltrials.gov/ct2/show/NCT03330691?term=NCT03330691&draw=2&rank=1.
Neelapu, et al., "Chimeric antigen receptor T-cell therapy—assessment and management of toxicities," Nat. Rev. Clin. Oncol., vol. 15, No. 1, 2018, pp. 47-62.
Norelli, et al., "Monocyte-derived IL-1 and IL-6 are differentially required for cytokine-release syndrome and neurotoxicity due to CAR T cells," Nat. Med., vol. 24, 2018, pp. 739-748.
Park, et al., "Long-Term Follow-up of CD19 CAR Therapy in Acute Lymphoblastic Leukemia," N. Engl. J. Med., vol. 378, No. 5, 2018, pp. 449-459.
Search Report and Written Opinion Dated Mar. 25, 2022 for International Application No. PCT/US2021/060198, 16 pages.
Porter, et al., "Grading of cytokine release syndrome associated with the CAR T cell therapy tisagenlecleucel," J. Hematol. Oncol., vol. 11, No. 1, 2018, 12 pages.
Rex, et al., "A comprehensive pathway map of IL-18-mediated signalling," J. Cell. Commun. Signal., vol. 14, No. 2, 2020, pp. 257-266.
Ruelle & Maus, "Catch me if you can: Leukemia Escape after CD19-Directed T Cell Immunotherapies," Comput. Struct. Biotechnol. J., vol. 14, 2016, pp. 357-362.
Shah, et al., "CD4/CD8 T-Cell Selection Affects Chimeric Antigen Receptor (CAR) T-Cell Potency and Toxicity: Updated Results From a Phase I Anti-CD22 CAR T-Cell Trial," J. Clin. Oncol., vol. 38, No. 17, 2020, pp. 1938-1950.
Silva, et al., "De novo design of potent and selective mimics of IL-2 and IL-15," Nature, vol. 565, No. 7738, 2019, pp. 186-191.
Thompson, John A., "New NCCN Guidelines: Recognition and Management of Immunotherapy-Related Toxicity," J. Natl. Compr. Canc. Netw., vol. 16, No. 5S, 2018, pp. 594-596.
Zhou, et al., "IL-18BP is a secreted immune checkpoint and barrier to IL-18 immunotherapy," Nature, vol. 583, No. 7817, 2020, pp. 609-614.
Biswas, et al., "Tumor-associated macrophages: functional diversity, clinical significance, and open questions," Semin. Immunopathol., vol. 35, No. 5, 2013, pp. 585-600.
Bonnardel & Guilliams, "Developmental control of macrophage function," Curr. Opin. Immunol., vol. 50, 2018, pp. 64-74.
Bossi, et al., "ImmTAC-redirected tumour cell killing induces and potentiates antigen cross-presentation by dendritic cells," Cancer Immunol Ommunother., vol. 63, No. 5, 2014, pp. 437-448.
Lefevre, et al., "Interferon-delta: the first member of a novel type I interferon family," Biochimie, vol. 80, No. 8, 1998, pp. 779-788.
Oritani and Tomiyama, "Interferon-zeta/limitin: novel type I interferon that displays a narrow range of biological activity," Int. J. Hematol., vol. 80, No. 4, 2004, pp. 325-331.

* cited by examiner

FIG. 7C

| Day | Model # | Iteration | Cytokine | Cumulative Average AUC |
|---|---|---|---|---|
| 1 | 1 | 1 | IL-10 | 0.798 |
| | | 2 | SAA | 0.882 |
| | | 3 | GM-CSF | 0.831 |
| | | 4 | IFN-γ | 0.838 |
| 3 | 1 | 1 | IL-10 | 0.880 |
| | | 2 | CRP | 0.907 |
| | | 3 | IFN-γ | 0.918 |
| | | 4 | GM-CSF | 0.932 |
| 3 | 2 | 1 | GM-CSF | 0.880 |
| | | 2 | IL-10 | 0.906 |
| | | 3 | siL-2Ra | 0.916 |
| | | 4 | IL-5 | 0.931 |
| 7 | 1 | 1 | IL-18 | 0.805 |
| | | 2 | IL18BP | 0.917 |
| | | 3 | IFN-γ | 0.923 |
| 7 | 2 | 1 | IL-18 | 0.805 |
| | | 2 | IL18BP | 0.917 |
| | | 3 | IL-22 | 0.917 |

FIG. 13

| # | Cytokine | GROUP | Int (DAY) | GROUP (DAY1) | GROUP (DAY3) | GROUP (DAY7) |
|---|---|---|---|---|---|---|
| 5 | IL-10 | 5.3E-4^ | 0.0653 | 0.0018^ | 1.6E-4^ | 0.1971 |
| 12 | IL-5 | 0.0025^ | 0.7771 | 0.0032^ | 0.0162^ | 0.0475# |
| 18 | PlGF | 0.0035^ | 0.2152 | 7.0E-4^ | 0.0120^ | 0.1128 |
| 4 | IFNy | 0.0079^ | 0.5679 | 0.0072^ | 6.5E-4^ | 0.0130^ |
| 20 | sIL-2Ra | 0.0123# | 0.0164# | 0.0171^ | 0.0029^ | 5.4E-4^ |
| 6 | IL-18 | 0.3324 | 1.8E-4^ | 0.3201 | 0.1430 | 6.8E-4^ |
| 10 | IL-2 | 0.0137# | 0.0625^ | 0.0137^ | 0.0167^ | 0.4724 |
| 13 | IL-6 | 0.0202# | 0.9929^ | 0.0134^ | 0.0128^ | 0.0382# |
| 3 | GM-CSF | 0.0230# | 0.6674^ | 0.0110^ | 0.0030^ | 0.0518 |
| 1 | CRP | 0.0420# | 0.5491 | 0.0694 | 0.0155^ | 0.1210 |
| 16 | IP-10 | 0.0440# | 0.3675 | 0.0352# | 0.0095^ | 0.0038^ |
| 7 | IL18BP | 0.0482# | 0.6342 | 0.0274# | 0.0076^ | 0.0163# |
| 11 | IL-22 | 0.0612 | 0.0229# | 0.1081 | 0.0189^ | 0.0018^ |
| 19 | SAA | 0.0571 | 0.0679 | 0.0987 | 0.0125^ | 0.5422 |
| 22 | TNF-a | 0.0942 | 0.8315 | 0.1549 | 0.0467# | 0.0779 |
| 9 | IL-1RA | 0.1171 | 0.2743 | 0.1113 | 0.0425# | 0.0118^ |
| 14 | IL-8 | 0.1738 | 0.4217 | 0.2078 | 0.3321 | 0.0578 |
| 2 | Flt-1 | 0.2821 | 0.0649 | 0.2593 | 0.2639 | 0.0926 |
| 8 | Ratio BP/18 (pM) | 0.2860 | 0.0579 | 0.3381 | 0.1505 | 0.6891 |
| 23 | VEGF-A | 0.3286 | 0.3874 | 0.4599 | 0.4131 | 0.9777 |
| 17 | MCP-4 | 0.4656 | 0.3673 | 0.3323 | 0.3406 | 0.0918 |
| 15 | IL-9 | 0.6747 | 0.6572 | 0.7274 | 0.4907 | 0.9072 |
| 21 | Tie-2 | 0.9859 | 0.5373 | 0.8377 | 0.9701 | 0.4287 |

FIG. 14

| # | Cytokine | GROUP (DAY1) | GROUP (DAY3) | GROUP (DAY7) |
|---|---|---|---|---|
| 5 | IL-10 | **2.039*^** | **2.340*^** | 0.638 |
| 12 | IL-5 | **2.061*^** | **1.578*^** | **1.566*#** |
| 18 | PlGF | 0.656^ | 0.695^ | 0.369 |
| 4 | IFNy | **2.745*^** | **4.064*^** | **2.899*^** |
| 20 | sIL-2Ra | **1.051*^** | **1.245*^** | **1.931*^** |
| 6 | IL-18 | 0.382 | 0.530 | **1.557*^** |
| 10 | IL-2 | **2.000*^** | **2.056*^** | 0.439 |
| 13 | IL-6 | **2.245*^** | **2.345*^** | **2.279*#** |
| 3 | GM-CSF | **1.976*^** | **2.476*^** | **1.998*** |
| 1 | CRP | 1.605* | **1.920*^** | **1.254*** |
| 16 | IP-10 | 0.796# | **1.181*^** | **1.815*^** |
| 7 | IL18BP | 0.683# | 0.998^ | **1.069*#** |
| 11 | IL-22 | 1.375* | **1.560*^** | **2.820*^** |
| 19 | SAA | 1.804* | **2.385*^** | 0.698 |
| 22 | TNF-a | 0.797 | **1.010*#** | 0.714 |
| 9 | IL-1RA | 0.501 | 0.768# | **1.281*^** |
| 14 | IL-8 | 1.060* | 0.796 | 1.533* |
| 2 | Flt-1 | -0.252 | -0.105 | 0.857 |
| 8 | Ratio BP/18 (pM) | 0.302 | 0.468 | -0.488 |
| 23 | VEGF-A | -0.674 | -0.516 | -0.236 |
| 17 | MCP-4 | 0.218 | 0.387 | 0.985 |
| 15 | IL-9 | -0.229 | -0.711 | -0.466 |
| 21 | Tie-2 | 0.066 | 0.104 | 0.211 |

FIG. 16

| subject | CRS | NTX | Dysfunctional |
|---|---|---|---|
| 00961-S002 | 1 | 1 | no |
| 00961-S004 | 0 | 0 | yes |
| 00961-S005 | 1 | 0 | no |
| 00961-S007 | 1 | 0 | no |
| 00961-S008 | 1 | 0 | no |
| 00961-S010 | 0 | 0 | yes |
| 00961-S013 | 3 | 1 | no |
| 00961-S014 | 1 | 1 | no |
| 00961-S015 | 1 | 2 | no |
| 00961-S016 | 1 | 1 | yes |
| 00961-S017 | 3 | 2 | no |
| 00961-S018 | 2 | 0 | no |
| 00961-S020 | 0 | 0 | no |
| 00961-S021 | 2 | 1 | no |
| 00961-S025 | 3 | 0 | no |
| 00961-S027 | 1 | 3 | no |

FIG. 22 con'td.
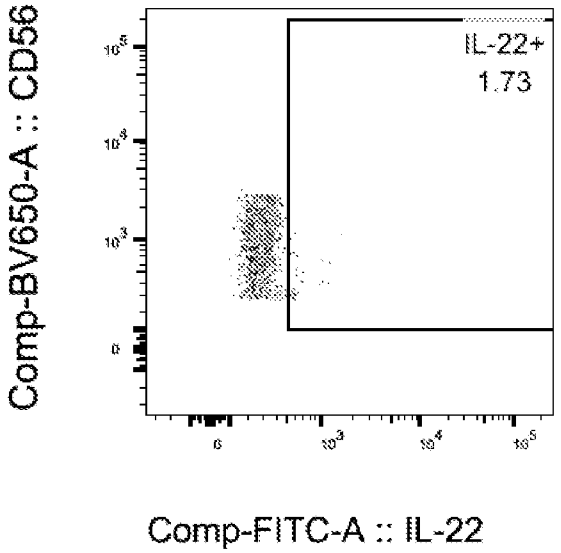
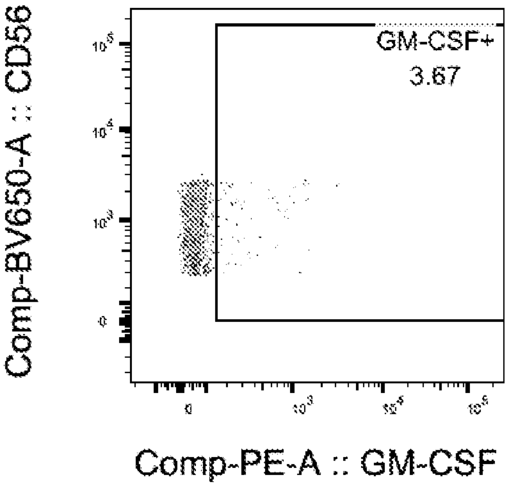
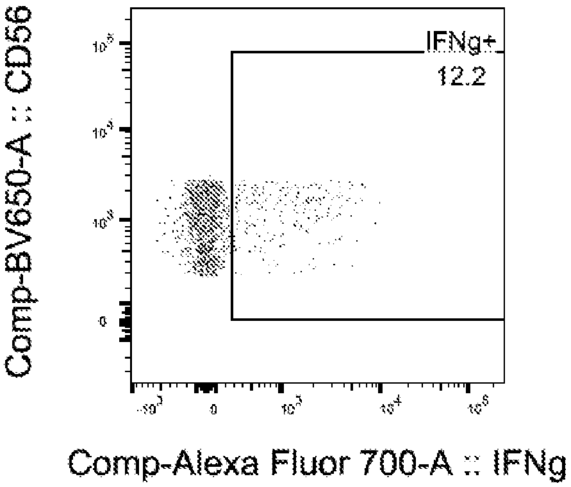

ICS Panel Analysis - 2nd Pass
Sample ID: 14602_CS_6

CD161+ of Live Cells

GM-CSF+ of CD4 Th IL-17-

Naive

Memory

NKT CD161+

FIG. 24

>Homo sapiens Interleukin-18 (IL-18) including pro-peptide (UniProt ID Q14116-1)
MAAEPVEDNCINFVAMKFIDNTLYFIAEDDENLESDYFGKLESKLSVIRNLNDQVLFIDQGNRPL
FEDMTDSDCRDNAPRTIFIISMYKDSQPRGMAVTISVKCEKISTLSCENKIISFKEMNPPDNIKDT
KSDIIFFQRSVPGHDNKMQFESSSYEGYFLACEKERDLFKLILKKEDELGDRSIMFTVQNED
(SEQ ID NO: 9)

>Homo sapiens IL-18 lacking pro-peptide (amino acids 37-193 of UniProt ID Q14116-1)
YFGKLESKLSVIRNLNDQVLFIDQGNRPLFEDMTDSDCRDNAPRTIFIISMYKDSQPRGMAVTIS
VKCEKISTLSCENKIISFKEMNPPDNIKDTKSDIIFFQRSVPGHDNKMQFESSSYEGYFLACEKE
RDLFKLILKKEDELGDRSIMFTVQNED (SEQ ID NO: 10)

>Homo sapiens IL-18 binding protein (IL-18BP) including signal peptide (UniProt ID O95998-2)
MTMRHNWTPDLSPLWVLLLCAHVVTLLVRATPVSQTTTAATASVRSTKDPCPSQPPVFPAAKQ
CPALEVTWPEVEVPLNGTLSLSCVACSRFPNFSILYWLGNGSFIEHLPGRLWEGSTSRERGST
GTQLCKALVLEQLTPALHSTNFSCVLVDPEQVVQRHVVLAQLWAGLRATLPPTQEALPSSHSS
PQQQG (SEQ ID NO: 11)

>Homo sapiens IL-18BP lacking signal peptide (amino acids 31-194 of UniProt ID O95998-2)
TPVSQTTTAATASVRSTKDPCPSQPPVFPAAKQCPALEVTWPEVEVPLNGTLSLSCVACSRFP
NFSILYWLGNGSFIEHLPGRLWEGSTSRERGSTGTQLCKALVLEQLTPALHSTNFSCVLVDPEQ
VVQRHVVLAQLWAGLRATLPPTQEALPSSHSSPQQQG (SEQ ID NO: 12)

>Homo sapiens IL-18 receptor 1 (IL-18R1) including signal peptide (UniProt ID Q13478)
MNCRELPLTLWVLISVSTAESCTSRPHITVVEGEPFYLKHCSCSLAHEIETTTKSWYKSSGSQE
HVELNPRSSSRIALHDCVLEFWPVELNDTGSYFFQMKNYTQKWKLNVIRRNKHSCFTERQVTS
KIVEVKKFFQITCENSYYQTLVNSTSLYKNCKKLLLENNKNPTIKKNAEFEDQGYYSCVHFLHHN
GKLFNITKTFNITIVEDRSNIVPVLLGPKLNHVAVELGKNVRLNCSALLNEEDVIYWMFGEENGS
DPNIHEEKEMRIMTPEGKWHASKVLRIENIGESNLNVLYNCTVASTGGTDTKSFILVRKADMADI
PGHVFTRGMIIAVLILVAVVCLVTVCVIYRVDLVLFYRHLTRRDETLTDGKTYDAFVSYLKECRPE
NGEEHTFAVEILPRVLEKHFGYKLCIFERDVVPGGAVVDEIHSLIEKSRRLIIVLSKSYMSNEVRY
ELESGLHEALVERKIKIILIEFTPVTDFTFLPQSLKLLKSHRVLKWKADKSLSYNSRFWKNLLYLM
PAKTVKPGRDEPEVLPVLSES (SEQ ID NO: 13)

>Homo sapiens IL-18R1 lacking signal peptide (amino acids 19-541 of UniProt ID Q13478)
AESCTSRPHITVVEGEPFYLKHCSCSLAHEIETTTKSWYKSSGSQEHVELNPRSSSRIALHDCV
LEFWPVELNDTGSYFFQMKNYTQKWKLNVIRRNKHSCFTERQVTSKIVEVKKFFQITCENSYY
QTLVNSTSLYKNCKKLLLENNKNPTIKKNAEFEDQGYYSCVHFLHHNGKLFNITKTFNITIVEDRS
NIVPVLLGPKLNHVAVELGKNVRLNCSALLNEEDVIYWMFGEENGSDPNIHEEKEMRIMTPEGK
WHASKVLRIENIGESNLNVLYNCTVASTGGTDTKSFILVRKADMADIPGHVFTRGMIIAVLILVAV
VCLVTVCVIYRVDLVLFYRHLTRRDETLTDGKTYDAFVSYLKECRPENGEEHTFAVEILPRVLEK
HFGYKLCIFERDVVPGGAVVDEIHSLIEKSRRLIIVLSKSYMSNEVRYELESGLHEALVERKIKIILI
EFTPVTDFTFLPQSLKLLKSHRVLKWKADKSLSYNSRFWKNLLYLMPAKTVKPGRDEPEVLPVL
SES (SEQ ID NO: 14)

FIG. 24 cont'd.

>Homo sapiens IL-18 receptor accessory protein (IL-18RAP) including signal peptide (UniProt ID O95256-1)
MLCLGWIFLWLVAGERIKGFNISGCSTKKLLWTYSTRSEEEFVLFCDLPEPQKSHFCHRNRLSP
KQVPEHLPFMGSNDLSDVQWYQQPSNGDPLEDIRKSYPHIIQDKCTLHFLTPGVNNSGSYICR
PKMIKSPYDVACCVKMILEVKPQTNASCEYSASHKQDLLLGSTGSISCPSLSCQSDAQSPAVT
WYKNGKLLSVERSNRIVVDEVYDYHQGTYVCDYTQSDTVSSWTVRAVVQVRTIVGDTKLKPDI
LDPVEDTLEVELGKPLTISCKARFGFERVFNPVIKWYIKDSDLEWEVSVPEAKSIKSTLKDEIIER
NIILEKVTQRDLRRKFVCFVQNSIGNTTQSVQLKEKRGVVLLYILLGTIGTLVAVLAASALLYRHWI
EIVLLYRTYQSKDQTLGDKKDFDAFVSYAKWSSFPSEATSSLSEEHLALSLFPDVLENKYGYSL
CLLERDVAPGGVYAEDIVSIIKRSRRGIFILSPNYVNGPSIFELQAAVNLALDDQTLKLILIKFCYFQ
EPESLPHLVKKALRVLPTVTWRGLKSVPPNSRFWAKMRYHMPVKNSQGFTWNQLRITSRIFQ
WKGLSRTETTGRSSQPKEW (SEQ ID NO: 15)

>Homo sapiens IL-18RAP lacking signal peptide (amino acids 20-599 of UniProt ID O95256-1)
FNISGCSTKKLLWTYSTRSEEEFVLFCDLPEPQKSHFCHRNRLSPKQVPEHLPFMGSNDLSDV
QWYQQPSNGDPLEDIRKSYPHIIQDKCTLHFLTPGVNNSGSYICRPKMIKSPYDVACCVKMILE
VKPQTNASCEYSASHKQDLLLGSTGSISCPSLSCQSDAQSPAVTWYKNGKLLSVERSNRIVVD
EVYDYHQGTYVCDYTQSDTVSSWTVRAVVQVRTIVGDTKLKPDILDPVEDTLEVELGKPLTISC
KARFGFERVFNPVIKWYIKDSDLEWEVSVPEAKSIKSTLKDEIIERNIILEKVTQRDLRRKFVCFV
QNSIGNTTQSVQLKEKRGVVLLYILLGTIGTLVAVLAASALLYRHWIEIVLLYRTYQSKDQTLGDK
KDFDAFVSYAKWSSFPSEATSSLSEEHLALSLFPDVLENKYGYSLCLLERDVAPGGVYAEDIVSI
IKRSRRGIFILSPNYVNGPSIFELQAAVNLALDDQTLKLILIKFCYFQEPESLPHLVKKALRVLPTV
TWRGLKSVPPNSRFWAKMRYHMPVKNSQGFTWNQLRITSRIFQWKGLSRTETTGRSSQPKE
W (SEQ ID NO: 16)

>Homo sapiens IL-2 including signal peptide (UniProt ID P60568)
MYRMQLLSCIALSLALVTNSAPTSSSTKKTQLQLEHLLLDLQMILNGINNYKNPKLTRMLTFKFY
MPKKATELKHLQCLEEELKPLEEVLNLAQSKNFHLRPRDLISNINVIVLELKGSETTFMCEYADE
TATIVEFLNRWITFCQSIISTLT (SEQ ID NO: 17)

>Homo sapiens IL-2 lacking signal peptide (amino acids 21-153 of UniProt ID P60568)
APTSSSTKKTQLQLEHLLLDLQMILNGINNYKNPKLTRMLTFKFYMPKKATELKHLQCLEEELKP
LEEVLNLAQSKNFHLRPRDLISNINVIVLELKGSETTFMCEYADETATIVEFLNRWITFCQSIISTLT
(SEQ ID NO: 18)

>Homo sapiens IL-2 receptor subunit alpha (IL-2RA) including signal peptide (UniProt ID P01589)
MDSYLLMWGLLTFIMVPGCQAELCDDDPPEIPHATFKAMAYKEGTMLNCECKRGFRRIKSGSL
YMLCTGNSSHSSWDNQCQCTSSATRNTTKQVTPQPEEQKERKTTEMQSPMQPVDQASLPG
HCREPPPWENEATERIYHFVVGQMVYYQCVQGYRALHRGPAESVCKMTHGKTRWTQPQLIC
TGEMETSQFPGEEKPQASPEGRPESETSCLVTTTDFQIQTEMAATMETSIFTTEYQVAVAGCV
FLLISVLLLSGLTWQRRQRKSRRTI (SEQ ID NO: 19)

FIG. 24 cont'd.

>Homo sapiens IL-2 receptor subunit alpha (IL-2RA) lacking signal peptide (amino acids 22-272 of UniProt ID P01589)
ELCDDDPPEIPHATFKAMAYKEGTMLNCECKRGFRRIKSGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTGEMETSQFPGEEKPQASPEGR
PESETSCLVTTTDFQIQTEMAATMETSIFTTEYQVAVAGCVFLLISVLLLSGLTWQRRQRKSRRT
I (SEQ ID NO: 20)

>Homo sapiens IL-12 subunit alpha (IL-12A) including signal peptide (NCBI Reference Sequence: NP_000873.2)
MWPPGSASQPPPSPAAATGLHPAARPVSLQCRLSMCPARSLLLVATLVLLDHLSLARNLPVAT
PDPGMFPCLHHSQNLLRAVSNMLQKARQTLEFYPCTSEEIDHEDITKDKTSTVEACLPLELTKN
ESCLNSRETSFITNGSCLASRKTSFMMALCLSSIYEDLKMYQVEFKTMNAKLLMDPKRQIFLDQ
NMLAVIDELMQALNFNSETVPQKSSLEEPDFYKTKIKLCILLHAFRIRAVTIDRVMSYLNAS (SEQ ID NO: 21)

>Homo sapiens IL-12A lacking signal peptide (amino acids 57-253 of NP_000873.2)
RNLPVATPDPGMFPCLHHSQNLLRAVSNMLQKARQTLEFYPCTSEEIDHEDITKDKTSTVEACL
PLELTKNESCLNSRETSFITNGSCLASRKTSFMMALCLSSIYEDLKMYQVEFKTMNAKLLMDPK
RQIFLDQNMLAVIDELMQALNFNSETVPQKSSLEEPDFYKTKIKLCILLHAFRIRAVTIDRVMSYL
NAS (SEQ ID NO: 22)

>Homo sapiens IL-12 subunit beta (IL-12B) including signal peptide (UniProt ID P29460-1)
MCHQQLVISWFSLVFLASPLVAIWELKKDVYVVELDWYPDAPGEMVVLTCDTPEEDGITWTLD
QSSEVLGSGKTLTIQVKEFGDAGQYTCHKGGEVLSHSLLLLHKKEDGIWSTDILKDQKEPKNKT
FLRCEAKNYSGRFTCWWLTTISTDLTFSVKSSRGSSDPQGVTCGAATLSAERVRGDNKEYEY
SVECQEDSACPAAEESLPIEVMVDAVHKLKYENYTSSFFIRDIIKPDPPKNLQLKPLKNSRQVEV
SWEYPDTWSTPHSYFSLTFCVQVQGKSKREKKDRVFTDKTSATVICRKNASISVRAQDRYYSS
SWSEWASVPCS (SEQ ID NO: 23)

>Homo sapiens IL-12B lacking signal peptide (amino acids 23-328 of UniProt ID P29460-1)
IWELKKDVYVVELDWYPDAPGEMVVLTCDTPEEDGITWTLDQSSEVLGSGKTLTIQVKEFGDA
GQYTCHKGGEVLSHSLLLLHKKEDGIWSTDILKDQKEPKNKTFLRCEAKNYSGRFTCWWLTTIS
TDLTFSVKSSRGSSDPQGVTCGAATLSAERVRGDNKEYEYSVECQEDSACPAAEESLPIEVMV
DAVHKLKYENYTSSFFIRDIIKPDPPKNLQLKPLKNSRQVEVSWEYPDTWSTPHSYFSLTFCVQ
VQGKSKREKKDRVFTDKTSATVICRKNASISVRAQDRYYSSSWSEWASVPCS (SEQ ID NO: 24)

>Homo sapiens IL-5 including signal peptide (UniProt ID P05113-1)
MRMLLHLSLLALGAAYVYAIPTEIPTSALVKETLALLSTHRTLLIANETLRIPVPVHKNHQLCTEEIF
QGIGTLESQTVQGGTVERLFKNLSLIKKYIDGQKKKCGEERRRVNQFLDYLQEFLGVMNTEWI
ES (SEQ ID NO: 25)

>Homo sapiens IL-5 lacking signal peptide (amino acids 20-134 of UniProt ID P05113-1)
IPTEIPTSALVKETLALLSTHRTLLIANETLRIPVPVHKNHQLCTEEIFQGIGTLESQTVQGGTVER
LFKNLSLIKKYIDGQKKKCGEERRRVNQFLDYLQEFLGVMNTEWIIES (SEQ ID NO: 26)

FIG. 24 cont'd.

>Homo sapiens IL-6 including signal peptide (UniProt ID P05231-1)
MNSFSTSAFGPVAFSLGLLLVLPAAFPAPVPPGEDSKDVAAPHRQPLTSSERIDKQIRYILDGIS
ALRKETCNKSNMCESSKEALAENNLNLPKMAEKDGCFQSGFNEETCLVKIITGLLEFEVYLEYL
QNRFESSEEQARAVQMSTKVLIQFLQKKAKNLDAITTPDPTTNASLLTKLQAQNQWLQDMTTH
LILRSFKEFLQSSLRALRQM (SEQ ID NO: 27)

>Homo sapiens IL-6 lacking signal peptide (amino acids 30-212 of UniProt ID P05231-1)
VPPGEDSKDVAAPHRQPLTSSERIDKQIRYILDGISALRKETCNKSNMCESSKEALAENNLNLPK
MAEKDGCFQSGFNEETCLVKIITGLLEFEVYLEYLQNRFESSEEQARAVQMSTKVLIQFLQKKA
KNLDAITTPDPTTNASLLTKLQAQNQWLQDMTTHLILRSFKEFLQSSLRALRQM (SEQ ID NO: 28)

>Homo sapiens IL-9 including signal peptide (UniProt ID P15248-1)
MLLAMVLTSALLLCSVAGQGCPTLAGILDINFLINKMQEDPASKCHCSANVTSCLCLGIPSDNCT
RPCFSERLSQMTNTTMQTRYPLIFSRVKKSVEVLKNNKCPYFSCEQPCNQTTAGNALTFLKSLL
EIFQKEKMRGMRGKI (SEQ ID NO: 29)

>Homo sapiens IL-9 lacking signal peptide (amino acids 19-144 of UniProt ID P15248-1)
QGCPTLAGILDINFLINKMQEDPASKCHCSANVTSCLCLGIPSDNCTRPCFSERLSQMTNTTMQ
TRYPLIFSRVKKSVEVLKNNKCPYFSCEQPCNQTTAGNALTFLKSLLEIFQKEKMRGMRGKI
(SEQ ID NO: 30)

>Homo sapiens IL-10 including signal peptide (UniProt ID P22301-1)
MHSSALLCCLVLLTGVRASPGQGTQSENSCTHFPGNLPNMLRDLRDAFSRVKTFFQMKDQLD
NLLLKESLLEDFKGYLGCQALSEMIQFYLEEVMPQAENQDPDIKAHVNSLGENLKTLRLRLRRC
HRFLPCENKSKAVEQVKNAFNKLQEKGIYKAMSEFDIFINYIEAYMTMKIRN (SEQ ID NO: 31)

>Homo sapiens IL-10 lacking signal peptide (amino acids 19-178 of UniProt ID P22301-1)
SPGQGTQSENSCTHFPGNLPNMLRDLRDAFSRVKTFFQMKDQLDNLLLKESLLEDFKGYLGC
QALSEMIQFYLEEVMPQAENQDPDIKAHVNSLGENLKTLRLRLRRCHRFLPCENKSKAVEQVK
NAFNKLQEKGIYKAMSEFDIFINYIEAYMTMKIRN (SEQ ID NO: 32)

>Homo sapiens IL-22 including signal peptide (UniProt ID Q9GZX6-1)
MAALQKSVSSFLMGTLATSCLLLLALLVQGGAAAPISSHCRLDKSNFQQPYITNRTFMLAKEAS
LADNNTDVRLIGEKLFHGVSMSERCYLMKQVLNFTLEEVLFPQSDRFQPYMQEVVPFLARLSN
RLSTCHIEGDDLHIQRNVQKLKDTVKKLGESGEIKAIGELDLLFMSLRNACI (SEQ ID NO: 33)

>Homo sapiens IL-22 lacking signal peptide (amino acids 34-179 of UniProt ID Q9GZX6-1)
APISSHCRLDKSNFQQPYITNRTFMLAKEASLADNNTDVRLIGEKLFHGVSMSERCYLMKQVLN
FTLEEVLFPQSDRFQPYMQEVVPFLARLSNRLSTCHIEGDDLHIQRNVQKLKDTVKKLGESGEI
KAIGELDLLFMSLRNACI (SEQ ID NO: 34)

>Homo sapiens interferon gamma (IFNγ) including signal peptide (UniProt ID P01579-1)
MKYTSYILAFQLCIVLGSLGCYCQDPYVKEAENLKKYFNAGHSDVADNGTLFLGILKNWKEESD
RKIMQSQIVSFYFKLFKNFKDDQSIQKSVETIKEDMNVKFFNSNKKKRDDFEKLTNYSVTDLNV
QRKAIHELIQVMAELSPAAKTGKRKRSQMLFRGRRASQ (SEQ ID NO: 35)

FIG. 24 cont'd.

>Homo sapiens IFNγ lacking signal peptide (amino acids 24-166 UniProt ID P01579-1)
QDPYVKEAENLKKYFNAGHSDVADNGTLFLGILKNWKEESDRKIMQSQIVSFYFKLFKNFKDDQ
SIQKSVETIKEDMNVKFFNSNKKKRDDFEKLTNYSVTDLNVQRKAIHELIQVMAELSPAAKTGKR
KRSQMLFRGRRASQ (SEQ ID NO: 36)

>Homo sapiens granulocyte-macrophage colony-stimulating factor (GM-CSF) including signal peptide (UniProt ID P04141-1)
MWLQSLLLLGTVACSISAPARSPSPSTQPWEHVNAIQEARRLLNLSRDTAAEMNETVEVISEMF
DLQEPTCLQTRLELYKQGLRGSLTKLKGPLTMMASHYKQHCPPTPETSCATQIITFESFKENLK
DFLLVIPFDCWEPVQE (SEQ ID NO: 37)

>Homo sapiens GM-CSF lacking signal peptide (amino acids 18-144 of UniProt ID P04141-1)
APARSPSPSTQPWEHVNAIQEARRLLNLSRDTAAEMNETVEVISEMFDLQEPTCLQTRLELYK
QGLRGSLTKLKGPLTMMASHYKQHCPPTPETSCATQIITFESFKENLKDFLLVIPFDCWEPVQE
(SEQ ID NO: 38)

>Homo sapiens serum amyloid A-1 (SAA) including signal peptide (UniProt ID P0DJI8-1)
MKLLTGLVFCSLVLGVSSRSFFSFLGEAFDGARDMWRAYSDMREANYIGSDKYFHARGNYDA
AKRGPGGVWAAEAISDARENIQRFFGHGAEDSLADQAANEWGRSGKDPNHFRPAGLPEKY
(SEQ ID NO: 39)

>Homo sapiens SAA lacking signal peptide (amino acids 19-122 of UniProt ID P0DJI8-1)
RSFFSFLGEAFDGARDMWRAYSDMREANYIGSDKYFHARGNYDAAKRGPGGVWAAEAISDA
RENIQRFFGHGAEDSLADQAANEWGRSGKDPNHFRPAGLPEKY (SEQ ID NO: 40)

>Homo sapiens C-reactive protein (CRP) including signal peptide (UniProt ID P02741-1)
MEKLLCFLVLTSLSHAFGQTDMSRKAFVFPKESDTSYVSLKAPLTKPLKAFTVCLHFYTELSSTR
GYSIFSYATKRQDNEILIFWSKDIGYSFTVGGSEILFEVPEVTVAPVHICTSWESASGIVEFWVD
GKPRVRKSLKKGYTVGAEASIILGQEQDSFGGNFEGSQSLVGDIGNVNMWDFVLSPDEINTIYL
GGPFSPNVLNWRALKYEVQGEVFTKPQLWP (SEQ ID NO: 41)

>Homo sapiens C-reactive protein (CRP) lacking signal peptide (amino acids 19-224 of UniProt ID P02741-1)
QTDMSRKAFVFPKESDTSYVSLKAPLTKPLKAFTVCLHFYTELSSTRGYSIFSYATKRQDNEILIF
WSKDIGYSFTVGGSEILFEVPEVTVAPVHICTSWESASGIVEFWVDGKPRVRKSLKKGYTVGAE
ASIILGQEQDSFGGNFEGSQSLVGDIGNVNMWDFVLSPDEINTIYLGGPFSPNVLNWRALKYEV
QGEVFTKPQLWP (SEQ ID NO: 42)

>Homo sapiens killer cell lectin-like receptor subfamily B member 1 (CD161 or KLRB1) (UniProt ID Q12918-1)
MDQQAIYAELNLPTDSGPESSSPSSLPRDVCQGSPWHQFALKLSCAGIILLVLVVTGLSVSVTS
LIQKSSIEKCSVDIQQSRNKTTERPGLLNCPIYWQQLREKCLLFSHTVNPWNNSLADCSTKESS
LLLIRDKDELIHTQNLIRDKAILFWIGLNFSLSEKNWKWINGSFLNSNDLEIRGDAKENSCISISQT
SVYSEYCSTEIRWICQKELTPVRNKVYPDS (SEQ ID NO: 43)

FIG. 24 cont'd.

>Homo sapiens neural cell adhesion molecule 1 (CD56 or NCAM1) including signal peptide (UniProt ID P13591-2)
MLQTKDLIWTLFFLGTAVSLQVDIVPSQGEISVGESKFFLCQVAGDAKDKDISWFSPNGEKLTP
NQQRISVVWNDDSSSTLTIYNANIDDAGIYKCVVTGEDGSESEATVNVKIFQKLMFKNAPTPQE
FREGEDAVIVCDVVSSLPPTIIWKHKGRDVILKKDVRFIVLSNNYLQIRGIKKTDEGTYRCEGRIL
ARGEINFKDIQVIVNVPPTIQARQNIVNATANLGQSVTLVCDAEGFPEPTMSWTKDGEQIEQEE
DDEKYIFSDDSSQLTIKKVDKNDEAEYICIAENKAGEQDATIHLKVFAKPKITYVENQTAMELEEQ
VTLTCEASGDPIPSITWRTSTRNISSEEKASWTRPEKQETLDGHMVVRSHARVSSLTLKSIQYT
DAGEYICTASNTIGQDSQSMYLEVQYAPKLQGPVAVYTWEGNQVNITCEVFAYPSATISWFRD
GQLLPSSNYSNIKIYNTPSASYLEVTPDSENDFGNYNCTAVNRIGQESLEFILVQADTPSSPSID
QVEPYSSTAQVQFDEPEATGGVPILKYKAEWRAVGEEVWHSKWYDAKEASMEGIVTIVGLKPE
TTYAVRLAALNGKGLGEISAASEFKTQPVQGEPSAPKLEGQMGEDGNSIKVNLIKQDDGGSPIR
HYLVRYRALSSEWKPEIRLPSGSDHVMLKSLDWNAEYEVYVVAENQQGKSKAAHFVFRTSAQ
PTAIPANGSPTSGLSTGAIVGILIVIFVLLLVVVDITCYFLNKCGLFMCIAVNLCGKAGPGAKGKDM
EEGKAAFSKDESKEPIVEVRTEEERTPNHDGGKHTEPNETTPLTEPEKGPVEAKPECQETETK
PAPAEVKTVPNDATQTKENESKA (SEQ ID NO: 44)

>Homo sapiens neural cell adhesion molecule 1 (CD56 or NCAM1) including signal peptide (amino acids 20-858 of UniProt ID P13591-2)
LQVDIVPSQGEISVGESKFFLCQVAGDAKDKDISWFSPNGEKLTPNQQRISVVWNDDSSSTLTI
YNANIDDAGIYKCVVTGEDGSESEATVNVKIFQKLMFKNAPTPQEFREGEDAVIVCDVVSSLPP
TIIWKHKGRDVILKKDVRFIVLSNNYLQIRGIKKTDEGTYRCEGRILARGEINFKDIQVIVNVPPTIQ
ARQNIVNATANLGQSVTLVCDAEGFPEPTMSWTKDGEQIEQEEDDEKYIFSDDSSQLTIKKVDK
NDEAEYICIAENKAGEQDATIHLKVFAKPKITYVENQTAMELEEQVTLTCEASGDPIPSITWRTST
RNISSEEKASWTRPEKQETLDGHMVVRSHARVSSLTLKSIQYTDAGEYICTASNTIGQDSQSMY
LEVQYAPKLQGPVAVYTWEGNQVNITCEVFAYPSATISWFRDGQLLPSSNYSNIKIYNTPSASY
LEVTPDSENDFGNYNCTAVNRIGQESLEFILVQADTPSSPSIDQVEPYSSTAQVQFDEPEATGG
VPILKYKAEWRAVGEEVWHSKWYDAKEASMEGIVTIVGLKPETTYAVRLAALNGKGLGEISAAS
EFKTQPVQGEPSAPKLEGQMGEDGNSIKVNLIKQDDGGSPIRHYLVRYRALSSEWKPEIRLPS
GSDHVMLKSLDWNAEYEVYVVAENQQGKSKAAHFVFRTSAQPTAIPANGSPTSGLSTGAIVGI
LIVIFVLLLVVVDITCYFLNKCGLFMCIAVNLCGKAGPGAKGKDMEEGKAAFSKDESKEPIVEVRT
EEERTPNHDGGKHTEPNETTPLTEPEKGPVEAKPECQETETKPAPAEVKTVPNDATQTKENES
KA (SEQ ID NO: 45)

>CDS for human IL-18 including pro-peptide sequence (nt 198-779 of NCBI Reference Sequence: NM_001562.4)
ATGGCTGCTGAACCAGTAGAAGACAATTGCATCAACTTTGTGGCAATGAAATTTATTGACAA
TACGCTTTACTTTATAGCTGAAGATGATGAAAACCTGGAATCAGATTACTTTGGCAAGCTTG
AATCTAAATTATCAGTCATAAGAAATTTGAATGACCAAGTTCTCTTCATTGACCAAGGAAATC
GGCCTCTATTTGAAGATATGACTGATTCTGACTGTAGAGATAATGCACCCCGGACCATATTT
ATTATAAGTATGTATAAAGATAGCCAGCCTAGAGGTATGGCTGTAACTATCTCTGTGAAGTG
TGAGAAAATTTCAACTCTCTCCTGTGAGAACAAAATTATTTCCTTTAAGGAAATGAATCCTCC
TGATAACATCAAGGATACAAAAAGTGACATCATATTCTTTCAGAGAAGTGTCCCAGGACATG
ATAATAAGATGCAATTTGAATCTTCATCATACGAAGGATACTTTCTAGCTTGTGAAAAAGAG
AGAGACCTTTTTAAACTCATTTTGAAAAAAGAGGATGAATTGGGGGATAGATCTATAATGTT
CACTGTTCAAAACGAAGACTAG (SEQ ID NO: 46)

FIG. 24 cont'd.

>CDS for human IL-18 lacking pro-peptide sequence
TACTTTGGCAAGCTTGAATCTAAATTATCAGTCATAAGAAATTTGAATGACCAAGTTCTCTTC
ATTGACCAAGGAAATCGGCCTCTATTTGAAGATATGACTGATTCTGACTGTAGAGATAATGC
ACCCCGGACCATATTTATTATAAGTATGTATAAAGATAGCCAGCCTAGAGGTATGGCTGTAA
CTATCTCTGTGAAGTGTGAGAAAATTTCAACTCTCTCCTGTGAGAACAAAATTATTTCCTTTA
AGGAAATGAATCCTCCTGATAACATCAAGGATACAAAAAGTGACATCATATTCTTTCAGAGA
AGTGTCCCAGGACATGATAATAAGATGCAATTTGAATCTTCATCATACGAAGGATACTTTCT
AGCTTGTGAAAAAGAGAGAGACCTTTTTAAACTCATTTTGAAAAAAGAGGATGAATTGGGG
GATAGATCTATAATGTTCACTGTTCAAAACGAAGACTAG (SEQ ID NO: 47)

>CDS for human IL-18BP including signal sequence (nt 282-866 of NCBI Reference Sequence: NM_001039659.2)
ATGACCATGAGACACAACTGGACACCAGACCTCAGCCCTTTGTGGGTCCTGCTCCTGTGT
GCCCACGTCGTCACTCTCCTGGTCAGAGCCACACCTGTCTCGCAGACCACCACAGCTGCC
ACTGCCTCAGTTAGAAGCACAAAGGACCCCTGCCCCTCCCAGCCCCCAGTGTTCCCAGCA
GCTAAGCAGTGTCCAGCATTGGAAGTGACCTGGCCAGAGGTGGAAGTGCCACTGAATGGA
ACGCTGAGCTTATCCTGTGTGGCCTGCAGCCGCTTCCCCAACTTCAGCATCCTCTACTGGC
TGGGCAATGGTTCCTTCATTGAGCACCTCCCAGGCCGACTGTGGGAGGGGAGCACCAGC
CGGGAACGTGGGAGCACAGGTACGCAGCTGTGCAAGGCCTTGGTGCTGGAGCAGCTGAC
CCCTGCCCTGCACAGCACCAACTTCTCCTGTGTGCTCGTGGACCCTGAACAGGTTGTCCA
GCGTCACGTCGTCCTGGCCCAGCTCTGGGCTGGGCTGAGGGCAACCTTGCCCCCCACCC
AAGAAGCCCTGCCCTCCAGCCACAGCAGTCCACAGCAGCAGGGTTAA (SEQ ID NO: 48)

>CDS for human IL-18BP lacking signal sequence
ACACCTGTCTCGCAGACCACCACAGCTGCCACTGCCTCAGTTAGAAGCACAAAGGACCCC
TGCCCCTCCCAGCCCCCAGTGTTCCCAGCAGCTAAGCAGTGTCCAGCATTGGAAGTGACC
TGGCCAGAGGTGGAAGTGCCACTGAATGGAACGCTGAGCTTATCCTGTGTGGCCTGCAGC
CGCTTCCCCAACTTCAGCATCCTCTACTGGCTGGGCAATGGTTCCTTCATTGAGCACCTCC
CAGGCCGACTGTGGGAGGGGAGCACCAGCCGGGAACGTGGGAGCACAGGTACGCAGCT
GTGCAAGGCCTTGGTGCTGGAGCAGCTGACCCCTGCCCTGCACAGCACCAACTTCTCCTG
TGTGCTCGTGGACCCTGAACAGGTTGTCCAGCGTCACGTCGTCCTGGCCCAGCTCTGGGC
TGGGCTGAGGGCAACCTTGCCCCCCACCCAAGAAGCCCTGCCCTCCAGCCACAGCAGTC
CACAGCAGCAGGGTTAA (SEQ ID NO: 49)

>CDS for human IL-18R1 including signal sequence (nt 634-2259 of NCBI Reference Sequence: NM_003855.5)
ATGAATTGTAGAGAATTACCCTTGACCCTTTGGGTGCTTATATCTGTAAGCACTGCAGAATC
TTGTACTTCACGTCCCCACATTACTGTGGTTGAAGGGGAACCTTTCTATCTGAAACATTGCT
CGTGTTCACTTGCACATGAGATTGAAACAACCACCAAAAGCTGGTACAAAAGCAGTGGATC
ACAGGAACATGTGGAGCTGAACCCAAGGAGTTCCTCGAGAATTGCTTTGCATGATTGTGTT
TTGGAGTTTTGGCCAGTTGAGTTGAATGACACAGGATCTTACTTTTTCCAAATGAAAAATTA
TACTCAGAAATGGAAATTAAATGTCATCAGAAGAAATAAACACAGCTGTTTCACTGAAAGAC
AAGTAACTAGTAAAATTGTGGAAGTTAAAAAATTTTTTCAGATAACCTGTGAAAACAGTTACT
ATCAAACACTGGTCAACAGCACATCATTGTATAAGAACTGTAAAAAGCTACTACTGGAGAAC
AATAAAAACCCAACGATAAAGAAGAACGCCGAGTTTGAAGATCAGGGGTATTACTCCTGCG
TGCATTTCCTTCATCATAATGGAAAACTATTTAATATCACCAAAACCTTCAATATAACAATAG

FIG. 24 cont'd.

TGGAAGATCGCAGTAATATAGTTCCGGTTCTTCTTGGACCAAAGCTTAACCATGTTGCAGT
GGAATTAGGAAAAAACGTAAGGCTCAACTGCTCTGCTTTGCTGAATGAAGAGGATGTAATT
TATTGGATGTTCGGGGAAGAAAATGGATCGGATCCTAATATACATGAAGAGAAAGAAATGA
GAATTATGACTCCAGAAGGCAAATGGCATGCTTCAAAAGTATTGAGAATTGAAAATATTGGT
GAAAGCAATCTAAATGTTTTATATAATTGCACTGTGGCCAGCACGGGAGGCACAGACACCA
AAAGCTTCATCTTGGTGAGAAAAGCAGACATGGCTGATATCCCAGGCCACGTCTTCACAAG
AGGAATGATCATAGCTGTTTTGATCTTGGTGGCAGTAGTGTGCCTAGTGACTGTGTGTGTC
ATTTATAGAGTTGACTTGGTTCTATTTTATAGACATTTAACGAGAAGAGATGAAACATTAACA
GATGGAAAAACATATGATGCTTTTGTGTCTTACCTAAAAGAATGCCGACCTGAAAATGGAGA
GGAGCACACCTTTGCTGTGGAGATTTTGCCCAGGGTGTTGGAGAAACATTTTGGGTATAAG
TTATGCATATTTGAAAGGGATGTAGTGCCTGGAGGAGCTGTTGTTGATGAAATCCACTCAC
TGATAGAGAAAAGCCGAAGACTAATCATTGTCCTAAGTAAAAGTTATATGTCTAATGAGGTC
AGGTATGAACTTGAAAGTGGACTCCATGAAGCATTGGTGGAAAGAAAAATTAAAATAATCTT
AATTGAATTTACACCTGTTACTGACTTCACATTCTTGCCCCAATCACTAAAGCTTTTGAAATC
TCACAGAGTTCTGAAGTGGAAGGCCGATAAATCTCTTTCTTATAACTCAAGGTTCTGGAAGA
ACCTTCTTTACTTAATGCCTGCAAAAACAGTCAAGCCAGGTAGAGACGAACCGGAAGTCTT
GCCTGTTCTTTCCGAGTCTTAA (SEQ ID NO: 50)

>CDS for human IL-18R1 lacking signal sequence
GCAGAATCTTGTACTTCACGTCCCCACATTACTGTGGTTGAAGGGGAACCTTTCTATCTGA
AACATTGCTCGTGTTCACTTGCACATGAGATTGAAACAACCACCAAAAGCTGGTACAAAAG
CAGTGGATCACAGGAACATGTGGAGCTGAACCCAAGGAGTTCCTCGAGAATTGCTTTGCAT
GATTGTGTTTTGGAGTTTTGGCCAGTTGAGTTGAATGACACAGGATCTTACTTTTTCCAAAT
GAAAAATTATACTCAGAAATGGAAATTAAATGTCATCAGAAGAAATAAACACAGCTGTTTCA
CTGAAAGACAAGTAACTAGTAAAATTGTGGAAGTTAAAAAATTTTTTCAGATAACCTGTGAA
AACAGTTACTATCAAACACTGGTCAACAGCACATCATTGTATAAGAACTGTAAAAAGCTACT
ACTGGAGAACAATAAAAACCCAACGATAAAGAAGAACGCCGAGTTTGAAGATCAGGGGTAT
TACTCCTGCGTGCATTTCCTTCATCATAATGGAAAACTATTTAATATCACCAAAACCTTCAAT
ATAACAATAGTGGAAGATCGCAGTAATATAGTTCCGGTTCTTCTTGGACCAAAGCTTAACCA
TGTTGCAGTGGAATTAGGAAAAAACGTAAGGCTCAACTGCTCTGCTTTGCTGAATGAAGAG
GATGTAATTTATTGGATGTTCGGGGAAGAAAATGGATCGGATCCTAATATACATGAAGAGA
AAGAAATGAGAATTATGACTCCAGAAGGCAAATGGCATGCTTCAAAAGTATTGAGAATTGAA
AATATTGGTGAAAGCAATCTAAATGTTTTATATAATTGCACTGTGGCCAGCACGGGAGGCA
CAGACACCAAAAGCTTCATCTTGGTGAGAAAAGCAGACATGGCTGATATCCCAGGCCACGT
CTTCACAAGAGGAATGATCATAGCTGTTTTGATCTTGGTGGCAGTAGTGTGCCTAGTGACT
GTGTGTGTCATTTATAGAGTTGACTTGGTTCTATTTTATAGACATTTAACGAGAAGAGATGA
AACATTAACAGATGGAAAAACATATGATGCTTTTGTGTCTTACCTAAAAGAATGCCGACCTG
AAAATGGAGAGGAGCACACCTTTGCTGTGGAGATTTTGCCCAGGGTGTTGGAGAAACATTT
TGGGTATAAGTTATGCATATTTGAAAGGGATGTAGTGCCTGGAGGAGCTGTTGTTGATGAA
ATCCACTCACTGATAGAGAAAAGCCGAAGACTAATCATTGTCCTAAGTAAAAGTTATATGTC
TAATGAGGTCAGGTATGAACTTGAAAGTGGACTCCATGAAGCATTGGTGGAAAGAAAAATT
AAAATAATCTTAATTGAATTTACACCTGTTACTGACTTCACATTCTTGCCCCAATCACTAAAG
CTTTTGAAATCTCACAGAGTTCTGAAGTGGAAGGCCGATAAATCTCTTTCTTATAACTCAAG
GTTCTGGAAGAACCTTCTTTACTTAATGCCTGCAAAAACAGTCAAGCCAGGTAGAGACGAA
CCGGAAGTCTTGCCTGTTCTTTCCGAGTCTTAA (SEQ ID NO: 51)

FIG. 24 cont'd.

>CDS for human IL-18RAP including signal sequence (nt 630-2429 of NCBI Reference Sequence: NM_003853.4)
ATGCTCTGTTTGGGCTGGATATTTCTTTGGCTTGTTGCAGGAGAGCGAATTAAAGGATTTAA
TATTTCAGGTTGTTCCACAAAAAAACTCCTTTGGACATATTCTACAAGGAGTGAAGAGGAAT
TTGTCTTATTTTGTGATTTACCAGAGCCACAGAAATCACATTTCTGCCACAGAAATCGACTC
TCACCAAAACAAGTCCCTGAGCACCTGCCCTTCATGGGTAGTAACGACCTATCTGATGTCC
AATGGTACCAACAACCTTCGAATGGAGATCCATTAGAGGACATTAGGAAAAGCTATCCTCA
CATCATTCAGGACAAATGTACCCTTCACTTTTTGACCCCAGGGGTGAATAATTCTGGGTCAT
ATATTTGTAGACCCAAGATGATTAAGAGCCCCTATGATGTAGCCTGTTGTGTCAAGATGATT
TTAGAAGTTAAGCCCCAGACAAATGCATCCTGTGAGTATTCCGCATCACATAAGCAAGACC
TACTTCTTGGGAGCACTGGCTCTATTTCTTGCCCCAGTCTCAGCTGCCAAAGTGATGCACA
AAGTCCAGCGGTAACCTGGTACAAGAATGGAAAACTCCTCTCTGTGGAAAGGAGCAACCG
AATCGTAGTGGATGAAGTTTATGACTATCACCAGGGCACATATGTATGTGATTACACTCAGT
CGGATACTGTGAGTTCGTGGACAGTCAGAGCTGTTGTTCAAGTGAGAACCATTGTGGGAG
ACACTAAACTCAAACCAGATATTCTGGATCCTGTCGAGGACACACTGGAAGTAGAACTTGG
AAAGCCTTTAACTATTAGCTGCAAAGCACGATTTGGCTTTGAAAGGGTCTTTAACCCTGTCA
TAAAATGGTACATCAAAGATTCTGACCTAGAGTGGGAAGTCTCAGTACCTGAGGCGAAAAG
TATTAAATCCACTTTAAAGGATGAAATCATTGAGCGTAATATCATCTTGGAAAAAGTCACTCA
GCGTGATCTTCGCAGGAAGTTTGTTTGCTTTGTCCAGAACTCCATTGGAAACACAACCCAG
TCCGTCCAACTGAAAGAAAAGAGAGGAGTGGTGCTCCTGTACATCCTGCTTGGCACCATC
GGGACCCTGGTGGCCGTGCTGGCGGCGAGTGCCCTCCTCTACAGGCACTGGATTGAAAT
AGTGCTGCTGTACCGGACCTACCAGAGCAAGGATCAGACGCTTGGGGATAAAAAGGATTT
TGATGCTTTCGTATCCTATGCAAAATGGAGCTCTTTTCCAAGTGAGGCCACTTCATCTCTGA
GTGAAGAACACTTGGCCCTGAGCCTATTTCCTGATGTTTTAGAAAACAAATATGGATATAGC
CTGTGTTTGCTTGAAAGAGATGTGGCTCCAGGAGGAGTGTATGCAGAAGACATTGTGAGC
ATTATTAAGAGAAGCAGAAGAGGAATATTTATCTTGAGCCCCAACTATGTCAATGGACCCA
GTATCTTTGAACTACAAGCAGCAGTGAATCTTGCCTTGGATGATCAAACACTGAAACTCATT
TTAATTAAGTTCTGTTACTTCCAAGAGCCAGAGTCTCTACCTCATCTCGTGAAAAAAGCTCT
CAGGGTTTTGCCCACAGTTACTTGGAGAGGCTTAAAATCAGTTCCTCCCAATTCTAGGTTCT
GGGCCAAAATGCGCTACCACATGCCTGTGAAAAACTCTCAGGGATTCACGTGGAACCAGC
TCAGAATTACCTCTAGGATTTTTCAGTGGAAAGGACTCAGTAGAACAGAAACCACTGGGAG
GAGCTCCCAGCCTAAGGAATGGTGA (SEQ ID NO: 52)

>CDS for human IL-18RAP lacking signal sequence
TTTAATATTTCAGGTTGTTCCACAAAAAAACTCCTTTGGACATATTCTACAAGGAGTGAAGA
GGAATTTGTCTTATTTTGTGATTTACCAGAGCCACAGAAATCACATTTCTGCCACAGAAATC
GACTCTCACCAAAACAAGTCCCTGAGCACCTGCCCTTCATGGGTAGTAACGACCTATCTGA
TGTCCAATGGTACCAACAACCTTCGAATGGAGATCCATTAGAGGACATTAGGAAAAGCTAT
CCTCACATCATTCAGGACAAATGTACCCTTCACTTTTTGACCCCAGGGGTGAATAATTCTGG
GTCATATATTTGTAGACCCAAGATGATTAAGAGCCCCTATGATGTAGCCTGTTGTGTCAAGA
TGATTTTAGAAGTTAAGCCCCAGACAAATGCATCCTGTGAGTATTCCGCATCACATAAGCAA
GACCTACTTCTTGGGAGCACTGGCTCTATTTCTTGCCCCAGTCTCAGCTGCCAAAGTGATG
CACAAAGTCCAGCGGTAACCTGGTACAAGAATGGAAAACTCCTCTCTGTGGAAAGGAGCA
ACCGAATCGTAGTGGATGAAGTTTATGACTATCACCAGGGCACATATGTATGTGATTACACT
CAGTCGGATACTGTGAGTTCGTGGACAGTCAGAGCTGTTGTTCAAGTGAGAACCATTGTGG
GAGACACTAAACTCAAACCAGATATTCTGGATCCTGTCGAGGACACACTGGAAGTAGAACT

FIG. 24 cont'd.

TGGAAAGCCTTTAACTATTAGCTGCAAAGCACGATTTGGCTTTGAAAGGGTCTTTAACCCTG
TCATAAAATGGTACATCAAAGATTCTGACCTAGAGTGGGAAGTCTCAGTACCTGAGGCGAA
AAGTATTAAATCCACTTTAAAGGATGAAATCATTGAGCGTAATATCATCTTGGAAAAAGTCA
CTCAGCGTGATCTTCGCAGGAAGTTTGTTTGCTTTGTCCAGAACTCCATTGGAAACACAAC
CCAGTCCGTCCAACTGAAAGAAAAGAGAGGAGTGGTGCTCCTGTACATCCTGCTTGGCAC
CATCGGGACCCTGGTGGCCGTGCTGGCGGCGAGTGCCCTCCTCTACAGGCACTGGATTG
AAATAGTGCTGCTGTACCGGACCTACCAGAGCAAGGATCAGACGCTTGGGGATAAAAAGG
ATTTTGATGCTTTCGTATCCTATGCAAAATGGAGCTCTTTTCCAAGTGAGGCCACTTCATCT
CTGAGTGAAGAACACTTGGCCCTGAGCCTATTTCCTGATGTTTTAGAAAACAAATATGGATA
TAGCCTGTGTTTGCTTGAAAGAGATGTGGCTCCAGGAGGAGTGTATGCAGAAGACATTGTG
AGCATTATTAAGAGAAGCAGAAGAGGAATATTTATCTTGAGCCCCAACTATGTCAATGGAC
CCAGTATCTTTGAACTACAAGCAGCAGTGAATCTTGCCTTGGATGATCAAACACTGAAACTC
ATTTTAATTAAGTTCTGTTACTTCCAAGAGCCAGAGTCTCTACCTCATCTCGTGAAAAAAGC
TCTCAGGGTTTTGCCCACAGTTACTTGGAGAGGCTTAAAATCAGTTCCTCCCAATTCTAGGT
TCTGGGCCAAAATGCGCTACCACATGCCTGTGAAAAACTCTCAGGGATTCACGTGGAACCA
GCTCAGAATTACCTCTAGGATTTTTCAGTGGAAAGGACTCAGTAGAACAGAAACCACTGGG
AGGAGCTCCCAGCCTAAGGAATGGTGA (SEQ ID NO: 53)

>CDS for human IL-2 including signal sequence (nt 286-747 of NCBI Reference Sequence: NM_000586.4)
ATGTACAGGATGCAACTCCTGTCTTGCATTGCACTAAGTCTTGCACTTGTCACAAACAGTG
CACCTACTTCAAGTTCTACAAAGAAAACACAGCTACAACTGGAGCATTTACTGCTGGATTTA
CAGATGATTTTGAATGGAATTAATAATTACAAGAATCCCAAACTCACCAGGATGCTCACATT
TAAGTTTTACATGCCCAAGAAGGCCACAGAACTGAAACATCTTCAGTGTCTAGAAGAAGAA
CTCAAACCTCTGGAGGAAGTGCTAAATTTAGCTCAAAGCAAAAACTTTCACTTAAGACCCAG
GGACTTAATCAGCAATATCAACGTAATAGTTCTGGAACTAAAGGGATCTGAAACAACATTCA
TGTGTGAATATGCTGATGAGACAGCAACCATTGTAGAATTTCTGAACAGATGGATTACCTTT
TGTCAAAGCATCATCTCAACACTGACTTGA (SEQ ID NO: 54)

>CDS for human IL-2 lacking signal sequence
GCACCTACTTCAAGTTCTACAAAGAAAACACAGCTACAACTGGAGCATTTACTGCTGGATTT
ACAGATGATTTTGAATGGAATTAATAATTACAAGAATCCCAAACTCACCAGGATGCTCACAT
TTAAGTTTTACATGCCCAAGAAGGCCACAGAACTGAAACATCTTCAGTGTCTAGAAGAAGA
ACTCAAACCTCTGGAGGAAGTGCTAAATTTAGCTCAAAGCAAAAACTTTCACTTAAGACCCA
GGGACTTAATCAGCAATATCAACGTAATAGTTCTGGAACTAAAGGGATCTGAAACAACATTC
ATGTGTGAATATGCTGATGAGACAGCAACCATTGTAGAATTTCTGAACAGATGGATTACCTT
TTGTCAAAGCATCATCTCAACACTGACTTGA (SEQ ID NO: 55)

FIG. 24 cont'd.

>CDS for human IL-2RA including signal sequence (nt 217-1035 of NCBI Reference Sequence: NM_000417.3)
ATGGATTCATACCTGCTGATGTGGGGACTGCTCACGTTCATCATGGTGCCTGGCTGCCAG
GCAGAGCTCTGTGACGATGACCCGCCAGAGATCCCACACGCCACATTCAAAGCCATGGCC
TACAAGGAAGGAACCATGTTGAACTGTGAATGCAAGAGAGGTTTCCGCAGAATAAAAAGCG
GGTCACTCTATATGCTCTGTACAGGAAACTCTAGCCACTCGTCCTGGGACAACCAATGTCA
ATGCACAAGCTCTGCCACTCGGAACACAACGAAACAAGTGACACCTCAACCTGAAGAACA
GAAAGAAAGGAAAACCACAGAAATGCAAAGTCCAATGCAGCCAGTGGACCAAGCGAGCCT
TCCAGGTCACTGCAGGGAACCTCCACCATGGGAAAATGAAGCCACAGAGAGAATTTATCAT
TTCGTGGTGGGGCAGATGGTTTATTATCAGTGCGTCCAGGGATACAGGGCTCTACACAGA
GGTCCTGCTGAGAGCGTCTGCAAAATGACCCACGGGAAGACAAGGTGGACCCAGCCCCA
GCTCATATGCACAGGTGAAATGGAGACCAGTCAGTTTCCAGGTGAAGAGAAGCCTCAGGC
AAGCCCCGAAGGCCGTCCTGAGAGTGAGACTTCCTGCCTCGTCACAACAACAGATTTTCAA
ATACAGACAGAAATGGCTGCAACCATGGAGACGTCCATATTTACAACAGAGTACCAGGTAG
CAGTGGCCGGCTGTGTTTTCCTGCTGATCAGCGTCCTCCTCCTGAGTGGGCTCACCTGGC
AGCGGAGACAGAGGAAGAGTAGAAGAACAATCTAG (SEQ ID NO: 56)

>CDS for human IL-2RA lacking signal sequence
GAGCTCTGTGACGATGACCCGCCAGAGATCCCACACGCCACATTCAAAGCCATGGCCTAC
AAGGAAGGAACCATGTTGAACTGTGAATGCAAGAGAGGTTTCCGCAGAATAAAAAGCGGG
TCACTCTATATGCTCTGTACAGGAAACTCTAGCCACTCGTCCTGGGACAACCAATGTCAAT
GCACAAGCTCTGCCACTCGGAACACAACGAAACAAGTGACACCTCAACCTGAAGAACAGA
AAGAAAGGAAAACCACAGAAATGCAAAGTCCAATGCAGCCAGTGGACCAAGCGAGCCTTC
CAGGTCACTGCAGGGAACCTCCACCATGGGAAAATGAAGCCACAGAGAGAATTTATCATTT
CGTGGTGGGGCAGATGGTTTATTATCAGTGCGTCCAGGGATACAGGGCTCTACACAGAGG
TCCTGCTGAGAGCGTCTGCAAAATGACCCACGGGAAGACAAGGTGGACCCAGCCCCAGCT
CATATGCACAGGTGAAATGGAGACCAGTCAGTTTCCAGGTGAAGAGAAGCCTCAGGCAAG
CCCCGAAGGCCGTCCTGAGAGTGAGACTTCCTGCCTCGTCACAACAACAGATTTTCAAATA
CAGACAGAAATGGCTGCAACCATGGAGACGTCCATATTTACAACAGAGTACCAGGTAGCA
GTGGCCGGCTGTGTTTTCCTGCTGATCAGCGTCCTCCTCCTGAGTGGGCTCACCTGGCAG
CGGAGACAGAGGAAGAGTAGAAGAACAATCTAG (SEQ ID NO: 57)

>CDS for human IL-12 subunit alpha including signal sequence (nt 223-984 of NCBI Reference Sequence: NM_000882.4)
ATGTGGCCCCCTGGGTCAGCCTCCCAGCCACCGCCCTCACCTGCCGCGGCCACAGGTCT
GCATCCAGCGGCTCGCCCTGTGTCCCTGCAGTGCCGGCTCAGCATGTGTCCAGCGCGCA
GCCTCCTCCTTGTGGCTACCCTGGTCCTCCTGGACCACCTCAGTTTGGCCAGAAACCTCC
CCGTGGCCACTCCAGACCCAGGAATGTTCCCATGCCTTCACCACTCCCAAAACCTGCTGA
GGGCCGTCAGCAACATGCTCCAGAAGGCCAGACAAACTCTAGAATTTTACCCTTGCACTTC
TGAAGAGATTGATCATGAAGATATCACAAAAGATAAAACCAGCACAGTGGAGGCCTGTTTA
CCATTGGAATTAACCAAGAATGAGAGTTGCCTAAATTCCAGAGAGACCTCTTTCATAACTAA
TGGGAGTTGCCTGGCCTCCAGAAAGACCTCTTTTATGATGGCCCTGTGCCTTAGTAGTATT
TATGAAGACTTGAAGATGTACCAGGTGGAGTTCAAGACCATGAATGCAAAGCTTCTGATGG
ATCCTAAGAGGCAGATCTTTCTAGATCAAAACATGCTGGCAGTTATTGATGAGCTGATGCA
GGCCCTGAATTTCAACAGTGAGACTGTGCCACAAAAATCCTCCCTTGAAGAACCGGATTTT
TATAAAACTAAAATCAAGCTCTGCATACTTCTTCATGCTTTCAGAATTCGGGCAGTGACTAT
TGATAGAGTGATGAGCTATCTGAATGCTTCCTAA (SEQ ID NO: 58)

FIG. 24 cont'd.

>CDS for human IL-12 subunit alpha lacking signal sequence
AGAAACCTCCCCGTGGCCACTCCAGACCCAGGAATGTTCCCATGCCTTCACCACTCCCAA
AACCTGCTGAGGGCCGTCAGCAACATGCTCCAGAAGGCCAGACAAACTCTAGAATTTTACC
CTTGCACTTCTGAAGAGATTGATCATGAAGATATCACAAAAGATAAAACCAGCACAGTGGA
GGCCTGTTTACCATTGGAATTAACCAAGAATGAGAGTTGCCTAAATTCCAGAGAGACCTCT
TTCATAACTAATGGGAGTTGCCTGGCCTCCAGAAAGACCTCTTTTATGATGGCCCTGTGCC
TTAGTAGTATTTATGAAGACTTGAAGATGTACCAGGTGGAGTTCAAGACCATGAATGCAAA
GCTTCTGATGGATCCTAAGAGGCAGATCTTTCTAGATCAAAACATGCTGGCAGTTATTGAT
GAGCTGATGCAGGCCCTGAATTTCAACAGTGAGACTGTGCCACAAAAATCCTCCCTTGAAG
AACCGGATTTTTATAAAACTAAAATCAAGCTCTGCATACTTCTTCATGCTTTCAGAATTCGG
GCAGTGACTATTGATAGAGTGATGAGCTATCTGAATGCTTCCTAA (SEQ ID NO: 59)

>CDS for human IL-12 subunit beta including signal sequence (nt 57-1043 of NCBI Reference Sequence: NM_002187.3)
ATGTGTCACCAGCAGTTGGTCATCTCTTGGTTTTCCCTGGTTTTTCTGGCATCTCCCCTCGT
GGCCATATGGGAACTGAAGAAAGATGTTTATGTCGTAGAATTGGATTGGTATCCGGATGCC
CCTGGAGAAATGGTGGTCCTCACCTGTGACACCCCTGAAGAAGATGGTATCACCTGGACC
TTGGACCAGAGCAGTGAGGTCTTAGGCTCTGGCAAAACCCTGACCATCCAAGTCAAAGAG
TTTGGAGATGCTGGCCAGTACACCTGTCACAAAGGAGGCGAGGTTCTAAGCCATTCGCTC
CTGCTGCTTCACAAAAAGGAAGATGGAATTTGGTCCACTGATATTTTAAAGGACCAGAAAG
AACCCAAAAATAAGACCTTTCTAAGATGCGAGGCCAAGAATTATTCTGGACGTTTCACCTG
CTGGTGGCTGACGACAATCAGTACTGATTTGACATTCAGTGTCAAAAGCAGCAGAGGCTCT
TCTGACCCCCAAGGGGTGACGTGCGGAGCTGCTACACTCTCTGCAGAGAGAGTCAGAGG
GGACAACAAGGAGTATGAGTACTCAGTGGAGTGCCAGGAGGACAGTGCCTGCCCAGCTG
CTGAGGAGAGTCTGCCCATTGAGGTCATGGTGGATGCCGTTCACAAGCTCAAGTATGAAA
ACTACACCAGCAGCTTCTTCATCAGGGACATCATCAAACCTGACCCACCCAAGAACTTGCA
GCTGAAGCCATTAAAGAATTCTCGGCAGGTGGAGGTCAGCTGGGAGTACCCTGACACCTG
GAGTACTCCACATTCCTACTTCTCCCTGACATTCTGCGTTCAGGTCCAGGGCAAGAGCAAG
AGAGAAAAGAAAGATAGAGTCTTCACGGACAAGACCTCAGCCACGGTCATCTGCCGCAAA
AATGCCAGCATTAGCGTGCGGGCCCAGGACCGCTACTATAGCTCATCTTGGAGCGAATGG
GCATCTGTGCCCTGCAGTTAG (SEQ ID NO: 60)

>CDS for human IL-12 subunit beta lacking signal sequence
ATATGGGAACTGAAGAAAGATGTTTATGTCGTAGAATTGGATTGGTATCCGGATGCCCCTG
GAGAAATGGTGGTCCTCACCTGTGACACCCCTGAAGAAGATGGTATCACCTGGACCTTGG
ACCAGAGCAGTGAGGTCTTAGGCTCTGGCAAAACCCTGACCATCCAAGTCAAAGAGTTTG
GAGATGCTGGCCAGTACACCTGTCACAAAGGAGGCGAGGTTCTAAGCCATTCGCTCCTGC
TGCTTCACAAAAAGGAAGATGGAATTTGGTCCACTGATATTTTAAAGGACCAGAAAGAACC
CAAAAATAAGACCTTTCTAAGATGCGAGGCCAAGAATTATTCTGGACGTTTCACCTGCTGG
TGGCTGACGACAATCAGTACTGATTTGACATTCAGTGTCAAAAGCAGCAGAGGCTCTTCTG
ACCCCCAAGGGGTGACGTGCGGAGCTGCTACACTCTCTGCAGAGAGAGTCAGAGGGGAC
AACAAGGAGTATGAGTACTCAGTGGAGTGCCAGGAGGACAGTGCCTGCCCAGCTGCTGAG
GAGAGTCTGCCCATTGAGGTCATGGTGGATGCCGTTCACAAGCTCAAGTATGAAAACTACA
CCAGCAGCTTCTTCATCAGGGACATCATCAAACCTGACCCACCCAAGAACTTGCAGCTGAA
GCCATTAAAGAATTCTCGGCAGGTGGAGGTCAGCTGGGAGTACCCTGACACCTGGAGTAC
TCCACATTCCTACTTCTCCCTGACATTCTGCGTTCAGGTCCAGGGCAAGAGCAAGAGAGAA

FIG. 24 cont'd.

AAGAAAGATAGAGTCTTCACGGACAAGACCTCAGCCACGGTCATCTGCCGCAAAAATGCC
AGCATTAGCGTGCGGGCCCAGGACCGCTACTATAGCTCATCTTGGAGCGAATGGGCATCT
GTGCCCTGCAGTTAG (SEQ ID NO: 61)

>CDS for human IL-5 including signal sequence (nt 45-449 of NCBI Reference Sequence: NM_000879.3)
ATGAGGATGCTTCTGCATTTGAGTTTGCTAGCTCTTGGAGCTGCCTACGTGTATGCCATCC
CCACAGAAATTCCCACAAGTGCATTGGTGAAAGAGACCTTGGCACTGCTTTCTACTCATCG
AACTCTGCTGATAGCCAATGAGACTCTGAGGATTCCTGTTCCTGTACATAAAAATCACCAAC
TGTGCACTGAAGAAATCTTTCAGGGAATAGGCACACTGGAGAGTCAAACTGTGCAAGGGG
GTACTGTGGAAAGACTATTCAAAAACTTGTCCTTAATAAAGAAATACATTGACGGCCAAAAA
AAAAAGTGTGGAGAAGAAAGACGGAGAGTAAACCAATTCCTAGACTACCTGCAAGAGTTTC
TTGGTGTAATGAACACCGAGTGGATAATAGAAAGTTGA (SEQ ID NO: 62)

>CDS for human IL-5 lacking signal sequence
ATCCCCACAGAAATTCCCACAAGTGCATTGGTGAAAGAGACCTTGGCACTGCTTTCTACTC
ATCGAACTCTGCTGATAGCCAATGAGACTCTGAGGATTCCTGTTCCTGTACATAAAAATCAC
CAACTGTGCACTGAAGAAATCTTTCAGGGAATAGGCACACTGGAGAGTCAAACTGTGCAAG
GGGGTACTGTGGAAAGACTATTCAAAAACTTGTCCTTAATAAAGAAATACATTGACGGCCAA
AAAAAAAAGTGTGGAGAAGAAAGACGGAGAGTAAACCAATTCCTAGACTACCTGCAAGAGT
TTCTTGGTGTAATGAACACCGAGTGGATAATAGAAAGTTGA (SEQ ID NO: 63)

>CDS for human IL-6 including signal sequence (nt 64-702 of NCBI Reference Sequence: NM_000600.5)
ATGAACTCCTTCTCCACAAGCGCCTTCGGTCCAGTTGCCTTCTCCCTGGGGCTGCTCCTG
GTGTTGCCTGCTGCCTTCCCTGCCCCAGTACCCCCAGGAGAAGATTCCAAAGATGTAGCC
GCCCCACACAGACAGCCACTCACCTCTTCAGAACGAATTGACAAACAAATTCGGTACATCC
TCGACGGCATCTCAGCCCTGAGAAAGGAGACATGTAACAAGAGTAACATGTGTGAAAGCA
GCAAAGAGGCACTGGCAGAAAACAACCTGAACCTTCCAAAGATGGCTGAAAAAGATGGAT
GCTTCCAATCTGGATTCAATGAGGAGACTTGCCTGGTGAAAATCATCACTGGTCTTTTGGA
GTTTGAGGTATACCTAGAGTACCTCCAGAACAGATTTGAGAGTAGTGAGGAACAAGCCAGA
GCTGTGCAGATGAGTACAAAAGTCCTGATCCAGTTCCTGCAGAAAAAGGCAAAGAATCTAG
ATGCAATAACCACCCCTGACCCAACCACAAATGCCAGCCTGCTGACGAAGCTGCAGGCAC
AGAACCAGTGGCTGCAGGACATGACAACTCATCTCATTCTGCGCAGCTTTAAGGAGTTCCT
GCAGTCCAGCCTGAGGGCTCTTCGGCAAATGTAG (SEQ ID NO: 64)

>CDS for human IL-6 lacking signal sequence
GTACCCCCAGGAGAAGATTCCAAAGATGTAGCCGCCCCACACAGACAGCCACTCACCTCT
TCAGAACGAATTGACAAACAAATTCGGTACATCCTCGACGGCATCTCAGCCCTGAGAAAGG
AGACATGTAACAAGAGTAACATGTGTGAAAGCAGCAAAGAGGCACTGGCAGAAAACAACCT
GAACCTTCCAAAGATGGCTGAAAAAGATGGATGCTTCCAATCTGGATTCAATGAGGAGACT
TGCCTGGTGAAAATCATCACTGGTCTTTTGGAGTTTGAGGTATACCTAGAGTACCTCCAGA
ACAGATTTGAGAGTAGTGAGGAACAAGCCAGAGCTGTGCAGATGAGTACAAAAGTCCTGAT
CCAGTTCCTGCAGAAAAAGGCAAAGAATCTAGATGCAATAACCACCCCTGACCCAACCACA
AATGCCAGCCTGCTGACGAAGCTGCAGGCACAGAACCAGTGGCTGCAGGACATGACAACT
CATCTCATTCTGCGCAGCTTTAAGGAGTTCCTGCAGTCCAGCCTGAGGGCTCTTCGGCAAA
TGTAG (SEQ ID NO: 65)

FIG. 24 cont'd.

>CDS for human IL-9 including signal sequence (nt 26-460 of NCBI Reference Sequence: NM_000590.2)
ATGCTTCTGGCCATGGTCCTTACCTCTGCCCTGCTCCTGTGCTCCGTGGCAGGCCAGGGG
TGTCCAACCTTGGCGGGGATCCTGGACATCAACTTCCTCATCAACAAGATGCAGGAAGATC
CAGCTTCCAAGTGCCACTGCAGTGCTAATGTGACCAGTTGTCTCTGTTTGGGCATTCCCTC
TGACAACTGCACCAGACCATGCTTCAGTGAGAGACTGTCTCAGATGACCAATACCACCATG
CAAACAAGATACCCACTGATTTTCAGTCGGGTGAAAAAATCAGTTGAAGTACTAAAGAACAA
CAAGTGTCCATATTTTTCCTGTGAACAGCCATGCAACCAAACCACGGCAGGCAACGCGCTG
ACATTTCTGAAGAGTCTTCTGGAAATTTTCCAGAAAGAAAAGATGAGAGGGATGAGAGGCA
AGATATGA (SEQ ID NO: 66)

>CDS for human IL-9 lacking signal sequence
CAGGGGTGTCCAACCTTGGCGGGGATCCTGGACATCAACTTCCTCATCAACAAGATGCAG
GAAGATCCAGCTTCCAAGTGCCACTGCAGTGCTAATGTGACCAGTTGTCTCTGTTTGGGCA
TTCCCTCTGACAACTGCACCAGACCATGCTTCAGTGAGAGACTGTCTCAGATGACCAATAC
CACCATGCAAACAAGATACCCACTGATTTTCAGTCGGGTGAAAAAATCAGTTGAAGTACTAA
AGAACAACAAGTGTCCATATTTTTCCTGTGAACAGCCATGCAACCAAACCACGGCAGGCAA
CGCGCTGACATTTCTGAAGAGTCTTCTGGAAATTTTCCAGAAAGAAAAGATGAGAGGGATG
AGAGGCAAGATATGA (SEQ ID NO: 67)

>CDS for human IL-10 including signal sequence (nt 60-596 of NCBI Reference Sequence: NM_000572.3)
ATGCACAGCTCAGCACTGCTCTGTTGCCTGGTCCTCCTGACTGGGGTGAGGGCCAGCCCA
GGCCAGGGCACCCAGTCTGAGAACAGCTGCACCCACTTCCCAGGCAACCTGCCTAACATG
CTTCGAGATCTCCGAGATGCCTTCAGCAGAGTGAAGACTTTCTTTCAAATGAAGGATCAGC
TGGACAACTTGTTGTTAAAGGAGTCCTTGCTGGAGGACTTTAAGGGTTACCTGGGTTGCCA
AGCCTTGTCTGAGATGATCCAGTTTTACCTGGAGGAGGTGATGCCCCAAGCTGAGAACCA
AGACCCAGACATCAAGGCGCATGTGAACTCCCTGGGGGAGAACCTGAAGACCCTCAGGCT
GAGGCTACGGCGCTGTCATCGATTTCTTCCCTGTGAAAACAAGAGCAAGGCCGTGGAGCA
GGTGAAGAATGCCTTTAATAAGCTCCAAGAGAAAGGCATCTACAAAGCCATGAGTGAGTTT
GACATCTTCATCAACTACATAGAAGCCTACATGACAATGAAGATACGAAACTGA (SEQ ID NO: 68)

>CDS for human IL-10 lacking signal sequence
AGCCCAGGCCAGGGCACCCAGTCTGAGAACAGCTGCACCCACTTCCCAGGCAACCTGCC
TAACATGCTTCGAGATCTCCGAGATGCCTTCAGCAGAGTGAAGACTTTCTTTCAAATGAAG
GATCAGCTGGACAACTTGTTGTTAAAGGAGTCCTTGCTGGAGGACTTTAAGGGTTACCTGG
GTTGCCAAGCCTTGTCTGAGATGATCCAGTTTTACCTGGAGGAGGTGATGCCCCAAGCTG
AGAACCAAGACCCAGACATCAAGGCGCATGTGAACTCCCTGGGGGAGAACCTGAAGACCC
TCAGGCTGAGGCTACGGCGCTGTCATCGATTTCTTCCCTGTGAAAACAAGAGCAAGGCCG
TGGAGCAGGTGAAGAATGCCTTTAATAAGCTCCAAGAGAAAGGCATCTACAAAGCCATGAG
TGAGTTTGACATCTTCATCAACTACATAGAAGCCTACATGACAATGAAGATACGAAACTGA
(SEQ ID NO: 69)

FIG. 24 cont'd.

>CDS for human IL-22 including signal sequence (nt 69-608 of NCBI Reference Sequence: NM_020525.5)
ATGGCCGCCCTGCAGAAATCTGTGAGCTCTTTCCTTATGGGGACCCTGGCCACCAGCTGC
CTCCTTCTCTTGGCCCTCTTGGTACAGGGAGGAGCAGCTGCGCCCATCAGCTCCCACTGC
AGGCTTGACAAGTCCAACTTCCAGCAGCCCTATATCACCAACCGCACCTTCATGCTGGCTA
AGGAGGCTAGCTTGGCTGATAACAACACAGACGTTCGTCTCATTGGGGAGAAACTGTTCCA
CGGAGTCAGTATGAGTGAGCGCTGCTATCTGATGAAGCAGGTGCTGAACTTCACCCTTGA
AGAAGTGCTGTTCCCTCAATCTGATAGGTTCCAGCCTTATATGCAGGAGGTGGTGCCCTTC
CTGGCCAGGCTCAGCAACAGGCTAAGCACATGTCATATTGAAGGTGATGACCTGCATATCC
AGAGGAATGTGCAAAAGCTGAAGGACACAGTGAAAAAGCTTGGAGAGAGTGGAGAGATCA
AAGCAATTGGAGAACTGGATTTGCTGTTTATGTCTCTGAGAAATGCCTGCATTTGA (SEQ ID NO: 70)

>CDS for human IL-22 lacking signal sequence
GCGCCCATCAGCTCCCACTGCAGGCTTGACAAGTCCAACTTCCAGCAGCCCTATATCACC
AACCGCACCTTCATGCTGGCTAAGGAGGCTAGCTTGGCTGATAACAACACAGACGTTCGT
CTCATTGGGGAGAAACTGTTCCACGGAGTCAGTATGAGTGAGCGCTGCTATCTGATGAAG
CAGGTGCTGAACTTCACCCTTGAAGAAGTGCTGTTCCCTCAATCTGATAGGTTCCAGCCTT
ATATGCAGGAGGTGGTGCCCTTCCTGGCCAGGCTCAGCAACAGGCTAAGCACATGTCATA
TTGAAGGTGATGACCTGCATATCCAGAGGAATGTGCAAAAGCTGAAGGACACAGTGAAAAA
GCTTGGAGAGAGTGGAGAGATCAAAGCAATTGGAGAACTGGATTTGCTGTTTATGTCTCTG
AGAAATGCCTGCATTTGA (SEQ ID NO: 71)

>CDS for human IFNγ including signal sequence (nt 126-626 of NCBI Reference Sequence: NM_000619.3)
ATGAAATATACAAGTTATATCTTGGCTTTTCAGCTCTGCATCGTTTTGGGTTCTCTTGGCTG
TTACTGCCAGGACCCATATGTAAAAGAAGCAGAAAACCTTAAGAAATATTTTAATGCAGGTC
ATTCAGATGTAGCGGATAATGGAACTCTTTTCTTAGGCATTTTGAAGAATTGGAAAGAGGAG
AGTGACAGAAAAATAATGCAGAGCCAAATTGTCTCCTTTTACTTCAAACTTTTTAAAAACTTT
AAAGATGACCAGAGCATCCAAAAGAGTGTGGAGACCATCAAGGAAGACATGAATGTCAAGT
TTTTCAATAGCAACAAAAAGAAACGAGATGACTTCGAAAAGCTGACTAATTATTCGGTAACT
GACTTGAATGTCCAACGCAAAGCAATACATGAACTCATCCAAGTGATGGCTGAACTGTCGC
CAGCAGCTAAAACAGGGAAGCGAAAAAGGAGTCAGATGCTGTTTCGAGGTCGAAGAGCAT
CCCAGTAA (SEQ ID NO: 72)

>CDS for human IFNγ lacking signal sequence
CAGGACCCATATGTAAAAGAAGCAGAAAACCTTAAGAAATATTTTAATGCAGGTCATTCAGA
TGTAGCGGATAATGGAACTCTTTTCTTAGGCATTTTGAAGAATTGGAAAGAGGAGAGTGAC
AGAAAAATAATGCAGAGCCAAATTGTCTCCTTTTACTTCAAACTTTTTAAAAACTTTAAAGAT
GACCAGAGCATCCAAAAGAGTGTGGAGACCATCAAGGAAGACATGAATGTCAAGTTTTTCA
ATAGCAACAAAAAGAAACGAGATGACTTCGAAAAGCTGACTAATTATTCGGTAACTGACTTG
AATGTCCAACGCAAAGCAATACATGAACTCATCCAAGTGATGGCTGAACTGTCGCCAGCAG
CTAAAACAGGGAAGCGAAAAAGGAGTCAGATGCTGTTTCGAGGTCGAAGAGCATCCCAGT
AA (SEQ ID NO: 73)

FIG. 24 cont'd.

>CDS for human GM-CSF including signal sequence (nt 36-470 of NCBI Reference Sequence: NM_000758.4)
ATGTGGCTGCAGAGCCTGCTGCTCTTGGGCACTGTGGCCTGCAGCATCTCTGCACCCGCC
CGCTCGCCCAGCCCCAGCACGCAGCCCTGGGAGCATGTGAATGCCATCCAGGAGGCCCG
GCGTCTCCTGAACCTGAGTAGAGACACTGCTGCTGAGATGAATGAAACAGTAGAAGTCATC
TCAGAAATGTTTGACCTCCAGGAGCCGACCTGCCTACAGACCCGCCTGGAGCTGTACAAG
CAGGGCCTGCGGGGCAGCCTCACCAAGCTCAAGGGCCCCTTGACCATGATGGCCAGCCA
CTACAAGCAGCACTGCCCTCCAACCCCGGAAACTTCCTGTGCAACCCAGATTATCACCTTT
GAAAGTTTCAAAGAGAACCTGAAGGACTTTCTGCTTGTCATCCCCTTTGACTGCTGGGAGC
CAGTCCAGGAGTGA (SEQ ID NO: 74)

>CDS for human GM-CSF lacking signal sequence
GCACCCGCCCGCTCGCCCAGCCCCAGCACGCAGCCCTGGGAGCATGTGAATGCCATCCA
GGAGGCCCGGCGTCTCCTGAACCTGAGTAGAGACACTGCTGCTGAGATGAATGAAACAGT
AGAAGTCATCTCAGAAATGTTTGACCTCCAGGAGCCGACCTGCCTACAGACCCGCCTGGA
GCTGTACAAGCAGGGCCTGCGGGGCAGCCTCACCAAGCTCAAGGGCCCCTTGACCATGA
TGGCCAGCCACTACAAGCAGCACTGCCCTCCAACCCCGGAAACTTCCTGTGCAACCCAGA
TTATCACCTTTGAAAGTTTCAAAGAGAACCTGAAGGACTTTCTGCTTGTCATCCCCTTTGAC
TGCTGGGAGCCAGTCCAGGAGTGA (SEQ ID NO: 75)

>CDS for human SAA including signal sequence (nt 185-553 of NCBI Reference Sequence: NM_000331.6)
ATGAAGCTTCTCACGGGCCTGGTTTTCTGCTCCTTGGTCCTGGGTGTCAGCAGCCGAAGC
TTCTTTTCGTTCCTTGGCGAGGCTTTTGATGGGGCTCGGGACATGTGGAGAGCCTACTCTG
ACATGAGAGAAGCCAATTACATCGGCTCAGACAAATACTTCCATGCTCGGGGGAACTATGA
TGCTGCCAAAAGGGGACCTGGGGGTGCCTGGGCTGCAGAAGTGATCACCGATGCCAGAG
AGAATATCCAGAGATTCTTTGGCCATGGTGCGGAGGACTCGCTGGCTGATCAGGCTGCCA
ATGAATGGGGCAGGAGTGGCAAAGACCCCAATCACTTCCGACCTGCTGGCCTGCCTGAGA
AATACTGA (SEQ ID NO: 776)

>CDS for human SAA lacking signal sequence
CGAAGCTTCTTTTCGTTCCTTGGCGAGGCTTTTGATGGGGCTCGGGACATGTGGAGAGCC
TACTCTGACATGAGAGAAGCCAATTACATCGGCTCAGACAAATACTTCCATGCTCGGGGGA
ACTATGATGCTGCCAAAAGGGGACCTGGGGGTGCCTGGGCTGCAGAAGTGATCACCGAT
GCCAGAGAGAATATCCAGAGATTCTTTGGCCATGGTGCGGAGGACTCGCTGGCTGATCAG
GCTGCCAATGAATGGGGCAGGAGTGGCAAAGACCCCAATCACTTCCGACCTGCTGGCCTG
CCTGAGAAATACTGA (SEQ ID NO: 77)

>CDS for human CRP including signal sequence (nt 105-779 of NCBI Reference Sequence: NM_000567.3)
ATGGAGAAGCTGTTGTGTTTCTTGGTCTTGACCAGCCTCTCTCATGCTTTTGGCCAGACAG
ACATGTCGAGGAAGGCTTTTGTGTTTCCCAAAGAGTCGGATACTTCCTATGTATCCCTCAAA
GCACCGTTAACGAAGCCTCTCAAAGCCTTCACTGTGTGCCTCCACTTCTACACGGAACTGT
CCTCGACCCGTGGGTACAGTATTTTCTCGTATGCCACCAAGAGACAAGACAATGAGATTCT
CATATTTTGGTCTAAGGATATAGGATACAGTTTTACAGTGGGTGGGTCTGAAATATTATTCG
AGGTTCCTGAAGTCACAGTAGCTCCAGTACACATTTGTACAAGCTGGGAGTCCGCCTCAG

FIG. 24 cont'd.

GGATCGTGGAGTTCTGGGTAGATGGGAAGCCCAGGGTGAGGAAGAGTCTGAAGAAGGGA
TACACTGTGGGGGCAGAAGCAAGCATCATCTTGGGGCAGGAGCAGGATTCCTTCGGTGG
GAACTTTGAAGGAAGCCAGTCCCTGGTGGGAGACATTGGAAATGTGAACATGTGGGACTT
TGTGCTGTCACCAGATGAGATTAACACCATCTATCTTGGCGGGCCCTTCAGTCCTAATGTC
CTGAACTGGCGGGCACTGAAGTATGAAGTGCAAGGCGAAGTGTTCACCAAACCCCAGCTG
TGGCCCTGA (SEQ ID NO: 78)

>CDS for human CRP lacking signal sequence
CAGACAGACATGTCGAGGAAGGCTTTTGTGTTTCCCAAAGAGTCGGATACTTCCTATGTAT
CCCTCAAAGCACCGTTAACGAAGCCTCTCAAAGCCTTCACTGTGTGCCTCCACTTCTACAC
GGAACTGTCCTCGACCCGTGGGTACAGTATTTTCTCGTATGCCACCAAGAGACAAGACAAT
GAGATTCTCATATTTTGGTCTAAGGATATAGGATACAGTTTTACAGTGGGTGGGTCTGAAAT
ATTATTCGAGGTTCCTGAAGTCACAGTAGCTCCAGTACACATTTGTACAAGCTGGGAGTCC
GCCTCAGGGATCGTGGAGTTCTGGGTAGATGGGAAGCCCAGGGTGAGGAAGAGTCTGAA
GAAGGGATACACTGTGGGGGCAGAAGCAAGCATCATCTTGGGGCAGGAGCAGGATTCCTT
CGGTGGGAACTTTGAAGGAAGCCAGTCCCTGGTGGGAGACATTGGAAATGTGAACATGTG
GGACTTTGTGCTGTCACCAGATGAGATTAACACCATCTATCTTGGCGGGCCCTTCAGTCCT
AATGTCCTGAACTGGCGGGCACTGAAGTATGAAGTGCAAGGCGAAGTGTTCACCAAACCC
CAGCTGTGGCCCTGA (SEQ ID NO: 79)

>CDS for human CD161 (nt 63-740 of NCBI Reference Sequence: NM_002258.2)
ATGGACCAACAAGCAATATATGCTGAGTTAAACTTACCCACAGACTCAGGCCCAGAAAGTT
CTTCACCTTCATCTCTTCCTCGGGATGTCTGTCAGGGTTCACCTTGGCATCAATTTGCCCT
GAAACTTAGCTGTGCTGGGATTATTCTCCTTGTCTTGGTTGTTACTGGGTTGAGTGTTTCAG
TGACATCCTTAATACAGAAATCATCAATAGAAAAATGCAGTGTGGACATTCAACAGAGCAG
GAATAAAACAACAGAGAGACCGGGTCTCTTAAACTGCCCAATATATTGGCAGCAACTCCGA
GAGAAATGCTTGTTATTTTCTCACACTGTCAACCCTTGGAATAACAGTCTAGCTGATTGTTC
CACCAAAGAATCCAGCCTGCTGCTTATTCGAGATAAGGATGAATTGATACACACACAGAAC
CTGATACGTGACAAAGCAATTCTGTTTTGGATTGGATTAAATTTTTCATTATCAGAAAAGAAC
TGGAAGTGGATAAACGGCTCTTTTTTAAATTCTAATGACTTAGAAATTAGAGGTGATGCTAA
AGAAAACAGCTGTATTTCCATCTCACAGACATCTGTGTATTCTGAGTACTGTAGTACAGAAA
TCAGATGGATCTGCCAAAAAGAACTAACACCTGTGAGAAATAAAGTGTATCCTGACTCTTGA
(SEQ ID NO: 80)

>CDS for human CD56 including signal sequence (nt 194-2770 of NCBI Reference Sequence: NM_181351.5)
ATGCTGCAAACTAAGGATCTCATCTGGACTTTGTTTTTCCTGGGAACTGCAGTTTCTCTGCA
GGTGGATATTGTTCCCAGCCAGGGGGAGATCAGCGTTGGAGAGTCCAAATTCTTCTTATGC
CAAGTGGCAGGAGATGCCAAAGATAAAGACATCTCCTGGTTCTCCCCCAATGGAGAAAAG
CTCACCCCAAACCAGCAGCGGATCTCAGTGGTGTGGAATGATGATTCCTCCTCCACCCTCA
CCATCTATAACGCCAACATCGACGACGCCGGCATTTACAAGTGTGTGGTTACAGGCGAGG
ATGGCAGTGAGTCAGAGGCCACCGTCAACGTGAAGATCTTTCAGAAGCTCATGTTCAAGAA
TGCGCCAACCCCACAGGAGTTCCGGGAGGGGGAAGATGCCGTGATTGTGTGTGATGTGG
TCAGCTCCCTCCCACCAACCATCATCTGGAAACACAAAGGCCGAGATGTCATCCTGAAAAA
AGATGTCCGATTCATAGTCCTGTCCAACAACTACCTGCAGATCCGGGGCATCAAGAAAACA
GATGAGGGCACTTATCGCTGTGAGGGCAGAATCCTGGCACGGGGGGAGATCAACTTCAAG

FIG. 24 cont'd.

GACATTCAGGTCATTGTGAATGTGCCACCTACCATCCAGGCCAGGCAGAATATTGTGAATG
CCACCGCCAACCTCGGCCAGTCCGTCACCCTGGTGTGCGATGCCGAAGGCTTCCCAGAG
CCCACCATGAGCTGGACAAAGGATGGGGAACAGATAGAGCAAGAGGAAGACGATGAGAA
GTACATCTTCAGCGACGATAGTTCCCAGCTGACCATCAAAAAGGTGGATAAGAACGACGAG
GCTGAGTACATCTGCATTGCTGAGAACAAGGCTGGCGAGCAGGATGCGACCATCCACCTC
AAAGTCTTTGCAAAACCCAAAATCACATATGTAGAGAACCAGACTGCCATGGAATTAGAGG
AGCAGGTCACTCTTACCTGTGAAGCCTCCGGAGACCCCATTCCCTCCATCACCTGGAGGA
CTTCTACCCGGAACATCAGCAGCGAAGAAAAGGCTTCGTGGACTCGACCAGAGAAGCAAG
AGACTCTGGATGGGCACATGGTGGTGCGTAGCCATGCCCGTGTGTCGTCGCTGACCCTGA
AGAGCATCCAGTACACTGATGCCGGAGAGTACATCTGCACCGCCAGCAACACCATCGGCC
AGGACTCCCAGTCCATGTACCTTGAAGTGCAATATGCCCCAAAGCTACAGGGCCCTGTGG
CTGTGTACACTTGGGAGGGGAACCAGGTGAACATCACCTGCGAGGTATTTGCCTATCCCA
GTGCCACGATCTCATGGTTTCGGGATGGCCAGCTGCTGCCAAGCTCCAATTACAGCAATAT
CAAGATCTACAACACCCCCTCTGCCAGCTATCTGGAGGTGACCCCAGACTCTGAGAATGAT
TTTGGGAACTACAACTGTACTGCAGTGAACCGCATTGGGCAGGAGTCCTTGGAATTCATCC
TTGTTCAAGCAGACACCCCCTCTTCACCATCCATCGACCAGGTGGAGCCATACTCCAGCAC
AGCCCAGGTGCAGTTTGATGAACCAGAGGCCACAGGTGGGGTGCCCATCCTCAAATACAA
AGCTGAGTGGAGAGCAGTTGGTGAAGAAGTATGGCATTCCAAGTGGTATGATGCCAAGGA
AGCCAGCATGGAGGGCATCGTCACCATCGTGGGCCTGAAGCCCGAAACAACGTACGCCG
TAAGGCTGGCGGCGCTCAATGGCAAAGGGCTGGGTGAGATCAGCGCGGCCTCCGAGTTC
AAGACGCAGCCAGTCCAAGGGGAACCCAGTGCACCTAAGCTCGAAGGGCAGATGGGAGA
GGATGGAAACTCTATTAAAGTGAACCTGATCAAGCAGGATGACGGCGGCTCCCCCATCAG
ACACTATCTGGTCAGGTACCGAGCGCTCTCCTCCGAGTGGAAACCAGAGATCAGGCTCCC
GTCTGGCAGTGACCACGTCATGCTGAAGTCCCTGGACTGGAATGCTGAGTATGAGGTCTA
CGTGGTGGCTGAGAACCAGCAAGGAAAATCCAAGGCGGCTCATTTTGTGTTCAGGACCTC
GGCCCAGCCCACAGCCATCCCAGCCAACGGCAGCCCCACCTCAGGCCTGAGCACCGGGG
CCATCGTGGGCATCCTCATCGTCATCTTCGTCCTGCTCCTGGTGGTTGTGGACATCACCTG
CTACTTCCTGAACAAGTGTGGCCTGTTCATGTGCATTGCGGTCAACCTGTGTGGAAAAGCC
GGGCCCGGGGCCAAGGGCAAGGACATGGAGGAGGGCAAGGCCGCCTTCTCGAAAGATG
AGTCCAAGGAGCCCATCGTGGAGGTTCGAACGGAGGAGGAGAGGACCCCAAACCATGAT
GGAGGGAAACACACAGAGCCCAACGAGACCACGCCACTGACGGAGCCCGAGAAGGGCCC
CGTAGAAGCAAAGCCAGAGTGCCAGGAGACAGAAACGAAGCCAGCGCCAGCCGAAGTCA
AGACGGTCCCCAATGACGCCACACAGACAAAGGAGAACGAGAGCAAAGCATGA (SEQ ID NO: 81)

>CDS for human CD56 lacking signal sequence
CTGCAGGTGGATATTGTTCCCAGCCAGGGGGAGATCAGCGTTGGAGAGTCCAAATTCTTC
TTATGCCAAGTGGCAGGAGATGCCAAAGATAAAGACATCTCCTGGTTCTCCCCCAATGGAG
AAAAGCTCACCCCAAACCAGCAGCGGATCTCAGTGGTGTGGAATGATGATTCCTCCTCCAC
CCTCACCATCTATAACGCCAACATCGACGACGCCGGCATTTACAAGTGTGTGGTTACAGGC
GAGGATGGCAGTGAGTCAGAGGCCACCGTCAACGTGAAGATCTTTCAGAAGCTCATGTTC
AAGAATGCGCCAACCCCACAGGAGTTCCGGGAGGGGGAAGATGCCGTGATTGTGTGTGAT
GTGGTCAGCTCCCTCCCACCAACCATCATCTGGAAACACAAAGGCCGAGATGTCATCCTG
AAAAAAGATGTCCGATTCATAGTCCTGTCCAACAACTACCTGCAGATCCGGGGCATCAAGA
AAACAGATGAGGGCACTTATCGCTGTGAGGGCAGAATCCTGGCACGGGGGGAGATCAACT
TCAAGGACATTCAGGTCATTGTGAATGTGCCACCTACCATCCAGGCCAGGCAGAATATTGT

FIG. 24 cont'd.

GAATGCCACCGCCAACCTCGGCCAGTCCGTCACCCTGGTGTGCGATGCCGAAGGCTTCC
CAGAGCCCACCATGAGCTGGACAAAGGATGGGGAACAGATAGAGCAAGAGGAAGACGAT
GAGAAGTACATCTTCAGCGACGATAGTTCCCAGCTGACCATCAAAAAGGTGGATAAGAACG
ACGAGGCTGAGTACATCTGCATTGCTGAGAACAAGGCTGGCGAGCAGGATGCGACCATCC
ACCTCAAAGTCTTTGCAAAACCCAAAATCACATATGTAGAGAACCAGACTGCCATGGAATTA
GAGGAGCAGGTCACTCTTACCTGTGAAGCCTCCGGAGACCCCATTCCCTCCATCACCTGG
AGGACTTCTACCCGGAACATCAGCAGCGAAGAAAAGGCTTCGTGGACTCGACCAGAGAAG
CAAGAGACTCTGGATGGGCACATGGTGGTGCGTAGCCATGCCCGTGTGTCGTCGCTGACC
CTGAAGAGCATCCAGTACACTGATGCCGGAGAGTACATCTGCACCGCCAGCAACACCATC
GGCCAGGACTCCCAGTCCATGTACCTTGAAGTGCAATATGCCCCAAAGCTACAGGGCCCT
GTGGCTGTGTACACTTGGGAGGGGAACCAGGTGAACATCACCTGCGAGGTATTTGCCTAT
CCCAGTGCCACGATCTCATGGTTTCGGGATGGCCAGCTGCTGCCAAGCTCCAATTACAGC
AATATCAAGATCTACAACACCCCCTCTGCCAGCTATCTGGAGGTGACCCCAGACTCTGAGA
ATGATTTTGGGAACTACAACTGTACTGCAGTGAACCGCATTGGGCAGGAGTCCTTGGAATT
CATCCTTGTTCAAGCAGACACCCCCTCTTCACCATCCATCGACCAGGTGGAGCCATACTCC
AGCACAGCCCAGGTGCAGTTTGATGAACCAGAGGCCACAGGTGGGGTGCCCATCCTCAAA
TACAAAGCTGAGTGGAGAGCAGTTGGTGAAGAAGTATGGCATTCCAAGTGGTATGATGCC
AAGGAAGCCAGCATGGAGGGCATCGTCACCATCGTGGGCCTGAAGCCCGAAACAACGTA
CGCCGTAAGGCTGGCGGCGCTCAATGGCAAAGGGCTGGGTGAGATCAGCGCGGCCTCCG
AGTTCAAGACGCAGCCAGTCCAAGGGGAACCCAGTGCACCTAAGCTCGAAGGGCAGATG
GGAGAGGATGGAAACTCTATTAAAGTGAACCTGATCAAGCAGGATGACGGCGGCTCCCCC
ATCAGACACTATCTGGTCAGGTACCGAGCGCTCTCCTCCGAGTGGAAACCAGAGATCAGG
CTCCCGTCTGGCAGTGACCACGTCATGCTGAAGTCCCTGGACTGGAATGCTGAGTATGAG
GTCTACGTGGTGGCTGAGAACCAGCAAGGAAAATCCAAGGCGGCTCATTTTGTGTTCAGG
ACCTCGGCCCAGCCCACAGCCATCCCAGCCAACGGCAGCCCCACCTCAGGCCTGAGCAC
CGGGGCCATCGTGGGCATCCTCATCGTCATCTTCGTCCTGCTCCTGGTGGTTGTGGACAT
CACCTGCTACTTCCTGAACAAGTGTGGCCTGTTCATGTGCATTGCGGTCAACCTGTGTGGA
AAAGCCGGGCCCGGGGCCAAGGGCAAGGACATGGAGGAGGGCAAGGCCGCCTTCTCGA
AAGATGAGTCCAAGGAGCCCATCGTGGAGGTTCGAACGGAGGAGGAGAGGACCCCAAAC
CATGATGGAGGGAAACACACAGAGCCCAACGAGACCACGCCACTGACGGAGCCCGAGAA
GGGCCCCGTAGAAGCAAAGCCAGAGTGCCAGGAGACAGAAACGAAGCCAGCGCCAGCCG
AAGTCAAGACGGTCCCCAATGACGCCACACAGACAAAGGAGAACGAGAGCAAAGCATGA
(SEQ ID NO: 82)

SEQUENCE LISTING

<160> NUMBER OF SEQ ID NOS: 82

<210> SEQ ID NO 1
<211> LENGTH: 21
<212> TYPE: DNA
<213> ORGANISM: Artificial Sequence
<220> FEATURE:
<223> OTHER INFORMATION: forward PCR primer for actin

<400> SEQUENCE: 1
gagaaaatct ggcaccacac c 21

<210> SEQ ID NO 2
<211> LENGTH: 23
<212> TYPE: DNA
<213> ORGANISM: Artificial Sequence
<220> FEATURE:
<223> OTHER INFORMATION: reverse PCR primer for actin

<400> SEQUENCE: 2
ggatagcaca gcctggatag caa 23

<210> SEQ ID NO 3
<211> LENGTH: 28
<212> TYPE: DNA
<213> ORGANISM: Artificial Sequence
<220> FEATURE:
<223> OTHER INFORMATION: forward PCR primer for IL-18R1

<400> SEQUENCE: 3
gtggaagatc gcagtaatat agttccgg 28

<210> SEQ ID NO 4
<211> LENGTH: 24
<212> TYPE: DNA
<213> ORGANISM: Artificial Sequence
<220> FEATURE:
<223> OTHER INFORMATION: reverse PCR primer for IL-18R1

<400> SEQUENCE: 4
cattcagcaa agcagagcag ttga 24

<210> SEQ ID NO 5
<211> LENGTH: 22
<212> TYPE: DNA
<213> ORGANISM: Artificial Sequence
<220> FEATURE:
<223> OTHER INFORMATION: forward PCR primer for IL-18RAP

<400> SEQUENCE: 5
gattctgtag attctcccag cg 22

<210> SEQ ID NO 6
<211> LENGTH: 24
<212> TYPE: DNA
<213> ORGANISM: Artificial Sequence
<220> FEATURE:
<223> OTHER INFORMATION: reverse PCR primer for IL-18RAP

<400> SEQUENCE: 6
cctgagtatc cccttcattt ctgg 24

<210> SEQ ID NO 7
<211> LENGTH: 21
<212> TYPE: DNA
<213> ORGANISM: Artificial Sequence
<220> FEATURE:
<223> OTHER INFORMATION: forward PCR primer for CD161

<400> SEQUENCE: 7
aaatgcagtg tggacattca a 21

<210> SEQ ID NO 8
<211> LENGTH: 19
<212> TYPE: DNA
<213> ORGANISM: Artificial Sequence
<220> FEATURE:
<223> OTHER INFORMATION: reverse PCR primer for CD161

<400> SEQUENCE: 8
ctcggagttg ctgccaata 19

<210> SEQ ID NO 9
<211> LENGTH: 193
<212> TYPE: PRT
<213> ORGANISM: Homo sapiens

<400> SEQUENCE: 9

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 10
<211> LENGTH: 157
<212> TYPE: PRT
<213> ORGANISM: Homo sapiens

<400> SEQUENCE: 10

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30
```

Met Thr Asp Ser Asp Cys Arg Asp Asn Ala Pro Arg Thr Ile Phe Ile
35 40 45

Ile Ser Met Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Ser Val Pro Gly His Asp Asn Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 11
<211> LENGTH: 194
<212> TYPE: PRT
<213> ORGANISM: Homo sapiens

<400> SEQUENCE: 11

Met Thr Met Arg His Asn Trp Thr Pro Asp Leu Ser Pro Leu Trp Val
1 5 10 15

Leu Leu Leu Cys Ala His Val Val Thr Leu Leu Val Arg Ala Thr Pro
20 25 30

Val Ser Gln Thr Thr Thr Ala Ala Thr Ala Ser Val Arg Ser Thr Lys
35 40 45

Asp Pro Cys Pro Ser Gln Pro Pro Val Phe Pro Ala Ala Lys Gln Cys
50 55 60

Pro Ala Leu Glu Val Thr Trp Pro Glu Val Glu Val Pro Leu Asn Gly
65 70 75 80

Thr Leu Ser Leu Ser Cys Val Ala Cys Ser Arg Phe Pro Asn Phe Ser
85 90 95

Ile Leu Tyr Trp Leu Gly Asn Gly Ser Phe Ile Glu His Leu Pro Gly
100 105 110

Arg Leu Trp Glu Gly Ser Thr Ser Arg Glu Arg Gly Ser Thr Gly Thr
115 120 125

Gln Leu Cys Lys Ala Leu Val Leu Glu Gln Leu Thr Pro Ala Leu His
130 135 140

Ser Thr Asn Phe Ser Cys Val Leu Val Asp Pro Glu Gln Val Val Gln
145 150 155 160

Arg His Val Val Leu Ala Gln Leu Trp Ala Gly Leu Arg Ala Thr Leu
165 170 175

Pro Pro Thr Gln Glu Ala Leu Pro Ser Ser His Ser Ser Pro Gln Gln
180 185 190

Gln Gly

<210> SEQ ID NO 12
<211> LENGTH: 164
<212> TYPE: PRT
<213> ORGANISM: Homo sapiens

<400> SEQUENCE: 12

Thr Pro Val Ser Gln Thr Thr Thr Ala Ala Thr Ala Ser Val Arg Ser

```
1               5                   10                  15

Thr Lys Asp Pro Cys Pro Ser Gln Pro Pro Val Phe Pro Ala Ala Lys
            20                  25                  30

Gln Cys Pro Ala Leu Glu Val Thr Trp Pro Glu Val Glu Val Pro Leu
        35                  40                  45

Asn Gly Thr Leu Ser Leu Ser Cys Val Ala Cys Ser Arg Phe Pro Asn
    50                  55                  60

Phe Ser Ile Leu Tyr Trp Leu Gly Asn Gly Ser Phe Ile Glu His Leu
65                  70                  75                  80

Pro Gly Arg Leu Trp Glu Gly Ser Thr Ser Arg Glu Arg Gly Ser Thr
                85                  90                  95

Gly Thr Gln Leu Cys Lys Ala Leu Val Leu Glu Gln Leu Thr Pro Ala
            100                 105                 110

Leu His Ser Thr Asn Phe Ser Cys Val Leu Val Asp Pro Glu Gln Val
        115                 120                 125

Val Gln Arg His Val Val Leu Ala Gln Leu Trp Ala Gly Leu Arg Ala
    130                 135                 140

Thr Leu Pro Pro Thr Gln Glu Ala Leu Pro Ser Ser His Ser Ser Pro
145                 150                 155                 160

Gln Gln Gln Gly


<210> SEQ ID NO 13
<211> LENGTH: 541
<212> TYPE: PRT
<213> ORGANISM: Homo sapiens

<400> SEQUENCE: 13

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Ser Gly Ser Gln Glu
    50                  55                  60

His Val Glu Leu Asn Pro Arg Ser Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Leu Gly Pro Lys Leu Asn His
```

```
    210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
                245                 250                 255

Ser Asp Pro Asn Ile His Glu Glu Lys Glu Met Arg Ile Met Thr Pro
            260                 265                 270

Glu Gly Lys Trp His Ala Ser Lys Val Leu Arg Ile Glu Asn Ile Gly
        275                 280                 285

Glu Ser Asn Leu Asn Val Leu Tyr Asn Cys Thr Val Ala Ser Thr Gly
    290                 295                 300

Gly Thr Asp Thr Lys Ser Phe Ile Leu Val Arg Lys Ala Asp Met Ala
305                 310                 315                 320

Asp Ile Pro Gly His Val Phe Thr Arg Gly Met Ile Ile Ala Val Leu
                325                 330                 335

Ile Leu Val Ala Val Val Cys Leu Val Thr Val Cys Val Ile Tyr Arg
            340                 345                 350

Val Asp Leu Val Leu Phe Tyr Arg His Leu Thr Arg Arg Asp Glu Thr
        355                 360                 365

Leu Thr Asp Gly Lys Thr Tyr Asp Ala Phe Val Ser Tyr Leu Lys Glu
    370                 375                 380

Cys Arg Pro Glu Asn Gly Glu Glu His Thr Phe Ala Val Glu Ile Leu
385                 390                 395                 400

Pro Arg Val Leu Glu Lys His Phe Gly Tyr Lys Leu Cys Ile Phe Glu
                405                 410                 415

Arg Asp Val Val Pro Gly Gly Ala Val Val Asp Glu Ile His Ser Leu
            420                 425                 430

Ile Glu Lys Ser Arg Arg Leu Ile Ile Val Leu Ser Lys Ser Tyr Met
        435                 440                 445

Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Leu Lys Ser His Arg
                485                 490                 495

Val Leu Lys Trp Lys Ala Asp Lys Ser Leu Ser Tyr Asn Ser Arg Phe
            500                 505                 510

Trp Lys Asn Leu Leu Tyr Leu Met Pro Ala Lys Thr Val Lys Pro Gly
        515                 520                 525

Arg Asp Glu Pro Glu Val Leu Pro Val Leu Ser Glu Ser
    530                 535                 540


<210> SEQ ID NO 14
<211> LENGTH: 523
<212> TYPE: PRT
<213> ORGANISM: Homo sapiens

<400> SEQUENCE: 14

Ala Glu Ser Cys Thr Ser Arg Pro His Ile Thr Val Val Glu Gly Glu
1               5                   10                  15

Pro Phe Tyr Leu Lys His Cys Ser Cys Ser Leu Ala His Glu Ile Glu
            20                  25                  30

Thr Thr Thr Lys Ser Trp Tyr Lys Ser Ser Gly Ser Gln Glu His Val
        35                  40                  45
```

```
Glu Leu Asn Pro Arg Ser Ser Ser Arg Ile Ala Leu His Asp Cys Val
    50                  55                  60

Leu Glu Phe Trp Pro Val Glu Leu Asn Asp Thr Gly Ser Tyr Phe Phe
65                  70                  75                  80

Gln Met Lys Asn Tyr Thr Gln Lys Trp Lys Leu Asn Val Ile Arg Arg
                85                  90                  95

Asn Lys His Ser Cys Phe Thr Glu Arg Gln Val Thr Ser Lys Ile Val
            100                 105                 110

Glu Val Lys Lys Phe Phe Gln Ile Thr Cys Glu Asn Ser Tyr Tyr Gln
        115                 120                 125

Thr Leu Val Asn Ser Thr Ser Leu Tyr Lys Asn Cys Lys Lys Leu Leu
    130                 135                 140

Leu Glu Asn Asn Lys Asn Pro Thr Ile Lys Lys Asn Ala Glu Phe Glu
145                 150                 155                 160

Asp Gln Gly Tyr Tyr Ser Cys Val His Phe Leu His His Asn Gly Lys
                165                 170                 175

Leu Phe Asn Ile Thr Lys Thr Phe Asn Ile Thr Ile Val Glu Asp Arg
            180                 185                 190

Ser Asn Ile Val Pro Val Leu Leu Gly Pro Lys Leu Asn His Val Ala
        195                 200                 205

Val Glu Leu Gly Lys Asn Val Arg Leu Asn Cys Ser Ala Leu Leu Asn
    210                 215                 220

Glu Glu Asp Val Ile Tyr Trp Met Phe Gly Glu Glu Asn Gly Ser Asp
225                 230                 235                 240

Pro Asn Ile His Glu Glu Lys Glu Met Arg Ile Met Thr Pro Glu Gly
                245                 250                 255

Lys Trp His Ala Ser Lys Val Leu Arg Ile Glu Asn Ile Gly Glu Ser
            260                 265                 270

Asn Leu Asn Val Leu Tyr Asn Cys Thr Val Ala Ser Thr Gly Gly Thr
        275                 280                 285

Asp Thr Lys Ser Phe Ile Leu Val Arg Lys Ala Asp Met Ala Asp Ile
    290                 295                 300

Pro Gly His Val Phe Thr Arg Gly Met Ile Ile Ala Val Leu Ile Leu
305                 310                 315                 320

Val Ala Val Val Cys Leu Val Thr Val Cys Val Ile Tyr Arg Val Asp
                325                 330                 335

Leu Val Leu Phe Tyr Arg His Leu Thr Arg Arg Asp Glu Thr Leu Thr
            340                 345                 350

Asp Gly Lys Thr Tyr Asp Ala Phe Val Ser Tyr Leu Lys Glu Cys Arg
        355                 360                 365

Pro Glu Asn Gly Glu Glu His Thr Phe Ala Val Glu Ile Leu Pro Arg
    370                 375                 380

Val Leu Glu Lys His Phe Gly Tyr Lys Leu Cys Ile Phe Glu Arg Asp
385                 390                 395                 400

Val Val Pro Gly Gly Ala Val Val Asp Glu Ile His Ser Leu Ile Glu
                405                 410                 415

Lys Ser Arg Arg Leu Ile Ile Val Leu Ser Lys Ser Tyr Met Ser Asn
            420                 425                 430

Glu Val Arg Tyr Glu Leu Glu Ser Gly Leu His Glu Ala Leu Val Glu
        435                 440                 445

Arg Lys Ile Lys Ile Ile Leu Ile Glu Phe Thr Pro Val Thr Asp Phe
    450                 455                 460

Thr Phe Leu Pro Gln Ser Leu Lys Leu Leu Lys Ser His Arg Val Leu
```

```
465                 470                 475                 480

Lys Trp Lys Ala Asp Lys Ser Leu Ser Tyr Asn Ser Arg Phe Trp Lys
                485                 490                 495

Asn Leu Leu Tyr Leu Met Pro Ala Lys Thr Val Lys Pro Gly Arg Asp
            500                 505                 510

Glu Pro Glu Val Leu Pro Val Leu Ser Glu Ser
        515                 520


<210> SEQ ID NO 15
<211> LENGTH: 599
<212> TYPE: PRT
<213> ORGANISM: Homo sapiens

<400> SEQUENCE: 15

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320
```

```
Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365

Gly Thr Leu Val Ala Val Leu Ala Ala Ser Ala Leu Leu Tyr Arg His
    370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
        435                 440                 445

Ser Leu Cys Leu Leu Glu Arg Asp Val Ala Pro Gly Gly Val Tyr Ala
    450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
        515                 520                 525

Lys Ala Leu Arg Val Leu Pro Thr Val Thr Trp Arg Gly Leu Lys Ser
    530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
            580                 585                 590

Ser Ser Gln Pro Lys Glu Trp
        595


<210> SEQ ID NO 16
<211> LENGTH: 580
<212> TYPE: PRT
<213> ORGANISM: Homo sapiens

<400> SEQUENCE: 16

Phe Asn Ile Ser Gly Cys Ser Thr Lys Lys Leu Leu Trp Thr Tyr Ser
1               5                   10                  15

Thr Arg Ser Glu Glu Glu Phe Val Leu Phe Cys Asp Leu Pro Glu Pro
            20                  25                  30

Gln Lys Ser His Phe Cys His Arg Asn Arg Leu Ser Pro Lys Gln Val
        35                  40                  45

Pro Glu His Leu Pro Phe Met Gly Ser Asn Asp Leu Ser Asp Val Gln
    50                  55                  60

Trp Tyr Gln Gln Pro Ser Asn Gly Asp Pro Leu Glu Asp Ile Arg Lys
65                  70                  75                  80

Ser Tyr Pro His Ile Ile Gln Asp Lys Cys Thr Leu His Phe Leu Thr
                85                  90                  95
```

```
Pro Gly Val Asn Asn Ser Gly Ser Tyr Ile Cys Arg Pro Lys Met Ile
            100                 105                 110

Lys Ser Pro Tyr Asp Val Ala Cys Cys Val Lys Met Ile Leu Glu Val
        115                 120                 125

Lys Pro Gln Thr Asn Ala Ser Cys Glu Tyr Ser Ala Ser His Lys Gln
    130                 135                 140

Asp Leu Leu Leu Gly Ser Thr Gly Ser Ile Ser Cys Pro Ser Leu Ser
145                 150                 155                 160

Cys Gln Ser Asp Ala Gln Ser Pro Ala Val Thr Trp Tyr Lys Asn Gly
                165                 170                 175

Lys Leu Leu Ser Val Glu Arg Ser Asn Arg Ile Val Val Asp Glu Val
            180                 185                 190

Tyr Asp Tyr His Gln Gly Thr Tyr Val Cys Asp Tyr Thr Gln Ser Asp
        195                 200                 205

Thr Val Ser Ser Trp Thr Val Arg Ala Val Val Gln Val Arg Thr Ile
    210                 215                 220

Val Gly Asp Thr Lys Leu Lys Pro Asp Ile Leu Asp Pro Val Glu Asp
225                 230                 235                 240

Thr Leu Glu Val Glu Leu Gly Lys Pro Leu Thr Ile Ser Cys Lys Ala
                245                 250                 255

Arg Phe Gly Phe Glu Arg Val Phe Asn Pro Val Ile Lys Trp Tyr Ile
            260                 265                 270

Lys Asp Ser Asp Leu Glu Trp Glu Val Ser Val Pro Glu Ala Lys Ser
        275                 280                 285

Ile Lys Ser Thr Leu Lys Asp Glu Ile Ile Glu Arg Asn Ile Ile Leu
    290                 295                 300

Glu Lys Val Thr Gln Arg Asp Leu Arg Arg Lys Phe Val Cys Phe Val
305                 310                 315                 320

Gln Asn Ser Ile Gly Asn Thr Thr Gln Ser Val Gln Leu Lys Glu Lys
                325                 330                 335

Arg Gly Val Val Leu Leu Tyr Ile Leu Leu Gly Thr Ile Gly Thr Leu
            340                 345                 350

Val Ala Val Leu Ala Ala Ser Ala Leu Leu Tyr Arg His Trp Ile Glu
        355                 360                 365

Ile Val Leu Leu Tyr Arg Thr Tyr Gln Ser Lys Asp Gln Thr Leu Gly
    370                 375                 380

Asp Lys Lys Asp Phe Asp Ala Phe Val Ser Tyr Ala Lys Trp Ser Ser
385                 390                 395                 400

Phe Pro Ser Glu Ala Thr Ser Ser Leu Ser Glu Glu His Leu Ala Leu
                405                 410                 415

Ser Leu Phe Pro Asp Val Leu Glu Asn Lys Tyr Gly Tyr Ser Leu Cys
            420                 425                 430

Leu Leu Glu Arg Asp Val Ala Pro Gly Gly Val Tyr Ala Glu Asp Ile
        435                 440                 445

Val Ser Ile Ile Lys Arg Ser Arg Arg Gly Ile Phe Ile Leu Ser Pro
    450                 455                 460

Asn Tyr Val Asn Gly Pro Ser Ile Phe Glu Leu Gln Ala Ala Val Asn
465                 470                 475                 480

Leu Ala Leu Asp Asp Gln Thr Leu Lys Leu Ile Leu Ile Lys Phe Cys
                485                 490                 495

Tyr Phe Gln Glu Pro Glu Ser Leu Pro His Leu Val Lys Lys Ala Leu
            500                 505                 510
```

```
Arg Val Leu Pro Thr Val Thr Trp Arg Gly Leu Lys Ser Val Pro Pro
        515                 520                 525

Asn Ser Arg Phe Trp Ala Lys Met Arg Tyr His Met Pro Val Lys Asn
    530                 535                 540

Ser Gln Gly Phe Thr Trp Asn Gln Leu Arg Ile Thr Ser Arg Ile Phe
545                 550                 555                 560

Gln Trp Lys Gly Leu Ser Arg Thr Glu Thr Thr Gly Arg Ser Ser Gln
                565                 570                 575

Pro Lys Glu Trp
            580


<210> SEQ ID NO 17
<211> LENGTH: 153
<212> TYPE: PRT
<213> ORGANISM: Homo sapiens

<400> SEQUENCE: 17

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150


<210> SEQ ID NO 18
<211> LENGTH: 133
<212> TYPE: PRT
<213> ORGANISM: Homo sapiens

<400> SEQUENCE: 18

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 19
<211> LENGTH: 272
<212> TYPE: PRT
<213> ORGANISM: Homo sapiens

<400> SEQUENCE: 19

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270


<210> SEQ ID NO 20
<211> LENGTH: 251
<212> TYPE: PRT
<213> ORGANISM: Homo sapiens

<400> SEQUENCE: 20

Glu Leu Cys Asp Asp Asp Pro Pro Glu Ile Pro His Ala Thr Phe Lys
1               5                   10                  15
```

```
Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250
```

<210> SEQ ID NO 21
<211> LENGTH: 253
<212> TYPE: PRT
<213> ORGANISM: Homo sapiens

<400> SEQUENCE: 21

```
Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140
```

```
Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250


<210> SEQ ID NO 22
<211> LENGTH: 197
<212> TYPE: PRT
<213> ORGANISM: Homo sapiens

<400> SEQUENCE: 22

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195


<210> SEQ ID NO 23
<211> LENGTH: 328
<212> TYPE: PRT
<213> ORGANISM: Homo sapiens

<400> SEQUENCE: 23

Met Cys His Gln Gln Leu Val Ile Ser Trp Phe Ser Leu Val Phe Leu
1               5                   10                  15
```

```
Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 24
<211> LENGTH: 306
<212> TYPE: PRT
<213> ORGANISM: Homo sapiens

<400> SEQUENCE: 24

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
```

```
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 25
<211> LENGTH: 134
<212> TYPE: PRT
<213> ORGANISM: Homo sapiens

<400> SEQUENCE: 25

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110
```

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 26
<211> LENGTH: 115
<212> TYPE: PRT
<213> ORGANISM: Homo sapiens

<400> SEQUENCE: 26

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 27
<211> LENGTH: 212
<212> TYPE: PRT
<213> ORGANISM: Homo sapiens

<400> SEQUENCE: 27

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

```
Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210


<210> SEQ ID NO 28
<211> LENGTH: 183
<212> TYPE: PRT
<213> ORGANISM: Homo sapiens

<400> SEQUENCE: 28

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180


<210> SEQ ID NO 29
<211> LENGTH: 144
<212> TYPE: PRT
<213> ORGANISM: Homo sapiens

<400> SEQUENCE: 29

Met Leu Leu Ala Met Val Leu Thr Ser Ala Leu Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
    50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95
```

```
Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140


<210> SEQ ID NO 30
<211> LENGTH: 126
<212> TYPE: PRT
<213> ORGANISM: Homo sapiens

<400> SEQUENCE: 30

Gln Gly Cys Pro Thr Leu Ala Gly Ile Leu Asp Ile Asn Phe Leu Ile
1               5                   10                  15

Asn Lys Met Gln Glu Asp Pro Ala Ser Lys Cys His Cys Ser Ala Asn
            20                  25                  30

Val Thr Ser Cys Leu Cys Leu Gly Ile Pro Ser Asp Asn Cys Thr Arg
        35                  40                  45

Pro Cys Phe Ser Glu Arg Leu Ser Gln Met Thr Asn Thr Thr Met Gln
    50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Ser Cys Glu Gln Pro Cys Asn
                85                  90                  95

Gln Thr Thr Ala Gly Asn Ala Leu Thr Phe Leu Lys Ser Leu Leu Glu
            100                 105                 110

Ile Phe Gln Lys Glu Lys Met Arg Gly Met Arg Gly Lys Ile
        115                 120                 125


<210> SEQ ID NO 31
<211> LENGTH: 178
<212> TYPE: PRT
<213> ORGANISM: Homo sapiens

<400> SEQUENCE: 31

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160
```

```
Phe Asp Ile Phe Ile Asn Tyr Ile Glu Ala Tyr Met Thr Met Lys Ile
                165                 170                 175

Arg Asn


<210> SEQ ID NO 32
<211> LENGTH: 160
<212> TYPE: PRT
<213> ORGANISM: Homo sapiens

<400> SEQUENCE: 32

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 33
<211> LENGTH: 179
<212> TYPE: PRT
<213> ORGANISM: Homo sapiens

<400> SEQUENCE: 33

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
```

145 150 155 160

Ile Lys Ala Ile Gly Glu Leu Asp Leu Leu Phe Met Ser Leu Arg Asn
165 170 175

Ala Cys Ile

<210> SEQ ID NO 34
<211> LENGTH: 146
<212> TYPE: PRT
<213> ORGANISM: Homo sapiens

<400> SEQUENCE: 34

Ala Pro Ile Ser Ser His Cys Arg Leu Asp Lys Ser Asn Phe Gln Gln
1 5 10 15

Pro Tyr Ile Thr Asn Arg Thr Phe Met Leu Ala Lys Glu Ala Ser Leu
20 25 30

Ala Asp Asn Asn Thr Asp Val Arg Leu Ile Gly Glu Lys Leu Phe His
35 40 45

Gly Val Ser Met Ser Glu Arg Cys Tyr Leu Met Lys Gln Val Leu Asn
50 55 60

Phe Thr Leu Glu Glu Val Leu Phe Pro Gln Ser Asp Arg Phe Gln Pro
65 70 75 80

Tyr Met Gln Glu Val Val Pro Phe Leu Ala Arg Leu Ser Asn Arg Leu
85 90 95

Ser Thr Cys His Ile Glu Gly Asp Asp Leu His Ile Gln Arg Asn Val
100 105 110

Gln Lys Leu Lys Asp Thr Val Lys Lys Leu Gly Glu Ser Gly Glu Ile
115 120 125

Lys Ala Ile Gly Glu Leu Asp Leu Leu Phe Met Ser Leu Arg Asn Ala
130 135 140

Cys Ile
145

<210> SEQ ID NO 35
<211> LENGTH: 166
<212> TYPE: PRT
<213> ORGANISM: Homo sapiens

<400> SEQUENCE: 35

Met Lys Tyr Thr Ser Tyr Ile Leu Ala Phe Gln Leu Cys Ile Val Leu
1 5 10 15

Gly Ser Leu Gly Cys Tyr Cys Gln Asp Pro Tyr Val Lys Glu Ala Glu
20 25 30

Asn Leu Lys Lys Tyr Phe Asn Ala Gly His Ser Asp Val Ala Asp Asn
35 40 45

Gly Thr Leu Phe Leu Gly Ile Leu Lys Asn Trp Lys Glu Glu Ser Asp
50 55 60

Arg Lys Ile Met Gln Ser Gln Ile Val Ser Phe Tyr Phe Lys Leu Phe
65 70 75 80

Lys Asn Phe Lys Asp Asp Gln Ser Ile Gln Lys Ser Val Glu Thr Ile
85 90 95

Lys Glu Asp Met Asn Val Lys Phe Phe Asn Ser Asn Lys Lys Lys Arg
100 105 110

Asp Asp Phe Glu Lys Leu Thr Asn Tyr Ser Val Thr Asp Leu Asn Val
115 120 125

Gln Arg Lys Ala Ile His Glu Leu Ile Gln Val Met Ala Glu Leu Ser
130 135 140

```
Pro Ala Ala Lys Thr Gly Lys Arg Lys Arg Ser Gln Met Leu Phe Arg
145                 150                 155                 160

Gly Arg Arg Ala Ser Gln
                165


<210> SEQ ID NO 36
<211> LENGTH: 143
<212> TYPE: PRT
<213> ORGANISM: Homo sapiens

<400> SEQUENCE: 36

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140


<210> SEQ ID NO 37
<211> LENGTH: 144
<212> TYPE: PRT
<213> ORGANISM: Homo sapiens

<400> SEQUENCE: 37

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140


<210> SEQ ID NO 38
```

<211> LENGTH: 127
<212> TYPE: PRT
<213> ORGANISM: Homo sapiens

<400> SEQUENCE: 38

Ala Pro Ala Arg Ser Pro Ser Pro Ser Thr Gln Pro Trp Glu His Val
1 5 10 15

Asn Ala Ile Gln Glu Ala Arg Arg Leu Leu Asn Leu Ser Arg Asp Thr
20 25 30

Ala Ala Glu Met Asn Glu Thr Val Glu Val Ile Ser Glu Met Phe Asp
35 40 45

Leu Gln Glu Pro Thr Cys Leu Gln Thr Arg Leu Glu Leu Tyr Lys Gln
50 55 60

Gly Leu Arg Gly Ser Leu Thr Lys Leu Lys Gly Pro Leu Thr Met Met
65 70 75 80

Ala Ser His Tyr Lys Gln His Cys Pro Pro Thr Pro Glu Thr Ser Cys
85 90 95

Ala Thr Gln Ile Ile Thr Phe Glu Ser Phe Lys Glu Asn Leu Lys Asp
100 105 110

Phe Leu Leu Val Ile Pro Phe Asp Cys Trp Glu Pro Val Gln Glu
115 120 125

<210> SEQ ID NO 39
<211> LENGTH: 122
<212> TYPE: PRT
<213> ORGANISM: Homo sapiens

<400> SEQUENCE: 39

Met Lys Leu Leu Thr Gly Leu Val Phe Cys Ser Leu Val Leu Gly Val
1 5 10 15

Ser Ser Arg Ser Phe Phe Ser Phe Leu Gly Glu Ala Phe Asp Gly Ala
20 25 30

Arg Asp Met Trp Arg Ala Tyr Ser Asp Met Arg Glu Ala Asn Tyr Ile
35 40 45

Gly Ser Asp Lys Tyr Phe His Ala Arg Gly Asn Tyr Asp Ala Ala Lys
50 55 60

Arg Gly Pro Gly Gly Val Trp Ala Ala Glu Ala Ile Ser Asp Ala Arg
65 70 75 80

Glu Asn Ile Gln Arg Phe Phe Gly His Gly Ala Glu Asp Ser Leu Ala
85 90 95

Asp Gln Ala Ala Asn Glu Trp Gly Arg Ser Gly Lys Asp Pro Asn His
100 105 110

Phe Arg Pro Ala Gly Leu Pro Glu Lys Tyr
115 120

<210> SEQ ID NO 40
<211> LENGTH: 104
<212> TYPE: PRT
<213> ORGANISM: Homo sapiens

<400> SEQUENCE: 40

Arg Ser Phe Phe Ser Phe Leu Gly Glu Ala Phe Asp Gly Ala Arg Asp
1 5 10 15

Met Trp Arg Ala Tyr Ser Asp Met Arg Glu Ala Asn Tyr Ile Gly Ser
20 25 30

Asp Lys Tyr Phe His Ala Arg Gly Asn Tyr Asp Ala Ala Lys Arg Gly
35 40 45

```
Pro Gly Gly Val Trp Ala Ala Glu Ala Ile Ser Asp Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100
```

<210> SEQ ID NO 41
<211> LENGTH: 224
<212> TYPE: PRT
<213> ORGANISM: Homo sapiens

<400> SEQUENCE: 41

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220
```

<210> SEQ ID NO 42
<211> LENGTH: 206
<212> TYPE: PRT
<213> ORGANISM: Homo sapiens

<400> SEQUENCE: 42

```
Gln Thr Asp Met Ser Arg Lys Ala Phe Val Phe Pro Lys Glu Ser Asp
1               5                   10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45
```

```
Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205


<210> SEQ ID NO 43
<211> LENGTH: 225
<212> TYPE: PRT
<213> ORGANISM: Homo sapiens

<400> SEQUENCE: 43

Met Asp Gln Gln Ala Ile Tyr Ala Glu Leu Asn Leu Pro Thr Asp Ser
1               5                   10                  15

Gly Pro Glu Ser Ser Ser Pro Ser Ser Leu Pro Arg Asp Val Cys Gln
            20                  25                  30

Gly Ser Pro Trp His Gln Phe Ala Leu Lys Leu Ser Cys Ala Gly Ile
        35                  40                  45

Ile Leu Leu Val Leu Val Val Thr Gly Leu Ser Val Ser Val Thr Ser
    50                  55                  60

Leu Ile Gln Lys Ser Ser Ile Glu Lys Cys Ser Val Asp Ile Gln Gln
65                  70                  75                  80

Ser Arg Asn Lys Thr Thr Glu Arg Pro Gly Leu Leu Asn Cys Pro Ile
                85                  90                  95

Tyr Trp Gln Gln Leu Arg Glu Lys Cys Leu Leu Phe Ser His Thr Val
            100                 105                 110

Asn Pro Trp Asn Asn Ser Leu Ala Asp Cys Ser Thr Lys Glu Ser Ser
        115                 120                 125

Leu Leu Leu Ile Arg Asp Lys Asp Glu Leu Ile His Thr Gln Asn Leu
    130                 135                 140

Ile Arg Asp Lys Ala Ile Leu Phe Trp Ile Gly Leu Asn Phe Ser Leu
145                 150                 155                 160

Ser Glu Lys Asn Trp Lys Trp Ile Asn Gly Ser Phe Leu Asn Ser Asn
                165                 170                 175

Asp Leu Glu Ile Arg Gly Asp Ala Lys Glu Asn Ser Cys Ile Ser Ile
            180                 185                 190

Ser Gln Thr Ser Val Tyr Ser Glu Tyr Cys Ser Thr Glu Ile Arg Trp
        195                 200                 205

Ile Cys Gln Lys Glu Leu Thr Pro Val Arg Asn Lys Val Tyr Pro Asp
    210                 215                 220
```

Ser
225

<210> SEQ ID NO 44
<211> LENGTH: 858
<212> TYPE: PRT
<213> ORGANISM: Homo sapiens

<400> SEQUENCE: 44

Met Leu Gln Thr Lys Asp Leu Ile Trp Thr Leu Phe Phe Leu Gly Thr
1 5 10 15

Ala Val Ser Leu Gln Val Asp Ile Val Pro Ser Gln Gly Glu Ile Ser
20 25 30

Val Gly Glu Ser Lys Phe Phe Leu Cys Gln Val Ala Gly Asp Ala Lys
35 40 45

Asp Lys Asp Ile Ser Trp Phe Ser Pro Asn Gly Glu Lys Leu Thr Pro
50 55 60

Asn Gln Gln Arg Ile Ser Val Val Trp Asn Asp Asp Ser Ser Ser Thr
65 70 75 80

Leu Thr Ile Tyr Asn Ala Asn Ile Asp Asp Ala Gly Ile Tyr Lys Cys
85 90 95

Val Val Thr Gly Glu Asp Gly Ser Glu Ser Glu Ala Thr Val Asn Val
100 105 110

Lys Ile Phe Gln Lys Leu Met Phe Lys Asn Ala Pro Thr Pro Gln Glu
115 120 125

Phe Arg Glu Gly Glu Asp Ala Val Ile Val Cys Asp Val Val Ser Ser
130 135 140

Leu Pro Pro Thr Ile Ile Trp Lys His Lys Gly Arg Asp Val Ile Leu
145 150 155 160

Lys Lys Asp Val Arg Phe Ile Val Leu Ser Asn Asn Tyr Leu Gln Ile
165 170 175

Arg Gly Ile Lys Lys Thr Asp Glu Gly Thr Tyr Arg Cys Glu Gly Arg
180 185 190

Ile Leu Ala Arg Gly Glu Ile Asn Phe Lys Asp Ile Gln Val Ile Val
195 200 205

Asn Val Pro Pro Thr Ile Gln Ala Arg Gln Asn Ile Val Asn Ala Thr
210 215 220

Ala Asn Leu Gly Gln Ser Val Thr Leu Val Cys Asp Ala Glu Gly Phe
225 230 235 240

Pro Glu Pro Thr Met Ser Trp Thr Lys Asp Gly Glu Gln Ile Glu Gln
245 250 255

Glu Glu Asp Asp Glu Lys Tyr Ile Phe Ser Asp Asp Ser Ser Gln Leu
260 265 270

Thr Ile Lys Lys Val Asp Lys Asn Asp Glu Ala Glu Tyr Ile Cys Ile
275 280 285

Ala Glu Asn Lys Ala Gly Glu Gln Asp Ala Thr Ile His Leu Lys Val
290 295 300

Phe Ala Lys Pro Lys Ile Thr Tyr Val Glu Asn Gln Thr Ala Met Glu
305 310 315 320

Leu Glu Glu Gln Val Thr Leu Thr Cys Glu Ala Ser Gly Asp Pro Ile
325 330 335

Pro Ser Ile Thr Trp Arg Thr Ser Thr Arg Asn Ile Ser Ser Glu Glu
340 345 350

Lys Ala Ser Trp Thr Arg Pro Glu Lys Gln Glu Thr Leu Asp Gly His

-continued

```
        355                 360                 365

Met Val Val Arg Ser His Ala Arg Val Ser Ser Leu Thr Leu Lys Ser
    370                 375                 380

Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
                405                 410                 415

Lys Leu Gln Gly Pro Val Ala Val Tyr Thr Trp Glu Gly Asn Gln Val
            420                 425                 430

Asn Ile Thr Cys Glu Val Phe Ala Tyr Pro Ser Ala Thr Ile Ser Trp
        435                 440                 445

Phe Arg Asp Gly Gln Leu Leu Pro Ser Ser Asn Tyr Ser Asn Ile Lys
    450                 455                 460

Ile Tyr Asn Thr Pro Ser Ala Ser Tyr Leu Glu Val Thr Pro Asp Ser
465                 470                 475                 480

Glu Asn Asp Phe Gly Asn Tyr Asn Cys Thr Ala Val Asn Arg Ile Gly
                485                 490                 495

Gln Glu Ser Leu Glu Phe Ile Leu Val Gln Ala Asp Thr Pro Ser Ser
            500                 505                 510

Pro Ser Ile Asp Gln Val Glu Pro Tyr Ser Ser Thr Ala Gln Val Gln
        515                 520                 525

Phe Asp Glu Pro Glu Ala Thr Gly Gly Val Pro Ile Leu Lys Tyr Lys
    530                 535                 540

Ala Glu Trp Arg Ala Val Gly Glu Glu Val Trp His Ser Lys Trp Tyr
545                 550                 555                 560

Asp Ala Lys Glu Ala Ser Met Glu Gly Ile Val Thr Ile Val Gly Leu
                565                 570                 575

Lys Pro Glu Thr Thr Tyr Ala Val Arg Leu Ala Ala Leu Asn Gly Lys
            580                 585                 590

Gly Leu Gly Glu Ile Ser Ala Ala Ser Glu Phe Lys Thr Gln Pro Val
        595                 600                 605

Gln Gly Glu Pro Ser Ala Pro Lys Leu Glu Gly Gln Met Gly Glu Asp
    610                 615                 620

Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
                645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Val Ala Glu Asn
        675                 680                 685

Gln Gln Gly Lys Ser Lys Ala Ala His Phe Val Phe Arg Thr Ser Ala
    690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
                725                 730                 735

Val Val Val Asp Ile Thr Cys Tyr Phe Leu Asn Lys Cys Gly Leu Phe
            740                 745                 750

Met Cys Ile Ala Val Asn Leu Cys Gly Lys Ala Gly Pro Gly Ala Lys
        755                 760                 765

Gly Lys Asp Met Glu Glu Gly Lys Ala Ala Phe Ser Lys Asp Glu Ser
    770                 775                 780
```

```
Lys Glu Pro Ile Val Glu Val Arg Thr Glu Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Glu Ala Lys Pro Glu Cys Gln Glu Thr
            820                 825                 830

Glu Thr Lys Pro Ala Pro Ala Glu Val Lys Thr Val Pro Asn Asp Ala
        835                 840                 845

Thr Gln Thr Lys Glu Asn Glu Ser Lys Ala
    850                 855
```

<210> SEQ ID NO 45
<211> LENGTH: 839
<212> TYPE: PRT
<213> ORGANISM: Homo sapiens

<400> SEQUENCE: 45

```
Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Ser Thr Leu Thr Ile
    50                  55                  60

Tyr Asn Ala Asn Ile Asp Asp Ala Gly Ile Tyr Lys Cys Val Val Thr
65                  70                  75                  80

Gly Glu Asp Gly Ser Glu Ser Glu Ala Thr Val Asn Val Lys Ile Phe
                85                  90                  95

Gln Lys Leu Met Phe Lys Asn Ala Pro Thr Pro Gln Glu Phe Arg Glu
            100                 105                 110

Gly Glu Asp Ala Val Ile Val Cys Asp Val Val Ser Ser Leu Pro Pro
        115                 120                 125

Thr Ile Ile Trp Lys His Lys Gly Arg Asp Val Ile Leu Lys Lys Asp
    130                 135                 140

Val Arg Phe Ile Val Leu Ser Asn Asn Tyr Leu Gln Ile Arg Gly Ile
145                 150                 155                 160

Lys Lys Thr Asp Glu Gly Thr Tyr Arg Cys Glu Gly Arg Ile Leu Ala
                165                 170                 175

Arg Gly Glu Ile Asn Phe Lys Asp Ile Gln Val Ile Val Asn Val Pro
            180                 185                 190

Pro Thr Ile Gln Ala Arg Gln Asn Ile Val Asn Ala Thr Ala Asn Leu
        195                 200                 205

Gly Gln Ser Val Thr Leu Val Cys Asp Ala Glu Gly Phe Pro Glu Pro
    210                 215                 220

Thr Met Ser Trp Thr Lys Asp Gly Glu Gln Ile Glu Gln Glu Glu Asp
225                 230                 235                 240

Asp Glu Lys Tyr Ile Phe Ser Asp Asp Ser Ser Gln Leu Thr Ile Lys
                245                 250                 255

Lys Val Asp Lys Asn Asp Glu Ala Glu Tyr Ile Cys Ile Ala Glu Asn
            260                 265                 270

Lys Ala Gly Glu Gln Asp Ala Thr Ile His Leu Lys Val Phe Ala Lys
        275                 280                 285

Pro Lys Ile Thr Tyr Val Glu Asn Gln Thr Ala Met Glu Leu Glu Glu
```

```
    290                 295                 300

Gln Val Thr Leu Thr Cys Glu Ala Ser Gly Asp Pro Ile Pro Ser Ile
305                 310                 315                 320

Thr Trp Arg Thr Ser Thr Arg Asn Ile Ser Ser Glu Glu Lys Ala Ser
                325                 330                 335

Trp Thr Arg Pro Glu Lys Gln Glu Thr Leu Asp Gly His Met Val Val
            340                 345                 350

Arg Ser His Ala Arg Val Ser Ser Leu Thr Leu Lys Ser Ile Gln Tyr
        355                 360                 365

Thr Asp Ala Gly Glu Tyr Ile Cys Thr Ala Ser Asn Thr Ile Gly Gln
    370                 375                 380

Asp Ser Gln Ser Met Tyr Leu Glu Val Gln Tyr Ala Pro Lys Leu Gln
385                 390                 395                 400

Gly Pro Val Ala Val Tyr Thr Trp Glu Gly Asn Gln Val Asn Ile Thr
                405                 410                 415

Cys Glu Val Phe Ala Tyr Pro Ser Ala Thr Ile Ser Trp Phe Arg Asp
            420                 425                 430

Gly Gln Leu Leu Pro Ser Ser Asn Tyr Ser Asn Ile Lys Ile Tyr Asn
        435                 440                 445

Thr Pro Ser Ala Ser Tyr Leu Glu Val Thr Pro Asp Ser Glu Asn Asp
    450                 455                 460

Phe Gly Asn Tyr Asn Cys Thr Ala Val Asn Arg Ile Gly Gln Glu Ser
465                 470                 475                 480

Leu Glu Phe Ile Leu Val Gln Ala Asp Thr Pro Ser Ser Pro Ser Ile
                485                 490                 495

Asp Gln Val Glu Pro Tyr Ser Ser Thr Ala Gln Val Gln Phe Asp Glu
            500                 505                 510

Pro Glu Ala Thr Gly Gly Val Pro Ile Leu Lys Tyr Lys Ala Glu Trp
        515                 520                 525

Arg Ala Val Gly Glu Glu Val Trp His Ser Lys Trp Tyr Asp Ala Lys
    530                 535                 540

Glu Ala Ser Met Glu Gly Ile Val Thr Ile Val Gly Leu Lys Pro Glu
545                 550                 555                 560

Thr Thr Tyr Ala Val Arg Leu Ala Ala Leu Asn Gly Lys Gly Leu Gly
                565                 570                 575

Glu Ile Ser Ala Ala Ser Glu Phe Lys Thr Gln Pro Val Gln Gly Glu
            580                 585                 590

Pro Ser Ala Pro Lys Leu Glu Gly Gln Met Gly Glu Asp Gly Asn Ser
        595                 600                 605

Ile Lys Val Asn Leu Ile Lys Gln Asp Asp Gly Gly Ser Pro Ile Arg
    610                 615                 620

His Tyr Leu Val Arg Tyr Arg Ala Leu Ser Ser Glu Trp Lys Pro Glu
625                 630                 635                 640

Ile Arg Leu Pro Ser Gly Ser Asp His Val Met Leu Lys Ser Leu Asp
                645                 650                 655

Trp Asn Ala Glu Tyr Glu Val Tyr Val Val Ala Glu Asn Gln Gln Gly
            660                 665                 670

Lys Ser Lys Ala Ala His Phe Val Phe Arg Thr Ser Ala Gln Pro Thr
        675                 680                 685

Ala Ile Pro Ala Asn Gly Ser Pro Thr Ser Gly Leu Ser Thr Gly Ala
    690                 695                 700

Ile Val Gly Ile Leu Ile Val Ile Phe Val Leu Leu Leu Val Val Val
705                 710                 715                 720
```

```
Asp Ile Thr Cys Tyr Phe Leu Asn Lys Cys Gly Leu Phe Met Cys Ile
                725                 730                 735

Ala Val Asn Leu Cys Gly Lys Ala Gly Pro Gly Ala Lys Gly Lys Asp
            740                 745                 750

Met Glu Glu Gly Lys Ala Ala Phe Ser Lys Asp Glu Ser Lys Glu Pro
        755                 760                 765

Ile Val Glu Val Arg Thr Glu Glu Glu Arg Thr Pro Asn His Asp Gly
    770                 775                 780

Gly Lys His Thr Glu Pro Asn Glu Thr Thr Pro Leu Thr Glu Pro Glu
785                 790                 795                 800

Lys Gly Pro Val Glu Ala Lys Pro Glu Cys Gln Glu Thr Glu Thr Lys
                805                 810                 815

Pro Ala Pro Ala Glu Val Lys Thr Val Pro Asn Asp Ala Thr Gln Thr
            820                 825                 830

Lys Glu Asn Glu Ser Lys Ala
        835


<210> SEQ ID NO 46
<211> LENGTH: 582
<212> TYPE: DNA
<213> ORGANISM: Homo sapiens

<400> SEQUENCE: 46

atggctgctg aaccagtaga agacaattgc atcaactttg tggcaatgaa atttattgac     60

aatacgcttt actttatagc tgaagatgat gaaaacctgg aatcagatta ctttggcaag    120

cttgaatcta aattatcagt cataagaaat ttgaatgacc aagttctctt cattgaccaa    180

ggaaatcggc ctctatttga agatatgact gattctgact gtagagataa tgcaccccgg    240

accatattta ttataagtat gtataaagat agccagccta gaggtatggc tgtaactatc    300

tctgtgaagt gtgagaaaat ttcaactctc tcctgtgaga acaaaattat ttcctttaag    360

gaaatgaatc ctcctgataa catcaaggat acaaaaagtg acatcatatt ctttcagaga    420

agtgtcccag gacatgataa taagatgcaa tttgaatctt catcatacga aggatacttt    480

ctagcttgtg aaaaagagag agaccttttt aaactcattt tgaaaaaaga ggatgaattg    540

ggggatagat ctataatgtt cactgttcaa aacgaagact ag                       582


<210> SEQ ID NO 47
<211> LENGTH: 474
<212> TYPE: DNA
<213> ORGANISM: Homo sapiens

<400> SEQUENCE: 47

tactttggca agcttgaatc taaattatca gtcataagaa atttgaatga ccaagttctc     60

ttcattgacc aaggaaatcg gcctctattt gaagatatga ctgattctga ctgtagagat    120

aatgcacccc ggaccatatt tattataagt atgtataaag atagccagcc tagaggtatg    180

gctgtaacta tctctgtgaa gtgtgagaaa atttcaactc tctcctgtga gaacaaaatt    240

atttccttta aggaaatgaa tcctcctgat aacatcaagg atacaaaaag tgacatcata    300

ttctttcaga gaagtgtccc aggacatgat aataagatgc aatttgaatc ttcatcatac    360

gaaggatact ttctagcttg tgaaaaagag agagaccttt ttaaactcat tttgaaaaaa    420

gaggatgaat tgggggatag atctataatg ttcactgttc aaaacgaaga ctag          474


<210> SEQ ID NO 48
```

<211> LENGTH: 585
<212> TYPE: DNA
<213> ORGANISM: Homo sapiens

<400> SEQUENCE: 48

```
atgaccatga gacacaactg gacaccagac ctcagccctt tgtgggtcct gctcctgtgt     60
gcccacgtcg tcactctcct ggtcagagcc acacctgtct cgcagaccac cacagctgcc    120
actgcctcag ttagaagcac aaaggacccc tgcccctccc agcccccagt gttcccagca    180
gctaagcagt gtccagcatt ggaagtgacc tggccagagg tggaagtgcc actgaatgga    240
acgctgagct tatcctgtgt ggcctgcagc cgcttcccca acttcagcat cctctactgg    300
ctgggcaatg gttccttcat tgagcacctc ccaggccgac tgtgggaggg gagcaccagc    360
cgggaacgtg ggagcacagg tacgcagctg tgcaaggcct tggtgctgga gcagctgacc    420
cctgccctgc acagcaccaa cttctcctgt gtgctcgtgg accctgaaca ggttgtccag    480
cgtcacgtcg tcctggccca gctctgggct gggctgaggg caaccttgcc ccccacccaa    540
gaagccctgc cctccagcca cagcagtcca cagcagcagg gttaa                    585
```

<210> SEQ ID NO 49
<211> LENGTH: 495
<212> TYPE: DNA
<213> ORGANISM: Homo sapiens

<400> SEQUENCE: 49

```
acacctgtct cgcagaccac cacagctgcc actgcctcag ttagaagcac aaaggacccc     60
tgcccctccc agcccccagt gttcccagca gctaagcagt gtccagcatt ggaagtgacc    120
tggccagagg tggaagtgcc actgaatgga acgctgagct tatcctgtgt ggcctgcagc    180
cgcttcccca acttcagcat cctctactgg ctgggcaatg gttccttcat tgagcacctc    240
ccaggccgac tgtgggaggg gagcaccagc cgggaacgtg ggagcacagg tacgcagctg    300
tgcaaggcct tggtgctgga gcagctgacc cctgccctgc acagcaccaa cttctcctgt    360
gtgctcgtgg accctgaaca ggttgtccag cgtcacgtcg tcctggccca gctctgggct    420
gggctgaggg caaccttgcc ccccacccaa gaagccctgc cctccagcca cagcagtcca    480
cagcagcagg gttaa                                                     495
```

<210> SEQ ID NO 50
<211> LENGTH: 1626
<212> TYPE: DNA
<213> ORGANISM: Homo sapiens

<400> SEQUENCE: 50

```
atgaattgta gagaattacc cttgaccctt tgggtgctta tatctgtaag cactgcagaa     60
tcttgtactt cacgtcccca cattactgtg gttgaagggg aacctttcta tctgaaacat    120
tgctcgtgtt cacttgcaca tgagattgaa acaaccacca aaagctggta caaaagcagt    180
ggatcacagg aacatgtgga gctgaaccca aggagttcct cgagaattgc tttgcatgat    240
tgtgttttgg agttttggcc agttgagttg aatgacacag gatcttactt tttccaaatg    300
aaaaattata ctcagaaatg gaaattaaat gtcatcagaa gaaataaaca cagctgtttc    360
actgaaagac aagtaactag taaaattgtg gaagttaaaa aatttttca gataacctgt     420
gaaaacagtt actatcaaac actggtcaac agcacatcat tgtataagaa ctgtaaaaag    480
ctactactgg agaacaataa aaacccaacg ataaagaaga acgccgagtt tgaagatcag    540
gggtattact cctgcgtgca tttccttcat cataatggaa aactatttaa tatcaccaaa    600
```

```
accttcaata taacaatagt ggaagatcgc agtaatatag ttccggttct tcttggacca    660

aagcttaacc atgttgcagt ggaattagga aaaaacgtaa ggctcaactg ctctgctttg    720

ctgaatgaag aggatgtaat ttattggatg ttcggggaag aaaatggatc ggatcctaat    780

atacatgaag agaaagaaat gagaattatg actccagaag gcaaatggca tgcttcaaaa    840

gtattgagaa ttgaaaatat tggtgaaagc aatctaaatg ttttatataa ttgcactgtg    900

gccagcacgg gaggcacaga caccaaaagc ttcatcttgg tgagaaaagc agacatggct    960

gatatcccag gccacgtctt cacaagagga atgatcatag ctgttttgat cttggtggca   1020

gtagtgtgcc tagtgactgt gtgtgtcatt tatagagttg acttggttct attttataga   1080

catttaacga gaagagatga aacattaaca gatggaaaaa catatgatgc ttttgtgtct   1140

tacctaaaag aatgccgacc tgaaaatgga gaggagcaca cctttgctgt ggagattttg   1200

cccagggtgt tggagaaaca ttttgggtat aagttatgca tatttgaaag ggatgtagtg   1260

cctggaggag ctgttgttga tgaaatccac tcactgatag agaaaagccg aagactaatc   1320

attgtcctaa gtaaaagtta tatgtctaat gaggtcaggt atgaacttga aagtggactc   1380

catgaagcat tggtggaaag aaaaattaaa ataatcttaa ttgaatttac acctgttact   1440

gacttcacat tcttgcccca atcactaaag cttttgaaat ctcacagagt tctgaagtgg   1500

aaggccgata aatctctttc ttataactca aggttctgga agaaccttct ttacttaatg   1560

cctgcaaaaa cagtcaagcc aggtagagac gaaccggaag tcttgcctgt tctttccgag   1620

tcttaa                                                              1626
```

<210> SEQ ID NO 51
<211> LENGTH: 1572
<212> TYPE: DNA
<213> ORGANISM: Homo sapiens

<400> SEQUENCE: 51

```
gcagaatctt gtacttcacg tccccacatt actgtggttg aaggggaacc tttctatctg     60

aaacattgct cgtgttcact tgcacatgag attgaaacaa ccaccaaaag ctggtacaaa    120

agcagtggat cacaggaaca tgtggagctg aacccaagga gttcctcgag aattgctttg    180

catgattgtg ttttggagtt ttggccagtt gagttgaatg acacaggatc ttactttttc    240

caaatgaaaa attatactca gaaatggaaa ttaaatgtca tcagaagaaa taaacacagc    300

tgtttcactg aaagacaagt aactagtaaa attgtggaag ttaaaaaatt ttttcagata    360

acctgtgaaa acagttacta tcaaacactg gtcaacagca catcattgta taagaactgt    420

aaaaagctac tactggagaa caataaaaac ccaacgataa agaagaacgc cgagtttgaa    480

gatcaggggt attactcctg cgtgcatttc cttcatcata atggaaaact atttaatatc    540

accaaaacct tcaatataac aatagtggaa gatcgcagta atatagttcc ggttcttctt    600

ggaccaaagc ttaaccatgt tgcagtggaa ttaggaaaaa acgtaaggct caactgctct    660

gctttgctga atgaagagga tgtaatttat tggatgttcg gggaagaaaa tggatcggat    720

cctaatatac atgaagagaa agaaatgaga attatgactc cagaaggcaa atggcatgct    780

tcaaaagtat tgagaattga aaatattggt gaaagcaatc taaatgtttt atataattgc    840

actgtggcca gcacgggagg cacagacacc aaaagcttca tcttggtgag aaaagcagac    900

atggctgata tcccaggcca cgtcttcaca agaggaatga tcatagctgt tttgatcttg    960

gtggcagtag tgtgcctagt gactgtgtgt gtcatttata gagttgactt ggttctattt   1020
```

```
tatagacatt taacgagaag agatgaaaca ttaacagatg gaaaaacata tgatgctttt   1080
gtgtcttacc taaaagaatg ccgacctgaa aatggagagg agcacacctt tgctgtggag   1140
attttgccca gggtgttgga gaaacatttt gggtataagt tatgcatatt tgaaagggat   1200
gtagtgcctg gaggagctgt tgttgatgaa atccactcac tgatagagaa aagccgaaga   1260
ctaatcattg tcctaagtaa aagttatatg tctaatgagg tcaggtatga acttgaaagt   1320
ggactccatg aagcattggt ggaaagaaaa attaaaataa tcttaattga atttacacct   1380
gttactgact tcacattctt gccccaatca ctaaagcttt tgaaatctca cagagttctg   1440
aagtggaagg ccgataaatc tctttcttat aactcaaggt tctggaagaa ccttctttac   1500
ttaatgcctg caaaaacagt caagccaggt agagacgaac cggaagtctt gcctgttctt   1560
tccgagtctt aa                                                       1572
```

```
<210> SEQ ID NO 52
<211> LENGTH: 1800
<212> TYPE: DNA
<213> ORGANISM: Homo sapiens

<400> SEQUENCE: 52

atgctctgtt tgggctggat atttctttgg cttgttgcag gagagcgaat taaaggattt     60
aatatttcag gttgttccac aaaaaaactc ctttggacat attctacaag gagtgaagag    120
gaatttgtct tattttgtga tttaccagag ccacagaaat cacatttctg ccacagaaat    180
cgactctcac caaaacaagt ccctgagcac ctgcccttca tgggtagtaa cgacctatct    240
gatgtccaat ggtaccaaca accttcgaat ggagatccat tagaggacat taggaaaagc    300
tatcctcaca tcattcagga caaatgtacc cttcactttt tgaccccagg ggtgaataat    360
tctgggtcat atatttgtag acccaagatg attaagagcc cctatgatgt agcctgttgt    420
gtcaagatga ttttagaagt taagccccag acaaatgcat cctgtgagta ttccgcatca    480
cataagcaag acctacttct tgggagcact ggctctattt cttgccccag tctcagctgc    540
caaagtgatg cacaaagtcc agcggtaacc tggtacaaga atggaaaact cctctctgtg    600
gaaaggagca accgaatcgt agtggatgaa gtttatgact atcaccaggg cacatatgta    660
tgtgattaca ctcagtcgga tactgtgagt tcgtggacag tcagagctgt tgttcaagtg    720
agaaccattg tgggagacac taaactcaaa ccagatattc tggatcctgt cgaggacaca    780
ctggaagtag aacttggaaa gcctttaact attagctgca aagcacgatt tggctttgaa    840
agggtcttta accctgtcat aaaatggtac atcaaagatt ctgacctaga gtgggaagtc    900
tcagtacctg aggcgaaaag tattaaatcc actttaaagg atgaaatcat tgagcgtaat    960
atcatcttgg aaaaagtcac tcagcgtgat cttcgcagga agtttgtttg ctttgtccag   1020
aactccattg gaaacacaac ccagtccgtc caactgaaag aaaagagagg agtggtgctc   1080
ctgtacatcc tgcttggcac catcgggacc ctggtggccg tgctggcggc gagtgccctc   1140
ctctacaggc actggattga aatagtgctg ctgtaccgga cctaccagag caaggatcag   1200
acgcttgggg ataaaaagga ttttgatgct ttcgtatcct atgcaaaatg gagctctttt   1260
ccaagtgagg ccacttcatc tctgagtgaa gaacacttgg ccctgagcct atttcctgat   1320
gttttagaaa acaaatatgg atatagcctg tgtttgcttg aaagagatgt ggctccagga   1380
ggagtgtatg cagaagacat tgtgagcatt attaagagaa gcagaagagg aatatttatc   1440
ttgagcccca actatgtcaa tggacccagt atctttgaac tacaagcagc agtgaatctt   1500
gccttggatg atcaaacact gaaactcatt ttaattaagt tctgttactt ccaagagcca   1560
```

gagtctctac ctcatctcgt gaaaaaagct ctcagggttt tgcccacagt tacttggaga 1620
ggcttaaaat cagttcctcc caattctagg ttctgggcca aaatgcgcta ccacatgcct 1680
gtgaaaaact ctcagggatt cacgtggaac cagctcagaa ttacctctag gatttttcag 1740
tggaaaggac tcagtagaac agaaaccact gggaggagct cccagcctaa ggaatggtga 1800

<210> SEQ ID NO 53
<211> LENGTH: 1743
<212> TYPE: DNA
<213> ORGANISM: Homo sapiens

<400> SEQUENCE: 53
tttaatattt caggttgttc cacaaaaaaa ctcctttgga catattctac aaggagtgaa 60
gaggaatttg tcttattttg tgatttacca gagccacaga aatcacattt ctgccacaga 120
aatcgactct caccaaaaca agtccctgag cacctgccct tcatgggtag taacgaccta 180
tctgatgtcc aatggtacca acaaccttcg aatggagatc cattagagga cattaggaaa 240
agctatcctc acatcattca ggacaaatgt acccttcact tttgacccc aggggtgaat 300 aattctgggt catatatttg tagacccaag atgattaaga gcccctatga tgtagcctgt 360
tgtgtcaaga tgattttaga agttaagccc cagacaaatg catcctgtga gtattccgca 420
tcacataagc aagacctact tcttgggagc actggctcta tttcttgccc cagtctcagc 480
tgccaaagtg atgcacaaag tccagcggta acctggtaca agaatggaaa actcctctct 540
gtggaaagga gcaaccgaat cgtagtggat gaagtttatg actatcacca gggcacatat 600
gtatgtgatt acactcagtc ggatactgtg agttcgtgga cagtcagagc tgttgttcaa 660
gtgagaacca ttgtgggaga cactaaactc aaaccagata ttctggatcc tgtcgaggac 720
acactggaag tagaacttgg aaagcccttta actattagct gcaaagcacg atttggcttt 780
gaaagggtct ttaaccctgt cataaaatgg tacatcaaag attctgacct agagtgggaa 840
gtctcagtac ctgaggcgaa aagtattaaa tccactttaa aggatgaaat cattgagcgt 900
aatatcatct tggaaaaagt cactcagcgt gatcttcgca ggaagtttgt ttgctttgtc 960
cagaactcca ttggaaacac aacccagtcc gtccaactga aagaaaagag aggagtggtg 1020
ctcctgtaca tcctgcttgg caccatcggg accctggtgg ccgtgctggc ggcgagtgcc 1080
ctcctctaca ggcactggat tgaaatagtg ctgctgtacc ggacctacca gagcaaggat 1140
cagacgcttg gggataaaaa ggattttgat gctttcgtat cctatgcaaa atggagctct 1200
tttccaagtg aggccacttc atctctgagt gaagaacact tggccctgag cctatttcct 1260
gatgttttag aaaacaaata tggatatagc ctgtgtttgc ttgaaagaga tgtggctcca 1320
ggaggagtgt atgcagaaga cattgtgagc attattaaga gaagcagaag aggaatattt 1380
atcttgagcc ccaactatgt caatggaccc agtatctttg aactacaagc agcagtgaat 1440
cttgccttgg atgatcaaac actgaaactc attttaatta agttctgtta cttccaagag 1500
ccagagtctc tacctcatct cgtgaaaaaa gctctcaggg ttttgcccac agttacttgg 1560
agaggcttaa aatcagttcc tcccaattct aggttctggg ccaaaatgcg ctaccacatg 1620
cctgtgaaaa actctcaggg attcacgtgg aaccagctca gaattacctc taggattttt 1680
cagtggaaag gactcagtag aacagaaacc actgggagga gctcccagcc taaggaatgg 1740
tga 1743

<210> SEQ ID NO 54

<211> LENGTH: 462
<212> TYPE: DNA
<213> ORGANISM: Homo sapiens

<400> SEQUENCE: 54
atgtacagga tgcaactcct gtcttgcatt gcactaagtc ttgcacttgt cacaaacagt 60
gcacctactt caagttctac aaagaaaaca cagctacaac tggagcattt actgctggat 120
ttacagatga ttttgaatgg aattaataat tacaagaatc ccaaactcac caggatgctc 180
acatttaagt tttacatgcc caagaaggcc acagaactga aacatcttca gtgtctagaa 240
gaagaactca aacctctgga ggaagtgcta aatttagctc aaagcaaaaa ctttcactta 300
agacccaggg acttaatcag caatatcaac gtaatagttc tggaactaaa gggatctgaa 360
acaacattca tgtgtgaata tgctgatgag acagcaacca ttgtagaatt tctgaacaga 420
tggattacct tttgtcaaag catcatctca acactgactt ga 462

<210> SEQ ID NO 55
<211> LENGTH: 402
<212> TYPE: DNA
<213> ORGANISM: Homo sapiens

<400> SEQUENCE: 55
gcacctactt caagttctac aaagaaaaca cagctacaac tggagcattt actgctggat 60
ttacagatga ttttgaatgg aattaataat tacaagaatc ccaaactcac caggatgctc 120
acatttaagt tttacatgcc caagaaggcc acagaactga aacatcttca gtgtctagaa 180
gaagaactca aacctctgga ggaagtgcta aatttagctc aaagcaaaaa ctttcactta 240
agacccaggg acttaatcag caatatcaac gtaatagttc tggaactaaa gggatctgaa 300
acaacattca tgtgtgaata tgctgatgag acagcaacca ttgtagaatt tctgaacaga 360
tggattacct tttgtcaaag catcatctca acactgactt ga 402

<210> SEQ ID NO 56
<211> LENGTH: 819
<212> TYPE: DNA
<213> ORGANISM: Homo sapiens

<400> SEQUENCE: 56
atggattcat acctgctgat gtggggactg ctcacgttca tcatggtgcc tggctgccag 60
gcagagctct gtgacgatga cccgccagag atcccacacg ccacattcaa agccatggcc 120
tacaaggaag gaaccatgtt gaactgtgaa tgcaagagag gtttccgcag aataaaaagc 180
gggtcactct atatgctctg tacaggaaac tctagccact cgtcctggga caaccaatgt 240
caatgcacaa gctctgccac tcggaacaca acgaaacaag tgacacctca acctgaagaa 300
cagaaagaaa ggaaaaccac agaaatgcaa agtccaatgc agccagtgga ccaagcgagc 360
cttccaggtc actgcaggga acctccacca tgggaaaatg aagccacaga gagaatttat 420
catttcgtgg tggggcagat ggtttattat cagtgcgtcc agggatacag ggctctacac 480
agaggtcctg ctgagagcgt ctgcaaaatg acccacggga agacaaggtg gacccagccc 540
cagctcatat gcacaggtga aatggagacc agtcagtttc caggtgaaga gaagcctcag 600
gcaagccccg aaggccgtcc tgagagtgag acttcctgcc tcgtcacaac aacagatttt 660
caaatacaga cagaaatggc tgcaaccatg gagacgtcca tatttacaac agagtaccag 720
gtagcagtgg ccggctgtgt tttcctgctg atcagcgtcc tcctcctgag tgggctcacc 780
tggcagcgga gacagaggaa gagtagaaga acaatctag 819

<210> SEQ ID NO 57
<211> LENGTH: 756
<212> TYPE: DNA
<213> ORGANISM: Homo sapiens

<400> SEQUENCE: 57
gagctctgtg acgatgaccc gccagagatc ccacacgcca cattcaaagc catggcctac 60
aaggaaggaa ccatgttgaa ctgtgaatgc aagagaggtt tccgcagaat aaaaagcggg 120
tcactctata tgctctgtac aggaaactct agccactcgt cctgggacaa ccaatgtcaa 180
tgcacaagct ctgccactcg gaacacaacg aaacaagtga cacctcaacc tgaagaacag 240
aaagaaagga aaaccacaga aatgcaaagt ccaatgcagc cagtggacca agcgagcctt 300
ccaggtcact gcagggaacc tccaccatgg gaaaatgaag ccacagagag aatttatcat 360
ttcgtggtgg ggcagatggt ttattatcag tgcgtccagg gatacagggc tctacacaga 420
ggtcctgctg agagcgtctg caaaatgacc cacgggaaga caaggtggac ccagccccag 480
ctcatatgca caggtgaaat ggagaccagt cagtttccag gtgaagagaa gcctcaggca 540
agccccgaag gccgtcctga gagtgagact tcctgcctcg tcacaacaac agattttcaa 600
atacagacag aaatggctgc aaccatggag acgtccatat ttacaacaga gtaccaggta 660
gcagtggccg gctgtgtttt cctgctgatc agcgtcctcc tcctgagtgg gctcacctgg 720
cagcggagac agaggaagag tagaagaaca atctag 756

<210> SEQ ID NO 58
<211> LENGTH: 762
<212> TYPE: DNA
<213> ORGANISM: Homo sapiens

<400> SEQUENCE: 58
atgtggcccc ctgggtcagc ctcccagcca ccgccctcac ctgccgcggc cacaggtctg 60
catccagcgg ctcgccctgt gtccctgcag tgccggctca gcatgtgtcc agcgcgcagc 120
ctcctccttg tggctaccct ggtcctcctg gaccacctca gtttggccag aaacctcccc 180
gtggccactc cagacccagg aatgttccca tgccttcacc actcccaaaa cctgctgagg 240
gccgtcagca acatgctcca gaaggccaga caaactctag aattttaccc ttgcacttct 300
gaagagattg atcatgaaga tatcacaaaa gataaaacca gcacagtgga ggcctgttta 360
ccattggaat taaccaagaa tgagagttgc ctaaattcca gagagacctc tttcataact 420
aatgggagtt gcctggcctc cagaaagacc tcttttatga tggccctgtg ccttagtagt 480
atttatgaag acttgaagat gtaccaggtg gagttcaaga ccatgaatgc aaagcttctg 540
atggatccta agaggcagat ctttctagat caaaacatgc tggcagttat tgatgagctg 600
atgcaggccc tgaatttcaa cagtgagact gtgccacaaa aatcctccct tgaagaaccg 660
gatttttata aaactaaaat caagctctgc atacttcttc atgctttcag aattcgggca 720
gtgactattg atagagtgat gagctatctg aatgcttcct aa 762

<210> SEQ ID NO 59
<211> LENGTH: 594
<212> TYPE: DNA
<213> ORGANISM: Homo sapiens

<400> SEQUENCE: 59
agaaacctcc ccgtggccac tccagaccca ggaatgttcc catgccttca ccactcccaa 60

```
aacctgctga gggccgtcag caacatgctc cagaaggcca gacaaactct agaattttac    120

ccttgcactt ctgaagagat tgatcatgaa gatatcacaa aagataaaac cagcacagtg    180

gaggcctgtt taccattgga attaaccaag aatgagagtt gcctaaattc cagagagacc    240

tctttcataa ctaatgggag ttgcctggcc tccagaaaga cctcttttat gatggccctg    300

tgccttagta gtatttatga agacttgaag atgtaccagg tggagttcaa gaccatgaat    360

gcaaagcttc tgatggatcc taagaggcag atctttctag atcaaaacat gctggcagtt    420

attgatgagc tgatgcaggc cctgaatttc aacagtgaga ctgtgccaca aaaatcctcc    480

cttgaagaac cggattttta taaaactaaa atcaagctct gcatacttct tcatgctttc    540

agaattcggg cagtgactat tgatagagtg atgagctatc tgaatgcttc ctaa          594
```

<210> SEQ ID NO 60
<211> LENGTH: 987
<212> TYPE: DNA
<213> ORGANISM: Homo sapiens

<400> SEQUENCE: 60

```
atgtgtcacc agcagttggt catctcttgg ttttccctgg tttttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagttag                                       987
```

<210> SEQ ID NO 61
<211> LENGTH: 921
<212> TYPE: DNA
<213> ORGANISM: Homo sapiens

<400> SEQUENCE: 61

```
atatgggaac tgaagaaaga tgtttatgtc gtagaattgg attggtatcc ggatgcccct     60

ggagaaatgg tggtcctcac ctgtgacacc cctgaagaag atggtatcac ctggaccttg    120

gaccagagca gtgaggtctt aggctctggc aaaaccctga ccatccaagt caaagagttt    180

ggagatgctg gccagtacac ctgtcacaaa ggaggcgagg ttctaagcca ttcgctcctg    240

ctgcttcaca aaaaggaaga tggaatttgg tccactgata ttttaaagga ccagaaagaa    300

cccaaaaata agacctttct aagatgcgag gccaagaatt attctggacg tttcacctgc    360
```

```
tggtggctga cgacaatcag tactgatttg acattcagtg tcaaaagcag cagaggctct    420

tctgaccccc aaggggtgac gtgcggagct gctacactct ctgcagagag agtcagaggg    480

gacaacaagg agtatgagta ctcagtggag tgccaggagg acagtgcctg cccagctgct    540

gaggagagtc tgcccattga ggtcatggtg gatgccgttc acaagctcaa gtatgaaaac    600

tacaccagca gcttcttcat cagggacatc atcaaacctg acccacccaa gaacttgcag    660

ctgaagccat taaagaattc tcggcaggtg gaggtcagct gggagtaccc tgacacctgg    720

agtactccac attcctactt ctccctgaca ttctgcgttc aggtccaggg caagagcaag    780

agagaaaaga aagatagagt cttcacggac aagacctcag ccacggtcat ctgccgcaaa    840

aatgccagca ttagcgtgcg ggcccaggac cgctactata gctcatcttg gagcgaatgg    900

gcatctgtgc cctgcagtta g                                               921
```

```
<210> SEQ ID NO 62
<211> LENGTH: 405
<212> TYPE: DNA
<213> ORGANISM: Homo sapiens

<400> SEQUENCE: 62

atgaggatgc ttctgcattt gagtttgcta gctcttggag ctgcctacgt gtatgccatc     60

cccacagaaa ttcccacaag tgcattggtg aaagagacct tggcactgct ttctactcat    120

cgaactctgc tgatagccaa tgagactctg aggattcctg ttcctgtaca taaaaatcac    180

caactgtgca ctgaagaaat ctttcaggga ataggcacac tggagagtca aactgtgcaa    240

gggggtactg tggaaagact attcaaaaac ttgtccttaa taaagaaata cattgacggc    300

caaaaaaaaa agtgtggaga agaaagacgg agagtaaacc aattcctaga ctacctgcaa    360

gagtttcttg gtgtaatgaa caccgagtgg ataatagaaa gttga                   405
```

```
<210> SEQ ID NO 63
<211> LENGTH: 348
<212> TYPE: DNA
<213> ORGANISM: Homo sapiens

<400> SEQUENCE: 63

atccccacag aaattcccac aagtgcattg gtgaaagaga ccttggcact gctttctact     60

catcgaactc tgctgatagc caatgagact ctgaggattc ctgttcctgt acataaaaat    120

caccaactgt gcactgaaga aatctttcag ggaataggca cactggagag tcaaactgtg    180

caagggggta ctgtggaaag actattcaaa aacttgtcct taataaagaa atacattgac    240

ggccaaaaaa aaaagtgtgg agaagaaaga cggagagtaa accaattcct agactacctg    300

caagagtttc ttggtgtaat gaacaccgag tggataatag aaagttga                348
```

```
<210> SEQ ID NO 64
<211> LENGTH: 639
<212> TYPE: DNA
<213> ORGANISM: Homo sapiens

<400> SEQUENCE: 64

atgaactcct tctccacaag cgccttcggt ccagttgcct tctccctggg gctgctcctg     60

gtgttgcctg ctgccttccc tgccccagta cccccaggag aagattccaa agatgtagcc    120

gccccacaca gacagccact cacctcttca gaacgaattg acaaacaaat tcggtacatc    180

ctcgacggca tctcagccct gagaaaggag acatgtaaca agagtaacat gtgtgaaagc    240
```

agcaaagagg cactggcaga aaacaacctg aaccttccaa agatggctga aaaagatgga 300
tgcttccaat ctggattcaa tgaggagact tgcctggtga aaatcatcac tggtcttttg 360
gagtttgagg tatacctaga gtacctccag aacagatttg agagtagtga ggaacaagcc 420
agagctgtgc agatgagtac aaaagtcctg atccagttcc tgcagaaaaa ggcaaagaat 480
ctagatgcaa taaccacccc tgacccaacc acaaatgcca gcctgctgac gaagctgcag 540
gcacagaacc agtggctgca ggacatgaca actcatctca ttctgcgcag ctttaaggag 600
ttcctgcagt ccagcctgag ggctcttcgg caaatgtag 639

<210> SEQ ID NO 65
<211> LENGTH: 552
<212> TYPE: DNA
<213> ORGANISM: Homo sapiens

<400> SEQUENCE: 65
gtacccccag gagaagattc caaagatgta gccgccccac acagacagcc actcacctct 60
tcagaacgaa ttgacaaaca aattcggtac atcctcgacg gcatctcagc cctgagaaag 120
gagacatgta acaagagtaa catgtgtgaa agcagcaaag aggcactggc agaaaacaac 180
ctgaaccttc caaagatggc tgaaaaagat ggatgcttcc aatctggatt caatgaggag 240
acttgcctgg tgaaaatcat cactggtctt ttggagtttg aggtatacct agagtacctc 300
cagaacagat ttgagagtag tgaggaacaa gccagagctg tgcagatgag tacaaaagtc 360
ctgatccagt tcctgcagaa aaaggcaaag aatctagatg caataaccac ccctgaccca 420
accacaaatg ccagcctgct gacgaagctg caggcacaga accagtggct gcaggacatg 480
acaactcatc tcattctgcg cagctttaag gagttcctgc agtccagcct gagggctctt 540
cggcaaatgt ag 552

<210> SEQ ID NO 66
<211> LENGTH: 435
<212> TYPE: DNA
<213> ORGANISM: Homo sapiens

<400> SEQUENCE: 66
atgcttctgg ccatggtcct tacctctgcc ctgctcctgt gctccgtggc aggccagggg 60
tgtccaacct tggcggggat cctggacatc aacttcctca tcaacaagat gcaggaagat 120
ccagcttcca agtgccactg cagtgctaat gtgaccagtt gtctctgttt gggcattccc 180
tctgacaact gcaccagacc atgcttcagt gagagactgt ctcagatgac caataccacc 240
atgcaaacaa gatacccact gattttcagt cgggtgaaaa aatcagttga agtactaaag 300
aacaacaagt gtccatattt ttcctgtgaa cagccatgca accaaaccac ggcaggcaac 360
gcgctgacat ttctgaagag tcttctggaa attttccaga aagaaaagat gagagggatg 420
agaggcaaga tatga 435

<210> SEQ ID NO 67
<211> LENGTH: 381
<212> TYPE: DNA
<213> ORGANISM: Homo sapiens

<400> SEQUENCE: 67
caggggtgtc caaccttggc ggggatcctg gacatcaact tcctcatcaa caagatgcag 60
gaagatccag cttccaagtg ccactgcagt gctaatgtga ccagttgtct ctgtttgggc 120
attccctctg acaactgcac cagaccatgc ttcagtgaga gactgtctca gatgaccaat 180
accaccatgc aaacaagata cccactgatt ttcagtcggg tgaaaaaatc agttgaagta 240
ctaaagaaca acaagtgtcc atatttttcc tgtgaacagc catgcaacca aaccacggca 300
ggcaacgcgc tgacatttct gaagagtctt ctggaaattt tccagaaaga aaagatgaga 360
gggatgagag gcaagatatg a 381

<210> SEQ ID NO 68
<211> LENGTH: 537
<212> TYPE: DNA
<213> ORGANISM: Homo sapiens

<400> SEQUENCE: 68
atgcacagct cagcactgct ctgttgcctg gtcctcctga ctggggtgag ggccagccca 60
ggccagggca cccagtctga gaacagctgc acccacttcc caggcaacct gcctaacatg 120
cttcgagatc tccgagatgc cttcagcaga gtgaagactt tctttcaaat gaaggatcag 180
ctggacaact tgttgttaaa ggagtccttg ctggaggact ttaagggtta cctgggttgc 240
caagccttgt ctgagatgat ccagttttac ctggaggagg tgatgcccca agctgagaac 300
caagacccag acatcaaggc gcatgtgaac tccctggggg agaacctgaa gaccctcagg 360
ctgaggctac ggcgctgtca tcgatttctt ccctgtgaaa acaagagcaa ggccgtggag 420
caggtgaaga atgcctttaa taagctccaa gagaaaggca tctacaaagc catgagtgag 480
tttgacatct tcatcaacta catagaagcc tacatgacaa tgaagatacg aaactga 537

<210> SEQ ID NO 69
<211> LENGTH: 483
<212> TYPE: DNA
<213> ORGANISM: Homo sapiens

<400> SEQUENCE: 69
agcccaggcc agggcaccca gtctgagaac agctgcaccc acttcccagg caacctgcct 60
aacatgcttc gagatctccg agatgccttc agcagagtga agactttctt tcaaatgaag 120
gatcagctgg acaacttgtt gttaaaggag tccttgctgg aggactttaa gggttacctg 180
ggttgccaag ccttgtctga gatgatccag ttttacctgg aggaggtgat gccccaagct 240
gagaaccaag acccagacat caaggcgcat gtgaactccc tgggggagaa cctgaagacc 300
ctcaggctga ggctacggcg ctgtcatcga tttcttccct gtgaaaacaa gagcaaggcc 360
gtggagcagg tgaagaatgc ctttaataag ctccaagaga aaggcatcta caaagccatg 420
agtgagtttg acatcttcat caactacata gaagcctaca tgacaatgaa gatacgaaac 480
tga 483

<210> SEQ ID NO 70
<211> LENGTH: 540
<212> TYPE: DNA
<213> ORGANISM: Homo sapiens

<400> SEQUENCE: 70
atggccgccc tgcagaaatc tgtgagctct ttccttatgg ggaccctggc caccagctgc 60
ctccttctct tggccctctt ggtacaggga ggagcagctg cgcccatcag ctcccactgc 120
aggcttgaca agtccaactt ccagcagccc tatatcacca accgcacctt catgctggct 180
aaggaggcta gcttggctga taacaacaca gacgttcgtc tcattgggga gaaactgttc 240
cacggagtca gtatgagtga gcgctgctat ctgatgaagc aggtgctgaa cttcaccctt 300
gaagaagtgc tgttccctca atctgatagg ttccagcctt atatgcagga ggtggtgccc 360
ttcctggcca ggctcagcaa caggctaagc acatgtcata ttgaaggtga tgacctgcat 420
atccagagga atgtgcaaaa gctgaaggac acagtgaaaa agcttggaga gagtggagag 480
atcaaagcaa ttggagaact ggatttgctg tttatgtctc tgagaaatgc ctgcatttga 540

<210> SEQ ID NO 71
<211> LENGTH: 441
<212> TYPE: DNA
<213> ORGANISM: Homo sapiens

<400> SEQUENCE: 71
gcgcccatca gctcccactg caggcttgac aagtccaact tccagcagcc ctatatcacc 60
aaccgcacct tcatgctggc taaggaggct agcttggctg ataacaacac agacgttcgt 120
ctcattgggg agaaactgtt ccacggagtc agtatgagtg agcgctgcta tctgatgaag 180
caggtgctga acttcaccct tgaagaagtg ctgttccctc aatctgatag gttccagcct 240
tatatgcagg aggtggtgcc cttcctggcc aggctcagca acaggctaag cacatgtcat 300
attgaaggtg atgacctgca tatccagagg aatgtgcaaa agctgaagga cacagtgaaa 360
aagcttggag agagtggaga gatcaaagca attggagaac tggatttgct gtttatgtct 420
ctgagaaatg cctgcatttg a 441

<210> SEQ ID NO 72
<211> LENGTH: 501
<212> TYPE: DNA
<213> ORGANISM: Homo sapiens

<400> SEQUENCE: 72
atgaaatata caagttatat cttggctttt cagctctgca tcgttttggg ttctcttggc 60
tgttactgcc aggacccata tgtaaaagaa gcagaaaacc ttaagaaata ttttaatgca 120
ggtcattcag atgtagcgga taatggaact cttttcttag gcattttgaa gaattggaaa 180
gaggagagtg acagaaaaat aatgcagagc caaattgtct ccttttactt caaacttttt 240
aaaaacttta aagatgacca gagcatccaa aagagtgtgg agaccatcaa ggaagacatg 300
aatgtcaagt ttttcaatag caacaaaaag aaacgagatg acttcgaaaa gctgactaat 360
tattcggtaa ctgacttgaa tgtccaacgc aaagcaatac atgaactcat ccaagtgatg 420
gctgaactgt cgccagcagc taaaacaggg aagcgaaaaa ggagtcagat gctgtttcga 480
ggtcgaagag catcccagta a 501

<210> SEQ ID NO 73
<211> LENGTH: 432
<212> TYPE: DNA
<213> ORGANISM: Homo sapiens

<400> SEQUENCE: 73
caggacccat atgtaaaaga agcagaaaac cttaagaaat attttaatgc aggtcattca 60
gatgtagcgg ataatggaac tcttttctta ggcattttga agaattggaa agaggagagt 120
gacagaaaaa taatgcagag ccaaattgtc tccttttact tcaaactttt taaaaacttt 180
aaagatgacc agagcatcca aaagagtgtg gagaccatca aggaagacat gaatgtcaag 240
tttttcaata gcaacaaaaa gaaacgagat gacttcgaaa agctgactaa ttattcggta 300
actgacttga atgtccaacg caaagcaata catgaactca tccaagtgat ggctgaactg 360
tcgccagcag ctaaaacagg gaagcgaaaa aggagtcaga tgctgtttcg aggtcgaaga 420
gcatcccagt aa 432

<210> SEQ ID NO 74
<211> LENGTH: 435
<212> TYPE: DNA
<213> ORGANISM: Homo sapiens

<400> SEQUENCE: 74
atgtggctgc agagcctgct gctcttgggc actgtggcct gcagcatctc tgcacccgcc 60
cgctcgccca gccccagcac gcagccctgg gagcatgtga atgccatcca ggaggcccgg 120
cgtctcctga acctgagtag agacactgct gctgagatga atgaaacagt agaagtcatc 180
tcagaaatgt ttgacctcca ggagccgacc tgcctacaga cccgcctgga gctgtacaag 240
cagggcctgc ggggcagcct caccaagctc aagggcccct tgaccatgat ggccagccac 300
tacaagcagc actgccctcc aaccccggaa acttcctgtg caacccagat tatcaccttt 360
gaaagtttca aagagaacct gaaggacttt ctgcttgtca tcccctttga ctgctgggag 420
ccagtccagg agtga 435

<210> SEQ ID NO 75
<211> LENGTH: 384
<212> TYPE: DNA
<213> ORGANISM: Homo sapiens

<400> SEQUENCE: 75
gcacccgccc gctcgcccag ccccagcacg cagccctggg agcatgtgaa tgccatccag 60
gaggcccggc gtctcctgaa cctgagtaga gacactgctg ctgagatgaa tgaaacagta 120
gaagtcatct cagaaatgtt tgacctccag gagccgacct gcctacagac ccgcctggag 180
ctgtacaagc agggcctgcg gggcagcctc accaagctca agggcccctt gaccatgatg 240
gccagccact acaagcagca ctgccctcca accccggaaa cttcctgtgc aacccagatt 300
atcacctttg aaagtttcaa agagaacctg aaggactttc tgcttgtcat cccctttgac 360
tgctgggagc cagtccagga gtga 384

<210> SEQ ID NO 76
<211> LENGTH: 369
<212> TYPE: DNA
<213> ORGANISM: Homo sapiens

<400> SEQUENCE: 76
atgaagcttc tcacgggcct ggttttctgc tccttggtcc tgggtgtcag cagccgaagc 60
ttcttttcgt tccttggcga ggcttttgat ggggctcggg acatgtggag agcctactct 120
gacatgagag aagccaatta catcggctca gacaaatact tccatgctcg gggggaactat 180 gatgctgcca aaaggggacc tgggggtgcc tgggctgcag aagtgatcac cgatgccaga 240
gagaatatcc agagattctt tggccatggt gcggaggact cgctggctga tcaggctgcc 300
aatgaatggg gcaggagtgg caaagacccc aatcacttcc gacctgctgg cctgcctgag 360
aaatactga 369

<210> SEQ ID NO 77
<211> LENGTH: 315
<212> TYPE: DNA
<213> ORGANISM: Homo sapiens

<400> SEQUENCE: 77

```
cgaagcttct tttcgttcct tggcgaggct tttgatgggg ctcgggacat gtggagagcc      60

tactctgaca tgagagaagc caattacatc ggctcagaca aatacttcca tgctcggggg     120

aactatgatg ctgccaaaag gggacctggg ggtgcctggg ctgcagaagt gatcaccgat     180

gccagagaga atatccagag attctttggc catggtgcgg aggactcgct ggctgatcag     240

gctgccaatg aatggggcag gagtggcaaa gaccccaatc acttccgacc tgctggcctg     300

cctgagaaat actga                                                      315
```

<210> SEQ ID NO 78
<211> LENGTH: 675
<212> TYPE: DNA
<213> ORGANISM: Homo sapiens

<400> SEQUENCE: 78

```
atggagaagc tgttgtgttt cttggtcttg accagcctct ctcatgcttt tggccagaca      60

gacatgtcga ggaaggcttt tgtgtttccc aaagagtcgg atacttccta tgtatccctc     120

aaagcaccgt taacgaagcc tctcaaagcc ttcactgtgt gcctccactt ctacacggaa     180

ctgtcctcga cccgtgggta cagtattttc tcgtatgcca ccaagagaca agacaatgag     240

attctcatat tttggtctaa ggatatagga tacagtttta cagtgggtgg gtctgaaata     300

ttattcgagg ttcctgaagt cacagtagct ccagtacaca tttgtacaag ctgggagtcc     360

gcctcaggga tcgtggagtt ctgggtagat gggaagccca gggtgaggaa gagtctgaag     420

aagggataca ctgtgggggc agaagcaagc atcatcttgg ggcaggagca ggattccttc     480

ggtgggaact ttgaaggaag ccagtccctg gtgggagaca ttggaaatgt gaacatgtgg     540

gactttgtgc tgtcaccaga tgagattaac accatctatc ttggcgggcc cttcagtcct     600

aatgtcctga actggcgggc actgaagtat gaagtgcaag gcgaagtgtt caccaaaccc     660

cagctgtggc cctga                                                      675
```

<210> SEQ ID NO 79
<211> LENGTH: 621
<212> TYPE: DNA
<213> ORGANISM: Homo sapiens

<400> SEQUENCE: 79

```
cagacagaca tgtcgaggaa ggcttttgtg tttcccaaag agtcggatac ttcctatgta      60

tccctcaaag caccgttaac gaagcctctc aaagccttca ctgtgtgcct ccacttctac     120

acggaactgt cctcgacccg tgggtacagt attttctcgt atgccaccaa gagacaagac     180

aatgagattc tcatattttg gtctaaggat ataggataca gttttacagt gggtgggtct     240

gaaatattat tcgaggttcc tgaagtcaca gtagctccag tacacatttg tacaagctgg     300

gagtccgcct cagggatcgt ggagttctgg gtagatggga agcccagggt gaggaagagt     360

ctgaagaagg gatacactgt gggggcagaa gcaagcatca tcttggggca ggagcaggat     420

tccttcggtg ggaactttga aggaagccag tccctggtgg gagacattgg aaatgtgaac     480

atgtgggact ttgtgctgtc accagatgag attaacacca tctatcttgg cgggcccttc     540

agtcctaatg tcctgaactg gcgggcactg aagtatgaag tgcaaggcga agtgttcacc     600

aaaccccagc tgtggccctg a                                               621
```

<210> SEQ ID NO 80
<211> LENGTH: 678
<212> TYPE: DNA
<213> ORGANISM: Homo sapiens

<400> SEQUENCE: 80

```
atggaccaac aagcaatata tgctgagtta aacttaccca cagactcagg cccagaaagt     60
tcttcacctt catctcttcc tcgggatgtc tgtcagggtt caccttggca tcaatttgcc    120
ctgaaactta gctgtgctgg gattattctc cttgtcttgg ttgttactgg gttgagtgtt    180
tcagtgacat ccttaataca gaaatcatca atagaaaaat gcagtgtgga cattcaacag    240
agcaggaata aaacaacaga gagaccgggt ctcttaaact gcccaatata ttggcagcaa    300
ctccgagaga aatgcttgtt attttctcac actgtcaacc cttggaataa cagtctagct    360
gattgttcca ccaaagaatc cagcctgctg cttattcgag ataaggatga attgatacac    420
acacagaacc tgatacgtga caaagcaatt ctgttttgga ttggattaaa tttttcatta    480
tcagaaaaga actggaagtg gataaacggc tcttttttaa attctaatga cttagaaatt    540
agaggtgatg ctaaagaaaa cagctgtatt tccatctcac agacatctgt gtattctgag    600
tactgtagta cagaaatcag atggatctgc caaaaagaac taacacctgt gagaaataaa    660
gtgtatcctg actcttga                                                  678
```

<210> SEQ ID NO 81
<211> LENGTH: 2577
<212> TYPE: DNA
<213> ORGANISM: Homo sapiens

<400> SEQUENCE: 81

```
atgctgcaaa ctaaggatct catctggact ttgtttttcc tgggaactgc agtttctctg     60
caggtggata ttgttcccag ccaggggggag atcagcgttg gagagtccaa attcttctta    120
tgccaagtgg caggagatgc caaagataaa gacatctcct ggttctcccc caatggagaa    180
aagctcaccc caaaccagca gcggatctca gtggtgtgga atgatgattc ctcctccacc    240
ctcaccatct ataacgccaa catcgacgac gccggcattt acaagtgtgt ggttacaggc    300
gaggatggca gtgagtcaga ggccaccgtc aacgtgaaga tctttcagaa gctcatgttc    360
aagaatgcgc caaccccaca ggagttccgg gagggggaag atgccgtgat tgtgtgtgat    420
gtggtcagct ccctcccacc aaccatcatc tggaaacaca aaggccgaga tgtcatcctg    480
aaaaaagatg tccgattcat agtcctgtcc aacaactacc tgcagatccg gggcatcaag    540
aaaacagatg agggcactta tcgctgtgag ggcagaatcc tggcacgggg ggagatcaac    600
ttcaaggaca ttcaggtcat tgtgaatgtg ccacctacca tccaggccag gcagaatatt    660
gtgaatgcca ccgccaacct cggccagtcc gtcaccctgg tgtgcgatgc cgaaggcttc    720
ccagagccca ccatgagctg gacaaaggat ggggaacaga tagagcaaga ggaagacgat    780
gagaagtaca tcttcagcga cgatagttcc cagctgacca tcaaaaaggt ggataagaac    840
gacgaggctg agtacatctg cattgctgag aacaaggctg gcgagcagga tgcgaccatc    900
cacctcaaag tctttgcaaa acccaaaatc acatatgtag agaaccagac tgccatggaa    960
ttagaggagc aggtcactct tacctgtgaa gcctccggag accccattcc ctccatcacc   1020
tggaggactt ctacccggaa catcagcagc gaagaaaagg cttcgtggac tcgaccagag   1080
aagcaagaga ctctggatgg gcacatggtg gtgcgtagcc atgcccgtgt gtcgtcgctg   1140
accctgaaga gcatccagta cactgatgcc ggagagtaca tctgcaccgc cagcaacacc   1200
atcggccagg actcccagtc catgtacctt gaagtgcaat atgccccaaa gctacagggc   1260
cctgtggctg tgtacacttg ggaggggaac caggtgaaca tcacctgcga ggtatttgcc   1320
```

tatcccagtg ccacgatctc atggtttcgg gatggccagc tgctgccaag ctccaattac 1380
agcaatatca agatctacaa cacccccctct gccagctatc tggaggtgac cccagactct 1440
gagaatgatt ttgggaacta caactgtact gcagtgaacc gcattgggca ggagtccttg 1500
gaattcatcc ttgttcaagc agacaccccc tcttcaccat ccatcgacca ggtggagcca 1560
tactccagca cagcccaggt gcagtttgat gaaccagagg ccacaggtgg ggtgcccatc 1620
ctcaaataca aagctgagtg gagagcagtt ggtgaagaag tatggcattc caagtggtat 1680
gatgccaagg aagccagcat ggagggcatc gtcaccatcg tgggcctgaa gcccgaaaca 1740
acgtacgccg taaggctggc ggcgctcaat ggcaaagggc tgggtgagat cagcgcggcc 1800
tccgagttca agacgcagcc agtccaaggg gaacccagtg cacctaagct cgaagggcag 1860
atgggagagg atggaaactc tattaaagtg aacctgatca agcaggatga cggcggctcc 1920
cccatcagac actatctggt caggtaccga gcgctctcct ccgagtggaa accagagatc 1980
aggctcccgt ctggcagtga ccacgtcatg ctgaagtccc tggactggaa tgctgagtat 2040
gaggtctacg tggtggctga gaaccagcaa ggaaaatcca aggcggctca ttttgtgttc 2100
aggacctcgg cccagcccac agccatccca gccaacggca gccccacctc aggcctgagc 2160
accggggcca tcgtgggcat cctcatcgtc atcttcgtcc tgctcctggt ggttgtggac 2220
atcacctgct acttcctgaa caagtgtggc ctgttcatgt gcattgcggt caacctgtgt 2280
ggaaaagccg ggcccggggc caagggcaag gacatggagg agggcaaggc cgccttctcg 2340
aaagatgagt ccaaggagcc catcgtggag gttcgaacgg aggaggagag gaccccaaac 2400
catgatggag ggaaacacac agagcccaac gagaccacgc cactgacgga gcccgagaag 2460
ggccccgtag aagcaaagcc agagtgccag gagacagaaa cgaagccagc gccagccgaa 2520
gtcaagacgg tccccaatga cgccacacag acaaaggaga acgagagcaa agcatga 2577

<210> SEQ ID NO 82
<211> LENGTH: 2520
<212> TYPE: DNA
<213> ORGANISM: Homo sapiens

<400> SEQUENCE: 82
ctgcaggtgg atattgttcc cagccagggg gagatcagcg ttggagagtc caaattcttc 60
ttatgccaag tggcaggaga tgccaaagat aaagacatct cctggttctc ccccaatgga 120
gaaaagctca ccccaaacca gcagcggatc tcagtggtgt ggaatgatga ttcctcctcc 180
accctcacca tctataacgc caacatcgac gacgccggca tttacaagtg tgtggttaca 240
ggcgaggatg gcagtgagtc agaggccacc gtcaacgtga agatctttca gaagctcatg 300
ttcaagaatg cgccaacccc acaggagttc cgggaggggg aagatgccgt gattgtgtgt 360
gatgtggtca gctccctccc accaaccatc atctggaaac acaaaggccg agatgtcatc 420
ctgaaaaaag atgtccgatt catagtcctg tccaacaact acctgcagat ccggggcatc 480
aagaaaacag atgagggcac ttatcgctgt gagggcagaa tcctggcacg gggggagatc 540
aacttcaagg acattcaggt cattgtgaat gtgccaccta ccatccaggc caggcagaat 600
attgtgaatg ccaccgccaa cctcggccag tccgtcaccc tggtgtgcga tgccgaaggc 660
ttcccagagc ccaccatgag ctggacaaag gatggggaac agatagagca agaggaagac 720
gatgagaagt acatcttcag cgacgatagt tcccagctga ccatcaaaaa ggtggataag 780
aacgacgagg ctgagtacat ctgcattgct gagaacaagg ctggcgagca ggatgcgacc 840
atccacctca aagtctttgc aaaacccaaa atcacatatg tagagaacca gactgccatg 900

-continued

```
gaattagagg agcaggtcac tcttacctgt gaagcctccg gagaccccat tccctccatc    960
acctggagga cttctacccg gaacatcagc agcgaagaaa aggcttcgtg gactcgacca   1020
gagaagcaag agactctgga tgggcacatg gtggtgcgta gccatgcccg tgtgtcgtcg   1080
ctgaccctga agagcatcca gtacactgat gccggagagt acatctgcac cgccagcaac   1140
accatcggcc aggactccca gtccatgtac cttgaagtgc aatatgcccc aaagctacag   1200
ggccctgtgg ctgtgtacac ttgggagggg aaccaggtga acatcacctg cgaggtattt   1260
gcctatccca gtgccacgat ctcatggttt cgggatggcc agctgctgcc aagctccaat   1320
tacagcaata tcaagatcta caacaccccc tctgccagct atctggaggt gaccccagac   1380
tctgagaatg attttgggaa ctacaactgt actgcagtga accgcattgg gcaggagtcc   1440
ttggaattca tccttgttca agcagacacc ccctcttcac catccatcga ccaggtggag   1500
ccatactcca gcacagccca ggtgcagttt gatgaaccag aggccacagg tggggtgccc   1560
atcctcaaat acaaagctga gtggagagca gttggtgaag aagtatggca ttccaagtgg   1620
tatgatgcca aggaagccag catggagggc atcgtcacca tcgtgggcct gaagcccgaa   1680
acaacgtacg ccgtaaggct ggcggcgctc aatggcaaag ggctgggtga gatcagcgcg   1740
gcctccgagt tcaagacgca gccagtccaa ggggaaccca gtgcacctaa gctcgaaggg   1800
cagatgggag aggatggaaa ctctattaaa gtgaacctga tcaagcagga tgacggcggc   1860
tcccccatca gacactatct ggtcaggtac cgagcgctct cctccgagtg gaaaccagag   1920
atcaggctcc cgtctggcag tgaccacgtc atgctgaagt ccctggactg gaatgctgag   1980
tatgaggtct acgtggtggc tgagaaccag caaggaaaat ccaaggcggc tcattttgtg   2040
ttcaggacct cggcccagcc cacagccatc ccagccaacg gcagccccac ctcaggcctg   2100
agcaccgggg ccatcgtggg catcctcatc gtcatcttcg tcctgctcct ggtggttgtg   2160
gacatcacct gctacttcct gaacaagtgt ggcctgttca tgtgcattgc ggtcaacctg   2220
tgtggaaaag ccgggcccgg ggccaagggc aaggacatgg aggagggcaa ggccgccttc   2280
tcgaaagatg agtccaagga gcccatcgtg gaggttcgaa cggaggagga gaggacccca   2340
aaccatgatg gagggaaaca cacagagccc aacgagacca cgccactgac ggagcccgag   2400
aagggccccg tagaagcaaa gccagagtgc caggagacag aaacgaagcc agcgccagcc   2460
gaagtcaaga cggtccccaa tgacgccaca cagacaaagg agaacgagag caaagcatga   2520
```

IMMUNOMODULATORY CLINICAL BIOMARKER PROFILES AND USES THEREOF

CROSS-REFERENCE TO RELATED APPLICATION

This application is a U.S. National Phase Application based on International Patent Application No. PCT/US2021/060198, which claims priority to U.S. Provisional Patent Application No. 63/116,750 filed on Nov. 20, 2020, and to U.S. Provisional Patent Application No. 63/166,952, filed on Mar. 26, 2021, each of which is incorporated herein by reference in its entirety as if fully set forth herein.

STATEMENT REGARDING FEDERALLY SPONSORED RESEARCH OR DEVELOPMENT

This invention was made with government support under CA015704 awarded by the National Institutes of Health and Contract DE-AC0576RL01830 awarded by the U.S. Department of Energy. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2WC3141_ST25.txt. The text file is 124 KB, was created on May 18, 2023, and is being submitted electronically via Patent Center.

FIELD OF THE DISCLOSURE

The present disclosure relates to biomarker profiles and their use to predict a subject's response to an immunomodulatory treatment. The biomarker profiles can be used to predict responsiveness of subjects undergoing immunotherapy and to direct treatment toward better outcomes.

BACKGROUND OF THE DISCLOSURE

Immunotherapy encompasses therapeutic methods that target or modulate the immune system and is a powerful modality for treatment of many diseases. For example, T cells genetically modified to express a chimeric antigen receptor (CAR) is one form of immunotherapy to treat diseases such as cancer, infectious diseases, and autoimmune diseases. CAR T-cells have revolutionized the treatment of pediatric acute lymphoblastic leukemia (ALL). However, 10-30% of patients are non-responsive, and 20-30% of patients experience significant side effects, including life-threatening cytokine release syndrome (CRS) and neurotoxicity (NTX) (Maude et al. Cancer J 2014, 20(2):119-122; Maude et al. The New England Journal of Medicine 2014, 371(16):1507-1517). There is a crucial need for clinical biomarkers to predict response and toxicity and inform interventions for effective prevention of these adverse events. Biomarkers would help predict, identify, and target mechanisms of non-response and CRS/NTX to mitigate life-threatening toxicity in subjects undergoing immunotherapy.

SUMMARY OF THE DISCLOSURE

The present disclosure provides biomarker profiles to identify or predict a subject's response to an immunomodulatory treatment. The biomarker profiles are able to differentiate between: 1) subjects who have or will have a functional response to an immunomodulatory treatment with limited or no neurotoxicity (NTX); and 2) subjects who have or will have a toxic response to an immunomodulatory treatment with NTX and/or non-response (i.e. dysfunctional response) to an immunomodulatory treatment. Biomarkers in these profiles include cytokines and other proteins associated with the interleukin (IL)-1 family and the type 1 interferon (IFN) family. In particular embodiments, a biomarker disclosed herein is selected from interleukin (IL)-18, IL-18 binding protein (IL-18BP), IL-18 receptor 1 (IL-18R1), IL-18 receptor accessory protein (IL-18RAP), IL-2, soluble IL-2 receptor alpha (sIL-2RA), IL-5, IL-6, IL-9, IL-10, IL-22, Interferon gamma (IFNγ), Granulocyte Macrophage Colony Stimulating Factor (GM-CSF), serum amyloid A (SAA), and C-reactive protein (CRP). In particular embodiments, a biomarker disclosed herein includes a cell or population of cells. In particular embodiments, the cell or population of cells include T cells, mucosal associated invariant T (MAIT) cells, natural killer (NK) cells, natural killer T (NKT) cells, or a combination thereof. In particular embodiments, the cell or population of cells express C-type lectin-like receptor (CD161), CD56, produce GM-CSF, IL-22, produce IFNγ, or a combination thereof.

In particular embodiments, methods disclosed herein include obtaining a biological sample derived from a subject; measuring a level of at least one biomarker disclosed herein and/or a level of at least one biomarker cell population to generate a test biomarker profile; and comparing the test biomarker profile to a reference biomarker profile including the same biomarkers.

In particular embodiments, a subject is identified as having or predicted to have a toxic response and/or non-response to an immunomodulatory treatment when the level of interleukin (IL)-18, IL-18BP, IL-18R1, IL-18RAP, IL-2, sIL-2RA, IL-5, IL-6, IL-9, IL-10, IL-22, IFNγ, GM-CSF, SAA, CRP, CD161+ cells, CD56+ dim cells, or a combination thereof is increased as compared to the levels of the same biomarkers of a reference biomarker profile. In particular embodiments, the CD161+ cells include: CD161+ CD3+ T cells; CD161+ CD4+ T cells; CD161+ CD4+ CD45RA-T cells; CD161+ CD8+ T cells; CD161+ CD8+ CD45RA+ T cells; CD161+ CD56+ NK cells; CD161+ MAIT cells; CD161+ GM-CSF+ NK cells; CD161+ GM-CSF+ MAIT cells; CD161+ GM-CSF+ T cells; CD161+ IFNγ+ NK cells; CD161+ IFNγ+ MAIT cells; CD161+ IFNγ+ T cells; CD161+ IFNγ+ NKT cells; or a combination thereof.

The biomarkers disclosed herein can be used to identify or predict a subject's response to an immunomodulatory treatment before initiation of the immunomodulatory treatment (pre-immunomodulatory treatment) or after initiation of the immunomodulatory treatment. In particular embodiments, biomarkers disclosed herein can be used to predict a subject's response 1 day after an immunomodulatory treatment has initiated, 3 days after an immunomodulatory treatment has initiated, and/or 7 days after an immunomodulatory treatment has initiated.

In particular embodiments, an increase in the level of IL-18, IL-18BP, sIL-2RA, IL-10, IL-22, IFNγ, CD161+ cells, CD56+ dim cells, or a combination thereof, as compared to the level of the same biomarkers of a reference biomarker profile identifies or predicts a toxic response and/or non-response for a subject when the biomarker levels are measured before an immunomodulatory treatment has initiated.

In particular embodiments, an increase in the level of IL-18, IL-18BP, IL-5, IL-10, IL-22, sIL-2RA, IFNγ, GM-CSF, SAA, CRP, or a combination thereof, as compared to the level of the same biomarkers of a reference biomarker profile identifies or predicts a toxic response and/or non-response for a subject when the biomarker levels are measured after an immunomodulatory treatment has initiated. In particular embodiments, an increase in the level of IL-10, SAA, GM-CSF, IFNγ, or a combination thereof, as compared to the level of the same biomarkers of a reference biomarker profile identifies or predicts a toxic response and/or non-response for a subject when the biomarker levels are measured 1 day after an immunomodulatory treatment has initiated. In particular embodiments, an increase in the level of IL-10, CRP, IFNγ, GM-CSF, or a combination thereof, as compared to the level of the same biomarkers of a reference biomarker profile identifies or predicts a toxic response and/or non-response for a subject when the biomarker levels are measured 3 days after an immunomodulatory treatment has initiated. In particular embodiments, an increase in the level of IL-10, IL-5, sIL-2RA, GM-CSF, or a combination thereof, as compared to level of the same biomarkers of a reference biomarker profile identifies or predicts a toxic response and/or non-response for a subject when the biomarker levels are measured 3 days after an immunomodulatory treatment has initiated. In particular embodiments, an increase in the level of IL-18, IL-18BP, IFNγ, or a combination thereof, as compared to the level of the same biomarkers of a reference biomarker profile identifies or predicts a toxic response and/or non-response for a subject when the biomarker levels are measured 7 days after an immunomodulatory treatment has initiated. In particular embodiments, an increase in the level of IL-18, IL-18BP, IL-22, or a combination thereof, as compared to the level of the same biomarkers of a reference biomarker profile identifies or predicts a toxic response and/or non-response for a subject when the biomarker levels are measured 7 days after an immunomodulatory treatment has initiated.

In particular embodiments, a reference biomarker profile is from a subject or a population of subjects who have a functional response to an immunomodulatory treatment with limited or no neurotoxicity (NTX). In particular embodiments, a reference biomarker profile is from a healthy subject or a population of healthy subjects.

In particular embodiments, an immunomodulatory treatment includes chimeric antigen receptor (CAR) T cell immunotherapy, therapeutic agents to deplete regulatory T cells, recombinant cytokines, immune checkpoint inhibitors, monoclonal antibodies, bispecific antibodies, dual-affinity retargeting antibodies (DART), immune-mobilizing monoclonal T cell receptors against cancer (ImmTAC), and vaccines.

The biomarker profiles can be used to direct treatment or intervention for a subject that will undergo or is undergoing an immunomodulatory treatment to yield responsive and non-toxic outcomes to the immunomodulatory treatment.

BRIEF DESCRIPTION OF THE DRAWINGS

Some of the drawings submitted herein may be better understood in color. Applicant considers the color versions of the drawings as part of the original submission and reserve the right to present color images of the drawings in later proceedings.

(FIG. 6A) Standard principal component analysis (PCA) score plot showing unsupervised clustering based on subjects that are Functional (Group 1, circles) versus those that are either Dysfunctional or Toxicity (Group 2, circles with +). The inset is a scree plot demonstrating that one component describes the majority of the variance. (FIG. 6B) Probability of overall survival based on: unsupervised clustering (Group 1, dotted square; Group 2, black square with +); clinical CRS outcomes (no CRS, dotted square; mild CRS, black square; severe CRS, black square with +); clinical NTX outcomes (no NTX, dotted square; mild NTX, black square; severe NTX, black square with +); and clinical early CAR function (functional, dotted square; dysfunctional, black square with +). (FIG. 6C) Total antigen burden based on unsupervised clustering (Groups), clinical CRS outcomes (no, mild, severe), clinical NTX outcomes (no, mild, severe), and clinical early CAR function (functional or dysfunctional). (FIG. 6D) Age based on unsupervised clustering (Groups), clinical CRS outcomes (no, mild, severe), clinical NTX outcomes (no, mild, severe), and clinical early CAR function (functional or dysfunctional). (FIG. 6E) CAR T peak based on unsupervised clustering (Groups), clinical CRS outcomes (no, mild, severe), clinical NTX outcomes (no, mild, severe), and clinical early CAR function (functional or dysfunctional). (FIG. 6F) Day of CRS onset based on unsupervised clustering (Groups), clinical CRS outcomes (no, mild, severe), clinical NTX outcomes (no, mild, severe), clinical early CAR function (functional or dysfunctional). Mann-Whitney Test was performed for statistical analysis, significance is marked as follows *p value=0.05-0.01, p value=0.001-0.01, *p value=0.0001-0.001, ns=not significant.

FIGS. 7A-7D. Machine learning models are predictive of chronic interferon signaling events driving monocytic IL-18 signaling. (FIG. 7A) ROC curves for each time point. Models have a high Area Under the Curve (AUC) as described by the "optimal model". The optimal model was defined based on a forward feature selection. (FIG. 7B) Posterior probabilities for model fit for each of the subjects ordered from lowest to highest. There is a single probability estimate for each individual. Group 1, circles. Group 2, circles with +. (FIG. 7C) Model results from machine learning for each day. Results of machine learning for Day 1. 95-th Confidence interval for model is (0.733, 0.907). Results of machine learning for Day 3. 95-th Confidence interval for model is (0.867, 0.973) and (0.853, 0.987). Results of machine learning for Day 7. 95-th Confidence interval for model is (0.867, 0.973) and (0.840, 0.973). (FIG. 7D) Kinetic profiles for cytokines identified in machine learning models. Statically significant cytokines (statistical test were adjusted for age and gender) were at given time points are marked as follows *p value=0.05-0.01, p value=0.001-0.01, *p value=0.0001-0.001. All patients were assayed at Days 1-7; a subset were run on Days 10-14 (see Materials and Methods).

(FIG. 8A) IFNγ, interferon stimulated genes, sIL-2RA and IL-18, and IL-10 are chronically elevated in Group 2 both pre-CAR and 14 days post-CAR. Circles indicate patients with severe toxicity and triangles indicate dysfunctional patients within Group 2. All patients were assayed at Days 1-7; a subset were run on Days 10-14 (see Materials and Methods). (FIGS. 8B-8E) Phorbol myristate acetate (PMA) stimulated patient PBMCs were flow phenotyped for the indicated T cell markers. Significance was determined by Mann-Whitney statistical test in GraphPad Prism. (FIG. 8F) Patient PBMCs were stimulated with PMA/ionomycin for 2 hours prior to staining and flow cytometry, or (FIG. 8G) stimulated with CD3/CD28 beads for 3 hours prior to staining and flow cytometry. No significant differences were seen in function and exhaustion markers. No comparison was significant by Mann-Whitney test unless indicated. (FIG. 8H) Th22 almost achieved significance and GMCSF cells achieved significance by Mann-Whitney test. Patient PBMCs were stimulated with PMA/ionomycin for 2 hours prior to staining and flow cytometry.

(FIG. 9A) Proposed mechanism of NTX and non-response. (FIG. 9B) IL-12p70, IL-2, and sIL-2RA kinetic cytokine data for patient Group 1 and 2, pre and 14 days post-CAR. (representative of data from Cohort 1, see Material and Methods). (FIG. 9C) PMA/ionomycin stimulated healthy donors were flow phenotyped for CD161+ CD4+ CD45RA− and CD161+ CD4+CD45RA− IFNγ+ expression. (FIGS. 9D-9F) CD14+ cells isolated from healthy donors were primed with IFNγ (4 hours incubation followed by 20 hours rest) on day 1 and day 2, rested for 5 days, and activated with a lipopolysaccharide (LPS) prime. Cells were treated with nigericin to release IL-18. Supernatants were harvested and assayed for IL18BP (FIG. 9F), IL-6 (FIG. 9G), and IL-18 (FIG. 9H) by ELISA. Represents three experiments. (FIGS. 9G, 9H) Healthy donor CD4+ and CD8+ CAR T cells were incubated with IL-2 or IL-12p70 for 24 hours and RNA was harvested to assess IL-18R1 and IL-18RAP mRNA expression (FIG. 9G) and CD161 expression (FIG. 9I) relative to untreated CAR T cells by qPCR. FIG. 9G represents two experiments; FIG. 9I represents one. (FIG. 9I) Healthy donor CD4+ and CD8+ CAR T cells were pre-treated with IL-2 or IL-12 for 4 hours prior to exposure to IL-18 and target (Raji) cells. Supernatants were harvested after 3 days and assessed for IFNγ protein by ELISA. Represents three experiments.

FIGS. 11A-11C also includes Day 3. CD14+ cells isolated from healthy donors were primed with IFNγ (4 hours incubation followed by 20 hours rest) on day 1 and day 2, and then activated with a 4 hour LPS prime on either Day 3 or Day 6. Cells were treated with nigericin to release IL-18. Supernatants were harvested and assayed for IL-18BP (FIG. 11A), IL-6 (FIG. 11B), and IL-18 (FIG. 11C) by ELISA. Represents three experiments.

FIG. 13. Statistical results of kinetic cytokine machine learning panels. The linear mixed effects model p-values where the cells with ^ are significant after a multiple hypothesis test correction and the '#' cells are those that are significant with no correction.

FIG. 14. The log 2 fold change versus Functional with ^ and # symbols denoting significance as described in FIG. 13. Asterisks indicate those cytokines that have a fold-change greater than 2 on the log scale.

FIG. 16. Clinical characteristics of the 16 patient cohort from PLAT05. In this trial, patients were scored for CRS or neurotox on a scale of 1-4.

FIG. 24. Sequences of the disclosure.

DETAILED DESCRIPTION

Figure 1:
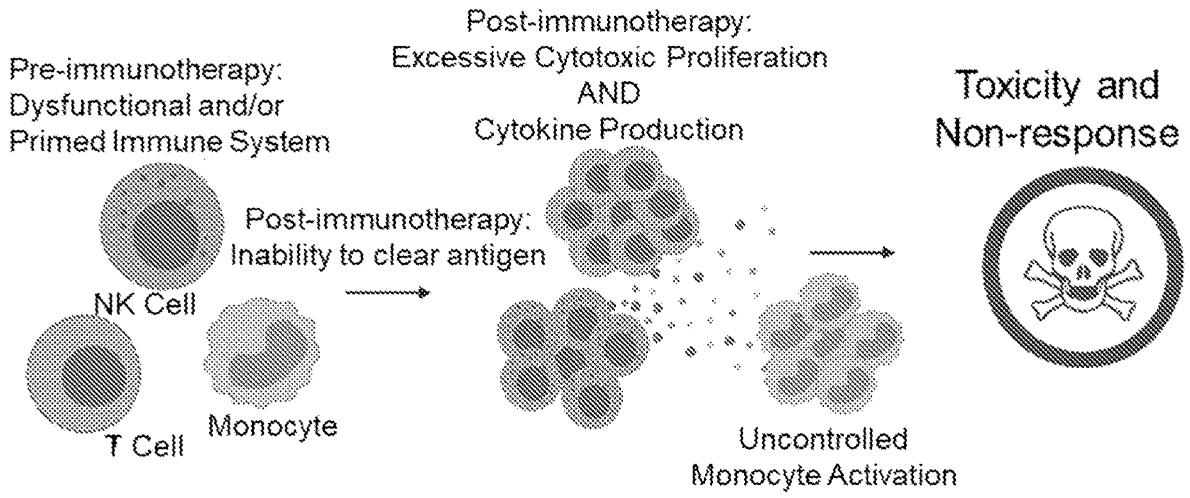
FIG. 1. Schematic of exemplary route to a toxic or non-responsive outcome to immunotherapy.
Figure 2:
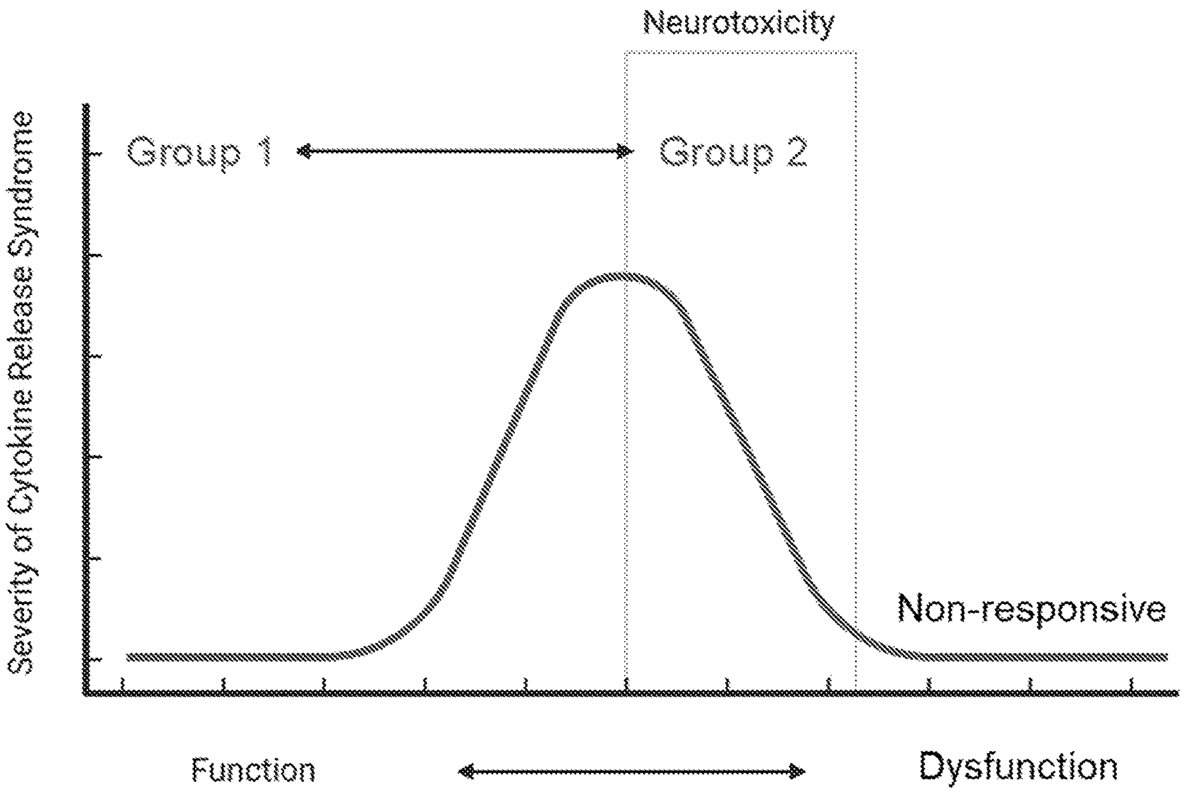
FIG. 2. Schematic of spectrum of toxicity and function in immunotherapy. Group 1 indicates functional immunotherapy with limited or no neurotoxicity. Group 2 indicates semi-functional immunotherapy with neurotoxicity and dysfunctional (or non-response) to immunotherapy. Cytokine release syndrome (CRS) is independent of neurotoxicity and function.

Chimeric antigen receptor (CAR) T cells as immunotherapies have revolutionized the treatment of childhood leukemia, inducing up to 80% remission rates in relapsed/refractory B-acute lymphoblastic leukemia (ALL). Of the patients who enter remission, close to 50% will eventually relapse (Ruella & Maus. *Computational and structural biotechnology journal* 14, 357-362 (2016)). In close to 20-30% of patients, the therapy induces adverse side effects such as neurotoxicity (NTX) and cytokine release syndrome (CRS) (Hay et al. Blood 130, 2295-2306 (2017)). These side effects can be devastating, leading to long-term neurological damage and in some cases death (Hay et al. Blood 130, 2295-2306 (2017)). As CAR therapies proliferate widely into standard clinical practice it will be necessary to predict and mitigate non-response, toxicity and relapse.

The reason for the variability of response, incidence and severity of CAR T toxicity between trials and products is poorly understood. CRS typically manifests during expansion of CAR Ts (3-10 days post-CAR) and NTX (7-14 days post-CAR) typically follows. While risk of CRS/NTX and non-response increases with antigen load and/or dose, these only partially explain toxicity and response. This, coupled with overlap in clinical presentations, raises the possibility of a common pathophysiology with hemophagocytic lymphohistiocytosis (HLH). HLH is characterized by defective lymphocyte cytotoxicity with increased cytokine production (simulated in CAR T through increased dosing and/or increased antigen exposure) coupled with uncontrolled Mϕ (myeloid) activation.

Mϕ characteristics have arisen both within the scientific literature and the clinic as strong predictive models for clinical outcomes, including response and toxicity in CAR T (Biswas & Mantovani. Seminars in immunopathology 35, 585-600 (2013); Bonnardel & Guilliams. Current opinion in immunology 50, 64-74 (2018); Murray & Wynn. Nature reviews. Immunology 11, 723-737 (2011)). Clinically, IL-6, a monocytic specific cytokine, although unproven to be causative for CRS, is able to alleviate adverse events caused by this toxicity. Physicians now dose tocilizumab (ant-IL-6 therapy) during presentation of adverse symptoms post-CAR to mitigate poor outcomes. Currently, over 90% of patients treated with CAR T present with CRS (defined by a high fever), suggesting that CRS is required for therapeutic efficacy (Gardner et al. Blood 129, 3322-3331 (2017)). However, IL-6 blockade does not alter severe neurological outcomes or tumor burden (Maude et al. Cancer J 20, 119-122 (2014)). The first humanized mouse models that could begin recapitulating both the NTX observed in human populations following CAR-T therapy were published in 2018 (Norelli et al. Nature medicine 24, 739-748 (2018)). NTX was shown to be caused by traditionally Mϕ-associated cytokine release, specifically IL-1β. Anakinra, an IL-1β receptor antagonist, ablates NTX in these models (Norelli et al. Nature medicine 24, 739-748 (2018)). Currently, there are a wide variety of open clinical trials to test the success of Anakinra in treating NTX post-CAR. However, despite wide acceptance that this molecule could be responsible for NTX outcomes, no reported prospective or retrospective studies have been able to identify this molecule in the serum or cerebral spinal fluid of patients. While IL-1β is present in clinical presentation of macrophage activation syndrome (MAS) and HLH, it is rarely linked to causative outcomes. In contrast, interleukin (IL)-18, an IL-1 family member, has been directly linked both clinically to symptom severity and lethality and in mouse models is linked to causal mechanisms. In primary HLH, IL-18BP (an IL-18 antagonist) is approved clinically. This molecule is now reported in multiple CD22 CAR trials as being elevated in the serum of severe toxicity patients presenting with classical HLH-like symptoms, albeit it's clear the timeline of presentation of these symptoms is very different from CD19 therapy (Shah et al. Journal of clinical oncology: official journal of the American Society of Clinical Oncology 38, 1938-1950 (2020)). Yet, this result suggests that agents that regulate signaling or processing of the IL-18 at early timepoints could be more efficacious than targeting either IL-6 or IL-1β. Regardless, myeloid associated cytokines appear to have a role in toxicity associated outcomes in CAR T.

IL-18 has long been implicated in tumor regression and progression, where it appears to both be responsible for poor therapeutic outcomes and successful treatment strategies. For example, IL-18 has been used in pre-clinical models to promote both CAR T efficacy and checkpoint blockade but serves as predictor clinically of poor survival in the context of a wide variety of tumors. The dichotomy of this molecule is likely linked to its ability to toggle the immune system within the context of disease. Importantly, while IL-18 is likely secreted and regulated (by the secreted antagonist IL-18BP) from the innate immune system to signal to the adaptive immune system, it requires a co-stimulatory molecule to induce expression of the IL-18 receptor. For example, in the presence of IL-12, IL-18 induces a robust cytotoxic immune response characterized robustly in pathogenesis and likely anti-tumor response. However, in the absence of IL-12 but presence of IL-2, IL-18 induces allergy and uncontrolled inflammation in mouse models. It is within the context of these co-stimulatory molecules that the functional differences of IL-18 in promoting and reducing tumorigenesis likely lies. These results at least highlight the important role of monocytic specific cytokines in regulating responsive CAR outcomes. It is possible that a basal level of cytokine excretion from MOs is necessary for overall therapeutic benefit, but highly amplified cytokine responses can be lethal or result in non-responsiveness. Without being bound by any one hypothesis, levels of cytokine secretion could be predicted by the inflammatory status of a patient prior to immunotherapy.

Figure 3:
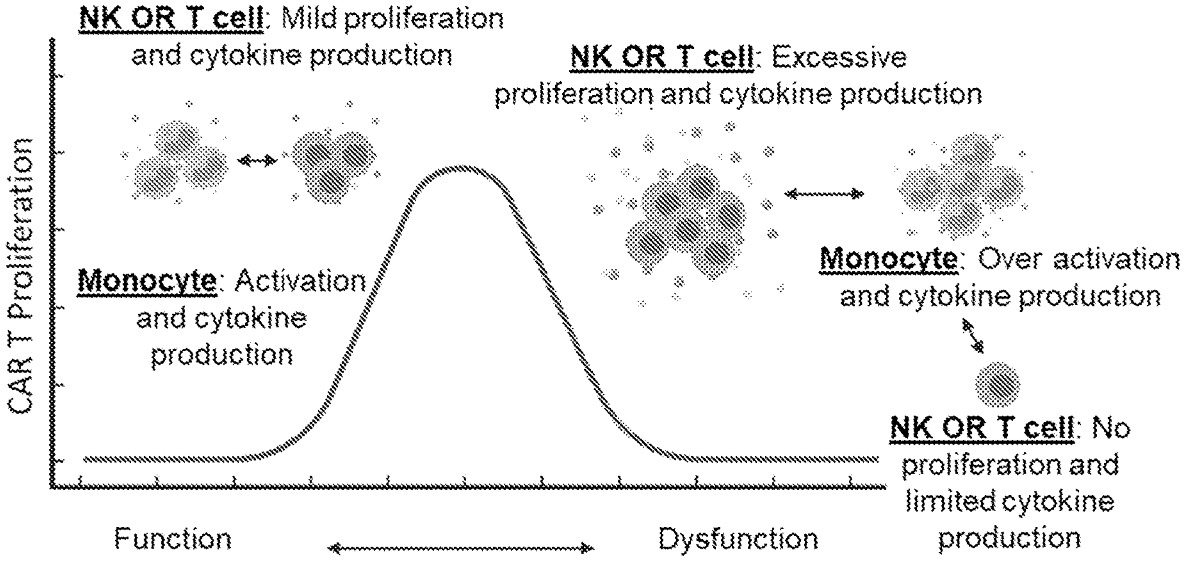
FIG. 3. Chimeric antigen receptor (CAR) T response and toxicity spectrum.
Figure 4:
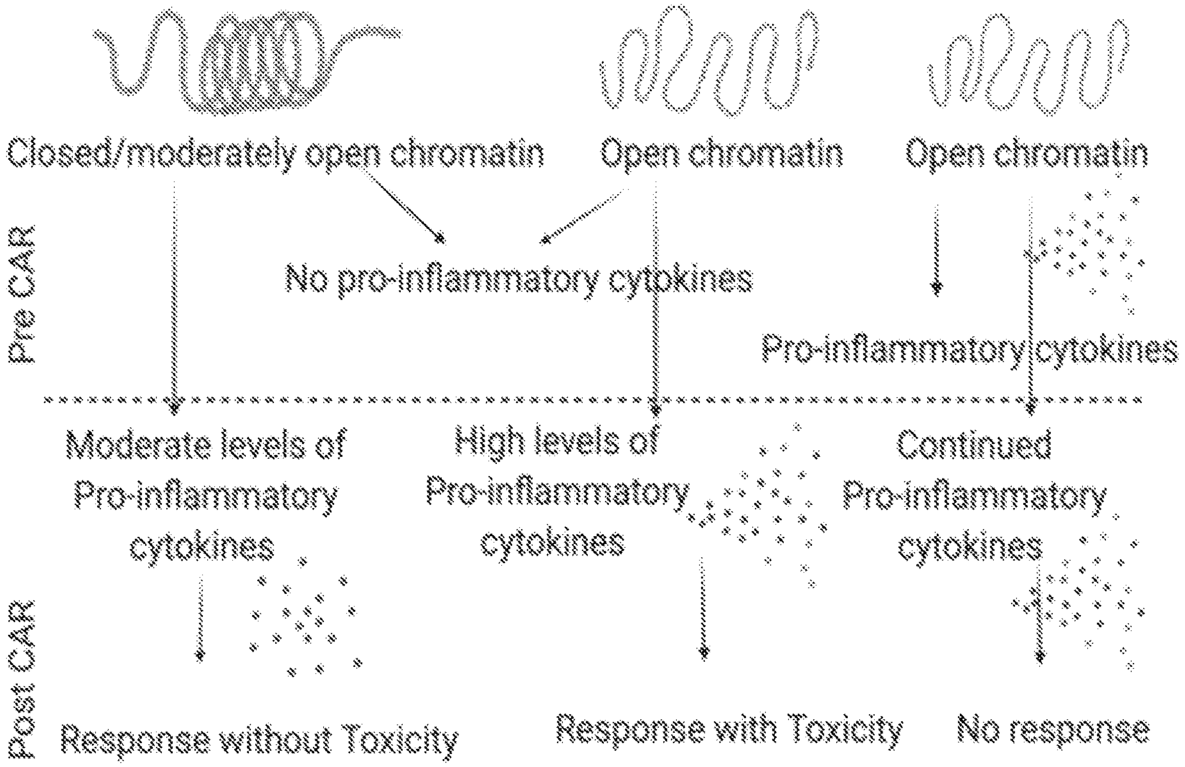
FIG. 4. CAR T cell function and toxic potential may be related to a patient's monocytic pro-inflammatory potential, which is driven by epigenetics. Proinflammatory cytokine elevation prior to CAR-T immunotherapy induces dysfunction and elevation post-CAR T immunotherapy induces toxicity.
Figure 5:
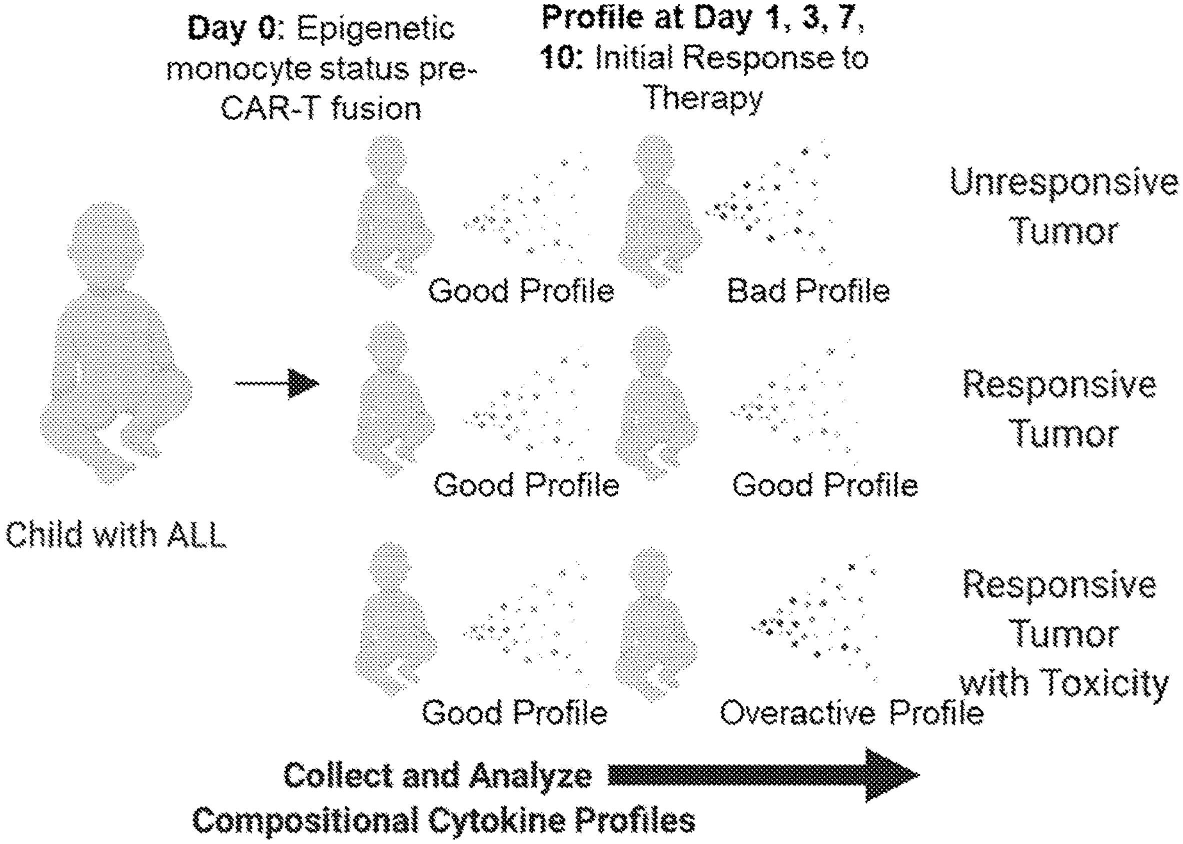
FIG. 5. Schematic depicting study described in Example 3 and outcomes.

Without being bound by any one hypothesis, the pre-inflammatory status of a patient's MO populations, defined by potential of the Mϕ to produce proinflammatory cytokines at early time points post-CAR, could predict therapeutic response and toxicity in patients undergoing an immunomodulatory treatment, such as pediatric ALL CAR T populations (FIGS. 3 and 4).

Studies on CAR patients thus far have focused on the T cell and have reduced the role of patient specific immune characteristics on CAR outcomes. Further, the role of monocytic cytokine kinetic/compositional profiles in immunotherapy outcomes have not been studied and there remains a lack of understanding of how these profiles either promote or inhibit efficacy of immunotherapy.

The present disclosure describes the generation of monocytic kinetic and compositional profiles. Retrospective machine learning was performed on 30 patients off the pediatric and young adult leukemia adoptive therapy trial (PLAT-02, NCT02028455) at days 1, 3, and 7 post-CAR. Using unbiased classifications, two distinct groups of patients were identified: a patient population that included initial non-responsive CAR T patients, patients with severe NTX and overall low survival (median survival 16.84 months, classified as Group 2); and another group that maintained high survival (median survival undefined, classified as Group 1) with varying degrees of CRS severity and mild/no NTX (FIGS. 6A-6F). A clear IL-18 (monocytic)-IFNγ (T cell) signaling axis emerged, differentiating these two groups of patients as early as day 1 post-CAR (FIGS. 7A-7D). Group 2 patients had had basal IFNγ signaling driving IL-18 outcomes. The characterization of the monocytic IL-18 signaling axis was extended in a subset of 14 patients to demonstrate that these profiles were also present pre-CAR treatment and that this axis defines differential peripheral blood mononuclear cell (PBMC) characteristics. Flow phenotyping performed on patient PBMCs isolated prior to apheresis showed that Group 2 had higher levels of CD161+ cells as well as CD161+ IFNγ+ cells than Group 1 patients. Variation in levels of CD4+CD161+ IFNγ+ cells in healthy adult donor PBMCs was also observed, and increased levels of these cells correlated with increased cytokine (e.g. IL-18, IL-6 and IL-18BP) production after IFNγ priming in the matched donor monocytes, correlating with Group 2 response, suggesting that humans with more CD4+CD161+ IFNγ+ cells may also have monocytes that are pre-disposed to be more responsive to stimulation. Healthy donor CAR T cells were able to be driven into a Group 2 like-phenotype by increasing IL18R1 and IL18RAP (the heterodimer responsible for IL-18 response), and CD161, which drove amplified IFNγ protein expression levels. Therefore, myeloid characteristics pre-CAR and early time points post-CAR can be used to aid in the prediction of patients who are set to fail treatment and allow medical teams to be more prepared to mitigate toxicity in those who are more prone to it. Further, these are potential intervention targets that might improve CD19+ CAR outcomes. These studies highlight the need to study patient specific immune characteristics prior to CAR therapy, as these may be more predictive of CAR success and failure.

Cytokines include proteins, peptides, and glycoproteins that are secreted by specific cells of the immune system. Cytokines can serve as signaling molecules in regulation of immunity, inflammation, and hematopoiesis. Immune responses can be mediated by two types of helper T cells. T helper type 1 (Th1) lymphocytes stimulate Type 1 immunity, characterized by intense phagocytic activity. Th1 cells secrete cytokines IL-2, interferon-γ (IFNγ), and lymphotoxin-α. Conversely, Th2 cells stimulate type 2 immunity, characterized by high antibody titers. Th2 cells secrete cytokines IL-4, IL-5, IL-9, IL-10, and IL-13. However, Th1 and Th2 cell functions are not clearly divided, as Th1 cells can stimulate antibody production, and Th2 cells can actively suppress phagocytosis. Generally, type 1 immunity is protective against infections, and type 2 responses help resolve cell-mediated inflammation. Th17 cells are distinct from Th1 and Th2 and include CD4+ T cells that produce the pro-inflammatory cytokine IL-17. Th17 cells function in host defense against infection; however, excessive Th17 cell activity may play a role in immune-mediated diseases, tumorigenesis, and transplant rejection.

Myeloid or myelogenous cells include white blood cells (leukocytes) that arise from a progenitor cell for granulocytes, monocytes, erythrocytes, or platelets. In particular embodiments, myeloid cells include granulocytes, monocytes, macrophages, and dendritic cells. Monocytes function in phagocytosis, antigen presentation, and cytokine production. Human blood has at least three types of monocytes: a classical monocyte characterized by high expression of the CD14 cell surface receptor (CD14++ CD16−); a non-classical monocyte characterized by low expression of CD14 and co-expression of the CD16 receptor (CD14+CD16++); and an intermediate monocyte with high expression of CD14 and low expression of CD16 (CD14++CD16+). In particular embodiments, the cell surface marker 6-Sulfo LacNAc (slan) can differentiate between non-classical and intermediate monocytes. In particular embodiments, the non-classical (CD14+CD16++) monocytes produce high amounts of pro-inflammatory cytokines like tumor necrosis factor (TNF) and IL-12 after stimulation with microbial products.

Macrophages are a type of white blood cell that functions in host defense against infection and injury in a process called phagocytosis. The macrophages engulf and digest biological entities that do not have molecular markers identifying them as part of the healthy host, such as cellular debris, foreign substances, microbes, and cancer cells. Macrophages function to retain homeostasis and achieve a balance of pro-inflammatory and immunosuppressive environments. Pro-inflammatory macrophages function in phagocytosis and promote an immune response, while pro-growth macrophages function in angiogenesis and immunosuppression. Macrophage activation may be predictive of inflammation and cancer survival (Buscher et al. (2017) Nature Communications 8:16041).

A T cell is a white blood cell that originates from hematopoietic stem cells in the bone marrow but matures in the thymus. Most T cells have a T-cell receptor (TCR) composed of two separate peptide chains (the α- and β-TCR chains). γδ T cells represent a small subset of T cells that possess a distinct T cell receptor (TCR) made up of one γ-chain and one δ-chain. CD3 is expressed on all mature T cells. T cells can further be classified into cytotoxic T cells (CD8+ T cells, also referred to as CTLs) and helper T cells (CD4+ T cells). Cytotoxic T cells destroy virally infected cells and tumor cells and are also implicated in transplant rejection. These cells recognize their targets by binding to antigen associated with major histocompatibility complex (MHC) class I, which is present on the surface of nearly every cell of the body. T cells have different maturation stages. In particular embodiments, naïve T cells express CD45RA (CD45RA+). After antigenic exposure, naïve T cells can convert to memory T cells. In particular embodiments, memory T cells express CD45RO (CD45RO+) and do not express CD45RA (CD45RA−).

Natural killer (NK) cells share a common progenitor with T and B cells but play a role in the innate immune system by rapidly responding to a wide variety of pathological challenges including infectious pathogens and tumor cells. NK cells are activated in response to inflammatory mediators such as interferons or cytokines. Once activated to destroy a target cell, NK cells can release cytotoxic granules including perforin and granzymes to lyse the target cell. NK cells also express a variety of activating and inhibitory receptors, as well as co-stimulatory receptors, to recognize and respond to inflamed or infected tissues. These receptors bind cellular stress ligands, which can lead to NK cell responses. Importantly, some of these receptors prevent activation of NK cells, so that NK cells do not target healthy tissue. In particular embodiments, NK cells can include CD3+ NK cells, CD4+ NK cells, and/or CD8+ NK cells. In particular embodiments, NK cells are CD56+. In particular embodiments, the majority of circulating NK cells are CD56+ dim.

Natural killer T (NKT) cells are lymphocytes that express both a TCR, a feature of adaptive immunity, and surface receptors for NK cells, which form part of the innate immune response. NKT cells play diverse roles in immune responses, including the surveillance for tumors, the maintenance of self-tolerance, and the regulation of autoimmune diseases. In particular embodiments, NKT cells can include CD3+ NKT cells, CD4+ NKT cells, and/or CD8+ NKT cells. In particular embodiments, NKT cells are CD3+ CD56+. A major population of NKT cells, called iNKT cells, expresses an invariant TCR α-chain. iNKT cells recognize lipids presented by CD1d molecules and protect a host against microbial pathogens, including bacteria, fungi, parasites and viruses.

The following aspects of the disclosure are now described in more detail: (I) Biomarkers; (II) Responses to an immunomodulatory treatment; (III) Biological Samples; (IV) Assays for detection and quantification of biomarkers; (V) Reference levels and reference biomarker profiles; (VI) Methods of Use; (VII) Kits; (VIII) Exemplary Embodiments; (IX) Examples; (X) Variants; and (XI) Closing Paragraphs.

(I) Biomarkers. A biomarker can include any biological compound, such as a protein and a fragment thereof, a peptide, a polypeptide, a proteoglycan, a glycoprotein, a lipoprotein, a carbohydrate, a lipid, a nucleic acid, an organic or inorganic chemical, a natural polymer, or a small molecule that is present in a biological sample and that may be isolated from, or measured in, the biological sample. A biomarker can include a cell type, a cell expressing one or more specific molecules (e.g. a cell surface molecule and/or a molecule produced inside the cell), a cell population, or a cell population expressing one or more specific molecules (e.g. a cell surface molecule and/or a molecule produced inside a cell of a cell population). Furthermore, a biomarker can be the entire intact molecule, or it can be a portion thereof that may be partially functional or recognized, for example, by an antibody or other specific binding protein. A biomarker is considered to be informative if a measurable aspect of the biomarker is associated with a given state of a subject, such as responsiveness to an immunomodulatory treatment. Such a measurable aspect may include, for example, the presence, absence, or concentration of the biomarker in the biological sample from the subject and/or its presence as part of a profile of biomarkers. Such a measurable aspect of a biomarker can be referred to as a "feature." In particular embodiments, a feature can include a concentration, amount, or level of a biomarker. A feature may also be a ratio of two or more measurable aspects of biomarkers, which biomarkers may or may not be of known identity, for example. A biomarker profile includes at least one such feature, where the feature can be, for example, a nucleic acid or a protein. A biomarker profile may also include at least two, three, four, five, 10, 20, 30, or more features. In particular embodiments, a biomarker profile includes the concentrations, amounts, or levels of 1, 2, 3, 4, 5, 6, 7, 8, 9, 10, 11, 12, 13, 14, 15, 16, 17, 18, 19, 20, or more biomarker(s). In particular embodiments, a biomarker profile includes the amount, size, or level of at least one cell population. In particular embodiments, a biomarker profile includes the concentrations, amounts, or levels of one or more biomarkers and the amount, size, or level of at least one cell population. In particular embodiments, a biomarker profile includes at least one measurable aspect of at least one internal standard.

The terms "nucleic acid", "nucleotide sequence", and "polynucleotide" are interchangeable. All refer to a polymeric form of nucleotides. The nucleotides may be deoxyribonucleotides (DNA) or ribonucleotides (RNA), or analogs thereof, and they may be of any length.

In particular embodiments, biomarkers to predict a subject's responsiveness to an immunomodulatory treatment can include cytokines and proteins associated with the interleukin (IL)-1 (IL-1) family. The IL-1 family of cytokines and proteins function in inflammatory and non-specific host defense responses (innate immunity) and in response to foreign antigens (acquired immunity). Receptors of the IL-1 family have a cytosolic Toll interleukin-1 receptor (TIR) domain that is highly homologous to that of the Toll-like receptors (TLRs). Both the TLR and IL-1 families nonspecifically augment antigen recognition and activate lymphocyte function. Cytokines and associated proteins in the IL-1 family include: IL-1β, IL-1α, IL-33, IL-1 receptor antagonist, IL-18, IL-37, IL-36 receptor antagonist (IL-36Ra), IL-36α, IL36β, IL-36γ, and IL-38. An exemplary IL-1β sequence includes UniProt ID P01584. An exemplary IL-1a sequence includes UniProt ID P01583. An exemplary IL-33 sequence includes UniProt ID O95760. An exemplary IL-1 receptor antagonist sequence includes UniProt ID P18510. An exemplary IL-37 sequence includes UniProt ID Q9NZH6. An exemplary IL-36Ra sequence includes UniProt ID Q9UBH0. An exemplary IL-36α sequence includes UniProt ID Q9UHA7. An exemplary IL-36β sequence includes UniProt ID Q9NZH7. An exemplary IL-36Rγ sequence includes UniProt ID Q9NZH8. An exemplary IL-38 sequence includes UniProt ID Q8WWZ1.

In particular embodiments, a biomarker of the present disclosure includes interleukin-18 (IL-18). An exemplary IL-18 sequence includes UniProt ID Q14116-1, which includes a pro-peptide (SEQ ID NO: 9, encoded by SEQ ID NO: 46). IL-18 is synthesized as an inactive pre-cursor, and the pro-peptide of IL-18 (amino acids 1-36 of SEQ ID NO: 9) is cleaved by a caspase to yield an active mature IL-18 included in SEQ ID NO: 10, encoded by SEQ ID NO: 47. IL-18 is a proinflammatory cytokine primarily involved in polarized Th1 cell and NK cell immune responses. IL-18 forms a ternary complex with IL-18 receptor 1 (IL18R1) and IL-18 receptor accessory protein (IL18RAP), which activates NF-kappa-B, triggering synthesis of inflammatory mediators. IL-18 acts with IL-12 to induce IFNγ synthesis from Th1 cells and NK cells.

In particular embodiments, a biomarker of the present disclosure includes interleukin-18 binding protein (IL-18BP). An exemplary IL-18BP sequence includes UniProt ID 095998-2, which includes a signal peptide (SEQ ID NO: 11, encoded by SEQ ID NO: 48). In particular embodiments, IL-18BP lacks a signal peptide (SEQ ID NO: 12, encoded by SEQ ID NO: 49). IL-18BP binds to IL-18 and inhibits its activity. In particular embodiments, IL-18BP functions as an inhibitor of the early Th1 cytokine response.

In particular embodiments, a biomarker of the present disclosure includes IL-18 receptor 1 (IL-18R1). An exemplary IL-18R1 sequence includes UniProt ID Q13478, which includes a signal peptide (SEQ ID NO: 13, encoded by SEQ ID NO: 50). In particular embodiments, IL-18R1 lacks a signal peptide (SEQ ID NO: 14, encoded by SEQ ID NO: 51). IL-18R1 is part of the IL18 receptor complex and binds the proinflammatory cytokine IL18. IL-18R1 plays a role in IL18-mediated IFNγ synthesis from Th1 cells. It contributes to IL18-induced cytokine production.

In particular embodiments, a biomarker of the present disclosure includes IL-18 receptor accessory protein (IL-18RAP). An exemplary IL-18RAP sequence includes UniProt ID 095256-1, which includes a signal peptide (SEQ ID NO: 15, encoded by SEQ ID NO: 52). In particular embodiments, IL-18RAP lacks a signal peptide (SEQ ID NO: 16, encoded by SEQ ID NO: 53). Although IL-18RAP is part of the IL18 receptor complex, it does not mediate IL18-binding; rather, it is involved in IL18-dependent signal transduction, leading to NF-kappa-B and JNK activation. In particular embodiments, it may function in IL18-mediated IFNγ synthesis from Th1 cells.

In particular embodiments, a biomarker of the present disclosure includes IL-1 receptor-like 1 (IL-1RL1/ST2). An exemplary ST2 sequence includes UniProt ID Q01638. ST2 is a receptor for interleukin-33 (IL-33). In particular embodiments, signaling involves association of the coreceptor IL1RAP. The stimulation of ST2 recruits proteins of a signaling platform including myeloid differentiation primary response 88 (MYD88), IL-1 receptor-associated kinase (IRAK) 1, IRAK4, and TNF receptor-associated factor 6 (TRAF6), followed by phosphorylation of mitogen activated protein kinase (MAPK) 3/ERK1 and/or MAPK1/ERK2, MAPK14, and MAPK8. In particular embodiments, ST2 is involved in helper T-cell function.

In particular embodiments, biomarkers to predict a subject's responsiveness to an immunomodulatory treatment can include a type 1 IFN. Interferons function in antiviral, antiproliferative, and immunomodulatory effects in a host response to viral or bacterial infection. The different types of interferons are classified according to genetic, structural, and functional characteristics, along with their cell surface receptors. The type 1 IFN family includes 13-14 subtypes of IFN-α, IFN-β, IFN-ε, IFN-κ, IFN-ω, IFN-δ, IFN-ζ, and IFN-τ. IFN-α and IFN-β are used as standard treatments for chronic hepatitis B and C virus infections. IFN-ε controls mucosal immunity against viral and bacterial infections, and IFN-T has been shown to inhibit HIV infection. See Li et al. 2018 Cell Physiol Biochem 51:2377-2396 for a description of Type I interferons. Exemplary IFN-α sequences include: UniProt ID P05014 (interferon alpha-4); UniProt ID P01570 (interferon alpha-14); UniProt ID P01563 (interferon alpha-2); UniProt ID P01562 (interferon alpha-1/13); UniProt ID P32881 (interferon alpha-8); UniProt ID P05015 (interferon alpha-16); UniProt ID P01571 (interferon alpha-17); UniProt ID P01567 (interferon alpha-7); and UniProt ID P01568 (interferon alpha-21). An exemplary IFN-β sequence includes UniProt ID P01574. An exemplary IFN-ε sequence includes UniProt ID Q86WN2. An exemplary IFN-κ sequence includes UniProt ID Q9P0W0. An exemplary IFN-ω sequence includes UniProt ID P05000. An exemplary IFN-δ is described in Lefevre et al. 1998 Biochimie 80(8-9):779-788. An exemplary mouse IFN-ζ sequence includes UniProt ID Q8BQT1 and a human IFN-ζ is described in Oritani and Tomiyama 2004 Int J Hematol 80(4):325-331. Exemplary IFN-T sequences include: UniProt ID P56831 (*Bos Taurus* interferon tau-3); UniProt ID P15696 (*Bos taurus* interferon tau-1); UniProt ID P56830 (*Bos Taurus* interferon tau-2); UniProt ID P56829 (*Ovis aries* interferon tau-2); UniProt ID Q29429 (*Ovis aries* interferon tau-6); UniProt ID P28169 (*Ovis aries* interferon tau-11); UniProt ID P56832 (*Ovis aries* interferon tau-3); UniProt ID P56828 (*Ovis aries* interferon tau-1); UniProt ID Q08053 (*Ovis aries* interferon tau-10); UniProt ID Q28595 (*Ovis aries* interferon tau-5); UniProt ID Q08072 (*Ovis aries* interferon tau-8); UniProt ID Q08071 (*Ovis aries* interferon tau-7); and UniProt ID Q08070 (*Ovis aries* interferon tau-9); and UniProt ID Q28594 (*Ovis aries* interferon tau-4).

In particular embodiments, a biomarker of the present disclosure includes IL-2. An exemplary IL-2 sequence includes UniProt ID P60568, which includes a signal peptide (SEQ ID NO: 17, encoded by SEQ ID NO: 54). In particular embodiments, IL-2 lacks a signal peptide (SEQ ID NO: 18, encoded by SEQ ID NO: 55). IL-2 is a member of the IL-2 cytokine subfamily which also includes IL-4, IL-7, IL-9, IL-15, IL-21, erythropoietin, and thrombopoietin, The cytokine is secreted by activated CD4+ and CD8+T lymphocytes in response to antigenic or mitogenic stimulation. In particular embodiments, IL-2 stimulates B-cells, monocytes, lymphokine-activated killer cells, NK cells, and glioma cells. IL-2 functions in proliferation of T and B lymphocytes, regulates CD4+ T cell differentiation and function, and plays a role in the effector and memory responses of CD8+ T cells. The receptor of IL-2, IL-2R, is a heterotrimeric protein complex composed of an IL-2 receptor alpha (IL-2RA) chain, an IL-2 receptor beta (IL-2RB) chain, and a common gamma chain (IL-2RG) gamma chain. The IL-2RG is also shared by receptors for IL-4 and IL-7.

In particular embodiments, a biomarker of the present disclosure includes soluble IL-2 receptor alpha (sIL-2RA or CD25). An exemplary IL-2RA sequence includes UniProt ID P01589-1, which includes a signal peptide (SEQ ID NO: 19, encoded by SEQ ID NO: 56). In particular embodiments, IL-2RA lacks a signal peptide (SEQ ID NO: 20, encoded by SEQ ID NO: 57). IL-2RA, along with IL-2RB and IL-2RG, make up the high-affinity IL-2 receptor. Homodimeric IL-2RA yield a low-affinity receptor, while homodimeric IL-2RB yield a medium-affinity receptor. The receptor is involved in the regulation of immune tolerance by controlling the activity of regulatory T cells (TREGs). TREGs suppress the activation and expansion of autoreactive T-cells. IL-2RA expression increases rapidly after T-cell activation. Normally an integral-membrane protein, soluble IL-2RA results from extracellular proteolysis and can be measured in serum as a 45 kDa soluble form. sIL-2RA levels have been found to be elevated in patients with different types of carcinomas.

In particular embodiments, a biomarker of the present disclosure includes IL-12. In particular embodiments, IL-12 includes IL-12A (subunit alpha) and/or IL-12B (subunit beta). An exemplary IL-12A sequence includes NCBI Reference Sequence NP_000873.2, which includes a signal peptide (SEQ ID NO: 21, encoded by SEQ ID NO: 58). In particular embodiments, IL-2RA lacks a signal peptide (SEQ ID NO: 22, encoded by SEQ ID NO: 59). An exemplary IL-12B sequence includes UniProt ID P29460-1, which includes a signal peptide (SEQ ID NO: 23, encoded by SEQ ID NO: 60). In particular embodiments, IL-2RA lacks a signal peptide (SEQ ID NO: 24, encoded by SEQ ID NO: 61). IL-12 is a disulfide-linked heterodimer composed of a 35-kD alpha subunit and a 40-kD beta subunit. IL-12 can act as a growth factor for activated T and NK cells, enhance the lytic activity of NK/lymphokine-activated killer cells, and stimulate the production of IFNγ by resting peripheral blood mononuclear cells (PBMC). In particular embodiments, IL-12 is a cytokine that induces development of Th1 and/or Th2 cells. In particular embodiments, IL-12 is important for sustaining a sufficient number of memory/effector Th1 cells to mediate long-term protection to an intracellular pathogen. In particular embodiments, the responses of lymphocytes to IL-12 may be mediated by the activator of transcription protein STAT4.

In particular embodiments, a biomarker of the present disclosure includes IL-4. An exemplary IL-4 sequence includes UniProt ID P05112. IL-4 participates in at least several B-cell activation processes such as induction of expression of class II MHC molecules on resting B cells. It is a co-stimulator of DNA synthesis. It enhances both secretion and cell surface expression of IgE and IgG1. IL-4 also controls the expression of the low affinity Fc receptor for IgE (CD23) on both lymphocytes and monocytes.

In particular embodiments, a biomarker of the present disclosure includes IL-5. An exemplary IL-5 sequence includes UniProt ID P05113-1, which includes a signal peptide (SEQ ID NO: 25, encoded by SEQ ID NO: 62). In particular embodiments, IL-5 lacks a signal peptide (SEQ ID NO: 26, encoded by SEQ ID NO: 63). IL-5 is a disulfide-linked homodimer. It promotes the growth, differentiation, and activation of eosinophils, white blood cells that protect against parasites and infection. IL-5 induces terminal differentiation of late-developing B-cells to immunoglobulin secreting cells. IL-5 binds a heterodimeric receptor, whose beta subunit is shared with the receptors for IL-3 and granulocyte macrophage colony stimulating factor (GM-CSF).

In particular embodiments, a biomarker of the present disclosure includes IL-6. An exemplary IL-6 sequence includes UniProt ID P05231-1, which includes a signal peptide (SEQ ID NO: 27, encoded by SEQ ID NO: 64). In particular embodiments, IL-6 lacks a signal peptide (SEQ ID NO: 28, encoded by SEQ ID NO: 65). IL-6 has many biological functions in immunity, tissue regeneration, and metabolism. It binds to IL-6 receptor (IL-6R). It contributes to host defense during infection and tissue injury; however, excessive IL-6 synthesis is involved in disease pathology. In the innate immune response, IL-6 is produced by myeloid cells, such as macrophages and dendritic cells. In the adaptive immune response, it is involved in the differentiation of B cells into immunoglobulin-secreting cells. IL-6 is secreted into the serum and induces a transcriptional inflammatory response through IL-6 receptor alpha.

In particular embodiments, a biomarker of the present disclosure includes IL-9. An exemplary IL-9 sequence includes UniProt ID P15248-1, which includes a signal peptide (SEQ ID NO: 29, encoded by SEQ ID NO: 66). In particular embodiments, IL-9 lacks a signal peptide (SEQ ID NO: 30, encoded by SEQ ID NO: 67). IL-9 regulates a variety of hematopoietic cells, stimulates cell proliferation, and prevents apoptosis. Signal transducer and activator (STAT) proteins are activated when IL-9 binds to the IL-9 receptor (IL-9R). In particular embodiments, IL-9 may play a role in the pathogenesis of bronchial hyperresponsiveness in asthma.

In particular embodiments, a biomarker of the present disclosure includes IL-10. An exemplary IL-10 sequence includes UniProt ID P22301-1, which includes a signal peptide (SEQ ID NO: 31, encoded by SEQ ID NO: 68). In particular embodiments, IL-10 lacks a signal peptide (SEQ ID NO: 32, encoded by SEQ ID NO: 69). IL-10 has anti-inflammatory functions, including limiting excessive tissue disruption caused by inflammation. The binding of IL10 to a hetero-tetrameric receptor including IL10RA and IL10RB leads to JAK/STAT signaling and expression of anti-inflammatory mediators. IL-10 inhibits release of pro-inflammatory cytokines (e.g., GM-CSF, granulocyte colony-stimulating factor (G-CSF), IL-1α, IL-1β, IL-6, IL-8 and TNF-α) from antigen-presenting cells (APCs) such as macrophages and monocytes. In particular embodiments, IL-10 can interfere with antigen presentation by reducing the expression of MHC class II and co-stimulatory molecules, thereby inhibiting T cell activation. In particular embodiments, IL-10 can regulate macrophage inflammatory response by reprogramming metabolic pathways including mTOR signaling.

In particular embodiments, a biomarker of the present disclosure includes IL-17B. An exemplary IL-17B sequence includes UniProt ID Q9UHF5. IL-17B stimulates the release of TNFα and IL-1β from the monocytic cell line THP-1.

In particular embodiments, a biomarker of the present disclosure includes IL-17E/IL-25. An exemplary IL-17E/IL-25 sequence includes UniProt ID Q9H293. IL-17E is a proinflammatory cytokine favoring Th2-type immune responses. It induces activation of NF-kappa-β and stimulates production of the proinflammatory chemokine IL-8.

In particular embodiments, a biomarker of the present disclosure includes IL-22. An exemplary IL-22 sequence includes UniProt ID Q9GZX6-1, which includes a signal peptide (SEQ ID NO: 33, encoded by SEQ ID NO: 70). In particular embodiments, IL-22 lacks a signal peptide (SEQ ID NO: 34, encoded by SEQ ID NO: 71). IL-22 binds to a heterodimeric cell surface receptor including IL-10R2 and IL-22R1 subunits. IL-22 is produced by immune cells including αβ T cells, γδ T cells, NKT, ILC3, neutrophils, and macrophages. IL-22 can stimulate cell survival, cell proliferation, and synthesis of anti-microbials in non-hematopoietic cells and thus functions in wound healing and protection against microbes. In particular embodiments, IL-22 contributes to the inflammatory response in vivo through signal transduction via IL-10R2 and IL-22R1. In particular embodiments, IL-22 function can be regulated by IL-22BP, a soluble binding protein and/or cytokine IL-17A.

In particular embodiments, a biomarker of the present disclosure includes Intercellular Adhesion Molecule 1 (ICAM1). An exemplary ICAM1 sequence includes UniProt ID P05362. ICAM proteins are ligands for the leukocyte adhesion protein LFA-1 (integrin alpha-L/beta-2). During leukocyte trans-endothelial migration, ICAM1 engagement promotes the assembly of endothelial apical cups through Rho guanine nucleotide exchange factor 26 (ARHGEF26)/SGEF and RhoG GTPase (RHOG) activation.

In particular embodiments, a biomarker of the present disclosure includes Tumor Necrosis Factor alpha (TNFα). An exemplary TNFα sequence includes UniProt ID P01375. TNFα binds to TNFRSF1A/TNFR1 and TNFRSF1B/TNFBR. It is mainly secreted by macrophages and can induce cell death of certain tumor cell lines. It stimulates IL-1 secretion. In particular embodiments, TNFα can stimulate cell proliferation and induce cell differentiation. In particular embodiments, it impairs regulatory T-cell function. It functions in angiogenesis by inducing vascular endothelial growth factor (VEGF) production synergistically with IL-1B and IL6.

In particular embodiments, a biomarker of the present disclosure includes Interferon gamma (IFNγ). An exemplary IFNγ sequence includes UniProt ID P01579-1, which includes a signal peptide (SEQ ID NO: 35, encoded by SEQ ID NO: 72). In particular embodiments, IFNγ lacks a signal peptide (SEQ ID NO: 36, encoded by SEQ ID NO: 73). IFNγ is a member of the type II interferon class. IFNγ is produced by lymphocytes activated by specific antigens or mitogens. Active IFNγ is a homodimer that functions by binding to the IFNγ receptor to trigger a cellular response to viral and microbial infections. IFNγ is a potent activator of macrophages, has antiproliferative effects on transformed cells, and can potentiate the antiviral and antitumor effects of the type I interferons.

In particular embodiments, a biomarker of the present disclosure includes Thymic Stromal Lymphopoietin (TSLP). An exemplary TSLP sequence includes UniProt ID Q969D9. TSLP induces the release of T-cell-attracting chemokines from monocytes. In particular embodiments, it enhances the maturation of $CD11c^+$ dendritic cells. It can induce allergic inflammation by directly activating mast cells.

In particular embodiments, a biomarker of the present disclosure includes Vascular Cell Adhesion Molecule 1 (VCAM1). An exemplary VCAM1 sequence includes UniProt ID P19320. VCAM1 functions in in cell-cell recognition. In particular embodiments, VCAM1 functions in leukocyte-endothelial cell adhesion. It interacts with integrin alpha-4/beta-1 (ITGA4/ITGB1) on leukocytes and mediates both adhesion and signal transduction.

In particular embodiments, a biomarker of the present disclosure includes Transforming Growth Factor beta (TGFβ). An exemplary TGFβ sequence includes UniProt ID P01137. TGFβ includes a regulatory Latency-associated peptide (LAP) and an active subunit (TGFβ chain). TGFβ is a multifunctional protein that regulates the growth and differentiation of various cell types and plays a role in many processes, including normal development, immune function, microglia function and responses to neurodegeneration.

In particular embodiments, a biomarker of the present disclosure includes Cytotoxic T-Lymphocyte Associated Protein 4 (CTLA4). An exemplary CTLA4 sequence includes UniProt ID P16410. CTLA4 is an inhibitory receptor that negatively regulates T-cell responses. CTLA4 has a high affinity for its natural B7 family ligands, CD80 and CD86.

In particular embodiments, a biomarker of the present disclosure includes Granulocyte Macrophage Colony Stimulating Factor (GM-CSF), also known as colony stimulating factor 2 (CSF2). An exemplary GM-CSF sequence includes UniProt ID P04141-1, which includes a signal peptide (SEQ ID NO: 37, encoded by SEQ ID NO: 74). In particular embodiments, GM-CSF lacks a signal peptide (SEQ ID NO: 38, encoded by SEQ ID NO: 75). Active GM-CSF is found extracellularly as a homodimer. GM-CSF stimulates the growth and differentiation of hematopoietic precursor cells from various lineages, including granulocytes, macrophages, eosinophils and erythrocytes. In particular embodiments, GM-CSF promotes tissue inflammation.

In particular embodiments, a biomarker of the present disclosure includes serum amyloid A (SAA). An exemplary SAA sequence includes UniProt ID P0DJI8-1, which includes a signal peptide (SEQ ID NO: 39, encoded by SEQ ID NO: 76). In particular embodiments, SAA lacks a signal peptide (SEQ ID NO: 40, encoded by SEQ ID NO: 77). SAA is an acute phase protein that recycles and reuses cholesterol in the cell membranes of new cells produced in response to damaged tissue repair and inflammation. In particular embodiments, SAA is a biomarker of inflammation caused by tissue injury or other traumas. In particular embodiments, the concentration of SAA in human blood can increase 1000-fold or more during inflammation. SAA features in AA amyloidosis, a disorder characterized by the extracellular tissue deposition of fibrils that are composed of intact and/or fragments of SAA. The N-terminal portion of the mature SAA protein has antimicrobial activity against *S. aureus* and *E. coli*.

In particular embodiments, a biomarker of the present disclosure includes C-reactive protein (CRP). An exemplary CRP sequence includes UniProt ID P02741-1, which includes a signal peptide (SEQ ID NO: 41, encoded by SEQ ID NO: 78). In particular embodiments, CRP lacks a signal peptide (SEQ ID NO: 42, encoded by SEQ ID NO: 79). CRP belongs to the pentraxin family which also includes serum amyloid P component protein and pentraxin 3. CRP is made in the liver and its levels increase in the blood in response to inflammation. CRP circulates in blood as a pentamer and is a non-soluble monomer in tissues. CRP functions in host defense, including promoting agglutination, bacterial capsular swelling, phagocytosis, and complement fixation. In particular embodiments, CRP functions through its calcium-dependent binding to phosphorylcholine. CRP is able to interact with DNA and histones and may scavenge nuclear material released from damaged circulating cells.

In particular embodiments, a biomarker of the present disclosure includes C-type lectin-like receptor CD161 (also known as KLRB1). An exemplary CD161 sequence includes UniProt ID Q12918-1 (SEQ ID NO: 43, encoded by SEQ ID NO: 80). CD161 is a type II membrane protein having an extracellular domain with several motifs characteristic of C-type lectins, a transmembrane domain, and a cytoplasmic domain. CD161 is expressed by: a majority of NK cells, natural killer T (NKT) cells, T cells, and cells of the gut and liver. CD161 is an early marker expressed by an NK cell as it matures from a CD34+ hematopoietic stem cell precursor. Lectin-like transcript-1 (LLT-1, or osteoclast inhibitory lectin (CLEC2D)) is the ligand of CD161. In particular embodiments, a biomarker of the present disclosure includes CD161+ cells or a population of cells that are CD161+. In particular embodiments, CD161 is expressed by CD3+ T cells. In particular embodiments, CD161 is expressed by CD8+ T cells. In particular embodiments, CD161 is expressed by CD4+ T cells. In particular embodiments, CD161 is expressed by CD56+ cells. In particular embodiments, CD161 is expressed by mucosal invariant T (MAIT) cells. MAIT cells are enriched at mucosal sites and express a semi-invariant αβ TCR that recognizes biosynthetic derivatives of riboflavin synthesis presented by the non-classical class Ib molecule major histocompatibility complex (MHC)-related 1 (MR1). Though enriched at mucosal sites, MAIT cells are present in peripheral blood and part of airway T cells and liver T cells. MAIT cells function in defense against pathogens (e.g., bacterial, viral) and in tissue repair. In particular embodiments, MAIT cells can function in an MR1-TCR independent manner associated with an antiviral response and can be activated by cytokines including IL-7, IL-12, IL-15, IL-18, and type I IFNs.

In particular embodiments, a biomarker of the present disclosure includes CD56 (also known as neural cell adhesion molecule 1, NCAM1). An exemplary CD56 sequence includes UniProt ID P13591-2, which includes a signal peptide (SEQ ID NO: 44, encoded by SEQ ID NO: 81). In particular embodiments, CD56 lacks a signal peptide (SEQ ID NO: 45, encoded by SEQ ID NO: 82). CD56 is a homophilic binding glycoprotein expressed on the surface of neurons, glia, and skeletal muscle. In particular, the expression of CD56 is associated with NK cells. In addition to being a marker of neural lineage commitment, CD56 expression is also found in the hematopoietic system and is involved in expansion of T lymphocytes, B lymphocytes, and NK cells. CD56 has been detected on lymphoid cells, including gamma delta (γδ) T cells and activated CD8+ T cells, as well as on dendritic cells. CD56 has been implicated as having a role in cell-cell adhesion, neurite outgrowth, synaptic plasticity, and learning and memory. In particular embodiments, CD56 functions in signal transduction by interacting with fibroblast growth factor receptors, N-cadherin, and other components of the extracellular matrix and by triggering signaling cascades involving FYN-focal adhesion kinase (FAK), mitogen-activated protein kinase (MAPK), and phosphatidylinositol 3-kinase (PI3K).

Figure 22:
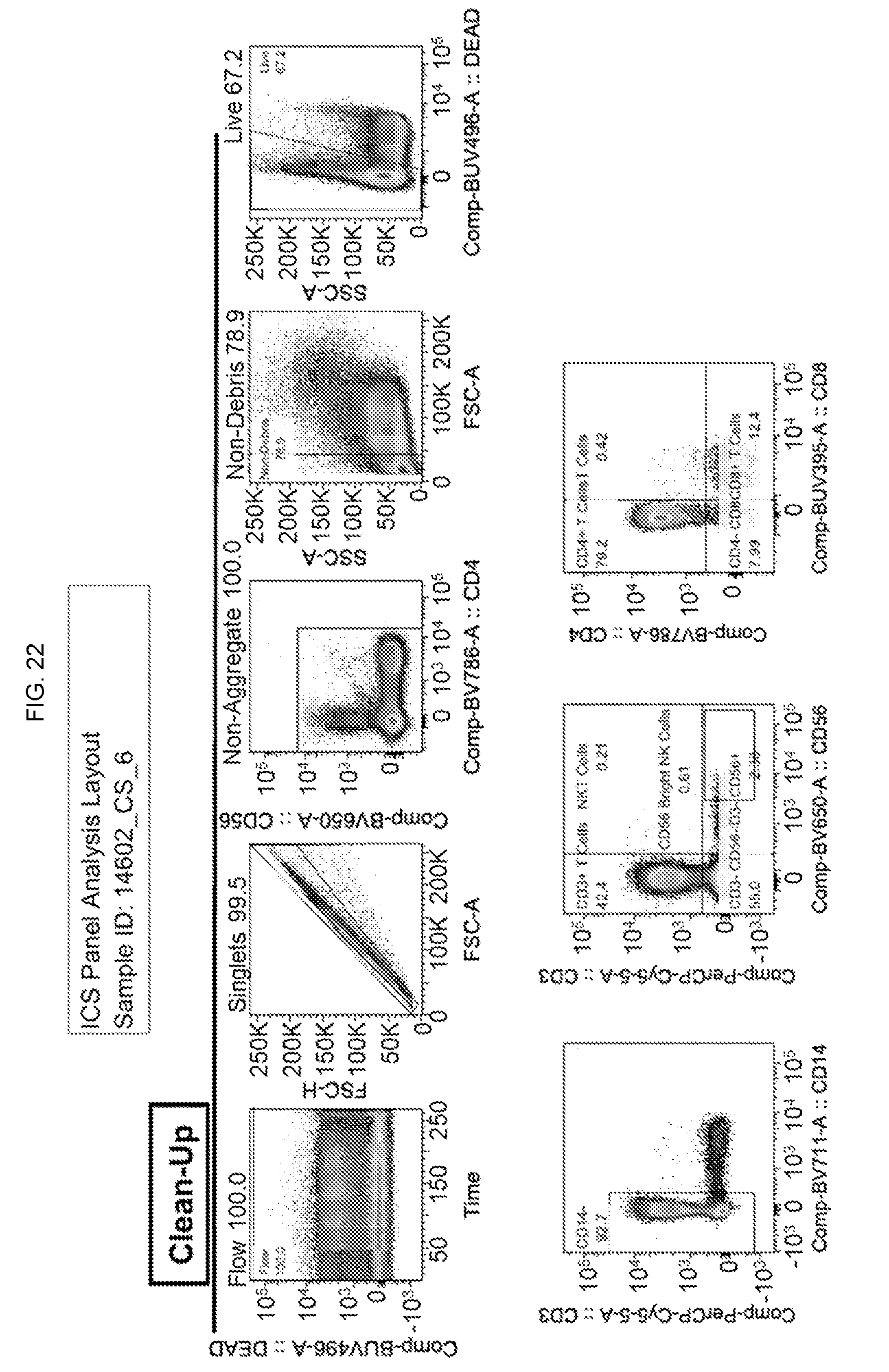
FIG. 22. Kinetics of the cytokines assayed pre-CAR (14 patient cohort). Meso Scale Discovery assay and ELISA assays were used to assess 10 cytokines: IFNγ, IL-10, IL-18 (ELISA), IL-18BP (ELISA), sIL-2ra, IL-2, IL-5, IL-6, IL-12p70, IL-13, IL-4, and IL-15. Example gating for intracellular staining panel.
Figure 22:
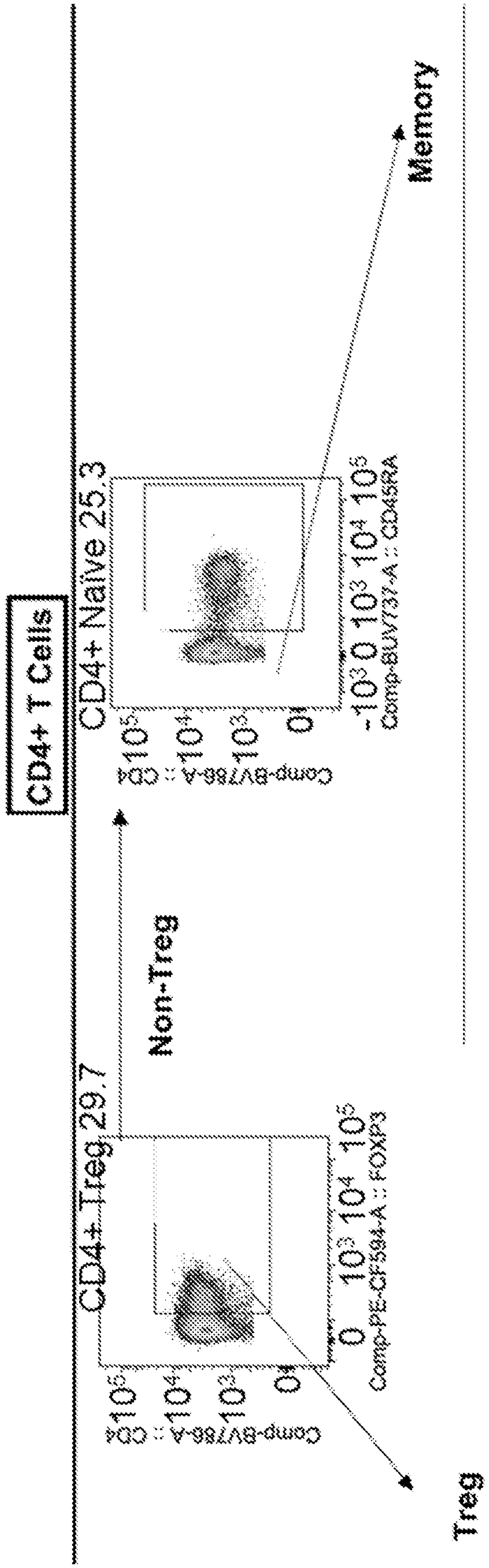
Figure 22:
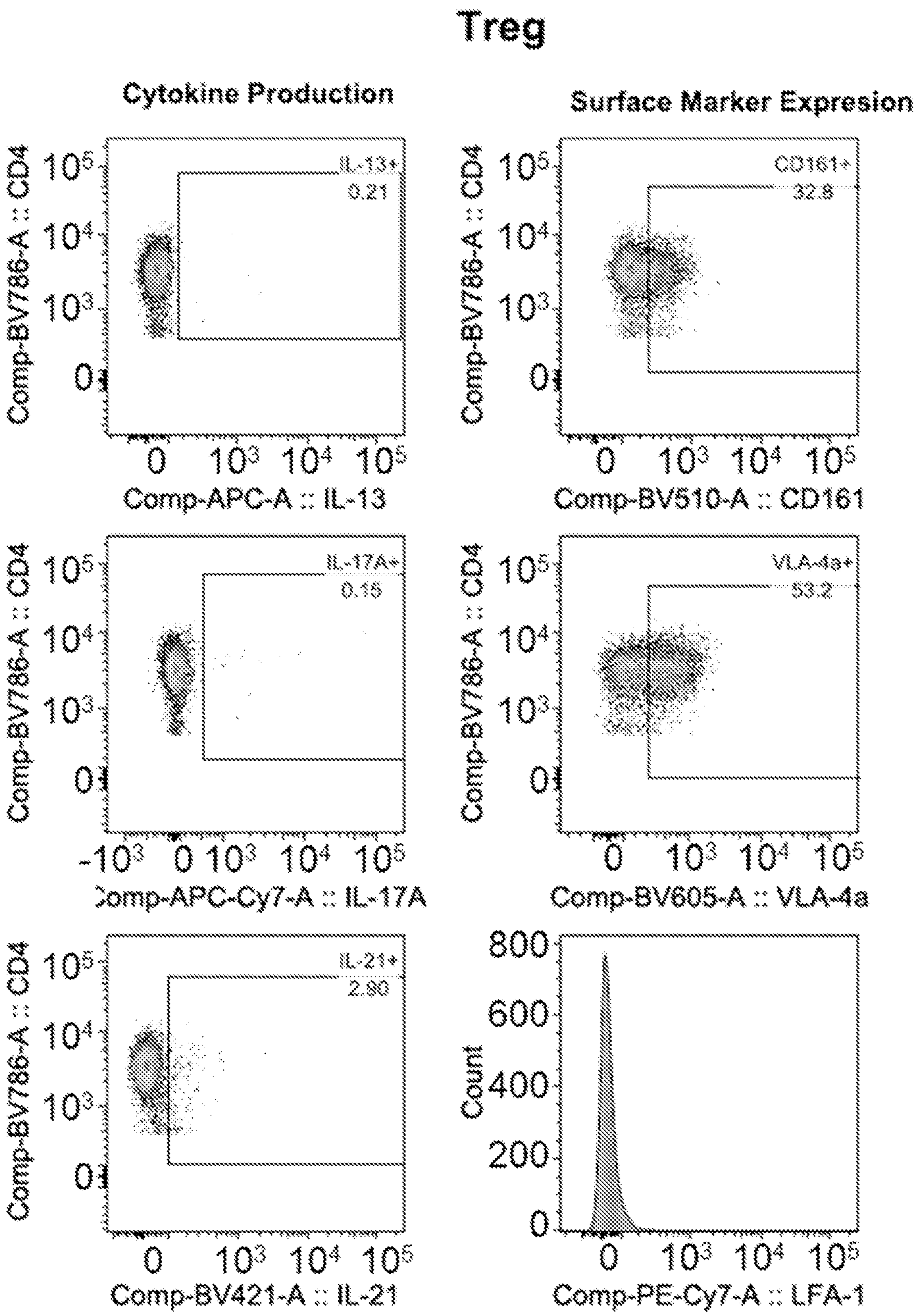
Figure 22:
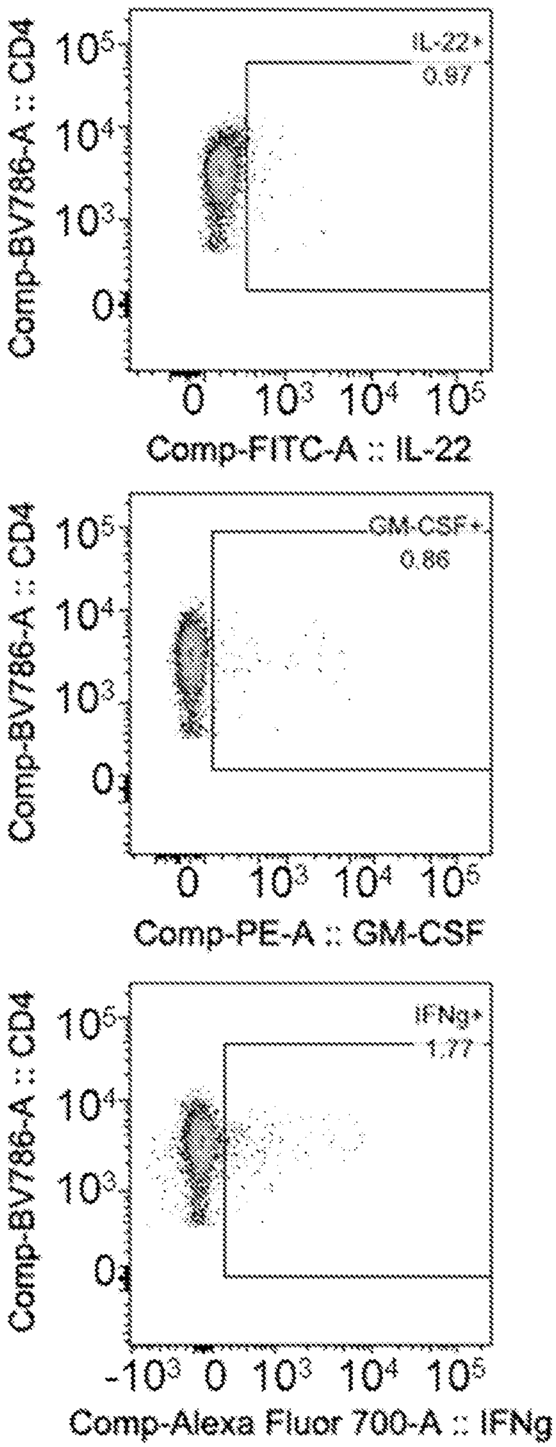
Figure 22:
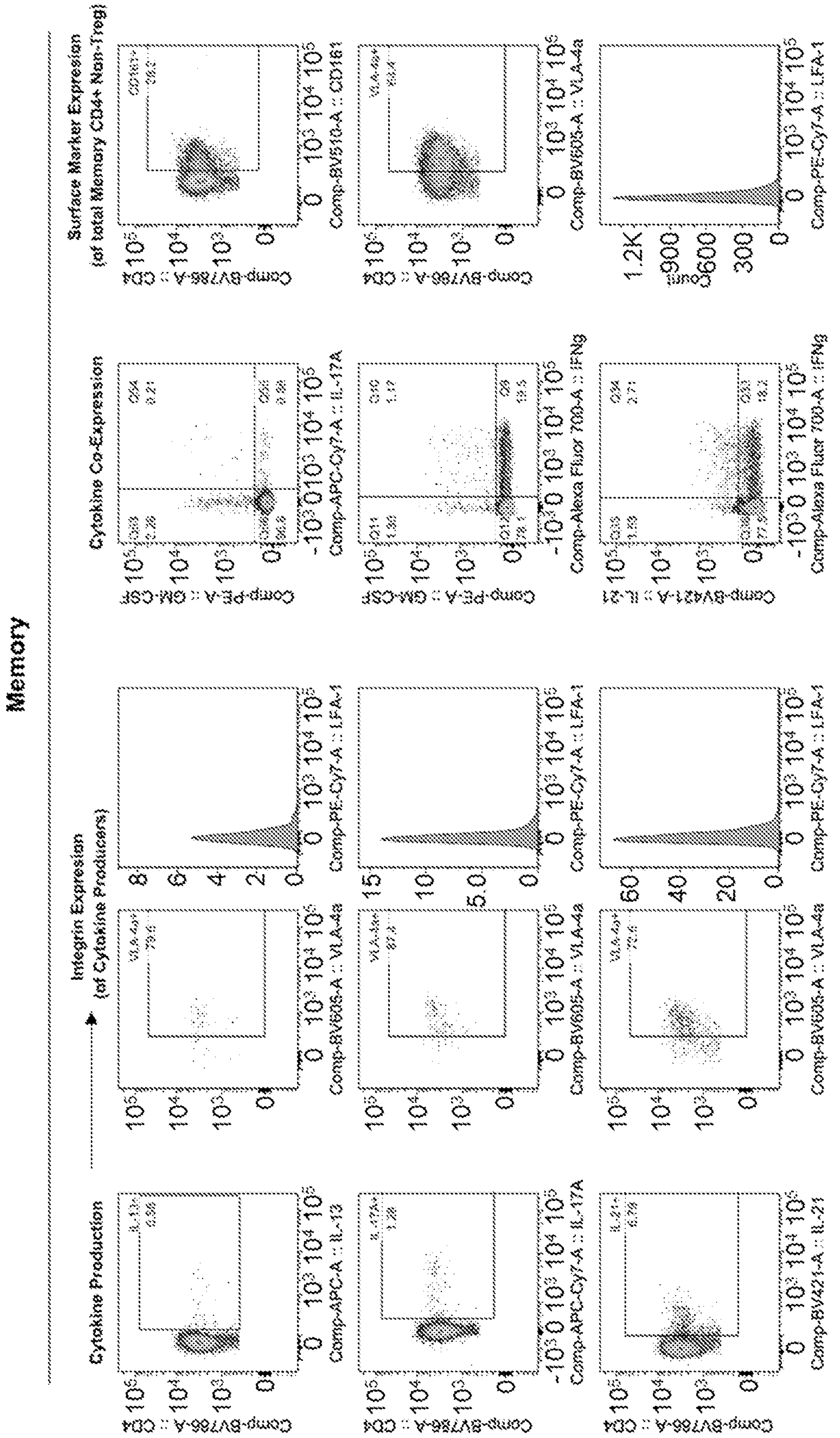
Figure 22:
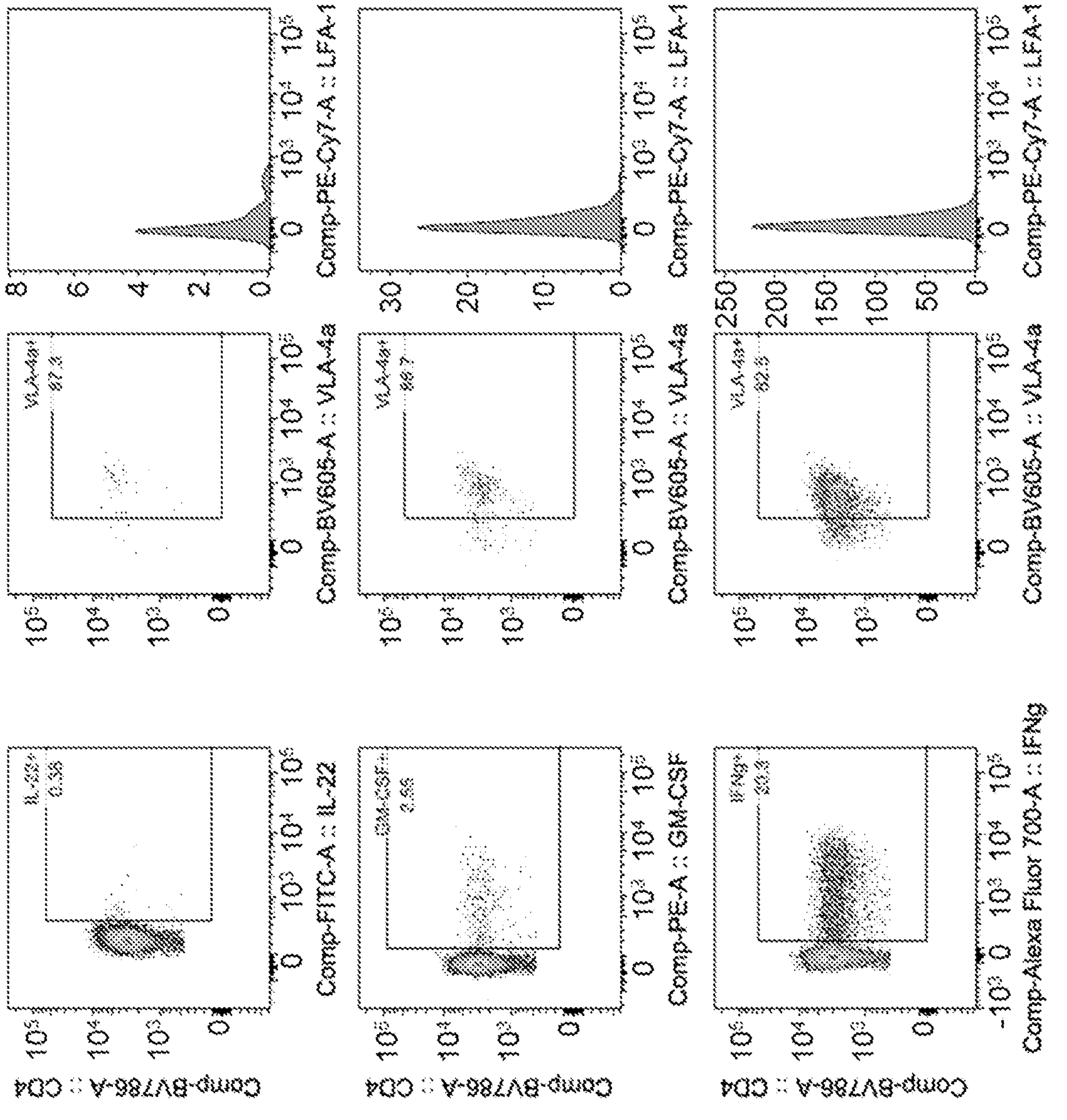
Figure 22:
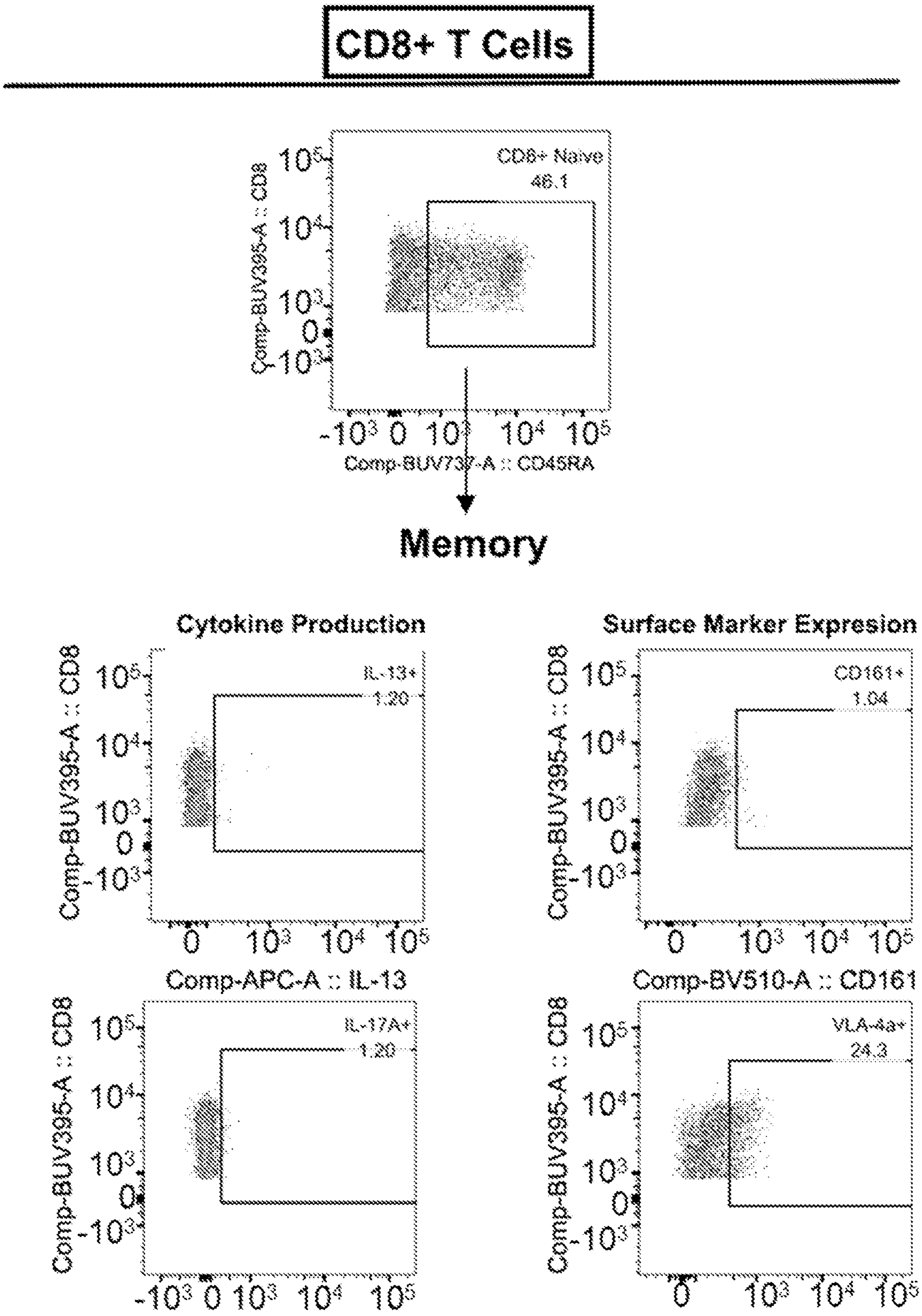
Figure 22:
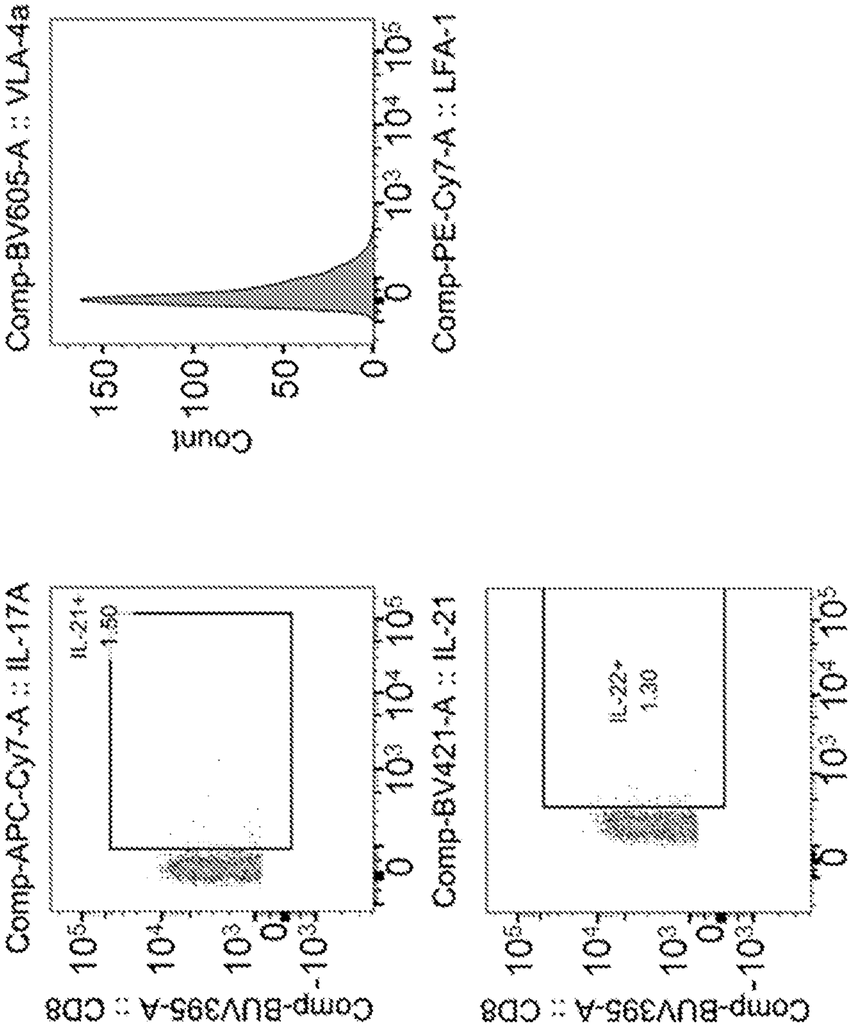
Figure 22:
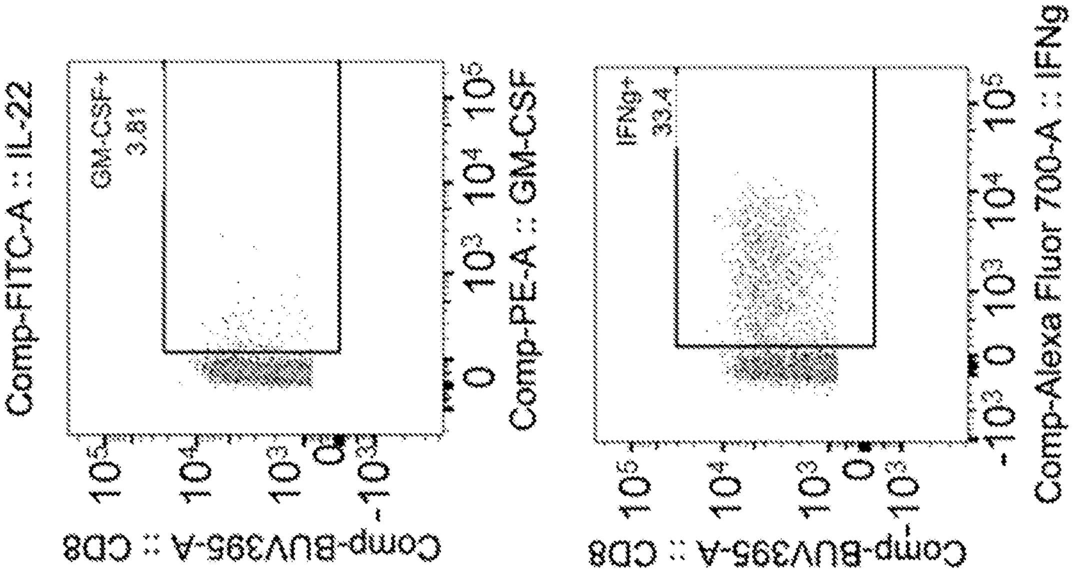
Figure 22:
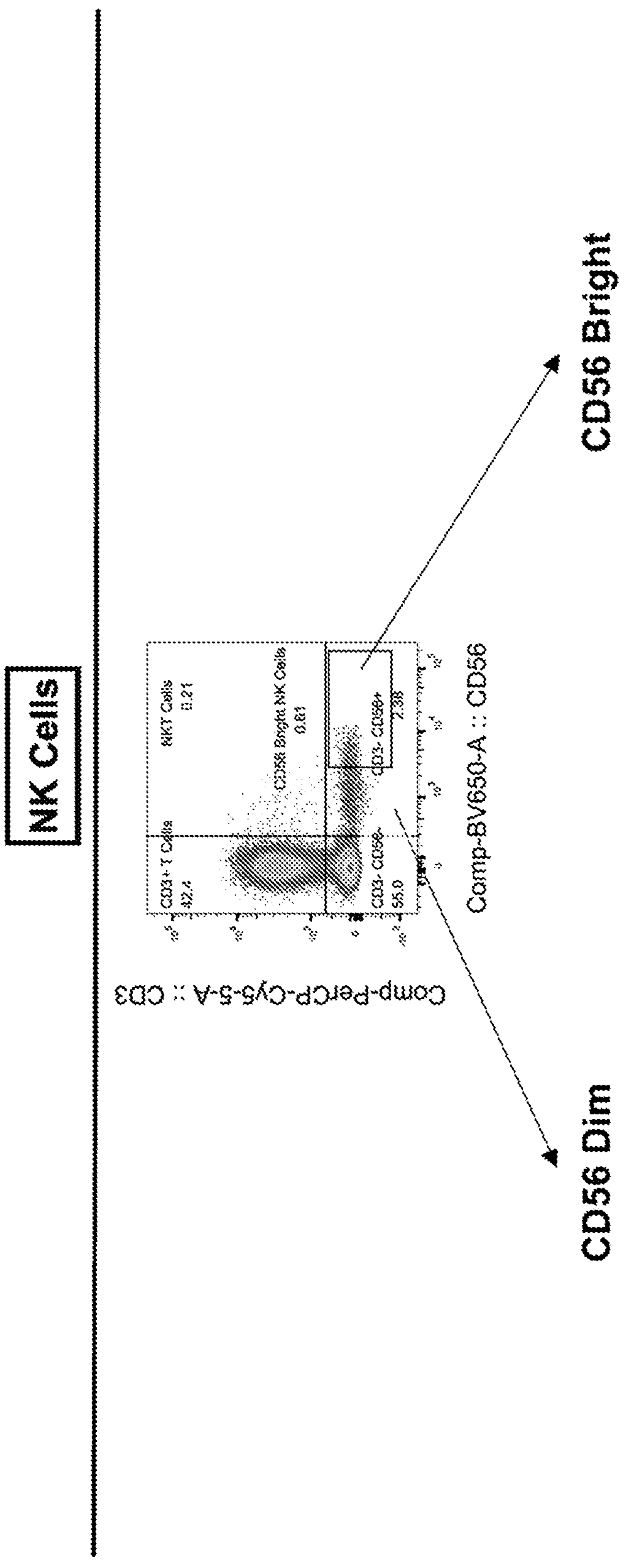
Figure 22:
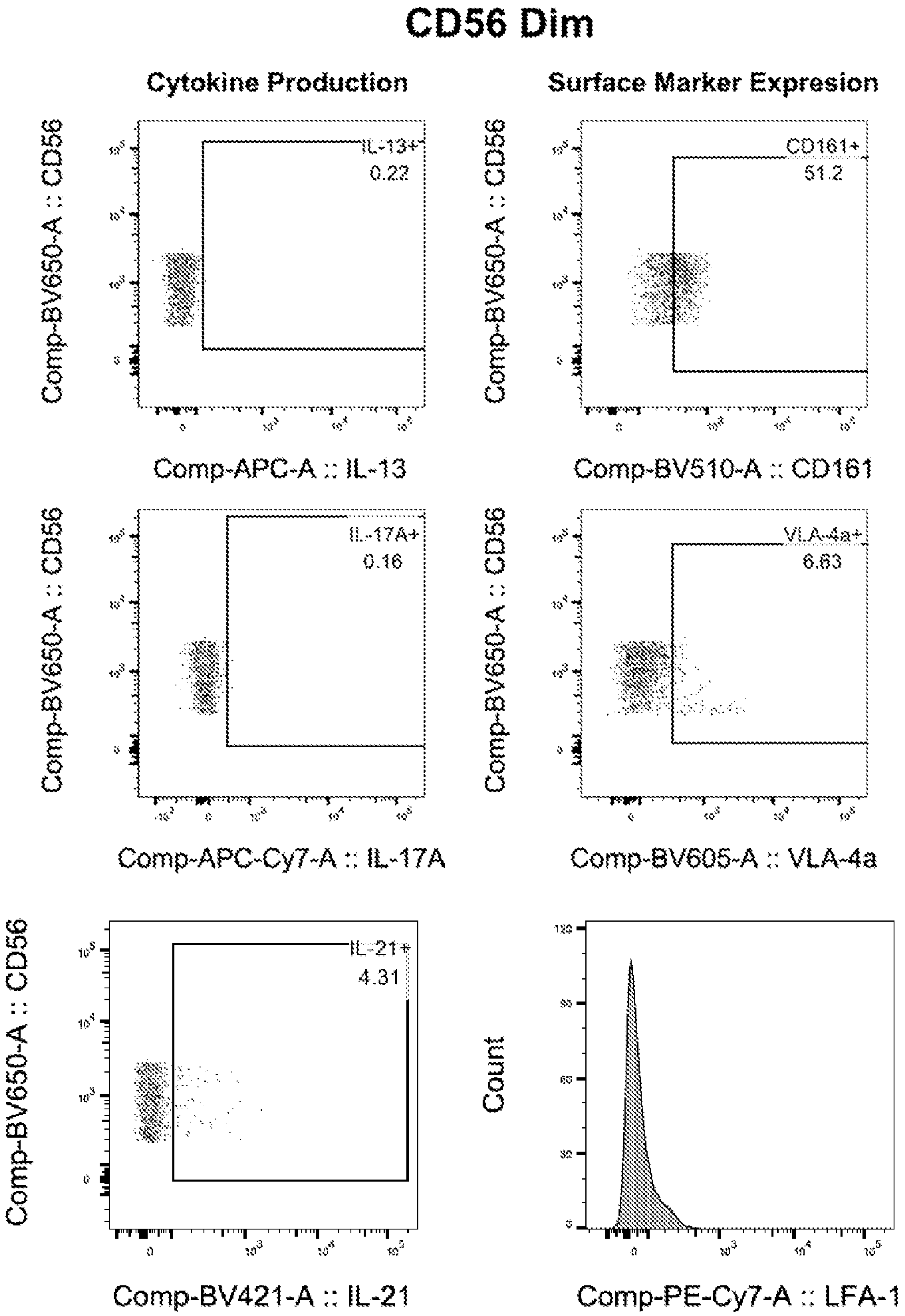
Figure 22:
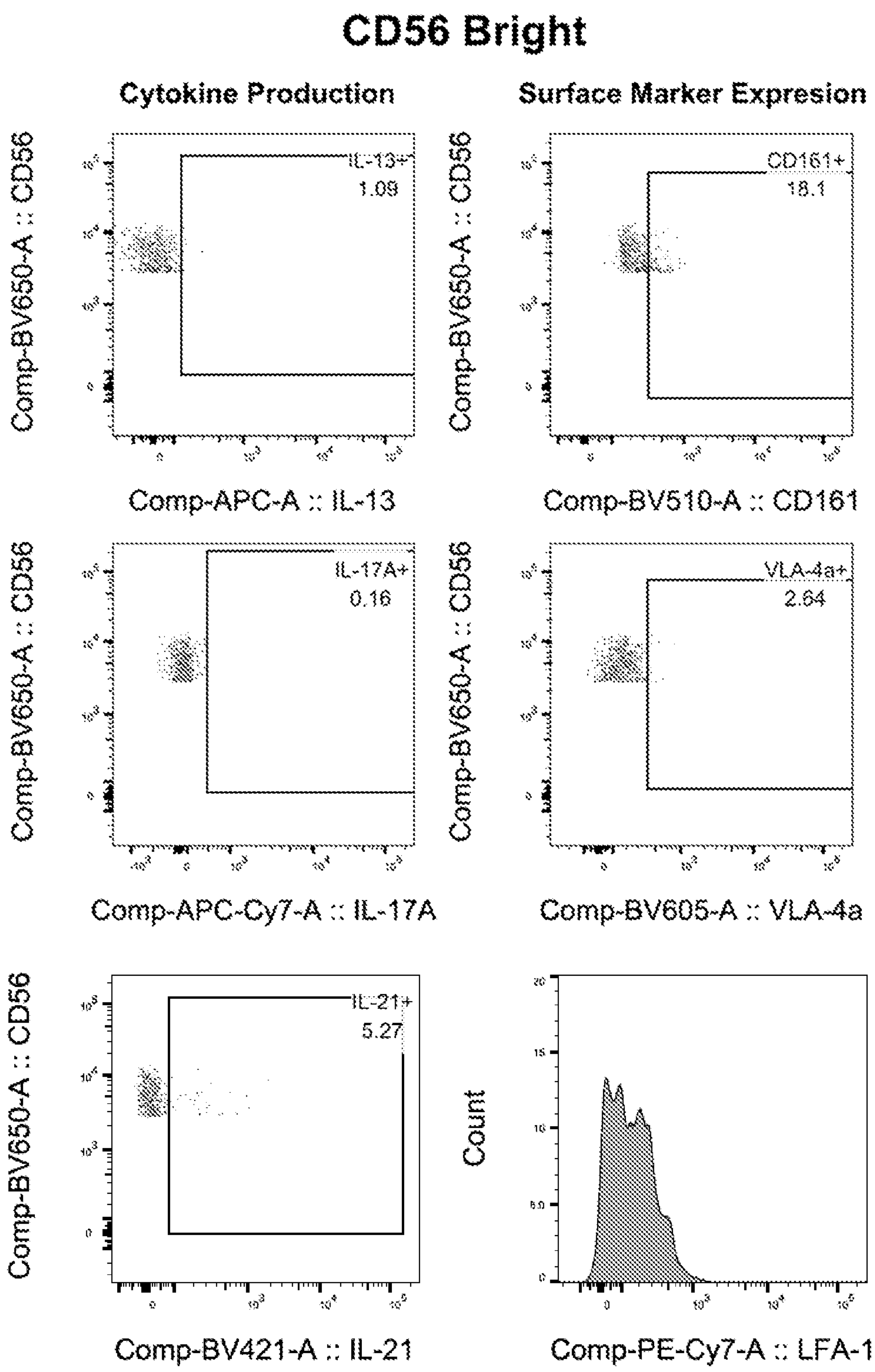
Figure 22:
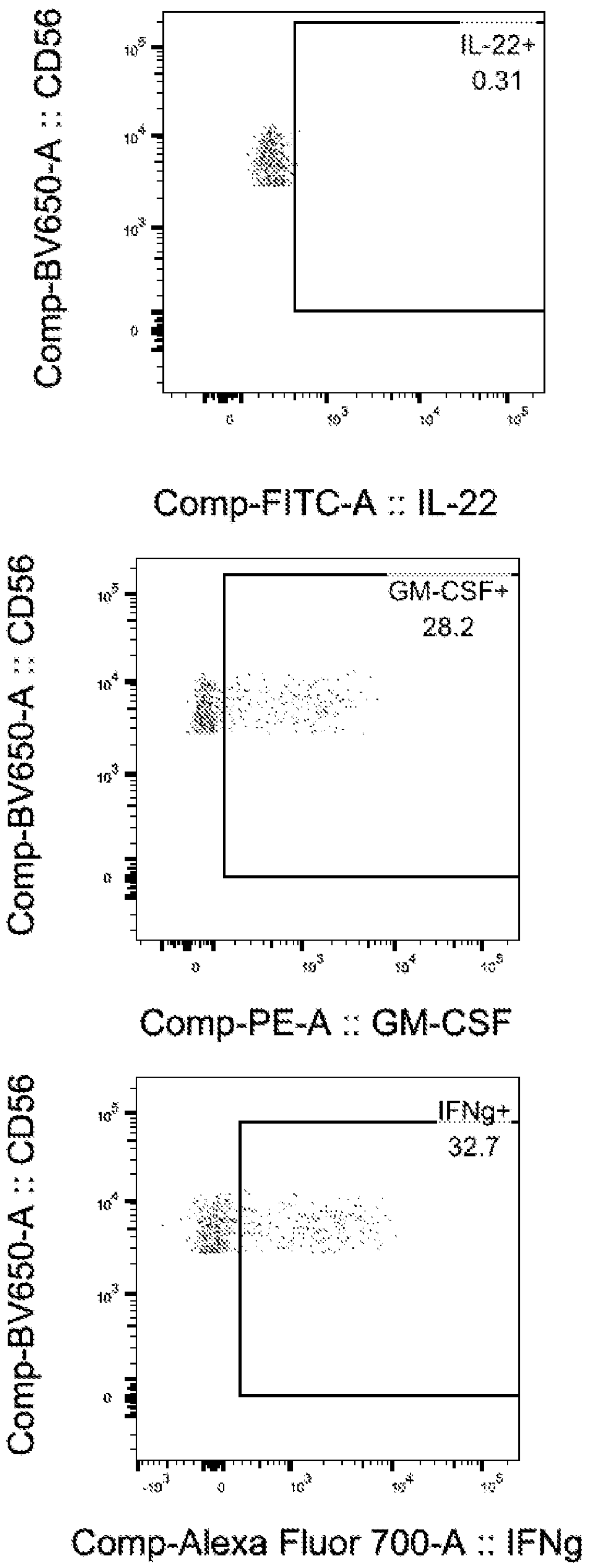
Figure 22:
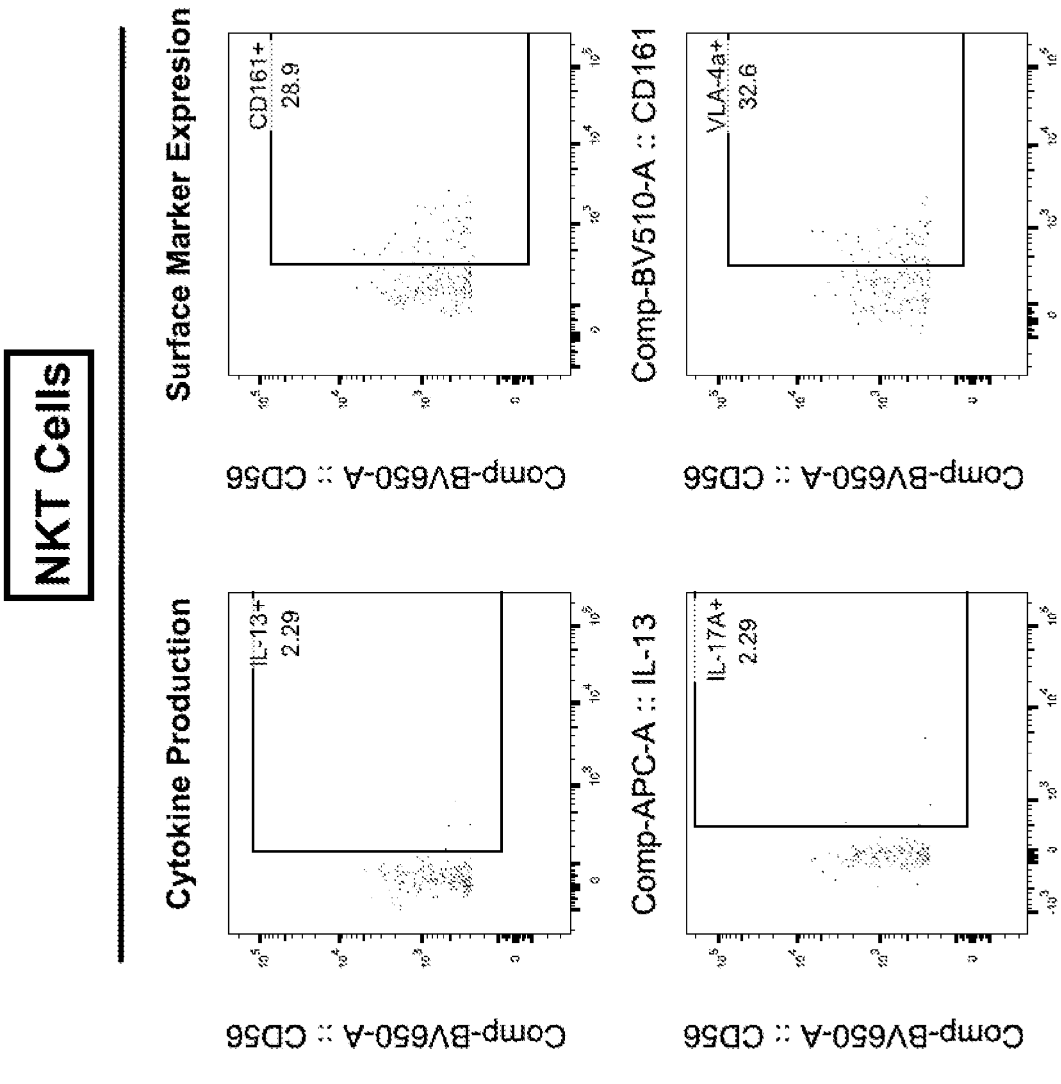
Figure 22:
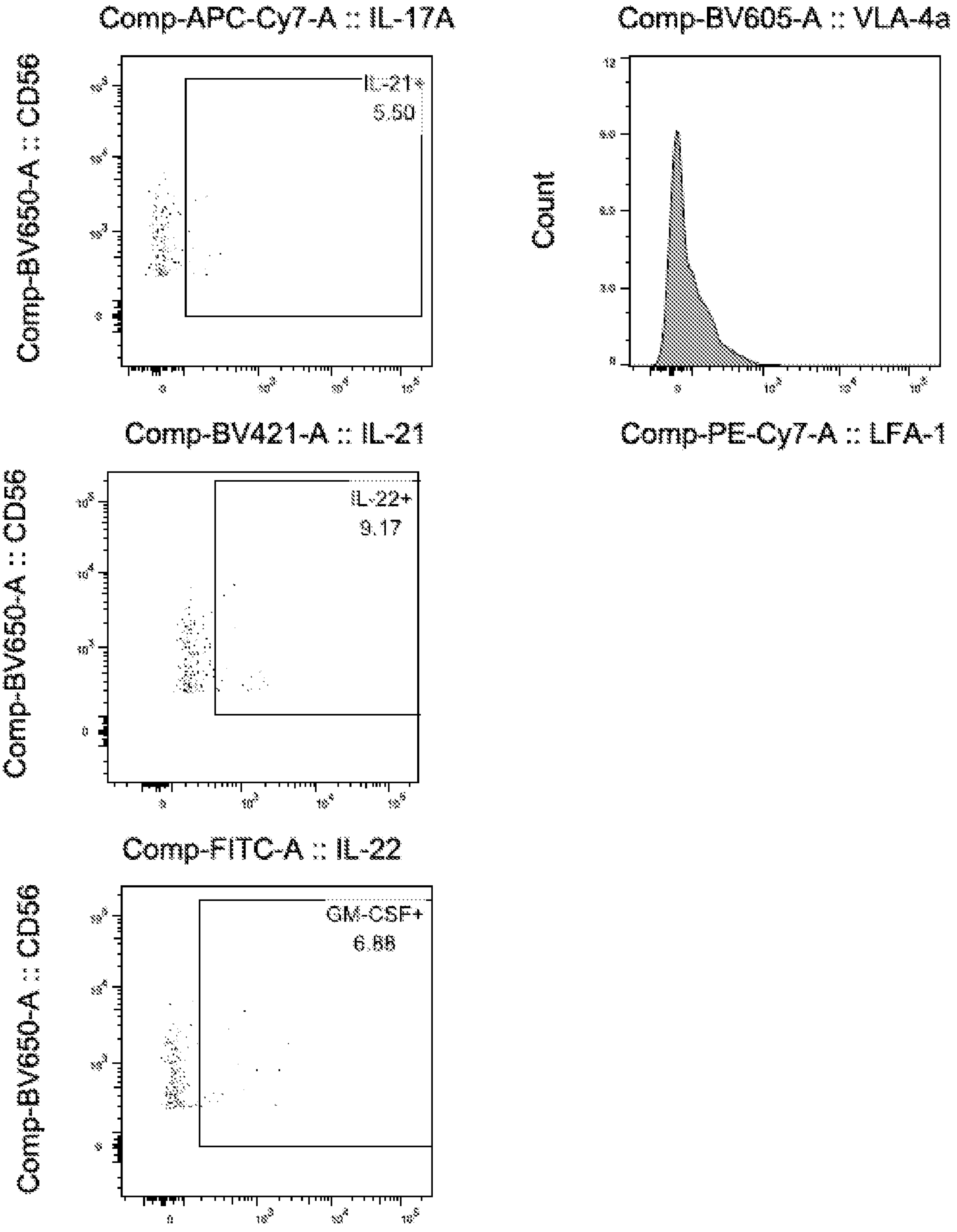
Figure 22:
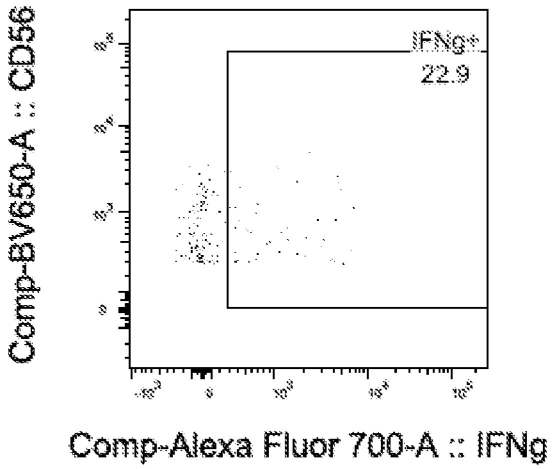
Figure 22:
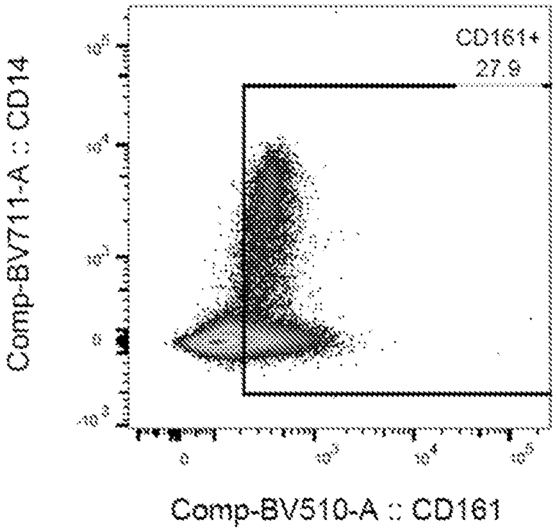
Figure 22:
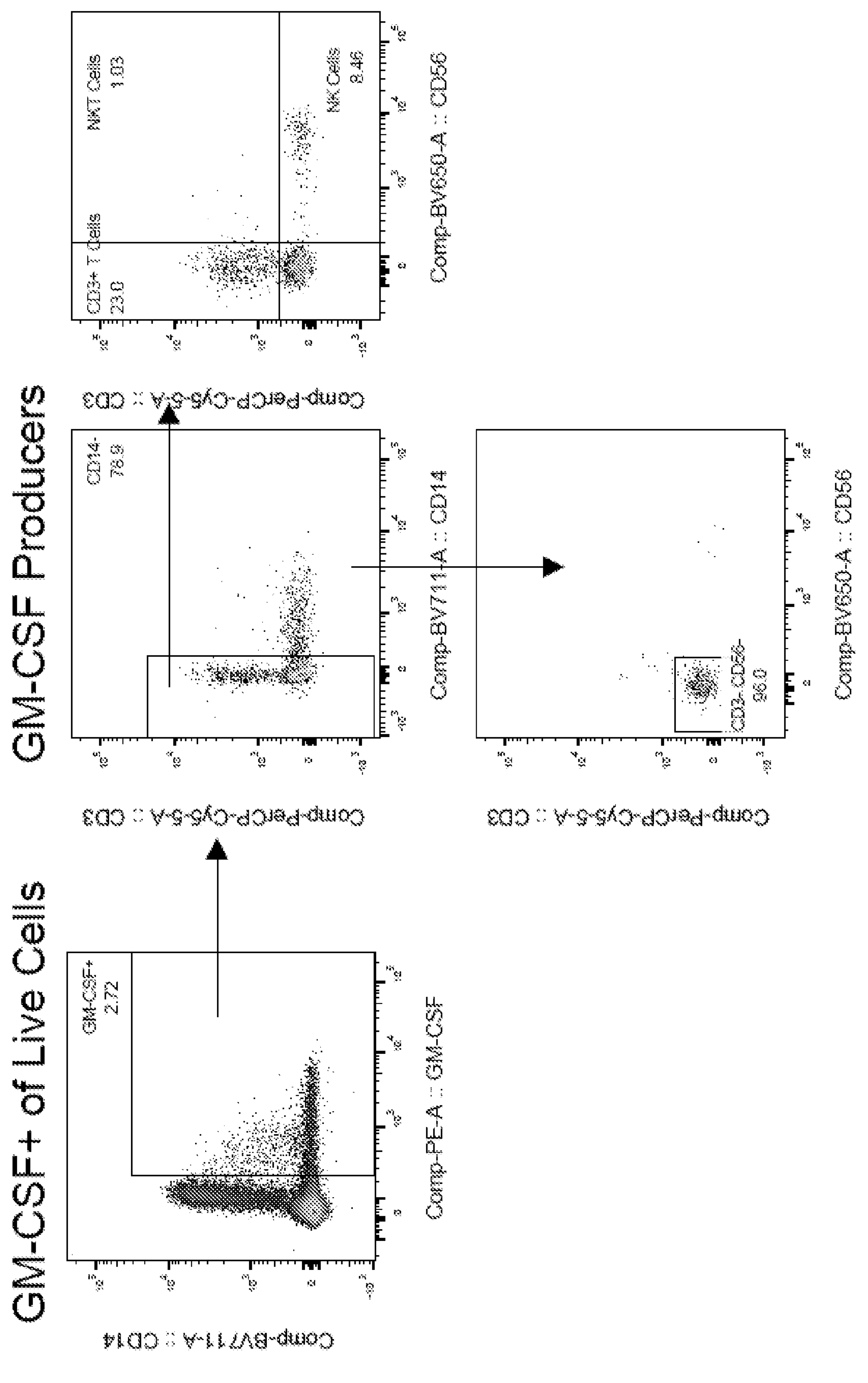
Figure 22:
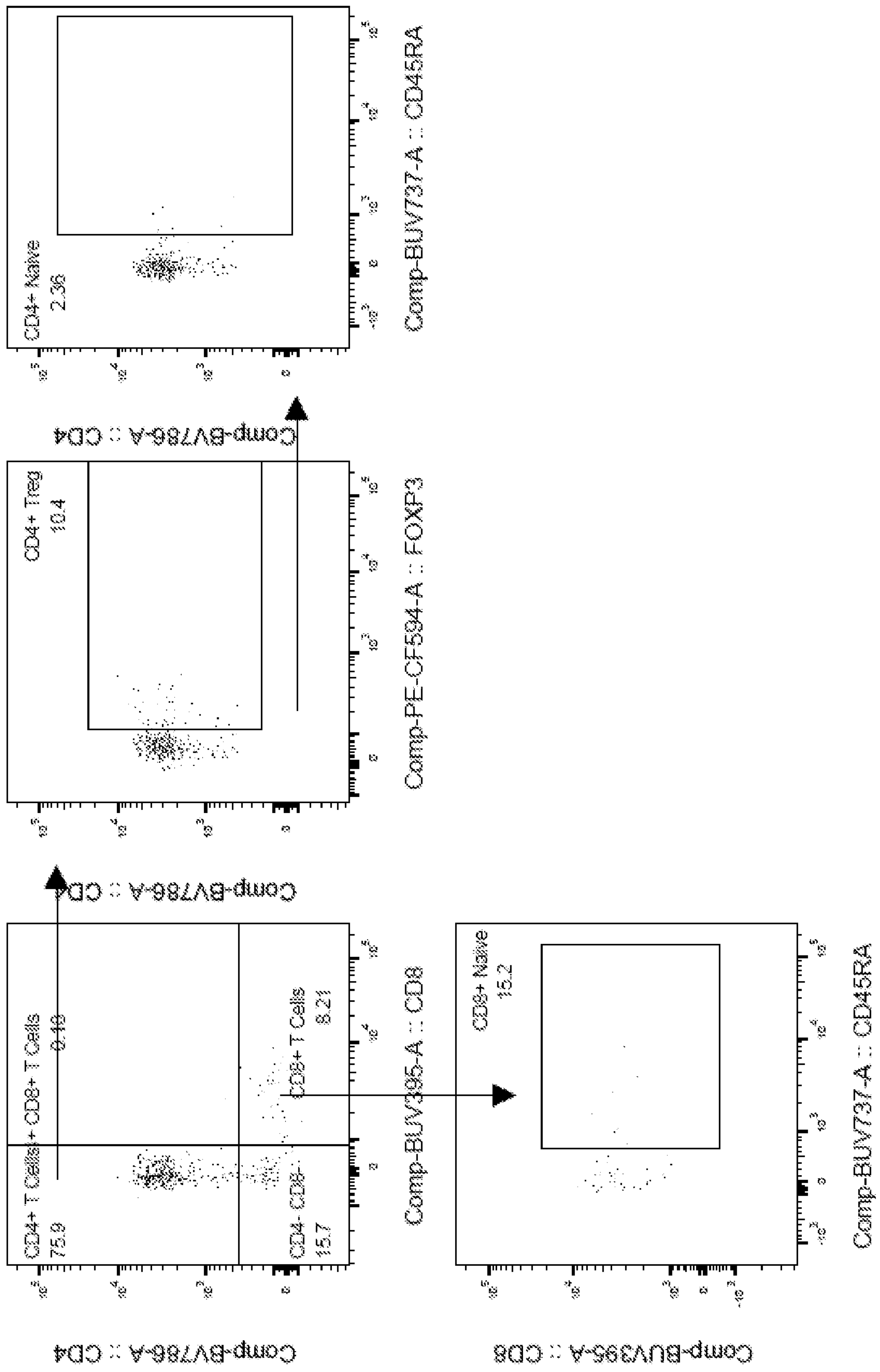
Figure 22:
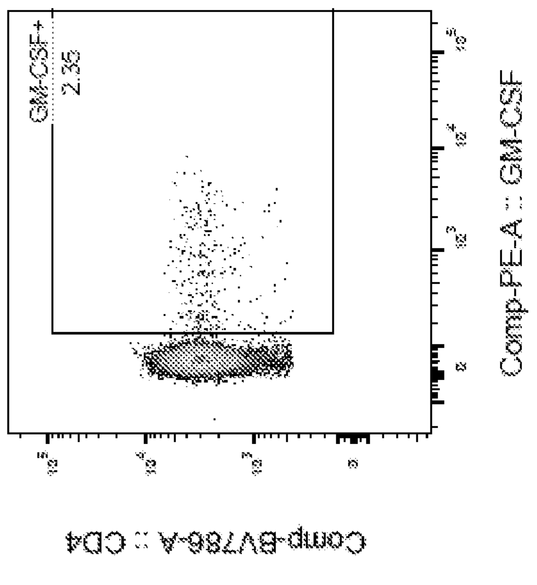
Figure 22:
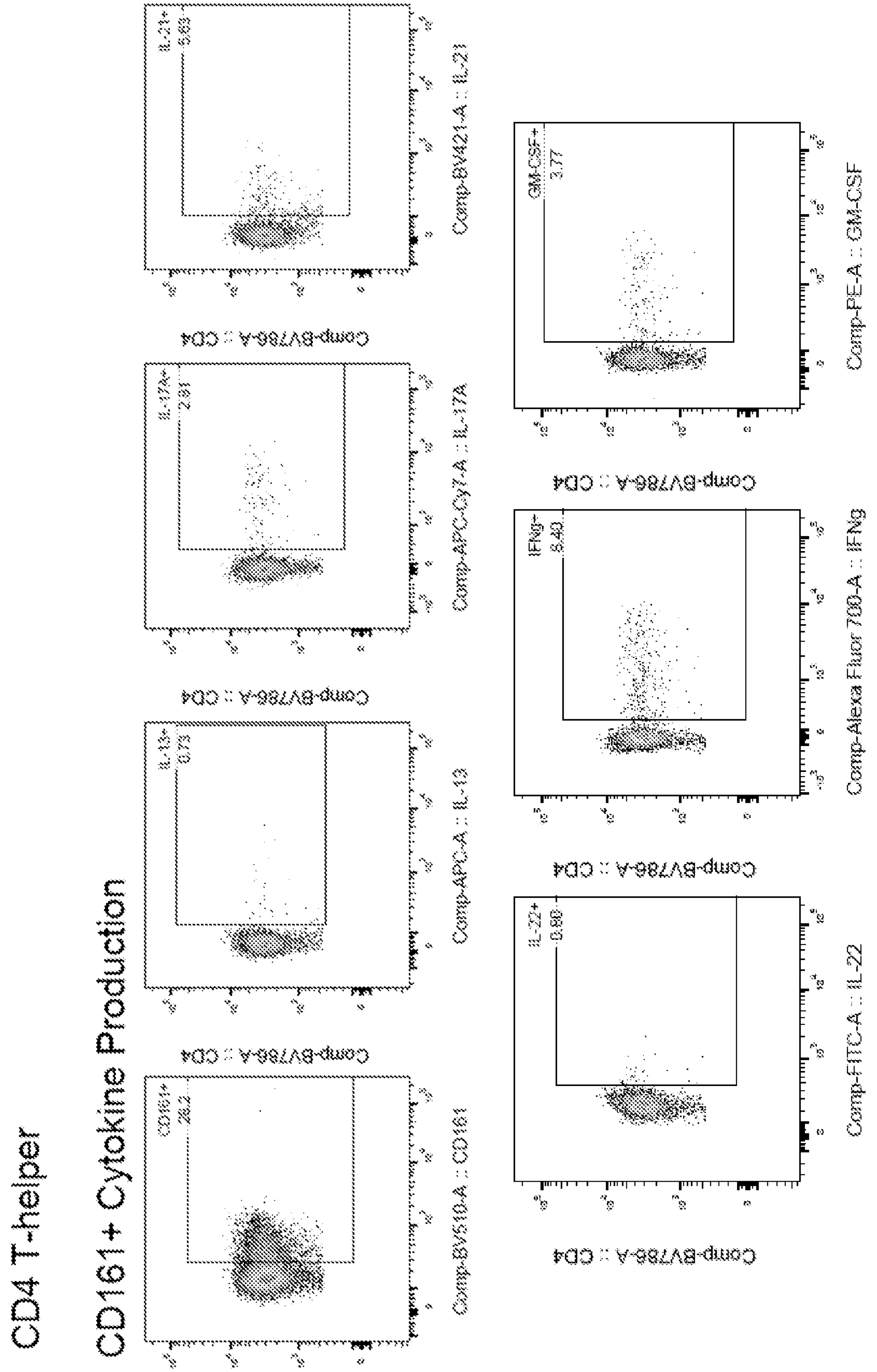
Figure 22:
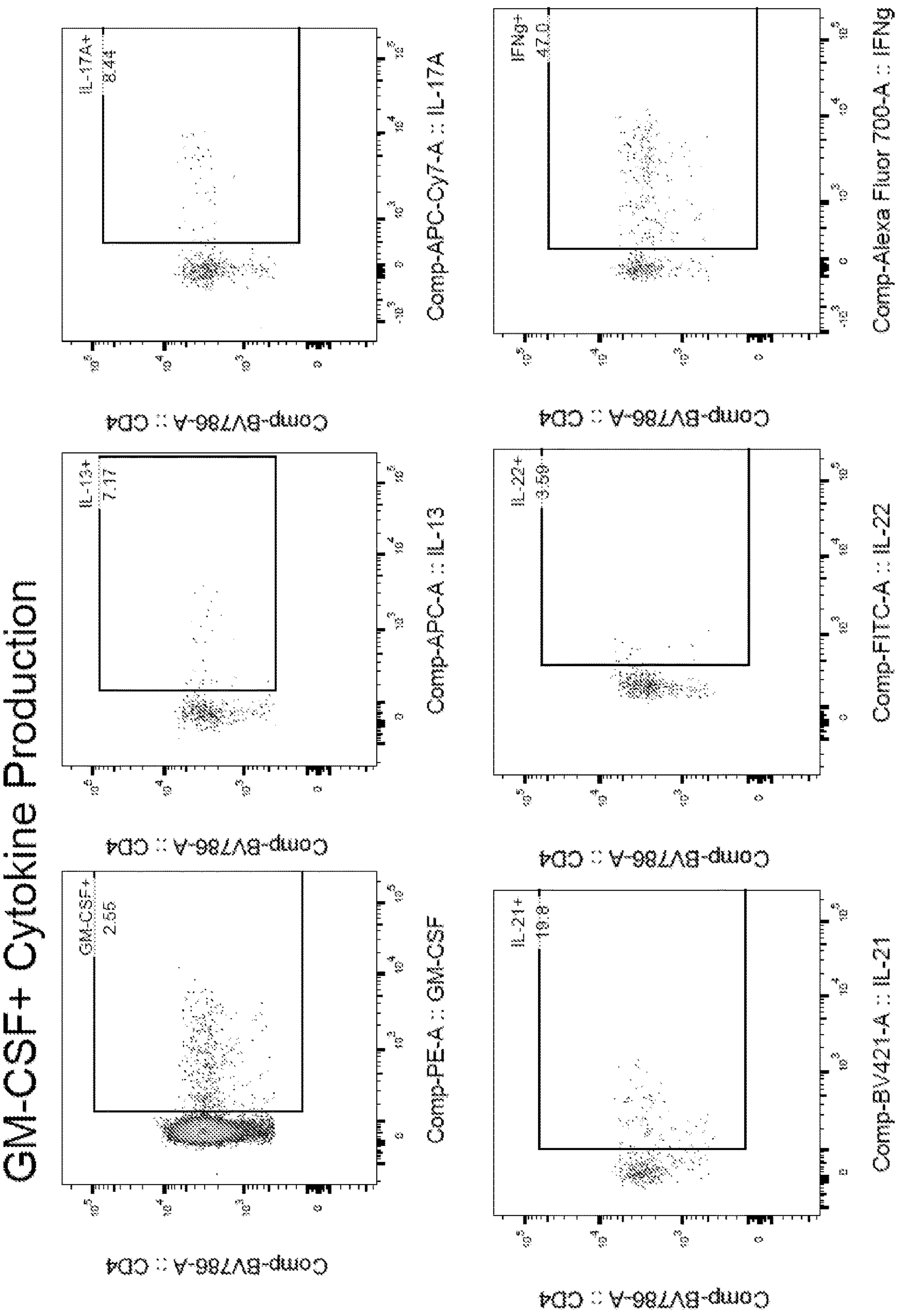
Figure 22:
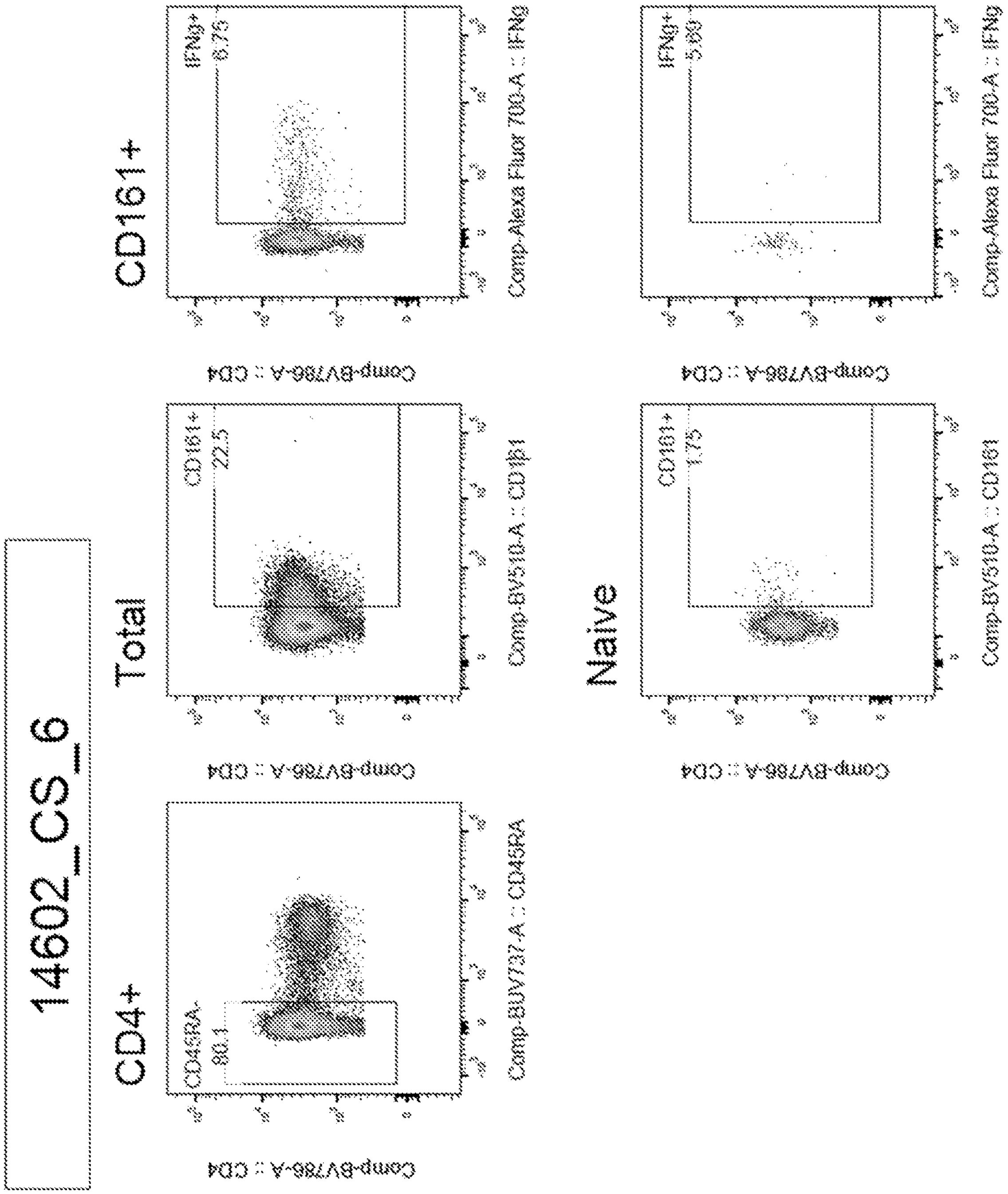
Figure 22:
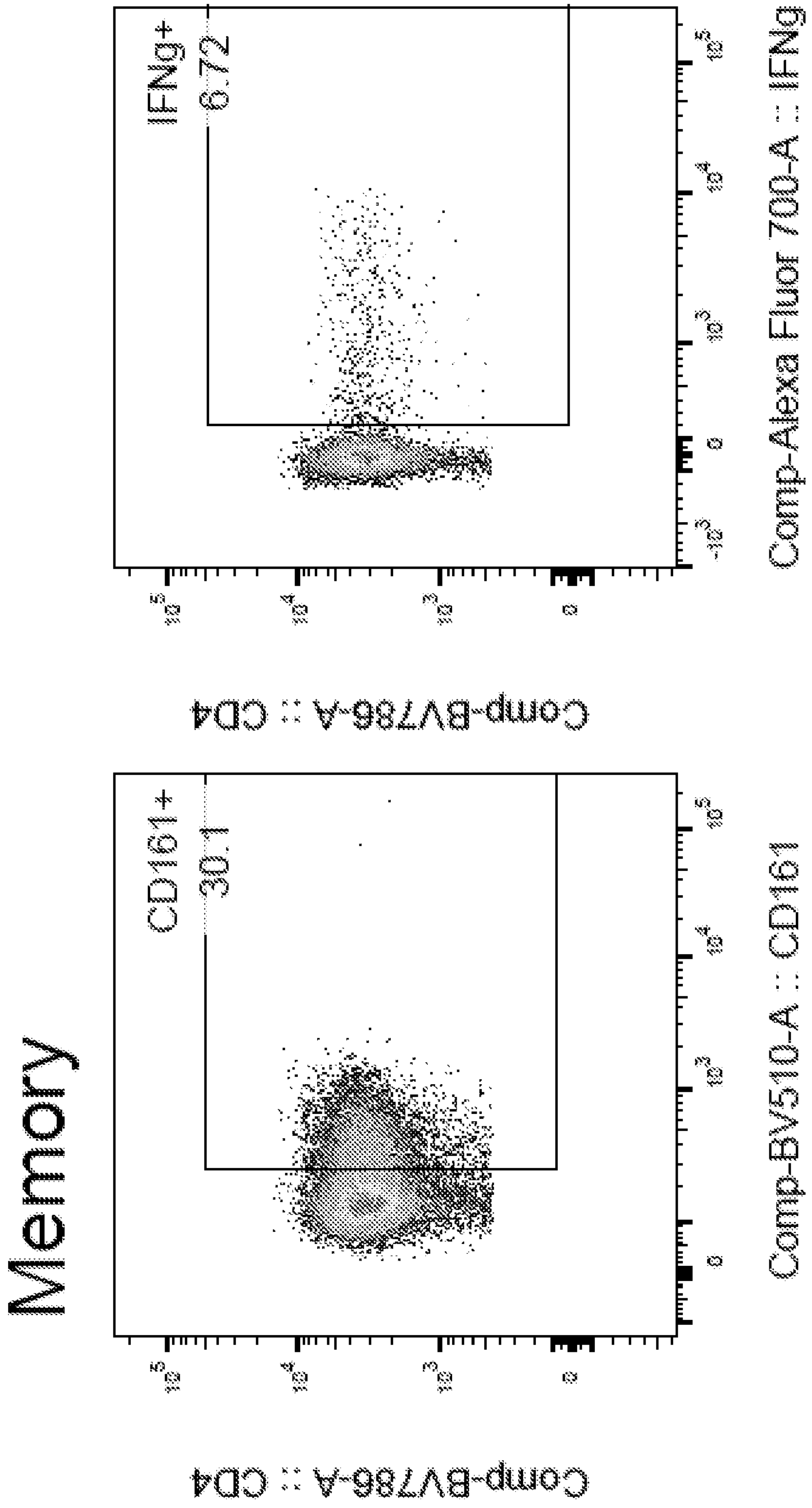
Figure 22:
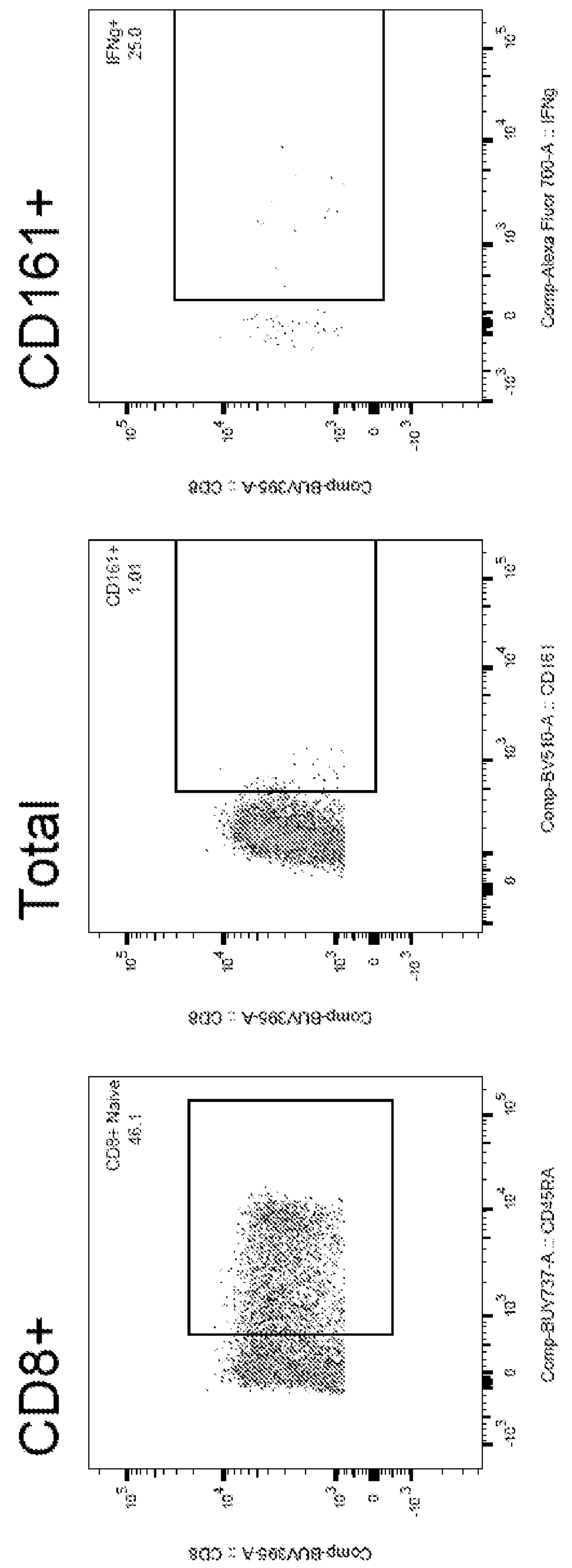
Figure 22:
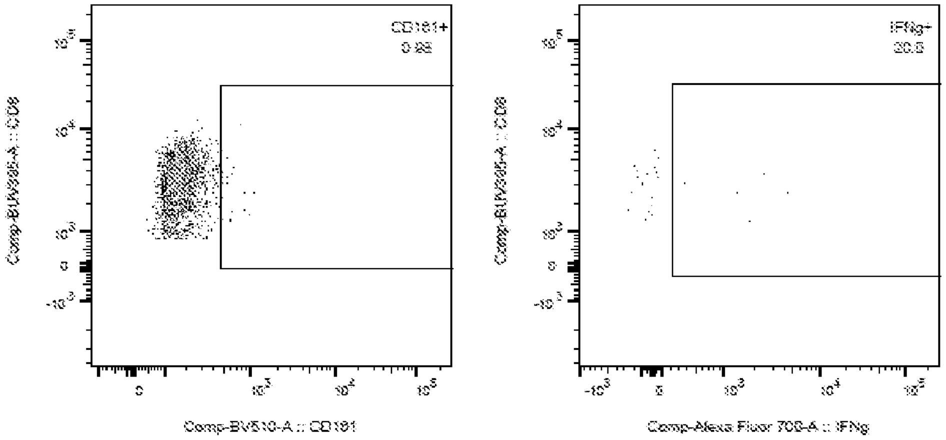
Figure 22:
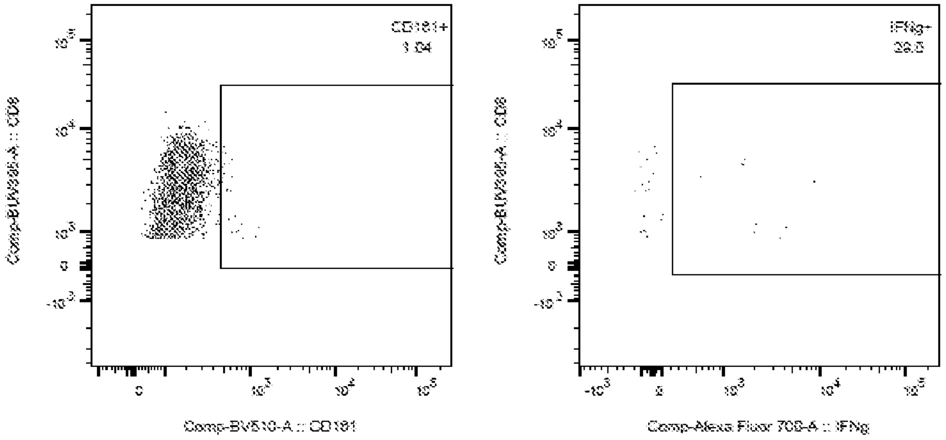
Figure 22:
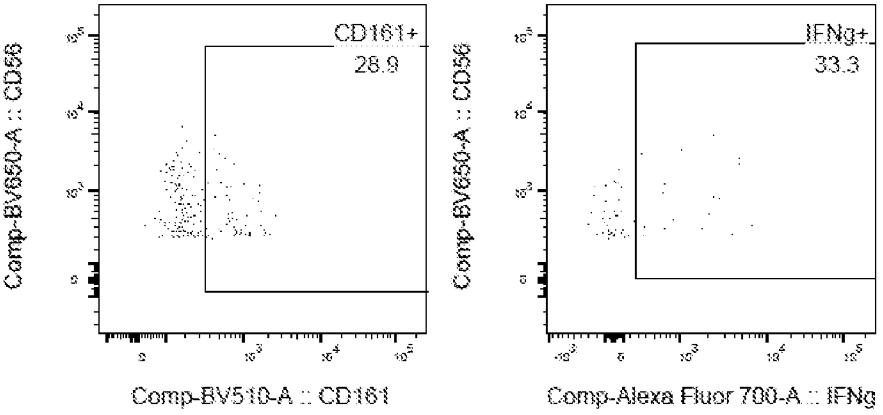
Figure 22:
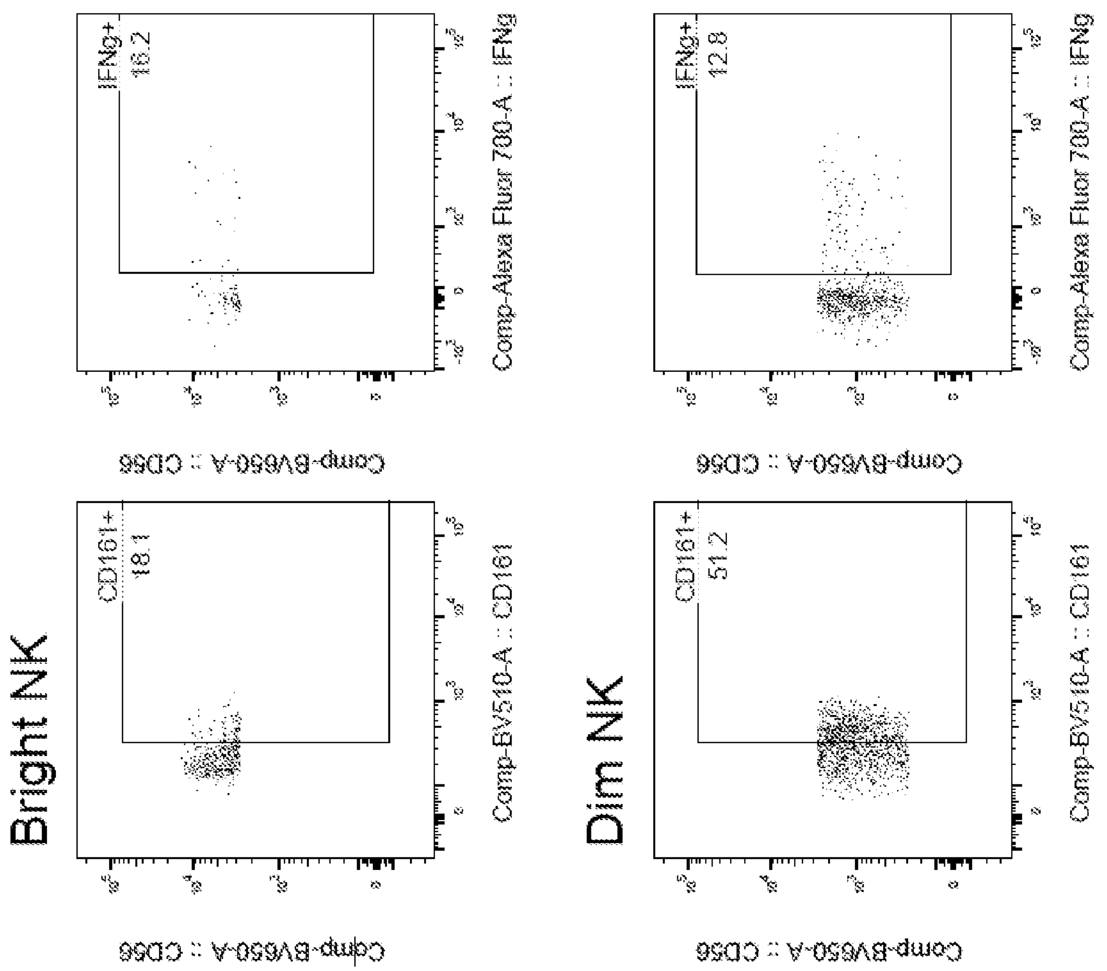
Figure 23:
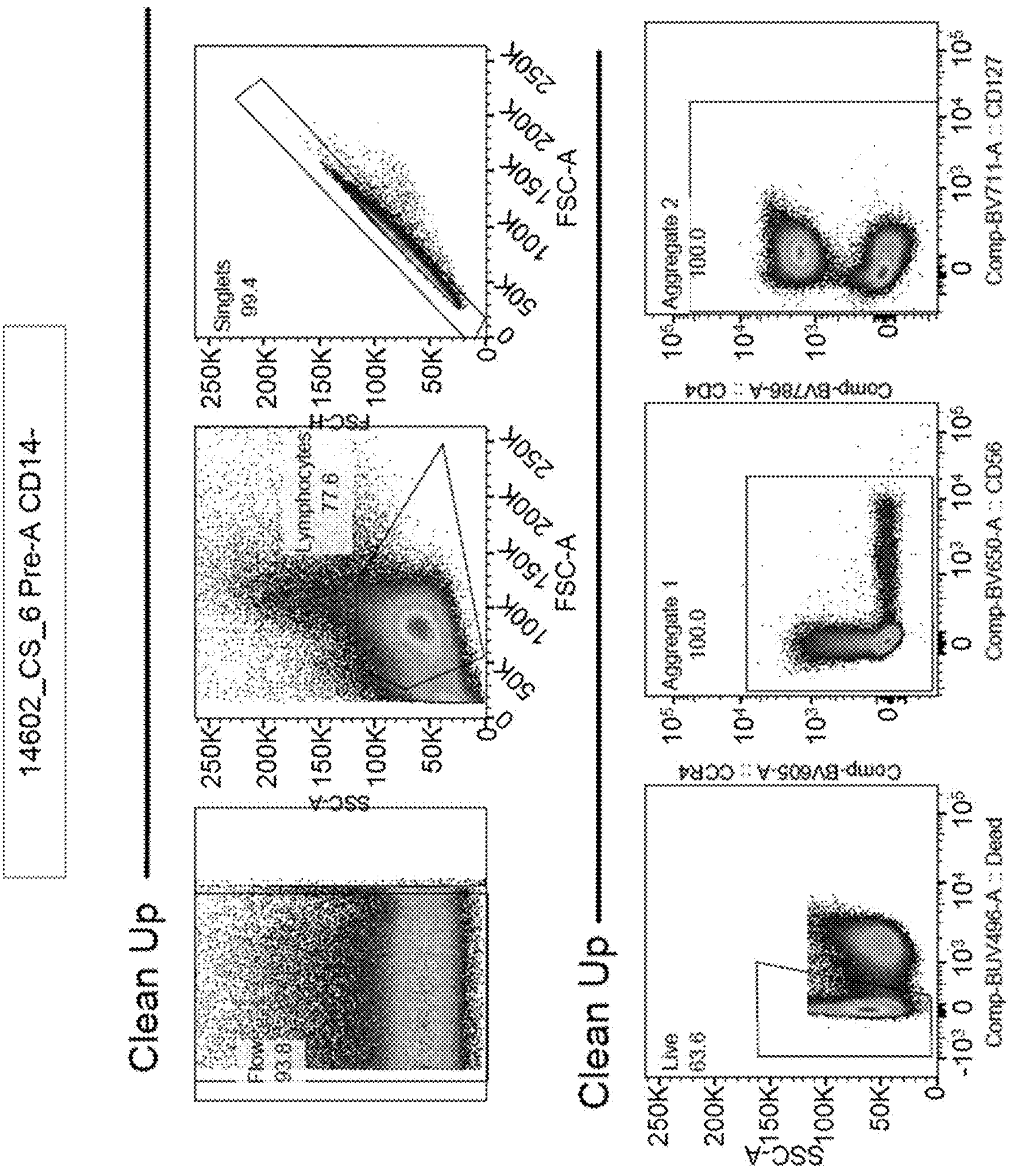
FIG. 23. Kinetics of the cytokines assayed pre-CAR (14 patient cohort). Meso Scale Discovery assay and ELISA assays were used to assess 10 cytokines: IFNγ, IL-10, IL-18 (ELISA), IL-18BP (ELISA), sIL-2ra, IL-2, IL-5, IL-6, IL-12p70, IL-13, IL-4, and IL-15. Example Gating for exhaustion and function panel.
Figure 23:
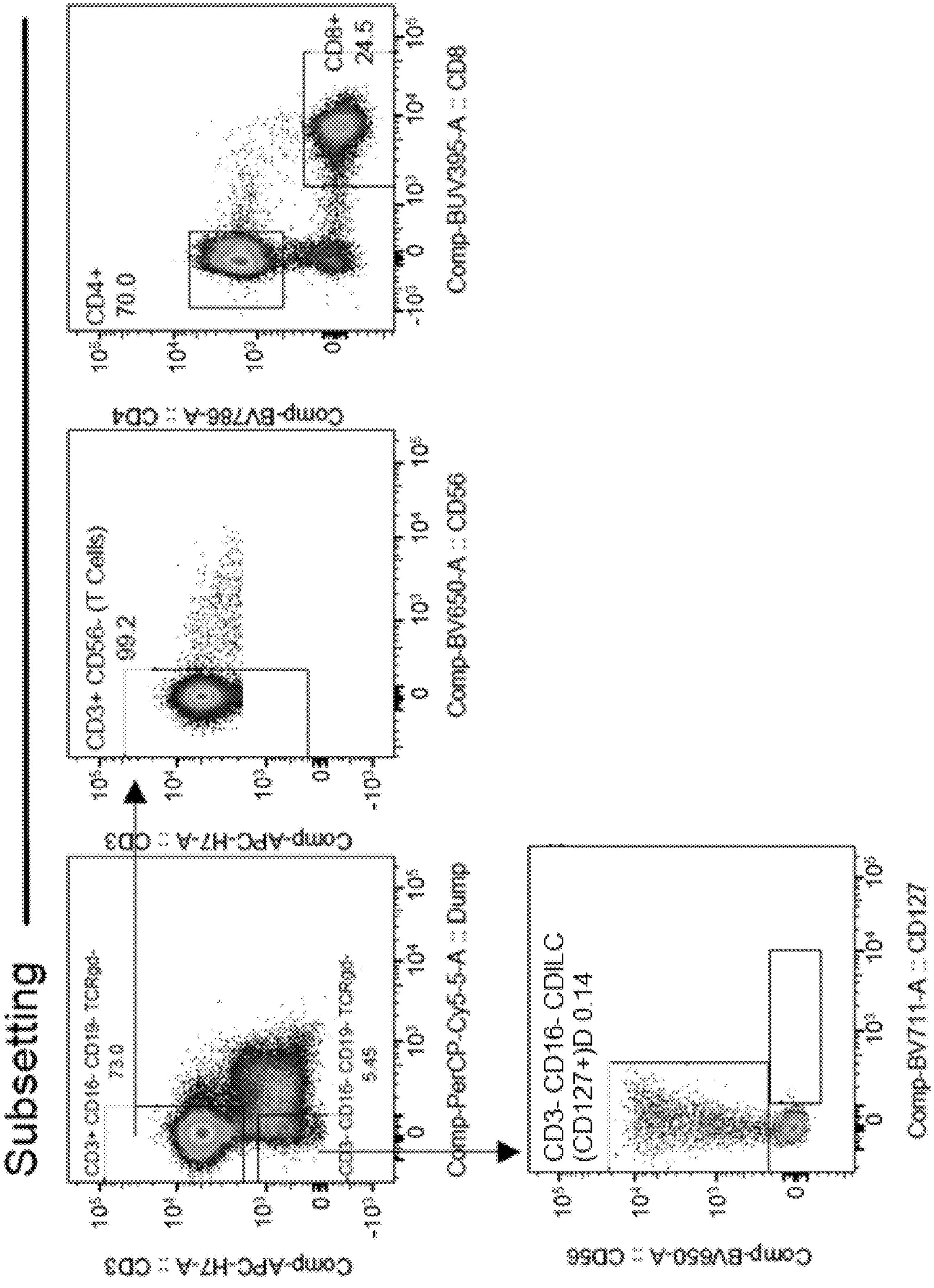
Figure 23:
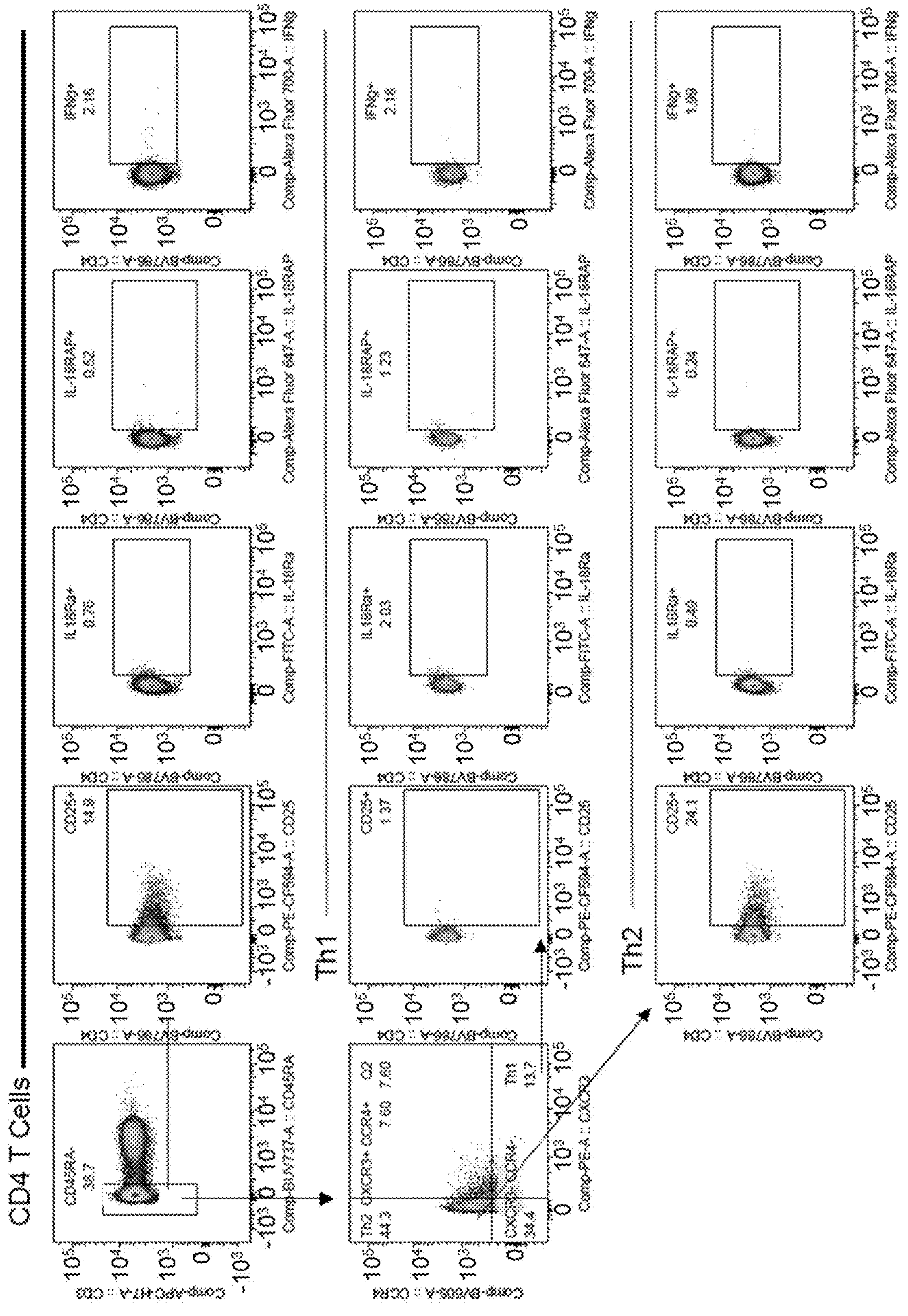
Figure 23:
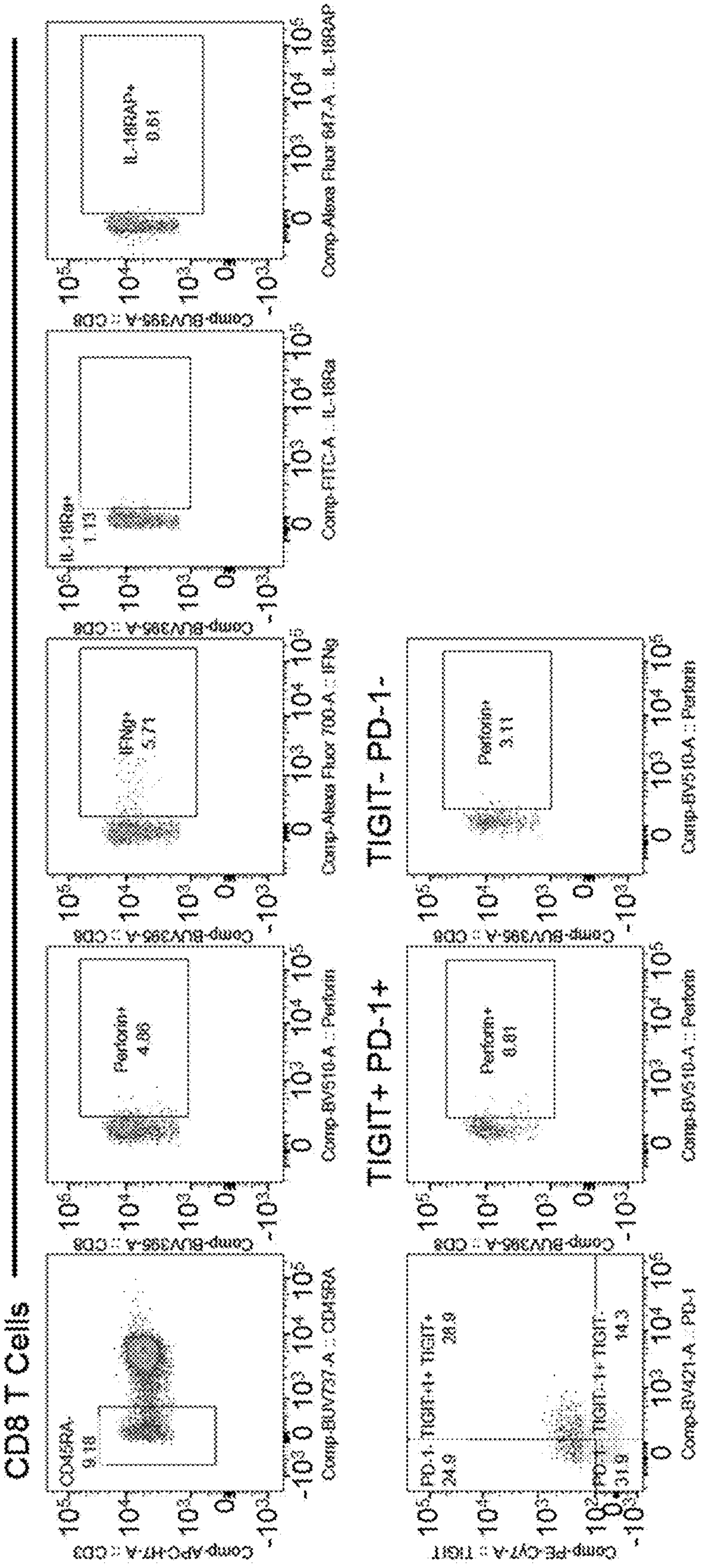
Figure 23:
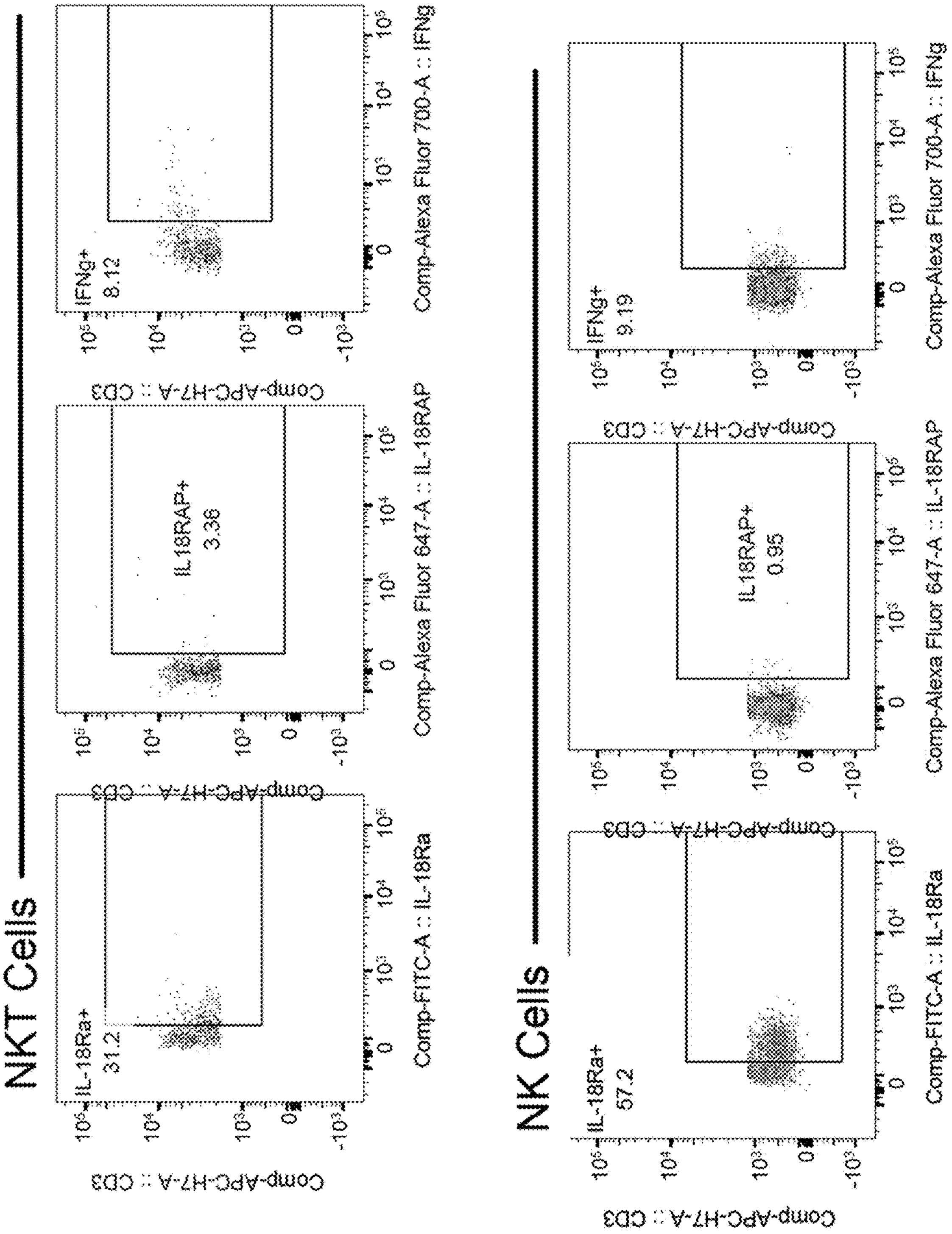

In particular embodiments, a biomarker of the present disclosure includes CD56+ dim cells or a population of cells that are CD56+ dim. Circulating NK cells (peripheral blood NK cells) may include CD56+ bright NK cells and CD56+ dim NK cells. CD56+ dim NK cells are more cytotoxic and express higher levels of Ig-like NK receptors and FCγ receptor III (CD16) than CD56+ bright NK cells. By contrast, CD56+ bright cells are immunoregulatory, less mature, and produce abundant cytokines following activation of monocytes, but have low cytotoxicity and are CD16dim or CD16−. In particular embodiments, 90% of circulating NK cells are CD56+ dim CD16+ bright and 10% of circulating NK cells are CD56+ bright and CD16−/dim. CD56+ dim and CD56+ bright cell populations, which reflect low and high cell surface density of CD56, respectively, may be distinguished by flow activated cell sorting (FACS) using an anti-CD56 antibody as described by Caligiuri et al. The Journal of experimental medicine. 1990; 171(5):1509-1526 and Cooper et al. Blood 2001; 97:3146-3151. In particular embodiments, CD56+ dim cells have fluorescence of <3000 while CD56+ bright cells have fluorescence of ≥3000, as measured by flow cytometry with a Brilliant Violet 650™ (BioLegend) fluorophore labeled antibody that binds CD56 (see FIG. 22).

(II) Responses to an immunomodulatory treatment. Biomarker profiles of the present disclosure can be used to predict the type of response a subject will have to an immunomodulatory treatment. In particular embodiments, an immunomodulatory treatment includes all therapeutic interventions directed to modulating an immune response. In particular embodiments, an immunomodulatory treatment includes immune effector cells. Immune effector cells include cells from the human body that have transformed into a form capable of modulating or effecting an immune response. The immune effector cells may be produced ex vivo (e.g., by genetically modifying T cells to express chimeric antigen receptors) and infused into a patient or may be produced in vivo following administration of an immunotherapy (e.g., immunotherapy with dendritic cells to stimulate endogenous T cells in the body). In particular embodiments, an immunomodulatory treatment includes immunotherapy, which treats a disease by activating or suppressing the immune system. In particular embodiments, immunotherapy includes therapies that use chimeric antigen receptor (CAR) modified T cells, therapeutic agents to deplete regulatory T cells, recombinant cytokines, immune checkpoint inhibitors, monoclonal antibodies, bispecific antibodies, dual-affinity retargeting antibodies (DART), immune-mobilizing monoclonal T cell receptors against cancer (ImmTAC), and vaccines. In particular embodiments, an immune response can be stimulated or increased to fight infections or cancer. In particular embodiments, an immune response can be suppressed or decreased in autoimmune diseases, allergic reactions, and organ transplantation with similar immunotherapies as used to fight cancer. For example, CAR T cells can target autoantigens to suppress autoimmunity, and activity of pathogenic cells that drive autoimmunity may be suppressed by immune checkpoint inhibitors. These immunotherapies, whether to activate the immune system or suppress it, may cause CRS and/or NTX.

CAR T cell therapy involves isolating T cells from a patient and genetically engineering the isolated T cells to express a CAR, a receptor that has been designed to recognize and bind to a specific molecule, or antigen, on tumor cells. The binding of the CAR to an antigen on a tumor cell triggers killing of the tumor cell. The CAR-modified T cells may be expanded in the lab before infusion back into the patient. Once inside the patient, the CAR-modified T cells may further divide in the patient, recognize and bind the particular antigen on tumor cells, and kill the tumor cells. Approved CAR T cell therapies include tisagenlecleucel (Kymriah™; Novartis) to treat pediatric and young adult B-cell acute lymphoblastic leukemia (ALL); axicabtagene ciloleucel (Yescarta®; Kite Pharma, Gilead Sciences Inc.) and lisocabtagene maraleucel (Breyanzi®; Bristol Myers Squibb) to treat large B cell lymphoma; and brexucabtagene autoleucel (Tecartus; Kite Pharma, Gilead Sciences Inc.) to treat mantle cell lymphoma and adult ALL. All use CD19-targeted CAR T cells. Other antigens are being targeted in development of CAR T cell therapies, including CD22, CD123, and BCMA.

Regulatory T cells (Treg cells) are immunosuppressive and may be an obstacle to initiating or enhancing an anti-tumor immune response. In particular embodiments, a therapeutic agent to deplete Treg cells may be an immunotherapy to fight cancer. Therapeutic agents may include low-dose cyclophosphamide (CTX), a common chemotherapeutic agent that targets rapidly dividing cells, as Treg cells have a higher rate of proliferation. In particular embodiments, anti-cancer agents including tyrosine kinase inhibitors sunitinib, sorafenib, and imatinib may reduce the levels of intra-tumoral Treg cells. Other agents to target Treg cells include daclizumab (CD25 blocking antibody) and denileukin diftitox (Ontak, IL-2-diphtheria toxin conjugate protein). A large number of receptors are upregulated on Treg cells in the tumor microenvironment including ICOS, OX40, GITR, TIGIT, PD-1, and CTLA-4, and these receptors may be targeted by, for example, antibodies to deplete Treg cells.

Recombinant cytokines may be used in cancer immunotherapy due to their anti-proliferative or pro-apoptotic effects against tumor cells or due to their ability to stimulate the cytotoxic function of immune cells. Examples of recombinant cytokines that are approved immunotherapies include: IL-2 to treat advanced renal cell carcinoma and metastatic melanoma; and IFN-α to treat hairy cell leukemia, follicular non-Hodgkin lymphoma, melanoma, and AIDS-related Kaposi's sarcoma. IL-2 promotes expansion of NK cells and T lymphocytes, while IFN-α has potent anti-angiogenic activity. Other cytokines being studied for immunotherapy include IL-15, IL-21, IL-12, IL-10, and GM-CSF.

Immune checkpoint proteins are useful to control over-active immune responses as part of the immune system. However, in the context of tumor cells, immune checkpoint proteins, which are found on the surface of T cells, can impede the function of T cells such that the T cells are not able to destroy tumor cells. Immune checkpoint inhibitors have been developed that target immune checkpoint proteins so that the immune checkpoint proteins are not able to bind their cognate ligands on tumor cells, allowing T cells to perform their cytotoxic functions against tumors. Approved immune checkpoint inhibitors include monoclonal antibodies: nivolumab (Opdivo®) and pembrolizumab (Keytruda®) that target the immune checkpoint protein PD-1; atezolizumab (Tecentriq®) and durvalumab (Imfinzi®) that target the ligand for PD-1, PD-L1; and ipilimumab (Yervoy®) that targets the immune checkpoint protein CTLA-4.

Monoclonal antibodies and bispecific antibodies may serve as immunotherapy in cancer by marking cancer cells for destruction by the immune system or by bringing immune cells close to their tumor cell targets for tumor cell killing. For example, the monoclonal antibody rituximab binds to CD20 on cells and triggers cell death. Rituximab is used to treat autoimmune diseases and certain types of cancer. Monoclonal antibody therapies include the monoclonal antibodies developed against immune checkpoint proteins. Bispecific antibodies for immunotherapy include antibodies that bind to an immune cell and to a tumor-associated antigen to re-direct the immune cell to a tumor. An example is blinatumomab (Blincyto®), which binds to both CD19 on the surface of leukemia cells, and CD3 on the surface of T cells. Bispecific antibodies also include tumor-targeted immunomodulators and dual immunomodulators that are being developed for immunotherapy. Tumor-targeted immunomodulators bind to a tumor-associated antigen and to a costimulatory molecule like CD40 or 4-1BB to direct potent costimulation to tumor-infiltrating cells. Dual immunomodulators bind to two distinct immunomodulatory targets to provoke a more powerful response against tumor cells (e.g., a bispecific that binds both PD-1 and CTLA-4). A DART (Dual-affinity Re-targeting Antibody) is another example of a bispecific antibody. A DART includes two engineered variable fragments (Fv) that allow greater flexibility of the variable heavy and variable light portions to improve binding to a target.

An ImmTAC® (Immune Mobilizing Monoclonal TCRs Against Cancer) includes a bispecific biologic that combines an engineered TCR that recognizes a tumor cell with immune activating complexes. In particular embodiments, an ImmTAC® includes a fusion protein of an engineered, soluble, affinity-enhanced monoclonal T cell receptor (to recognize MHC-presented tumor antigens) and a humanized anti-CD3 single chain antibody fragment (to re-direct non-tumor-specific T cells to a tumor) (Bossi et al. Cancer Immunol Immunother. 2014; 63(5):437-448; Boudousquie et al. Immunology. 2017; 152(3):425-438). An ImmTAC®, tebentafusp, is being developed against uveal melanoma (Immunocore Limited, Oxfordshire, UK).

Cancer vaccines help a patient's immune system recognize and eliminate cancer cells. Vaccines can include molecules (e.g. proteins, peptides, nucleic acids), cells, or parts of cells, that when introduced into a patient, increases the patient's immune response against cancer cells. Some cancers are caused by viral infections, so some vaccines have been developed to prevent viral infection. Preventive cancer vaccines include: human papillomavirus (HPV) vaccines that prevent infection from 2, 4, or 9 types of HPV, which can lead to cervical, head, and neck cancers; and a hepatitis B (HBV) vaccine that protects against development of HBV-related liver cancer. In embodiments, therapeutic cancer vaccines that treat existing cancers have been developed. These include: sipuleucel-T for advanced prostate cancer (activated dendritic cells and prostatic acid phosphatase antigen); talimogene laherparepvec (TVEC) for metastatic melanoma (genetically modified oncolytic type I herpes simplex virus); and *Bacillus* Calmette-Guerin (BCG) for early stage bladder cancer (a weakened bacteria).

Individuals undergoing an immunomodulatory treatment can have an aberrant or semi-functional response to the immunomodulatory treatment. In particular embodiments, an aberrant or semi-functional response to an immunomodulatory treatment includes having non-response (i.e. dysfunctional response) to the immunomodulatory treatment. In particular embodiments, a subject may be characterized as having a non-response to an immunomodulatory treatment when the subject does not have a complete response to an immunomodulatory treatment or briefly had a complete response to an immunomodulatory treatment but the disease has returned even in the presence of the agent of an immunomodulatory treatment (e.g., cancer relapse even in presence of CAR T cells in CAR T cell immunotherapy). Non-responses can include aspects of immune cell function, the particular target tissue that is undergoing an immunomodulatory treatment, the microenvironment in which an immunomodulatory treatment occurs, or a combination thereof. In particular embodiments, a non-response to CAR T cell therapy can include: no or reduced proliferation of CAR-modified cells (e.g., T or NK cells) and limited cytokine production; pro-inflammatory cytokine production prior to, during, and/or post CAR T cell therapy; CAR T cell exhaustion; impaired CAR T cell expansion; impaired CAR T cell cytotoxicity; target antigen loss from a tumor; diminished antigen expression; lineage switch; gene mutations in tumors; failed infiltration of CAR T cells; and CAR T cell rejection. T cell exhaustion refers to a state of dysfunction characterized by a progressive loss of effector function due to chronic antigen stimulation and/or increased expression of inhibitory receptors, usually in cancer and chronic infections. In particular embodiments, enhanced expression of regulators of aerobic glycolysis and/or CAR T cell differentiation (e.g., IL-6/STAT3 signaling) is associated with non-response to CAR T cell therapy. In particular embodiments, differentiated effector/memory T cells have decreased proliferation capacity when stimulated by antigen.

CRS can occur after treatment with immunotherapy. In particular embodiments, CRS is characterized by a large, rapid release of cytokines into the blood from immune cells affected by the immunotherapy. In particular embodiments, CRS may be more broadly defined as a supraphysiologic response following any immune therapy that results in the activation or engagement of endogenous or infused T cells and/or other immune effector cells. Symptoms can be progressive, includes fever at the onset, and may include hypotension, capillary leak (hypoxia), and end organ dysfunction (Lee et al. (2019) Biol Blood Marrow Transplant. 25:625-638). Fever is a hallmark of CRS. In particular embodiments, other CRS symptoms may include: tachypnea, dyspnea, tachycardia, headache, hypotension, hypoxia, rash, nausea, myalgias, malaise, capillary leak, and/or multiorgan dysfunction. Published grading systems for CRS include: Common Terminology Criteria for Adverse Events (CTCAE) version 4.03 (National Cancer Institute, available at World Wide Web at evs.nci.nih.gov/ftpl/CTCAE/CTCAE_4.03/CTCAE_4.03_2010-06-14_QuickReference_8.5×11.pdf.); CTCAE version 5.0 (National Cancer Institute, available at ctep.cancer.gov/protocol Development/electronic_applications/docs/CTCAE_v5_Quick_Reference_8.5×11.pdf); Lee criteria (Lee et al. (2014) Blood 124:188-195); Penn criteria (Porter et al. (2018) J Hematol Oncol 11:35); MSKCC criteria (Park et al. (2018) N Engl J Med 378:449-459); CARTOX criteria (Neelapu et al. (2018) Nat Rev Clin Oncol. 15:47-62); and American Society for Transplantation and Cellular Therapy (ASTCT) consensus grading (Lee et al. (2019) Biol Blood Marrow Transplant. 25:625-638).

For example, under the CTCAE version 5.0 grading system, the four grades of CRS include the following descriptions: Grade 1, fever with or without constitutional symptoms; Grade 2, hypotension responding to fluids and/or hypoxia responding to <40% $FiO_2$ (inspired oxygen); Grade 3, hypotension managed with one pressor and/or hypoxia requiring ≥40% $FiO_2$; and Grade 4, life-threatening consequences and/or urgent intervention indicated. In particular embodiments, severe CRS includes the need for vasopressors or inotropes, and/or includes respiratory failure.

In particular embodiments, an aberrant or semi-functional response to an immunomodulatory treatment includes having a toxic response to an immunomodulatory treatment. In particular embodiments, subjects who have a toxic response have neurological toxicities (neurotoxicities (NTX), or immune effector cell-associated neurotoxicity syndrome (ICANS)). NTX can affect the peripheral and central nervous system and include aphasia, dysgraphia, obtundation, stupor, lethargy, delirium, confusion, hallucinations, tremor, seizures, cerebral edema, coma, global encephalopathy, polyneuropathy, myositis, myasthenia gravis, demyelinating polyradiculopathy, myelitis, and encephalitis. In particular embodiments, NTX may occur during or after CRS symptoms but rarely before CRS. In particular embodiments, NTX may be characterized by a pathologic process involving the central nervous system following any immune therapy that results in the activation or engagement of endogenous or infused T cells and/or other immune effector cells (Lee et al. (2019) Biol Blood Marrow Transplant. 25:625-638). In particular embodiments, symptoms may be progressive and include aphasia, altered level of consciousness, impairment of cognitive skills, motor weakness, seizures, and cerebral edema. Published NTX grading systems include: CTCAE version 5.0, National Cancer Institute, available at ctep.cancer.gov/protocol Development/electronic_applications/docs/CTCAE_v5_Quick_Reference_8.5x11.pdf; CARTOX criteria (Neelapu et al. (2018) Nat Rev Clin Oncol. 15:47-62); and ASTCT consensus grading (Lee et al. (2019) Biol Blood Marrow Transplant. 25:625-638).

For example, under the CTCAE version 5.0 grading system, the four grades of NTX include the following descriptions for various adverse events: Grade 1, mild symptoms for encephalopathy, brief partial seizure and no loss of consciousness for seizure, awareness of receptive or expressive characteristics and/or not impairing ability to communicate for dysphasia, mild symptoms for tremor, mild pain for headache, mild disorientation for confusion, and decreased level of alertness for depressed level of consciousness; Grade 2, moderate symptoms and/or limiting instrumental activities of daily living (ADL) for encephalopathy, brief generalized seizure for seizure, moderate receptive or expressive characteristics and/or impairing ability to communicate spontaneously for dysphasia, moderate symptoms and/or limiting instrumental ADL for tremor, moderate pain and/or limiting instrumental ADL for headache, moderate disorientation and/or limiting instrumental ADL for confusion, and sedation, slow response to stimuli, and/or limiting instrumental ADL for depressed level of consciousness; Grade 3, severe symptoms and/or limiting self-care ADL for encephalopathy, new-onset seizures (partial or generalized) and/or multiple seizures despite medical intervention for seizure, severe receptive or expressive characteristics and/or impairing ability to read, write, and communicate intelligibly for dysphasia, severe symptoms and/or limiting self-care ADL for tremor, severe pain and/or limiting self-care ADL for headache, severe disorientation and/or limiting self-care ADL for confusion, difficult to arouse for depressed level of consciousness, and new onset and/or worsening from baseline for cerebral edema; Grade 4, life-threatening consequences and/or urgent intervention indicated for encephalopathy, life-threatening consequences for seizure, life-threatening consequences and/or urgent intervention indicated for confusion, life-threatening consequences and/or urgent intervention indicated for depressed level of consciousness, and life-threatening consequences and/or urgent intervention indicated for cerebral edema. In particular embodiments, severe NTX may be defined by grade 3/4 NTX exclusive of headache as defined by a grading system. In particular embodiments, limited NTX may include Grade 1 NTX as defined by a grading system. In particular embodiments, mild NTX may include any grade seizure as defined by a grading system.

Guidelines for grading and management of CRS and NTX are discussed in, for example, Thompson (2018) Natl Compr Canc Netw. 16(suppl 5):594-596; Neelapu et al. (2018) Nat Rev Clin Oncol. 15:47-62; Lee et al. (2014) Blood 124:188-195; and Lee et al. (2019) Biol Blood Marrow Transplant. 25:625-638.

In particular embodiments, a biomarker profile can predict a toxic response and/or a non-response to an immunomodulatory treatment by a subject. In particular embodiments, a toxic response and/or a non-response to an immunomodulatory treatment by a subject includes decreased overall survival, as compared to a reference. In particular embodiments, subjects who have a toxic response have NTX. In particular embodiments, a toxic response and/or a non-response to an immunomodulatory treatment by a subject includes CRS. In particular embodiments, a toxic response and/or a non-response to an immunomodulatory treatment by a subject includes decreased days to CRS onset, as compared to a reference. In particular embodiments, subjects who are non-responsive to an immunomodulatory treatment have a dysfunctional response. In particular embodiments, a subject who has a dysfunctional response to an immunomodulatory treatment either does not have or briefly had a functional response but had returned to disease while still having the therapeutic from the immunomodulatory treatment, with no or mild toxicity. In particular embodiments, a toxic response and/or a non-response to an immunomodulatory treatment by a subject includes increased levels of pro-inflammatory cytokines prior to an immunomodulatory treatment and continued increased levels of pro-inflammatory cytokines during or after an immunomodulatory treatment, as compared to a reference. In particular embodiments, a toxic and/or non-response to an immunomodulatory treatment by a subject includes no increase in levels of pro-inflammatory cytokines prior to an immunomodulatory treatment and increased levels of pro-inflammatory cytokines during or after an immunomodulatory treatment, as compared to a reference. In particular embodiments, a toxic and/or non-response to an immunomodulatory treatment by a subject includes active IL-18 signaling and/or IFNγ production, as compared to a reference. In particular embodiments, a reference includes a subject or population of subjects who have a functional response to an immunomodulatory treatment with limited or no NTX.

In particular embodiments, a toxic response and/or non-response to an immunomodulatory treatment by a subject includes: an increased level of IL-18; an increased level of IL-18BP; an increased level of IL-18R1; an increased level of IL-18RAP; an increased level of sIL-2RA; an increased level of IL-2; an increased level of IL-5; an increased level of IL-6; an increased level of IL-9; an increased level of IL-10; an increased level of IL-22; an increased level of IFNγ; an increased level of GM-CSF; an increased level of SAA; an increased level of CRP; an increased level of CD161+ cells; an increased level of CD56+ dim cells; or a combination thereof, as measured in a test sample from the subject as compared to the same biomarkers of a reference biomarker profile. In particular embodiments, CD161+ cells include: CD161+CD3+ T cells; CD161+CD4+ T cells; CD161+CD4+CD45RA-T cells; CD161+CD8+ T cells; CD161+CD8+CD45RA+ T cells; CD161+CD56+ NK cells; CD161+ MAIT cells; CD161+GM-CSF+NK cells; CD161+ GM-CSF+ MAIT cells; CD161+GM-CSF+ T cells; CD161+ IFNγ+NK cells; CD161+ IFNγ+ MAIT cells; CD161+ IFNγ+ T cells; CD161+ IFNγ+ NKT cells; or a combination thereof. In particular embodiments, the CD56+ dim cells are circulating NK cells.

In particular embodiments, a subject is identified as having a toxic response and/or non-response to an immunomodulatory treatment when the level of at least one biomarker selected from IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, CD56+ dim cells, or a combination thereof, as measured in a test sample from the subject, is increased as compared to the levels of the same biomarkers of a reference biomarker profile. In particular embodiments, a subject is identified as having a toxic response and/or non-response to an immunomodulatory treatment when the levels of at least two, of at least three, of at least four, of at least five, of at least six, of at least seven, of at least eight, of at least nine, of at least ten, of at least eleven, of at least twelve, of at least thirteen, of at least fourteen, of at least fifteen, or of at least sixteen, biomarkers including IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, as measured in a test sample from the subject, are increased as compared to the levels of the same biomarkers of a reference biomarker profile. In particular embodiments, a subject is identified as having a toxic response and/or non-response to an immunomodulatory treatment when the level(s) of one, two, three, four, five, six, seven, eight, nine, ten, eleven, twelve, thirteen, fourteen, fifteen, sixteen, or seventeen biomarkers including IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, as measured in a test sample from the subject, is/are increased as compared to the levels of the same biomarkers of a reference biomarker profile. In particular embodiments, a subject is identified as having a toxic response and/or non-response to an immunomodulatory treatment when the levels of all biomarkers including IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, as measured in a test sample from the subject, are increased as compared to the levels of the same biomarkers of a reference biomarker profile.

In particular embodiments, a subject is identified as having a toxic response and/or non-response to an immunomodulatory treatment when the level of at least one biomarker selected from IL-18, IL-18BP, sIL-2RA, IL-10, IL-22, IFNγ, CD161+ cells, or a combination thereof, as measured in a test sample from the subject, is increased as compared to the levels of the same biomarkers of a reference biomarker profile. In particular embodiments, a subject is identified as having a toxic response and/or non-response to an immunomodulatory treatment when the levels of at least two, of at least three, of at least four, of at least five, or of at least six, biomarkers including IL-18, IL-18BP, sIL-2RA, IL-10, IL-22, IFNγ, CD161+ cells, as measured in a test sample from the subject, are increased as compared to the levels of the same biomarkers of a reference biomarker profile. In particular embodiments, a subject is identified as having a toxic response and/or non-response to an immunomodulatory treatment when the level(s) of one, two, three, four, five, six, or seven biomarkers including IL-18, IL-18BP, sIL-2RA, IL-10, IL-22, IFNγ, CD161+ cells, as measured in a test sample from the subject, is/are increased as compared to the levels of the same biomarkers of a reference biomarker profile. In particular embodiments, a subject is identified as having a toxic response and/or non-response to an immunomodulatory treatment when the levels of all biomarkers including IL-18, IL-18BP, sIL-2RA, IL-10, IL-22, IFNγ, CD161+ cells, as measured in a test sample from the subject, are increased as compared to the levels of the same biomarkers of a reference biomarker profile.

In particular embodiments, a subject is identified as having a toxic response and/or non-response to an immunomodulatory treatment when the level of at least one biomarker selected from IL-10, IFNγ, GM-CSF, SAA, or a combination thereof, as measured in a test sample from the subject, is increased as compared to the levels of the same biomarkers of a reference biomarker profile. In particular embodiments, a subject is identified as having a toxic response and/or non-response to an immunomodulatory treatment when the level of at least one biomarker selected from IL-10, IFNγ, GM-CSF, CRP, or a combination thereof, as measured in a test sample from the subject, is increased as compared to the levels of the same biomarkers of a reference biomarker profile. In particular embodiments, a subject is identified as having a toxic response and/or non-response to an immunomodulatory treatment when the level of at least one biomarker selected from sIL-2RA, IL-5, IL-10, GM-CSF, or a combination thereof, as measured in a test sample from the subject, is increased as compared to the levels of the same biomarkers of a reference biomarker profile. In particular embodiments, a subject is identified as having a toxic response and/or non-response to an immunomodulatory treatment when the level of at least one biomarker selected from IL-18, IL-18BP, IFNγ, or a combination thereof, as measured in a test sample from the subject, is increased as compared to the levels of the same biomarkers of a reference biomarker profile. In particular embodiments, a subject is identified as having a toxic response and/or non-response to an immunomodulatory treatment when the level of at least one biomarker selected from IL-18, IL-18BP, IL-22, or a combination thereof, as measured in a test sample from the subject, is increased as compared to the levels of the same biomarkers of a reference biomarker profile.

The biomarkers disclosed herein can be used to identify or predict a subject's response to an immunomodulatory treatment before initiation of the immunomodulatory treatment (pre-immunomodulatory treatment). In particular embodiments, pre-immunomodulatory treatment includes a time before apheresis is performed on a subject to extract the subject's T cells for genetic modification to express a CAR. This would be valuable so that the most appropriate immunotherapy can be selected for a subject, or allow removal of detrimental cell populations from a subject's cells destined to be developed into CAR T cells (e.g., removal of CD161+ cells as described herein).

In particular embodiments, a subject is identified as having or predicted to have a toxic response and/or non-response to an immunomodulatory treatment when the level of at least one biomarker selected from IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, or a combination thereof, as measured in a test sample obtained from the subject pre-immunomodulatory treatment, is increased as compared to the same biomarkers of a reference biomarker profile. In particular embodiments, a subject is identified as having a toxic response and/or non-response to an immunomodulatory treatment when the levels of at least two, of at least three, of at least four, of at least five, of at least six, of at least seven, of at least eight, of at least nine, of at least ten, of at least eleven, of at least twelve, of at least thirteen, of at least fourteen, of at least fifteen, or of at least sixteen, biomarkers including IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, as measured in a test sample obtained from the subject pre-immunomodulatory treatment, are increased as compared to the levels of the same biomarkers of a reference biomarker profile. In particular embodiments, a subject is identified as having a toxic response and/or non-response to an immunomodulatory treatment when the level(s) of one, two, three, four, five, six, seven, eight, nine, ten, eleven, twelve, thirteen, fourteen, fifteen, sixteen, or seventeen biomarkers including IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, as measured in a test sample obtained from the subject pre-immunomodulatory treatment, is/are increased as compared to the levels of the same biomarkers of a reference biomarker profile. In particular embodiments, a subject is identified as having a toxic response and/or non-response to an immunomodulatory treatment when the levels of all biomarkers including IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, and CD56+ dim cells, as measured in a test sample obtained from the subject pre-immunomodulatory treatment, are increased as compared to the levels of the same biomarkers of a reference biomarker profile.

In particular embodiments, a subject is identified as having or predicted to have a toxic response and/or non-response to an immunomodulatory treatment when the level of at least one biomarker selected from IL-18, IL-18BP, IL-10, IL-22, sIL-2RA, IFNγ, CD161+ cells, CD56+ dim cells, or a combination thereof, as measured in a test sample obtained from the subject pre-immunomodulatory treatment, is increased as compared to the same biomarkers of a reference biomarker profile. In particular embodiments, a subject is predicted to have a toxic response and/or non-response to an immunomodulatory treatment when the levels of at least two, of at least three, of at least four, of at least five, of at least six, or of at least seven, biomarkers including IL-18, IL-18BP, IL-10, IL-22, sIL-2RA, IFNγ, CD161+ cells, and CD56+ dim cells, as measured in a test sample obtained from the subject pre-immunomodulatory treatment, are increased as compared to the levels of the same biomarkers of a reference biomarker profile. In particular embodiments, a subject is predicted pre-immunomodulatory treatment to have a toxic response and/or non-response to an immunomodulatory treatment when the level(s) of one, two, three, four, five, six, seven, or eight biomarkers including IL-18, IL-18BP, IL-10, IL-22, sIL-2RA, IFNγ, CD161+ cells, and CD56+ dim cells, as measured in a test sample obtained from the subject pre-immunomodulatory treatment, is/are increased as compared to the levels of the same biomarkers of a reference biomarker profile. In particular embodiments, a subject is predicted pre-immunomodulatory treatment to have a toxic response and/or non-response to an immunomodulatory treatment when the levels of all biomarkers including IL-18, IL-18BP, IL-10, IL-22, sIL-2RA, IFNγ, CD161+ cells, and CD56+ dim cells, as measured in a test sample obtained from the subject pre-immunomodulatory treatment, are increased as compared to the levels of the same biomarkers of a reference biomarker profile.

In particular embodiments, the CD161+ cells include: CD161+CD3+ T cells; CD161+CD4+ T cells; CD161+CD4+CD45RA-T cells; CD161+CD8+ T cells; CD161+CD8+CD45RA+ T cells; CD161+CD56+ NK cells; CD161+ MAIT cells; CD161+GM-CSF+NK cells; CD161+GM-CSF+ MAIT cells; CD161+GM-CSF+ T cells; CD161+IFNγ+NK cells; CD161+ IFNγ+ MAIT cells; CD161+IFNγ+ T cells; CD161+ IFNγ+ NKT cells; or a combination thereof. Importantly, an increase in the level of CD161+ cells can be detected in a subject who has or is predicted to have a toxic response and/or non-response in a pre-apheresis blood sample drawn from the subject. Pre-apheresis includes a time that occurs before a decision is made on whether to perform apheresis to obtain a subject's T cells to modify for CAR T cell therapy. Therefore, in particular embodiments, an increase in the level of CD161+ may be a prognostic diagnostic for doctors to decide to exclude a subject from a CAR T cell therapy clinical trial. In particular embodiments, an increase in the level of CD161+ may be a prognostic diagnostic for doctors to decide to remove CD161+ cells from an apheresis product obtained from a subject prior to CAR T cell therapy as a treatment to drive a potential toxic response and/or nonresponse to a functional response.

Apheresis is a process that uses an apparatus to remove whole blood from a subject, separate out components of the blood for particular uses, and return the remaining components to the subject. In particular embodiments, in autologous CAR T cell therapy, a subject's T cells are obtained by apheresis, genetically modified to express a CAR, and the CAR-modified T cells are then infused into the subject for immunotherapy. In particular embodiments, an apheresis product includes T cells. In particular embodiments, an apheresis product includes mononuclear cells.

In particular embodiments, an increase in the level of CD161+ cells includes a 2-fold increase to a 10-fold increase, or a 4-fold increase to a 10-fold increase as compared to the level of CD161+ cells of a reference biomarker profile. In particular embodiments, an increase in the level of CD161+ cells includes a 2-fold, a 2.5-fold, a 3-fold, a 3.5-fold, a 4-fold, a 4.5-fold, a 5-fold, a 5.5-fold, a 6-fold, a 6.5-fold, a 7-fold, a 7.5-fold, an 8-fold, an 8.5-fold, a 9-fold, a 9.5-fold, a 10-fold, or more increase as compared to the level of CD161+ cells of a reference biomarker profile. In particular embodiments, the percentage of CD161+ cells in a test sample from a subject who has a toxic response and/or non-response to an immunomodulatory treatment includes 10% to 30% or 10% to 20% of total live cells in the test sample. In particular embodiments, the percentage of CD161+ cells in a test sample from a subject who has a toxic response and/or non-response to an immunomodulatory treatment includes 10%, 11%, 12%, 13%, 14%, 15%, 16%, 17%, 18%, 19%, 20%, 21%, 22%, 23%, 24%, 25%, 26%, 27%, 28%, 29%, 30%, or more of total live cells in the test sample. In particular embodiments, the test sample includes PBMC cells. In particular embodiments, live cells can be determined using a viability dye in an assay such as LIVE/DEAD™ Fixable Blue Dead Cell Stain kit from ThermoFisher (Waltham, MA). The dye in the assay reacts with free amines both in the cell interior and on the cell surface of cells with compromised membranes, yielding intense fluorescent staining, while the dye's reactivity is restricted to the cell-surface amines in viable cells, resulting in less intense fluorescence. In particular embodiments, the difference in intensity is typically greater than 50-fold between live and dead cells, allowing for easy discrimination.

In particular embodiments, the CD56+ dim cells are circulating NK cells.

In particular embodiments, an increase in the level of CD56+ dim cells includes a 2-fold increase to a 10-fold increase, or a 4-fold increase to a 10-fold increase as compared to the level of CD56+ dim cells of a reference biomarker profile. In particular embodiments, an increase in the level of CD56+ dim cells includes 2-fold, a 2.5-fold, a 3-fold, a 3.5-fold, a 4-fold, a 4.5-fold, a 5-fold, a 5.5-fold, a 6-fold, a 6.5-fold, a 7-fold, a 7.5-fold, an 8-fold, an 8.5-fold, a 9-fold, a 9.5-fold, a 10-fold, or more increase as compared to the level of CD56+ dim cells of a reference biomarker profile. In particular embodiments, the test sample includes PBMC cells.

Biomarkers disclosed herein can be used to identify or predict a subject's response to an immunomodulatory treatment once the immunomodulatory treatment has initiated. In particular embodiments, biomarkers disclosed herein can be used to predict a subject's response to an immunomodulatory treatment once the immunomodulatory treatment has initiated but before any adverse symptoms of CRS and/or NTX are evident. This would be valuable so that a decision can be made early after an immunotherapy has started on whether the immunotherapy should be continued, adjusted (e.g., dosage), terminated, or terminated and another immunotherapy initiated, depending on the levels of biomarkers useful for predicting a subject's response after an immunomodulatory treatment has initiated as described herein. In particular embodiments, mean onset of NTX is 8 days after CAR T cell therapy has initiated, so being able to predict a subject's response before this time would allow early intervention points if the CAR T cell therapy needs to be adjusted, changed, or terminated. In particular embodiments, biomarkers disclosed herein can be used to predict a subject's response to an immunomodulatory treatment 1 day after an immunomodulatory treatment has initiated, 3 days after an immunomodulatory treatment has initiated, and/or 7 days after an immunomodulatory treatment has initiated. In particular embodiments, biomarkers disclosed herein can be used to predict a subject's response to an immunomodulatory treatment 1 day, 2 days, 3 days, 4 days, 5 days, 6 days, 7 days, 8 days, 9 days, 10 days, 11 days, 12 days, 13 days, 14 days, or more after an immunomodulatory treatment has initiated.

In particular embodiments, a subject is identified as having or predicted to have a toxic response and/or non-response to an immunomodulatory treatment when the level of at least one biomarker selected from IL-18, IL-18BP, IL-18R1, IL-18RAP, sIL-2RA, IL-2, IL-5, IL-6, IL-9, IL-10, IL-22, IFNγ, GM-CSF, SAA, CRP, or a combination thereof, as measured in a test sample obtained from the subject after an immunomodulatory treatment has initiated, is increased as compared to the same biomarkers of a reference biomarker profile. In particular embodiments, a subject is identified as having a toxic response and/or non-response to an immunomodulatory treatment when the levels of at least two, of at least three, of at least four, of at least five, of at least six, of at least seven, of at least eight, of at least nine, of at least ten, of at least eleven, of at least twelve, of at least thirteen, or of at least fourteen, biomarkers including IL-18, IL-18BP, IL-18R1, IL-18RAP, sIL-2RA, IL-2, IL-5, IL-6, IL-9, IL-10, IL-22, IFNγ, GM-CSF, SAA, and CRP, as measured in a test sample obtained from the subject after an immunomodulatory treatment has initiated, are increased as compared to the levels of the same biomarkers of a reference biomarker profile. In particular embodiments, a subject is identified as having a toxic response and/or non-response to an immunomodulatory treatment when the level(s) of one, two, three, four, five, six, seven, eight, nine, ten, eleven, twelve, thirteen, fourteen, or fifteen biomarkers including IL-18, IL-18BP, IL-18R1, IL-18RAP, sIL-2RA, IL-2, IL-5, IL-6, IL-9, IL-10, IL-22, IFNγ, GM-CSF, SAA, and CRP, as measured in a test sample obtained from the subject after an immunomodulatory treatment has initiated, is/are increased as compared to the levels of the same biomarkers of a reference biomarker profile. In particular embodiments, a subject is identified as having a toxic response and/or non-response to an immunomodulatory treatment when the levels of all biomarkers including IL-18, IL-18BP, IL-18R1, IL-18RAP, sIL-2RA, IL-2, IL-5, IL-6, IL-9, IL-10, IL-22, IFNγ, GM-CSF, SAA, and CRP, as measured in a test sample obtained from the subject after an immunomodulatory treatment has initiated, are increased as compared to the levels of the same biomarkers of a reference biomarker profile. In particular embodiments, a test sample is obtained from a subject 1 day, 3 days, or 7 days after an immunomodulatory treatment has initiated.

In particular embodiments, a subject is identified as having or predicted to have a toxic response and/or non-response to an immunomodulatory treatment when the level of at least one biomarker selected from IL-18, IL-18BP, IL-5, IL-10, IL-22, sIL-2RA, IFNγ, GM-CSF, SAA, CRP, or a combination thereof, as measured in a test sample obtained from the subject after an immunomodulatory treatment has initiated, is increased as compared to the level(s) of the same biomarkers of a reference biomarker profile. In particular embodiments, a subject is predicted to have a toxic response and/or non-response to an immunomodulatory treatment when the levels of at least two, of at least three, of at least four, of at least five, of at least six, of at least seven, of at least eight, or of at least nine, biomarkers including IL-18, IL-18BP, IL-5, IL-10, IL-22, sIL-2RA, IFNγ, GM-CSF, SAA, and CRP, as measured in a test sample obtained from the subject after an immunomodulatory treatment has initiated, are increased as compared to the levels of the same biomarkers of a reference biomarker profile. In particular embodiments, a subject is predicted to have a toxic response and/or non-response to an immunomodulatory treatment when the level(s) of one, two, three, four, five, six, seven, eight, nine, or ten biomarkers including IL-18, IL-18BP, IL-5, IL-10, IL-22, sIL-2RA, IFNγ, GM-CSF, SAA, and CRP, as measured in a test sample obtained from the subject after an immunomodulatory treatment has initiated, is/are increased as compared to the levels of the same biomarkers of a reference biomarker profile. In particular embodiments, a subject is predicted to have a toxic response and/or non-response to an immunomodulatory treatment when the levels of all biomarkers including IL-18, IL-18BP, IL-5, IL-10, IL-22, sIL-2RA, IFNγ, GM-CSF, SAA, and CRP, as measured in a test sample obtained from the subject after an immunomodulatory treatment has initiated, are increased as compared to the levels of the same biomarkers of a reference biomarker profile. In particular embodiments, a test sample is obtained from a subject 1 day, 3 days, or 7 days after an immunomodulatory treatment has initiated.

In particular embodiments, a subject is identified as having or predicted to have a toxic response and/or non-response to an immunomodulatory treatment when the level of at least one biomarker selected from IL-10, SAA, GM- CSF, IFNγ, or a combination thereof, as measured in a test sample obtained from the subject 1 day after an immunomodulatory treatment has initiated, is increased as compared to the level(s) of the same biomarkers of a reference biomarker profile. In particular embodiments, a subject is predicted to have a toxic response and/or non-response to an immunomodulatory treatment when the levels of at least two or of at least three biomarkers including IL-10, SAA, GM-CSF, and IFNγ, as measured in a test sample obtained from the subject 1 day after an immunomodulatory treatment has initiated, are increased as compared to the levels of the same biomarkers of a reference biomarker profile. In particular embodiments, a subject is predicted to have a toxic response and/or non-response to an immunomodulatory treatment when the level(s) of one, two, three, or four biomarkers including IL-10, SAA, GM-CSF, and IFNγ, as measured in a test sample obtained from the subject 1 day after an immunomodulatory treatment has initiated, is/are increased as compared to the levels of the same biomarkers of a reference biomarker profile. In particular embodiments, a subject is predicted to have a toxic response and/or non-response to an immunomodulatory treatment when the levels of all biomarkers including IL-10, SAA, GM-CSF, and IFNγ, as measured in a test sample obtained from the subject 1 day after an immunomodulatory treatment has initiated, are increased as compared to the levels of the same biomarkers of a reference biomarker profile.

In particular embodiments, a subject is identified as having or predicted to have a toxic response and/or non-response to an immunomodulatory treatment when the level of at least one biomarker selected from IL-10, CRP, IFNγ, GM-CSF, or a combination thereof, as measured in a test sample obtained from the subject 3 days after an immunomodulatory treatment has initiated, is increased as compared to the level(s) of the same biomarkers of a reference biomarker profile. In particular embodiments, a subject is predicted to have a toxic response and/or non-response to an immunomodulatory treatment when the levels of at least two or of at least three biomarkers including IL-10, CRP, IFNγ, and GM-CSF, as measured in a test sample obtained from the subject 3 days after an immunomodulatory treatment has initiated, are increased as compared to the levels of the same biomarkers of a reference biomarker profile. In particular embodiments, a subject is predicted to have a toxic response and/or non-response to an immunomodulatory treatment when the level(s) of one, two, three, or four biomarkers including IL-10, CRP, IFNγ, and GM-CSF, as measured in a test sample obtained from the subject 3 days after an immunomodulatory treatment has initiated, is/are increased as compared to the levels of the same biomarkers of a reference biomarker profile. In particular embodiments, a subject is predicted to have a toxic response and/or non-response to an immunomodulatory treatment when the levels of all biomarkers including IL-10, CRP, IFNγ, and GM-CSF, as measured in a test sample obtained from the subject 3 days after an immunomodulatory treatment has initiated, are increased as compared to the levels of the same biomarkers of a reference biomarker profile.

In particular embodiments, the subject is identified as having or predicted to have a toxic response and/or non-response to an immunomodulatory treatment when the level of at least one biomarker selected from IL-10, IL-5, sIL-2RA, GM-CSF, or a combination thereof, as measured in a test sample obtained from the subject 3 days after an immunomodulatory treatment has initiated, is increased as compared to the level(s) of the same biomarkers of a reference biomarker profile. In particular embodiments, a subject is predicted to have a toxic response and/or non-response to an immunomodulatory treatment when the levels of at least two or of at least three biomarkers including IL-10, IL-5, sIL-2RA, and GM-CSF, as measured in a test sample obtained from the subject 3 days after an immunomodulatory treatment has initiated, are increased as compared to the levels of the same biomarkers of a reference biomarker profile. In particular embodiments, a subject is predicted to have a toxic response and/or non-response to an immunomodulatory treatment when the level(s) of one, two, three, or four biomarkers including IL-10, IL-5, sIL-2RA, and GM-CSF, as measured in a test sample obtained from the subject 3 days after an immunomodulatory treatment has initiated, is/are increased as compared to the levels of the same biomarkers of a reference biomarker profile. In particular embodiments, a subject is predicted to have a toxic response and/or non-response to an immunomodulatory treatment when the levels of all biomarkers including IL-10, IL-5, sIL-2RA, and GM-CSF, as measured in a test sample obtained from the subject 3 days after an immunomodulatory treatment has initiated, are increased as compared to the levels of the same biomarkers of a reference biomarker profile.

In particular embodiments, a subject is identified as having or predicted to have a toxic response and/or non-response to an immunomodulatory treatment when the level of at least one biomarker selected from IL-18, IL-18BP, IFNγ, or a combination thereof, as measured in a test sample obtained from the subject 7 days after an immunomodulatory treatment has initiated, is increased as compared to the level(s) of the same biomarkers of a reference biomarker profile. In particular embodiments, a subject is predicted to have a toxic response and/or non-response to an immunomodulatory treatment when the levels of at least two biomarkers including IL-18, IL-18BP, and IFNγ, as measured in a test sample obtained from the subject 7 days after an immunomodulatory treatment has initiated, are increased as compared to the levels of the same biomarkers of a reference biomarker profile. In particular embodiments, a subject is predicted to have a toxic response and/or non-response to an immunomodulatory treatment when the level(s) of one, two, or three biomarkers including IL-18, IL-18BP, and IFNγ, as measured in a test sample obtained from the subject 7 days after an immunomodulatory treatment has initiated, is/are increased as compared to the levels of the same biomarkers of a reference biomarker profile. In particular embodiments, a subject is predicted to have a toxic response and/or non-response to an immunomodulatory treatment when the levels of all biomarkers including IL-18, IL-18BP, and IFNγ, as measured in a test sample obtained from the subject 7 days after an immunomodulatory treatment has initiated, are increased as compared to the levels of the same biomarkers of a reference biomarker profile.

In particular embodiments, a subject is predicted to have a toxic response and/or non-response to an immunomodulatory treatment when the level of at least one biomarker selected from IL-18, IL-18BP, IL-22, or a combination thereof, as measured in a test sample obtained from the subject 7 days after an immunomodulatory treatment has initiated, is increased as compared to the level(s) of the same biomarkers of a reference biomarker profile. In particular embodiments, a subject is predicted to have a toxic response and/or non-response to an immunomodulatory treatment when the levels of at least two biomarkers including IL-18, IL-18BP, and IL-22, as measured in a test sample obtained from the subject 7 days after an immunomodulatory treatment has initiated, are increased as compared to the levels of the same biomarkers of a reference biomarker profile. In particular embodiments, a subject is predicted to have a toxic response and/or non-response to an immunomodulatory treatment when the level(s) of one, two, or three biomarkers including IL-18, IL-18BP, and IL-22, as measured in a test sample obtained from the subject 7 days after an immunomodulatory treatment has initiated, is/are increased as compared to the levels of the same biomarkers of a reference biomarker profile. In particular embodiments, a subject is predicted to have a toxic response and/or non-response to an immunomodulatory treatment when the levels of all biomarkers including IL-18, IL-18BP, and IL-22, as measured in a test sample obtained from the subject 7 days after an immunomodulatory treatment has initiated, are increased as compared to the levels of the same biomarkers of a reference biomarker profile.

In particular embodiments, a reference biomarker profile includes levels of the same biomarkers as measured in a test sample and is from a subject or a population of subjects who have a functional response to an immunomodulatory treatment with limited or no NTX. In particular embodiments, a reference biomarker profile includes levels of the same biomarkers as measured in a test sample and is from a healthy subject or a population of healthy subjects. In particular embodiments, a reference biomarker profile includes levels of the same biomarkers measured at the same time points pre-immunomodulatory treatment or after an immunomodulatory treatment has initiated as the test sample, and is from a subject or a population of subjects who have a functional response to an immunomodulatory treatment with limited or no NTX.

In particular embodiments, an increase in the level of any one of biomarkers including IL-18, IL-18BP, IL-18R1, IL-18RAP, sIL-2RA, IL-2, IL-5, IL-6, IL-9, IL-10, IL-22, IFNγ, GM-CSF, SAA, and CRP includes a 1.1-fold increase to a 20-fold increase, or a 2-fold increase to a 20-fold increase as compared to the level of the same biomarker of a reference biomarker profile. In particular embodiments, an increase in the level of any one of biomarkers including IL-18, IL-18BP, IL-18R1, IL-18RAP, sIL-2RA, IL-2, IL-5, IL-6, IL-9, IL-10, IL-22, IFNγ, GM-CSF, SAA, and CRP includes a 1.1-fold, a 1.2-fold, a 1.3-fold, a 1.4-fold, a 1.5-fold, a 1.6-fold, a 1.7-fold, a 1.8-fold, a 1.9-fold, a 2-fold, a 2.5-fold, a 3-fold, a 3.5-fold, a 4-fold, a 4.5-fold, a 5-fold, a 5.5-fold, a 6-fold, a 6.5-fold, a 7-fold, a 7.5-fold, an 8-fold, an 8.5-fold, a 9-fold, a 9.5-fold, a 10-fold, a 15-fold, a 20-fold, or more increase as compared to the level of the same biomarker of a reference biomarker profile. In particular embodiments, the level of IFNγ is increased 2-fold to 100-fold or 5-fold to 100-fold as compared to the IFNγ level of a reference biomarker profile. In particular embodiments, the level of IFNγ in a test sample is increased 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or more as compared to the IFNγ level of a reference biomarker profile.

In particular embodiments, a biomarker profile can predict a functional response to an immunomodulatory treatment by a subject. In particular embodiments, a functional response to an immunomodulatory treatment by a subject includes increased overall survival, as compared to a reference. In particular embodiments, a functional response to an immunomodulatory treatment includes moderate levels of pro-inflammatory cytokines (e.g., IL-18 and IL-12) to allow T cells to produce IFNγ and polarize to Th1 cells. In particular embodiments, a functional response to an immunomodulatory treatment has limited or no NTX. In particular embodiments, a functional response to an immunomodulatory treatment by a subject includes CRS grades 1-4. In particular embodiments, a subject who has a functional response to an immunomodulatory treatment has an increase in Th22 cells as compared to a reference. Th22 cells are specialized T helper cells that secrete IL-22 and lack IL-4, IL-17, and IFNγ. Th22 cells function to protect epithelial barrier organs and modulate inflamed and/or injured tissue. In particular embodiments, the reference includes a subject or population of subjects who have a toxic response and/or non-response to an immunomodulatory treatment.

(III) Biological samples. "Sample" or "biological sample" refers to a biological material isolated from or derived from a subject. The biological sample may contain any biological material suitable for detecting a mRNA, polypeptide or other marker of a physiologic or pathologic process in a subject, and may include fluid, tissue, cellular and/or non-cellular material obtained from the individual. In particular embodiments, a biological sample may include blood, serum, cells, plasma, cerebral spinal fluid, and urine. In particular embodiments, a biological sample may include serum. Serum from blood is a light yellow, clear liquid that remains after blood has clotted. Serum may be obtained by centrifuging clotted blood. Serum does not include an anticoagulant. In particular embodiments, a biological sample may include plasma. Plasma is a light yellow, clear liquid that remains when blood clotting is prevented and can be obtained by centrifuging whole blood containing an anticoagulant. In particular embodiments, a biological sample can be obtained prior to an immunomodulatory treatment (pre-immunomodulatory treatment). In particular embodiments, a biological sample obtained pre-immunomodulatory treatment includes a pre-apheresis blood sample. A pre-apheresis blood sample is obtained at a time before a decision is made to perform apheresis on a subject. In particular embodiments, a pre-apheresis blood sample is obtained at a time before a decision is made to perform apheresis to obtain a subject's T cells to modify for CAR T cell therapy. In particular embodiments, a pre-apheresis blood sample includes a cell sample. In particular embodiments, a pre-apheresis blood sample includes a PBMC sample. In particular embodiments, a pre-apheresis blood sample includes a blood sample. In particular embodiments, a biological sample can be obtained 1 day, 2 days, 3 days, 4 days, 5 days, 6 days, 7 days, or more after an immunomodulatory treatment has initiated. In particular embodiments, a biological sample can be obtained after an immunomodulatory treatment has completed (post an immunomodulatory treatment). In particular embodiments, a biological sample isolated from or derived from a subject to measure levels of biomarkers and/or biomarker cell populations is referred to as a test sample. In particular embodiments, levels of biomarkers including IL-18, IL-18BP, IL-18R1, IL-18RAP, sIL-2RA, IL-2, IL-5, IL-6, IL-9, IL-10, IL-22, IFNγ, GM-CSF, SAA, and CRP may be measured in a blood sample. In particular embodiments, the blood sample is a serum sample. In particular embodiments, the blood sample is a plasma sample.

In particular embodiments, a biological sample is derived from a subject or source. Particular embodiments of "derived from" refer to a biological sample being obtained from a subject or other source and including any modification to the sample, addition to the sample, or removal from the sample, as long as biomarkers of the present disclosure can be measured from the sample using the systems and methods of the present disclosure.

In particular embodiments, a biological sample may include cells. In particular embodiments, samples used in the methods of the present disclosure include peripheral blood mononuclear cells (PBMCs). PBMCs come from peripheral blood and originate from hematopoietic stem cells (HSCs) that reside in the bone marrow. A PBMC is a blood cell with a round nucleus and can include many types of cells including monocytes, lymphocytes (including T cells, B cells, and NK cells), dendritic cells, and stem cells. PBMC can be isolated by any technique known in the art, including density centrifugation (e.g., with Ficoll-Paque). Density gradient centrifugation separates cells by cell density. In particular embodiments, whole blood or buffy coat layer may be layered over or under a density medium without mixing of the two layers followed by centrifugation. In particular embodiments, the PBMC appears as a thin white layer at the interface between the plasma and the density gradient medium. In particular embodiments, Vacutainer® blood draw tubes containing Ficoll-Hypaque and a gel plug that separates the Ficoll solution from the blood to be drawn can be used (cell preparation tubes CPT™, BD Biosciences, San Jose, CA; Puleo et al. (2017) *Bio-protocol* 7(2): e2103). In particular embodiments, SepMate™ tubes (STEMCELL™ Technologies, Vancouver, CA) designed with an insert to keep the density gradient medium and the sample from mixing prior to centrifugation can be used. (Kerfoot et al., Proteomics Clin Appl, 2012. 6(7-8):394-402; Grievink et al., Biopreserv Biobank. 2016 October; 14(5):410-415; Corkum et al. (2015) BMC Immunol. 16:48; Jia et al. (2018) Biopreserv Biobank 16(2):82-91). In particular embodiments, PBMC can be isolated by leukapheresis. A leukapheresis machine is an automated device that takes whole blood from a donor and separates out the target PBMC fraction using high-speed centrifugation while returning the remaining portion of the blood, including plasma, red blood cells, and granulocytes, back to the donor. In particular embodiments, isolated PBMCs can be solubilized with 0.1% Triton X-100 in 50 mM ammonium bicarbonate. In particular embodiments, the level of a biomarker cell population including CD161+ and CD56+ dim cells may be measured in a PBMC sample.

In particular embodiments, a control sample includes a sample from a healthy subject or a population of healthy subjects. A healthy subject may include a subject who is not in need of immunotherapy and has no known diseases. In particular embodiments, a control sample includes a sample from a subject or a population of subjects who has/have a functional response to an immunomodulatory treatment with limited or no NTX. In particular embodiments, a control sample includes a sample from a subject or a population of subjects who has/have a functional response to an immunomodulatory treatment with limited or no NTX.

(IV) Assays for detection and quantification of biomarkers. Up- or down-regulation of biomarkers, as indicated elsewhere herein for particular biomarkers, can be assessed by comparing a measured value (from a test or subject sample) to a relevant reference level. For example, the quantity of one or more biomarkers can be indicated as a value. The value can be expressed numerically and result from assaying a sample, and can be derived, e.g., by measuring level(s) of the biomarker(s) in the sample by an assay performed in a laboratory, by measuring the ratio or ratios of the levels of two or more of the biomarkers, or from a dataset obtained from a provider such as a laboratory, or from a dataset stored on a server. A biomarker profile includes the level(s) of one or more measured biomarker(s). The biomarkers disclosed herein can be a protein biomarker, a nucleic acid biomarker (e.g., gene encoding the protein biomarker), a small molecule, one or more cell types, and/or one or more cell populations.

In the broadest sense, the value may be qualitative or quantitative. As such, where detection is qualitative, the systems and methods provide a reading or evaluation, e.g., assessment, of whether or not the biomarker is present in the sample being assayed. In yet other embodiments, the systems and methods provide a quantitative detection of whether the biomarker is present in the sample being assayed, i.e., an evaluation or assessment of the actual amount or relative abundance of the biomarker in the sample being assayed. In such embodiments, the quantitative detection may be absolute or, if the method is a method of detecting two or more different biomarkers in a sample, relative. As such, the term "quantifying" when used in the context of quantifying a biomarker in a sample can refer to absolute or to relative quantification. Absolute quantification can be accomplished by inclusion of known concentration(s) of one or more control biomarkers and referencing, e.g., normalizing, the detected level of the biomarker with the known control biomarkers (e.g., through generation of a standard curve). Alternatively, relative quantification can be accomplished by comparison of detected levels or amounts between two or more different biomarkers to provide a relative quantification of each of the two or more biomarkers, e.g., relative to each other. The actual measurement of values of the biomarkers can be determined using any method known in the art. In some embodiments, a biomarker is detected by contacting a sample with reagents (e.g., antibodies or nucleic acids), generating complexes of reagent and biomarker(s), and detecting the complexes.

The reagent can include a probe. A probe is a molecule that binds a target, either directly or indirectly. The target can be a biomarker, a fragment of a biomarker, or any molecule that is to be detected, In particular embodiments, the probe includes a nucleic acid or a protein. As an example, a protein probe can be an antibody. An antibody can be a whole antibody or a binding fragment of an antibody. A probe can be labeled with a detectable label Examples of detectable labels include fluorescent chromophores, chemiluminescent emitters, dyes, enzymes, enzyme substrates, enzyme cofactors, enzyme inhibitors, enzyme subunits, metal ions, and radioactive isotopes.

"Protein" detection includes detection of full-length proteins, mature proteins, pre-proteins, polypeptides, isoforms, mutant forms, post-translationally modified proteins and variants thereof, and can be detected in any suitable manner.

Those skilled in the art will be familiar with numerous specific immunoassay formats and variations thereof which can be used to carry out the methods disclosed herein. See, e.g., E. Maggio, Enzyme-Immunoassay (1980), CRC Press, Inc., Boca Raton, Fla; and U.S. Pat. Nos. 4,727,022; 4,659,678; 4,376,110; 4,275,149; 4,233,402; and 4,230,797.

Antibodies can be conjugated or immobilized to a solid support suitable for a diagnostic assay (e.g., beads such as protein A or protein G agarose, microspheres, plates, slides or wells formed from materials such as latex or polystyrene) in accordance with known techniques, such as passive binding. Antibodies can be conjugated to detectable labels or groups such as radioisotopes (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Examples of suitable immunoassays include immunoblotting, immunoprecipitation, immunofluorescence, chemiluminescence, electro-chemiluminescence (ECL), and/or enzyme-linked immunosorbent assays (ELISA). In particular embodiments, cytokines can be measured by ELISAs. In particular embodiments, cytokines can be measured by enzyme-linked immunospot (ELISpot) to detect cytokine-secreting cells at the single-cell level. Cytokine antibody arrays have been developed for multiplex analysis of cytokines in a single microplate. Multiplex arrays to profile multiple biomarkers simultaneously may include Meso Scale Discovery custom U-PLEX, Angiogenesis V-PLEX Panel 1 (K15190D-1), and Vascular Injury V-PLEX Panel 2 (K15198D-1) (Meso Scale Discovery (MSD), Rockville, MD). A U-PLEX assay, for example, may provide a 10-spot U-PLEX plate and unique linkers to create custom multiplex panels to detect any combination of biomarkers. Users provide their own biotinylated capture reagents that recognize analytes of interest. In U-PLEX assays, biotinylated capture reagents (e.g., antibodies, peptides, proteins, nucleic acids) are coupled to U-PLEX Linkers. The U-PLEX Linkers then self-assemble onto unique spots on the U-PLEX plate. After analytes (e.g., cytokines) in the sample bind to the capture reagents, detection antibodies conjugated with labels (e.g., electro-chemiluminescent MSD GOLD SULFO-TAG) bind to the analytes to complete the sandwich immunoassay. Once the sandwich immunoassay is complete, the plate is placed into an appropriate instrument to measure the amount of analyte present in the sample by detecting the label. For example, an instrument to detect an electro-chemiluminescent MSD GOLD SULFO-TAG applies a voltage to the plate electrodes to cause the captured labels to emit light. The instrument can measure the intensity of the emitted light, which is proportional to the amount of analyte present in the sample, providing a quantitative measure of each analyte in the sample. Angiogenesis V-PLEX Panel 1 assay allows measurement of levels of VEGF-A, VEGF-C, VEGF-D, Tie-2, Flt-1, PIGF, and FGF in a sample. Vascular Injury V-PLEX Panel 2 assay allows measurement of levels of SAA, CRP, VCAM-1, and ICAM-1.

In particular embodiments, biomarker levels can be assessed by flow cytometry or high performance liquid electrophoresis. In particular embodiments, flow cytometry can be used for intracellular cytokine detection. In particular embodiments, flow cytometry can be used to measure the level of a cell type or population of cells expressing one or more biomarkers, including: CD161+ CD3+ T cells; CD161+ CD4+ T cells; CD161+ CD4+ CD45RA-T cells; CD161+ CD8+ T cells; CD161+ CD8+ CD45RA+ T cells; CD161+ CD56+ NK cells; CD161+ MAIT cells; CD161+ GM-CSF+ NK cells; CD161+ GM-CSF+ MAIT cells; CD161+ GM-CSF+ T cells; CD161+ IFNγ+ NK cells; CD161+ IFNγ+ MAIT cells; CD161+ IFNγ+ T cells; CD161+ IFNγ+ NKT cells; or a combination thereof.

Antibodies that can be used to detect biomarkers of the present disclosure are available commercially. In particular embodiments, antibodies to detect IL-18 include: rabbit monoclonal clone 11 (ThermoFisher Scientific, #MA5-30764); rabbit polyclonal (LifeSpan BioSciences, #LS-C313397); and mouse monoclonal clone 5C6F8 (Proteintech Group Inc., #60070-1-Ig). In particular embodiments, antibodies to detect IL-18BP include: goat polyclonal (R&D Systems, #AF119); mouse monoclonal clone 136007 (R&D Systems, #MAB1191); and mouse monoclonal clone MM0379-10G36 (Santa Cruz Biotechnology, #sc-517545). In particular embodiments, antibodies to detect IL-18R1 include: clone H44 (BioLegend, #313810); mouse monoclonal clone 2B7E6 (ThermoFisher, #MA5-38474); and rabbit polyclonal (Novus Biologicals, #NBP1-85782). In particular embodiments, antibodies to detect IL-18RAP include: clone FAB118R (R&D Systems, #FAB118R-100); rabbit polyclonal (LifeSpan BioSciences, #LS-C165182); and rabbit polyclonal (Abnova Corporation, #H00008807-W01P). In particular embodiments, antibodies to detect sIL-2RA include: mouse monoclonal clone SB-647 (ProSci, #38-230); mouse monoclonal clone TC-758 (Creative Diagnostics, #CABT-B8954); and mouse monoclonal clone YNRhIL2R (Prospec Protein Specialists, #ANT-104). In particular embodiments, antibodies to detect IL-2 include: rat monoclonal clone MQ1-17H12 (ThermoFisher, #25-7029-42); rabbit polyclonal (GeneTex, #GTX101138); and mouse monoclonal (LifeSpan BioSciences, #LS-C104534). In particular embodiments, antibodies to detect IL-5 include: rat monoclonal clone TRFK5 (BioLegend, #504303); rabbit polyclonal (ThermoFisher, #PA5-96761); and mouse monoclonal clone 9906 (R&D Systems, #MAB-605). In particular embodiments, antibodies to detect IL-6 include: mouse monoclonal clone 5IL6 (ThermoFisher, #M620); mouse monoclonal clone 6708 (R&D Systems, #MAB206); and rabbit polyclonal (Millipore Sigma, #12143). In particular embodiments, antibodies to detect IL-9 include: rabbit monoclonal clone 1043G (R&D Systems, #MAB2091); mouse monoclonal clone MH9D1 (ThermoFisher, #12-7098-42); and mouse monoclonal clone MH9A4 (BioLegend, #507603). In particular embodiments, antibodies to detect IL-10 include: rabbit monoclonal clone 2050B (R&D Systems, #MAB9210); rat monoclonal clone JES3-9D7 (ThermoFisher, #53-7108-42); and rabbit polyclonal (Abcam, #ab34843). In particular embodiments, antibodies to detect IL-22 include: clone 2G12A41 (BioLegend, #366711); mouse monoclonal clone 22URTI (ThermoFisher, #25-7229-42); and mouse monoclonal clone 142928 (R&D Systems, #1C7821). In particular embodiments, antibodies to detect IFNγ include: mouse monoclonal clone B27 (BioLegend, #506516); mouse monoclonal clone 4SB3 (ThermoFisher, #53-7319-42); and mouse monoclonal clone 25723 (R&D Systems, #MAB2851). In particular embodiments, antibodies to detect GM-CSF include: clone BVD2-21C11 (BioLegend, #502305); mouse monoclonal clone 6804 (R&D Systems, #MAB615); and rabbit monoclonal clone EPR23689-17 (Abcam, #ab227031). In particular embodiments, antibodies to detect SAA include: mouse monoclonal clone mcl (ThermoFisher, #MA5-11729); mouse monoclonal clone Reu86.1 (Novus Biologicals, #NB600-1418); and mouse monoclonal (LifeSpan BioSciences, #LS-B2130). In particular embodiments, antibodies to detect CRP include: mouse monoclonal clone 232007 (R&D Systems, #MAB17071); mouse monoclonal clone 987313 (Novus Biologicals, #MAB17073); and mouse monoclonal clone 3F10A11 (Proteintech Group Inc., #66250-1-Ig). In particular embodiments, antibodies to detect CD161 include: mouse monoclonal clone HP-3G10 (BioLegend, #339922); mouse monoclonal clone 191B8 (Miltenyi Biotec, #130-113-591); and mouse monoclonal clone B199.2 (Bio-Rad, #MCA1855). In particular embodiments, antibodies to detect CD56 include: clone HCD56 (BioLegend, #318344); clone NCAM16.2 (BD Biosciences, #564057); and rabbit monoclonal clone 3H15L12 (ThermoFisher, #701379).

In particular embodiments, biomarker levels can be assessed by nanoparticle-modified aptamers. Aptamer pairs can bind to a target biomarker to form a sandwich complex fixed onto a microplate. In particular embodiments, the nanoparticle is a gold nanoparticle whose signal can be amplified by silver-enhancement technology and a microplate reader can measure absorbance.

Up- or down-regulation of genes encoding biomarkers of the disclosure also can be detected using, for example, cDNA arrays, cDNA fragment fingerprinting, cDNA sequencing, clone hybridization, differential display, differential screening, fluorescence resonance energy transfer (FRET) detection, liquid microarrays, PCR, RT-PCR, quantitative real-time RT-PCR analysis with TaqMan assays, molecular beacons, microelectric arrays, oligonucleotide arrays, polynucleotide arrays, serial analysis of gene expression (SAGE), and/or subtractive hybridization. In particular embodiments, nucleic acid sequences that correspond to nucleic acids encoding biomarkers can be used to construct primers and probes for detecting and/or measuring biomarker nucleic acids.

As an example, Northern hybridization analysis using probes which specifically recognize one or more biomarker nucleic acid sequences can be used to determine gene expression. Alternatively, expression can be measured using RT-PCR; e.g., polynucleotide primers specific for the differentially expressed biomarker mRNA sequences are used to reverse-transcribe the mRNA into complementary DNA, which is then amplified in PCR and can be visualized and quantified. Biomarker RNA can also be quantified using, for example, other target amplification methods, such as transcription mediated amplification (TMA), strand displacement amplification (SDA), and nucleic acid sequence based amplification (NASBA), or signal amplification methods (e.g., bDNA), and the like. Ribonuclease protection assays can also be used, using probes that specifically recognize one or more biomarker mRNA sequences, to quantify gene expression.

Further hybridization technologies that may be used are described in, for example, U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; and 5,800,992 as well as WO 95/21265; WO 96/31622; WO 97/10365; WO 97/27317; EP 373 203; and EP 785 280.

Proteins and nucleic acids can be conjugated to or immobilized on chips, such as microarray chips. See, for example, U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138. Microarray refers to a solid carrier or support that has a plurality of molecules bound to its surface at defined locations. The solid carrier or support can be made of any material. As an example, the material can be hard, such as metal, glass, plastic, silicon, ceramics, and textured and porous materials; or soft materials, such as gels, rubbers, polymers, and other non-rigid materials. The material can also be nylon membranes, epoxy-glass and borofluorate-glass. The solid carrier or support can be flat but need not be and can include any type of shape such as spherical shapes (e.g., beads or microspheres). The solid carrier or support can have a flat surface as in slides and micro-titer plates having one or more wells. In particular embodiments, an array or microarray can include small molecules.

Binding to proteins or nucleic acids on microarrays can be detected by scanning the microarray with a variety of laser or CCD-based scanners, and extracting features with software packages, for example, Imagene (Biodiscovery, Hawthorne, CA), Feature Extraction Software (Agilent), Scanalyze (Eisen, M. 1999. SCANALYZE User Manual; Stanford Univ., Stanford, Calif. Ver 2.32.), or GenePix (Axon Instruments).

In particular embodiments, levels, amounts, or ratios of biomarkers of the present disclosure can be measured by mass spectrometry. Mass spectrometry (MS) refers to an analytical technique to identify compounds by their mass. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector. See, e.g., U.S. Pat. Nos. 6,204,500; 6,107,623; 6,268,144; 6,124,137; Wright et al., Prostate Cancer and Prostatic Diseases 2:264-76 (1999); and Merchant and Weinberger, Electrophoresis 21:1164-67 (2000).

Embodiments disclosed herein can be used with high throughput screening (HTS). Typically, HTS refers to a format that performs at least 100 assays, at least 500 assays, at least 1000 assays, at least 5000 assays, at least 10,000 assays, or more per day. When enumerating assays, either the number of samples or the number of protein, nucleic acid, or other biomarkers assayed can be considered.

Generally HTS methods involve a logical or physical array of either the subject samples, or the protein or nucleic acid biomarkers, or both. Appropriate array formats include both liquid and solid phase arrays. For example, assays employing liquid phase arrays, e.g., for hybridization of nucleic acids, binding of antibodies or other receptors to ligand, etc., can be performed in multi-well or microtiter plates. Microtiter plates with 96, 384, or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis.

HTS assays and screening systems are commercially available from, for example, Zymark Corp. (Hopkinton, MA); Air Technical Industries (Mentor, OH); Beckman Instruments, Inc. (Fullerton, CA); Precision Systems, Inc. (Natick, MA), etc. These systems typically automate entire procedures including all sample and reagent pipetting, liquid dispensing, timed incubations, and final readings of the microplate in detector(s) appropriate for the assay. These configurable systems provide HTS as well as a high degree of flexibility and customization. The manufacturers of such systems provide detailed protocols for the various methods of HTS.

Methods disclosed herein can include assessing cell proliferation. Cell proliferation can be determined using assays including: staining of living cells with a fluorescent dye and measuring cell division by flow cytometry; measuring DNA synthesis during S phase of the cell cycle using nucleotide analogs (e.g., 5-bromo-2'-deoxyuridine, BrdU); measuring lactate dehydrogenase activity in metabolic cell proliferation assays; detecting proliferation markers present in proliferating cells but not in non-proliferating cells (e.g., detecting Ki-67 with an antibody); and measuring ATP concentration, as there is a linear relationship between cell number and ATP concentration (e.g., bioluminescence-based detection of ATP using luciferase enzyme). A cellular test for monocyte activation has been described (Ivanova et al. J Immunol Res. 2016; 2016:4789279).

(V) Reference levels and reference biomarker profiles. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. In particular embodiments, a dataset includes a biomarker profile including level(s) of one or more biomarker(s). As is understood by one of ordinary skill in the art, the reference level can be based on e.g., any mathematical or statistical formula useful and known in the art for arriving at a meaningful aggregate reference level from a collection of individual datapoints; e.g., mean, median, median of the mean, etc. Alternatively, a reference level or dataset to create a reference level can be obtained from a service provider such as a laboratory, or from a database or a server on which the dataset has been stored. In certain embodiments of the present disclosure, a dataset of values is determined by measuring biomarkers from a population known to have a functional response to an immunomodulatory treatment with limited or no NTX which can provide a quantitative measure of responsiveness to an immunomodulatory treatment in a subject.

Reference levels or reference biomarker profiles can be obtained from one or more relevant datasets. A reference level or reference biomarker profile from a dataset can be derived from previous measures derived from a population. A "population" is any grouping of subjects or samples of like specified characteristics. The grouping could be according to, for example, clinical parameters, clinical assessments, therapeutic regimens, disease status, severity of condition, etc.

Reference levels or reference biomarker profiles can include "normal" or "control" levels or profiles, defined according to, e.g., discrimination limits or risk defining thresholds, in order to define cut-off points and/or abnormal values or profiles for responsiveness to an immunomodulatory treatment. In particular embodiments, the reference level is the level of one or more biomarkers or combined biomarker indices typically found in a subject or a population of subjects who is/are healthy and is/are not undergoing immunotherapy. In particular embodiments, the reference level is from a subject or a population of subjects who has/have a functional response to an immunomodulatory treatment with limited or no NTX. Other terms for "reference levels" include "functional", "index," "baseline," "standard," "healthy," "uninfected," "normal," etc. Alternatively, the reference level can be a database of biomarker profiles from previously tested subjects who have a functional response to an immunomodulatory treatment with limited or no NTX over a clinically relevant time period, such as pre-immunomodulatory treatment, or 1 day, 3 days, and 7 days after an immunomodulatory treatment has initiated. Reference levels can also be derived from, e.g., a control subject or a control population of subjects whose response to an immunomodulatory treatment is known. In particular embodiments, the reference value or reference biomarker profile can be derived from: a subject or a population of subjects who is/are healthy and not undergoing immunotherapy; a subject or a population of subjects who is/are non-responsive to an immunomodulatory treatment; a subject or a population of subjects who has/have an overactive or toxic response to an immunomodulatory treatment; or a subject or a population of subjects who was/were non-responsive and/or had a toxic response to an immunomodulatory treatment but had been administered a treatment (intervention) to drive the non-response and/or toxic response to a functional response. In particular embodiments, a reference level or reference biomarker profile is an average of biomarker levels (corresponding to the same biomarkers in a test biomarker profile) from a population of subjects who have a functional response, do not respond, or have a toxic response to an immunomodulatory treatment. A reference level can also be derived from disease activity algorithms or computed indices from population studies.

The profile of biomarkers obtained from an individual, i.e., the test biomarker profile, can be compared to a reference biomarker profile. The reference biomarker profile can be generated from one individual or a population of two or more individuals. The population, for example, may include three, four, five, ten, 15, 20, 30, 40, 50 or more individuals. Furthermore, the reference biomarker profile and the individual's (test) biomarker profile that are compared in the methods of the present disclosure may be generated from the same individual, provided that the test and reference profiles are generated from biological samples taken at different time points and compared to one another. For example, a sample may be obtained from an individual at the start of a study period. A reference biomarker profile taken from that sample may then be compared to biomarker profiles generated from subsequent samples from the same individual. Such a comparison may be used, for example, to determine if the individual's response to an immunomodulatory treatment becomes more functional and/or less toxic over time.

The methods of the present disclosure include comparing an individual's biomarker profile with a reference biomarker profile. A "comparison" includes any means to discern at least one difference in the individual's and the reference biomarker profiles. Thus, a comparison may include a visual inspection of biomarker expression levels, and a comparison may include arithmetical or statistical comparisons of biomarker expression values in a biomarker profile. Such statistical comparisons include, but are not limited to, applying a decision rule. If the biomarker profiles include at least one internal standard, the comparison to discern a difference in the biomarker profiles may also include features of these internal standards, such that features of the biomarker are correlated to features of the internal standards. The comparison can predict the type of response a subject has to an immunomodulatory treatment or the comparison can indicate whether an intervention has changed the type of response a subject has to an immunomodulatory treatment. Conclusions can be drawn based on whether a test biomarker profile is statistically significantly different or not statistically significantly different from a reference biomarker profile. A measure is not statistically significantly different if the difference is within a level that would be expected to occur based on chance alone. In contrast, a statistically significant difference is one that is greater than what would be expected to occur by chance alone. Statistical significance or lack thereof can be determined by any of various methods well-known in the art. Examples of commonly used measures of statistical significance include the t-test and the p-value. The p-value represents the probability of obtaining a given result equivalent to a particular datapoint, where the datapoint is the result of random chance alone. A result is often considered significant (not random chance) at a p-value less than or equal to 0.05.

In particular embodiments, "significantly elevated" (or significantly up-regulated or significantly increased) refers to an increase of more than 10%, more than 20%, more than 30%, more than 40%, more than 50%, more than 60%, more than 70%, more than 80%, more than 90%, more than 100%, more than 150%, more than 200%, or more, compared to a reference level. In particular embodiments, "significantly downregulated" or "significantly decreased" refers to a decrease of more than 10%, more than 20%, more than 30%, more than 40%, more than 50%, more than 60%, more than 70%, more than 80%, more than 90%, or more, compared to a reference level.

In particular embodiments, values obtained about the biomarkers and/or other dataset components can be subjected to an analytic process with chosen parameters. The parameters of the analytic process may be those disclosed herein or those derived using guidelines described herein. The analytic process used to generate a result may be any type of process capable of providing a result useful for classifying a sample, for example, comparison of the obtained value with a reference level, a linear algorithm, a quadratic algorithm, a decision tree algorithm, or a voting algorithm. The analytic process may set a threshold for determining the probability that a sample belongs to a given class. The probability preferably is at least 60%, at least 70%, at least 80%, at least 90%, at least 95%, or higher.

"Interpretation functions," refers to the transformation of a set of observed data into a meaningful determination of particular interest; e.g., an interpretation function may be a predictive model that is created by utilizing one or more statistical algorithms to transform a dataset of observed biomarker data into a meaningful determination of a subject's responsiveness to an immunomodulatory treatment.

In particular embodiments, values of the measured biomarkers in a biomarker profile can be calculated into a score. Each value can be weighted evenly within an algorithm generating a score, or the values for particular biomarkers can be weighted more heavily in reaching the score. For example, biomarkers with higher sensitivity and/or specificity can be weighted more heavily than biomarkers with lower sensitivity and/or specificity to determine scores. Biomarkers may also be grouped into classes, and each class given a weighted score. For example, biomarker values for predicting a subject who will have a toxic and/or non-response to an immunomodulatory treatment may be grouped into classes and weighted as follows (from highest weight to lowest weight): Class 1: IL-18, IL-18BP, sIL-2RA, IFNγ, IL-10, IL-22, IL-5, GM-CSF, CD161+ cells, and CD56+ dim cells; and Class 2: IL-18R1, IL-18RAP, IL-2, IL-6, IL-9, CRP, SAA.

In particular embodiments, weighting scores involves converting the measurement of one biomarker that is identified and quantified in a test sample into one of many potential scores. A receiver operating characteristic (ROC) curve can be used to standardize the scoring between different biomarkers by enabling the use of a weighted score based on the inverse of a false positive % or false negative % defined from the ROC curve. The weighted score can be calculated by multiplying the AUC by a factor for a biomarker and then dividing by the false positive % or false negative % based on a ROC curve. The weighted score can be calculated using the formula:

$$\text{Weighted Score}=(\text{AUC}_x \times \text{factor})/(1-\%\ \text{specificity}_x)$$

wherein x is the biomarker; the, "factor," is a real number (such as 0, 1, 2, 3, 4, 5, 6, 7, 8, 9, 10, 11, 12, 13, 14, 15, 16, 17, 18, 19, 20, 21, 22, 23, 24, 25 and so on) throughout a particular set of biomarkers; and the specificity is a chosen value that does not exceed 95%. Multiplication of a factor for the particular set of primary biomarkers allows the user to scale the weighted score.

(VI) Methods of Use. Particular embodiments disclosed herein include obtaining a sample (e.g., blood, a sample including cells) derived from a subject; and measuring a level of at least one biomarker disclosed herein to generate a biomarker profile. In particular embodiments, the level of the at least one biomarker disclosed herein is measured using immunoassay, flow cytometry, or a combination thereof. In particular embodiments, methods disclosed herein include obtaining a biological sample derived from a subject; measuring a level of at least one biomarker disclosed herein to generate a test biomarker profile; comparing the test biomarker profile to a reference biomarker profile including the same measured biomarkers; and identifying the subject as having a toxic response or non-response to an immunomodulatory treatment when the level of the at least one measured biomarker is increased compared to the levels of the same biomarkers of a reference biomarker profile. In particular embodiments, the at least one biomarker is selected from interleukin (IL)-18, IL-18 binding protein (IL-18BP), IL-18 receptor 1 (IL-18R1), IL-18 receptor accessory protein (IL-18RAP), IL-2, soluble IL-2 receptor alpha (sIL-2RA), IL-5, IL-6, IL-9, IL-10, IL-22, Interferon gamma (IFNγ), Granulocyte Macrophage Colony Stimulating Factor (GM-CSF), serum amyloid A (SAA), C-reactive protein (CRP), CD161+ cells, CD56+ dim cells, or a combination thereof. In particular embodiments, the at least one biomarker is selected from IL-18, IL-18BP, sIL-2RA, IL-10, IL-22, IFNγ, CD161+ cells, or a combination thereof.

The biomarkers disclosed herein can be used to predict a subject's response to an immunomodulatory treatment before initiation of the immunomodulatory treatment (pre-immunomodulatory treatment). In particular embodiments, pre-immunomodulatory treatment includes a time before a decision is made to perform apheresis to obtain a subject's T cells to modify for CAR T cell therapy. In particular embodiments, a biological sample obtained from a subject pre-immunomodulatory treatment includes a pre-apheresis blood sample. In particular embodiments, a subject is identified as having or predicted to have a toxic response and/or non-response to an immunomodulatory treatment when the level of CD161+ cells, as measured in a test sample obtained from the subject pre-immunomodulatory treatment, is increased as compared to a level of CD161+ cells of a reference biomarker profile. In particular embodiments, a subject is identified as having or predicted to have a toxic response and/or non-response to an immunomodulatory treatment when the level of at least one biomarker selected from IL-18, IL-18BP, IL-18R1, IL-18RAP, sIL-2RA, IL-2, IL-5, IL-6, IL-9, IL-10, IL-22, IFNγ, GM-CSF, SAA, CRP, CD161+ cells, CD56+ dim cells, or a combination thereof, as measured in a test sample obtained from the subject pre-immunomodulatory treatment, is increased as compared to the same biomarkers of a reference biomarker profile. In particular embodiments, the subject is identified as having or predicted to have a toxic response and/or non-response to an immunomodulatory treatment when the level of the at least one biomarker selected from IL-18, IL-10, sIL-2RA, IFNγ, CD161+ cells, CD56+ dim cells, or a combination thereof, as measured in a test sample obtained from the subject pre-immunomodulatory treatment, is increased as compared to the same biomarkers of a reference biomarker profile. In particular embodiments, the CD161+ cells include: CD161+ CD3+ T cells; CD161+ CD4+ T cells; CD161+ CD4+ CD45RA-T cells; CD161+ CD8+ T cells; CD161+ CD8+ CD45RA+ T cells; CD161+ CD56+ NK cells; CD161+ MAIT cells; CD161+GM-CSF+ NK cells; CD161+ GM-CSF+ MAIT cells; CD161+ GM-CSF+ T cells; CD161+ IFNγ+NK cells; CD161+ IFNγ+ MAIT cells; CD161+ IFNγ+ T cells; or a combination thereof.

The biomarkers disclosed herein can be used to identify or predict a subject's response to an immunomodulatory treatment once an immunomodulatory treatment has initiated. In particular embodiments, biomarkers disclosed herein can be used to identify or predict a subject's response to an immunomodulatory treatment once an immunomodulatory treatment has initiated but before any adverse symptoms of CRS and/or NTX are evident. In particular embodiments, biomarkers disclosed herein can be used to predict a subject's response to an immunomodulatory treatment 1 day after an immunomodulatory treatment has initiated, 3 days after an immunomodulatory treatment has initiated, and/or 7 days after an immunomodulatory treatment has initiated.

In particular embodiments, the subject is identified as having or predicted to have a toxic response and/or non-response to an immunomodulatory treatment when the level of at least one biomarker selected from IL-18, IL-18BP, IL-18R1, IL-18RAP, IL-2, IL-5, IL-6, IL-9, IL-10, IL-22, sIL-2RA, IFNγ, GM-CSF, SAA, CRP, or a combination thereof, as measured in a test sample obtained from the subject after an immunomodulatory treatment has initiated, is increased as compared to the level(s) of the same biomarkers of a reference biomarker profile. In particular embodiments, the subject is identified as having or predicted to have a toxic response and/or non-response to an immunomodulatory treatment when the level of the at least one biomarker selected from IL-10, SAA, GM-CSF, IFNγ, or a combination thereof, as measured in a test sample obtained from the subject 1 day after an immunomodulatory treatment has initiated, is increased as compared to the level(s) of the same biomarkers of a reference biomarker profile. In particular embodiments, the subject is identified as having or predicted to have a toxic response and/or non-response to an immunomodulatory treatment when the level of the at least one biomarker selected from IL-10, CRP, IFNγ, GM-CSF, or a combination thereof, as measured in a test sample obtained from the subject 3 days after an immunomodulatory treatment has initiated, is increased as compared to the level(s) of the same biomarkers of a reference biomarker profile. In particular embodiments, the subject is identified as having or predicted to have a toxic response and/or non-response to an immunomodulatory treatment when the level of the at least one biomarker selected from IL-10, IL-5, sIL-2RA, GM-CSF, or a combination thereof, as measured in a test sample obtained from the subject 3 days after an immunomodulatory treatment has initiated, is increased as compared to the level(s) of the same biomarkers of a reference biomarker profile. In particular embodiments, the subject is identified as having or predicted to have a toxic response and/or non-response to an immunomodulatory treatment when the level of the at least one biomarker selected from IL-18, IL-18BP, IFNγ, or a combination thereof, as measured in a test sample obtained from the subject 7 days after an immunomodulatory treatment has initiated, is increased as compared to the level(s) of the same biomarkers of a reference biomarker profile. In particular embodiments, the subject is identified as having or predicted to have a toxic response and/or non-response to an immunomodulatory treatment when the level of the at least one biomarker selected from IL-18, IL-18BP, IL-22, or a combination thereof, as measured in a test sample obtained from the subject 7 days after an immunomodulatory treatment has initiated, is increased as compared to the level(s) of the same biomarkers of a reference biomarker profile.

In particular embodiments, the reference biomarker profile is from a subject or a population of subjects having a functional response to an immunomodulatory treatment with limited or no NTX. In particular embodiments, the reference biomarker profile is from a healthy subject or a population of healthy subjects. In particular embodiments, a reference biomarker profile includes levels of the same biomarkers as measured in a test sample and is from a subject or a population of subjects who have a functional response to an immunomodulatory treatment with limited or no NTX. In particular embodiments, a reference biomarker profile includes levels of the same biomarkers as measured in a test sample and is from a healthy subject or a population of healthy subjects. In particular embodiments, a reference biomarker profile includes levels of the same biomarkers measured at the same time points pre-immunomodulatory treatment or after an immunomodulatory treatment has initiated as the test sample, and is from a subject or a population of subjects who have a functional response to an immunomodulatory treatment with limited or no NTX.

In particular embodiments, the subject whose biomarker levels are being measured has not undergone an immunomodulatory treatment, is undergoing an immunomodulatory treatment, or has completed an immunomodulatory treatment. In particular embodiments, an immunomodulatory treatment includes immunotherapy. In particular embodiments, the immunotherapy includes a therapy that uses chimeric antigen receptor (CAR) modified T cells, therapeutic agents to deplete regulatory T cells, recombinant cytokines, immune checkpoint inhibitors, monoclonal antibodies, bispecific antibodies, dual-affinity retargeting antibodies (DART), immune-mobilizing monoclonal T cell receptors against cancer (ImmTAC®), vaccines, or combinations thereof.

In particular embodiments, the method further includes accepting the subject into or excluding the subject from a clinical trial when the subject has not undergone an immunomodulatory treatment. In particular embodiments, an increase in the level of CD161+ cells, as measured in a sample pre-immunomodulatory treatment (e.g. in a pre-apheresis blood sample), predicts that a subject will have a toxic response and/or nonresponse to CAR T cell therapy and that the subject should therefore be excluded from a clinical trial involving CAR T cell therapy. In particular embodiments, the method further includes terminating the existing immunomodulatory treatment and initiating another type of immunomodulatory treatment when the subject is undergoing the existing immunomodulatory treatment. In particular embodiments, the method further includes initiating another type of immunomodulatory treatment after a subject has completed an existing immunomodulatory treatment. For example, if a subject is identified as a non-responder to CAR T cell therapy, the CAR T cell therapy can be terminated an another type of immunomodulatory treatment can be initiated, such as recombinant cytokines, monoclonal antibodies, immune checkpoint inhibitors, bispecific antibodies, dual-affinity retargeting antibodies (DART), immune-mobilizing monoclonal T cell receptors against cancer (ImmTAC®), or vaccines.

In particular embodiments, methods of the disclosure further includes: selecting a therapeutic agent to administer to a subject, including measuring a level of at least one biomarker selected from the group consisting of interleukin (IL)-18; IL-18 binding protein (IL-18BP), interferon gamma (IFNγ), and CD161+ cells to generate a test biomarker profile; comparing the test biomarker profile to a reference biomarker profile including the level(s) of the same biomarker(s); and identifying the subject as having or predicting that the subject will have a toxic response and/or non-response to an immunomodulatory treatment when the test biomarker profile includes increased levels of the at least one biomarker as compared to the reference biomarker profile; and selecting a therapeutic agent to administer to the subject. In particular embodiments, the reference biomarker profile is from a subject or a population of subjects having a functional response to the immunomodulatory treatment with limited or no neurotoxicity (NTX). In particular embodiments, the biological sample includes a blood sample and/or a cell sample. In particular embodiments, the biological sample is obtained before the immunomodulatory treatment has initiated, and wherein the at least one biomarker is selected from IL-18BP and/or CD161+ cells. In particular embodiments, the biological sample is obtained 1 day, 3 days, and/or 7 days after the immunomodulatory treatment has initiated, and wherein the at least one biomarker is selected from the group consisting of IL-18, IL-18BP, and IFNγ. In particular embodiments, the immunomodulatory treatment includes administration of chimeric antigen receptor (CAR) T cell immunotherapy and the therapeutic agent includes: an anti-CD161 antibody, an anti-IL-18 antibody, an anti-IFNγ antibody, an IL-18BP, or a combination thereof. In particular embodiments, the immunomodulatory treatment includes administration of chimeric antigen receptor (CAR) T cell immunotherapy, and wherein the method further includes removing CD161+ cells from an apheresis product obtained from the subject prior to the immunomodulatory treatment to produce an apheresis product reduced in CD161+ cells. In particular embodiments, the method further includes contacting the apheresis product obtained from the subject with an anti-CD161 antibody.

In particular embodiments, methods of the disclosure further includes selecting a therapeutic agent to administer to a subject, including measuring a level of CD161+ cells in a biological sample obtained from a subject; comparing the level of CD161+ cells to a level of CD161+ cells of a control sample; identifying the subject as having or predicting that the subject will have a toxic response and/or non-response to an immunomodulatory treatment when the level of CD161+ cells in the biological sample is increased as compared to the level of CD161+ cells in the control sample; and selecting a therapeutic agent to administer to the subject. In particular embodiments, the subject has not undergone an immunomodulatory treatment. In particular embodiments, the biological sample includes a cell sample. In particular embodiments, the cell sample is a PBMC sample. In particular embodiments, the immunomodulatory treatment includes chimeric antigen receptor (CAR) T cell immunotherapy and the therapeutic agent includes an anti-CD161 antibody.

In particular embodiments, a control sample is from a healthy subject or a population of healthy subjects. In particular embodiments, a control sample is from a subject or a population of subjects who has/have a functional response to the immunomodulatory treatment with limited or no NTX.

In particular embodiments, methods of the disclosure further includes treating subjects who have a toxic response and/or non-response to an immunomodulatory treatment with an anti-CD161 antibody. Commercially available anti-CD161 antibodies include: mouse anti-human CD161 clone HP-3G10 (BioLegend, San Diego, CA); mouse anti-human CD161 clone DX12 (BD Biosciences, San Jose, CA), and mouse anti-human CD161 clone B199.2 (Life Span BioSciences, Seattle, WA). In particular embodiments, an immunomodulatory treatment includes CAR T cell immunotherapy. In particular embodiments, treatment can occur before initiation of the immunomodulatory treatment, during the immunomodulatory treatment, or after the immunomodulatory treatment has been completed. In particular embodiments, an increase in the level of CD161+, as measured in a sample pre-immunomodulatory treatment (e.g. in a pre-apheresis blood sample) predicts that a subject will have a toxic response and/or nonresponse to CAR T cell therapy. Therefore, removing CD161+ cells from an apheresis product obtained from a subject prior to CAR T cell therapy may be a treatment to drive a potential toxic response and/or nonresponse to a functional response. In particular embodiments, treatment can occur at time points up to 7 days after initiation of the immunomodulatory treatment.

In particular embodiments, methods of the disclosure further includes treating subjects who have a toxic response and/or non-response to an immunomodulatory treatment with an anti-IL-18 antibody. Commercially available anti-IL-18 antibodies include: mouse anti-human IL-18 clone 50008-2 (Life Span BioSciences, Seattle, WA); rat anti-human IL-18 clone 159-12B (R&D Systems, Minneapolis, MN); and rat anti-human IL-18 (BioLegend, San Diego, CA). In particular embodiments, an immunomodulatory treatment includes CAR T cell immunotherapy. In particular embodiments, treatment can occur before initiation of the immunomodulatory treatment, during the immunomodulatory treatment, or after the immunomodulatory treatment has been completed. In particular embodiments, treatment can occur at time points up to 7 days after initiation of the immunomodulatory treatment.

In particular embodiments, methods of the disclosure further includes treating subjects who have a toxic response and/or non-response to an immunomodulatory treatment with an anti-IFNγ antibody. An anti-IFNγ monoclonal antibody, emapalumab (Gamifant®) is available to treat hemophagocytic lymphohistiocytosis. Commercially available anti-IL-IFNγ antibodies include: polyclonal rabbit anti-human IFNγ (LS-B7487, Life Span BioSciences, Seattle, WA); polyclonal rabbit anti-human IFNγ (RP1002, BosterBio, Pleasanton, CA); and polyclonal rabbit anti-human IFNγ (MBS821883, MyBioSource.com, San Diego, CA). In particular embodiments, an immunomodulatory treatment includes CAR T cell immunotherapy. In particular embodiments, treatment can occur before initiation of the immunomodulatory treatment, during the immunomodulatory treatment, or after the immunomodulatory treatment has been completed. In particular embodiments, treatment can occur at time points up to 7 days after initiation of the immunomodulatory treatment.

In particular embodiments, methods of the disclosure further includes treating subjects who have a toxic response and/or non-response to an immunomodulatory treatment with an IL-18BP. In particular embodiments, the IL-18BP is a recombinant human IL-18BP. In particular embodiments, the recombinant human IL-18BP can be obtained commercially, for example, from R&D Systems, Minneapolis, MN (Cat No. 119-BP). In particular embodiments, the recombinant human IL-18BP includes Tadekinig alfa (AB2 Bio Ltd., Lausanne, Switzerland). In particular embodiments, an immunomodulatory treatment includes CAR T cell immunotherapy. In particular embodiments, treatment can occur before initiation of the immunomodulatory treatment, during the immunomodulatory treatment, or after the immunomodulatory treatment has been completed. In particular embodiments, treatment can occur at time points up to 7 days after initiation of the immunomodulatory treatment.

In particular embodiments, methods of the disclosure further includes providing to a subject who will undergo CAR T cell immunotherapy a CAR T cell product that will promote a functional response from the subject. In particular embodiments, the CAR T cell product is produced by genetically modifying T cells that were obtained from the subject prior to genetically modifying the T cells to express a CAR. In particular embodiments, the CAR T cell product that promotes a functional response is depleted of CD161+ cells. In particular embodiments, depletion of CD161+ cells from a CAR T cell product can include contacting the CAR T cell product with an anti-CD161 antibody. Exemplary anti-CD161 antibodies are described herein.

In particular embodiments, non-responders can be treated with recombinant cytokines (e.g., IL-2, IFN-α, IL-15, IL-21, IL-12, IL-10, and GM-CSF), epigenetic blockade regulators (e.g., DNA methyltransferase inhibitors (e.g., azacytidine, 5-aza-2'-deoxycytidine), histone deacetylase inhibitors (e.g., suberoylanilide hydroxamic acid, romidepsin, belinostat, panobinostat, chidamide), inhibitors of demethylation of cells), probiotics and prebiotics to re-train or diversify gut microbiota, and/or nanoparticles conjugated with immunomodulatory agents to fine-tune the target microenvironment. Immunomodulatory agents that can be conjugated to nanoparticles include: tecemotide; RNAs targeting tumour-associated antigens MAGE-A3, NY-ESO-1, tyrosinase, and TPTE (Lipo-MERIT); human leukocyte antigen (HLA)-A2 restricted peptides (DPX-0907); survivin (DPX-Survivac); cholesteryl hydrophobized pullulan complexed with the cancer-testis antigen NY-ESO-1 protein (CHP-NY-ESO-1); recombinant human TNF (CYT-6091); IL-2 (Oncoquest-L); adjuvant (AS15, ISCOMATRIX™, JVRS-100); agent that targets dendritic cells (Lipovaxin MM); melanocyte differentiation antigen (Melan-A VLPs); viruses or viral antigens (Epaxal, Inflexal V); mycobacterial cordfactor (CAF01); and viral glycoproteins (e.g., Rpg120/HIV-1SF2).

In particular embodiments, the method further includes administering a therapeutic agent when the subject is undergoing the immunomodulatory treatment or has completed an immunomodulatory treatment to decrease a toxic response to immunotherapy. For example, if a subject is identified as having a toxic and/or non-response to an immunomodulatory treatment, a therapeutic agent can be administered to drive the aberrant response to a functional response, including: agents that interfere with antigen presentation (e.g., cyclooxygenase inhibitors (e.g., aspirin, ibuprofen), anti-CD154, CTLA4-Ig (abatacept)), agents that interfere with T-cell activation (e.g., calcineurin inhibitors, including cyclosporine A and tacrolimus; dasatinib); agents that interfere with T-cell proliferation (e.g., sirolimus, mycophenolate mofetil, leflunomide); agents that deplete T cells (e.g., alemtuzumab (anti-CD52 monoclonal antibody)), anti-thymocyte globulin (ATG), IL-1R-based inhibitors (e.g., anakinra, cyclophosphamide); an anti-IFNγ monoclonal antibody (e.g., emapalumab); or corticosteroids (e.g., dexamethasone, prednisone, budesonide, prednisolone, methylprednisolone). In particular embodiments, CRS associated with a toxic response to an immunomodulatory treatment can be treated with broad spectrum antibiotics, anti-histamines, antipyretics, and/or fluids. In particular embodiments, CRS associated with a toxic response to an immunomodulatory treatment can be treated with immunosuppressive drugs including: an anti-IL-6 receptor monoclonal antibody (e.g., tocilizumab); an anti-IL-6 monoclonal antibody (e.g., siltuximab, clazakizumab); an anti-TNFα therapeutic (e.g., soluble TNFα receptor etanercept, adalimumab, certolizumab, golimumab, infliximab); an anti-GM-CSF antibody (e.g., lenzilumab); an IL-1 receptor antagonist (e.g., anakinra); a monoclonal antibody targeting IL-2RA (basiliximab, daclizumab); a monoclonal antibody targeting anti-IL17A (ixekizumab, secukinumab); a monoclonal antibody targeting a cell adhesion molecule α4 integrin (natalizumab, vedolizumab); a monoclonal antibody targeting CD20 (rituximab); a monoclonal antibody targeting IL-12 and IL-23 (ustekinumab); small molecule inhibitors of the JAK/STAT pathway (e.g., ruxolitinib, itacitinib); Bruton's tyrosine kinase (BTK) or IL-2 inducible T cell kinase inhibitor (e.g., ibrutinib (Ruella et al. (2016) Leukemia 31:246)); mTOR inhibitors (sirolimus, everolimus); and/or steroids. In particular embodiments, CRS associated with a toxic response to an immunomodulatory treatment can be treated with cytokine adsorption (Frimmel et al. (2014) Liver Transpl. 20(12):1523-1524; Greil et al. (2017) J Clin Immunol. 37:273-276). In particular embodiments, NTX associated with a toxic response to an immunomodulatory treatment can be treated with: corticosteroids (e.g., dexamethasone, prednisone, budesonide, prednisolone, methylprednisolone); an IL-1 receptor antagonist (e.g., anakinra); an anti-GM-CSF antibody (e.g., lenzilumab); a suppressor of T cell activation (e.g., dasatinib, inhibitor of T cell receptor signaling kinases); and/or defibrotide (an FDA approved drug for the treatment of hepatic veno-occlusive disease (Richardson et al. (2016) Blood 127:1656-1665)).

In particular embodiments, identifying a subject as having a toxic response and/or non-response to an immunomodulatory treatment includes marking a biological sample appropriately so that the subject (from whom the marked biological sample was derived) receives or does not receive a selected, appropriate treatment or disease management procedure or protocol. The marking can include physically marking a container that the biological sample resides in with appropriate information or entering such appropriate information about the biological sample into a computer.

In particular embodiments, a biological sample can be assessed 1 time, 2 times, 3 times, 4 times, 5 times, 6 times, 7 times, 8 times, 9 times, 10 times and every remaining integer up to 100 times or more.

Particular embodiments include monitoring a response a subject will have to an immunomodulatory treatment including measuring a level of at least one biomarker described herein over a period of time. In particular embodiments, the subject will undergo, is undergoing, or has undergone an immunomodulatory treatment. In particular embodiments, a subject is selected for screening for responsiveness to an immunomodulatory treatment according to the systems and methods disclosed herein because they have been identified as a subject that would benefit from monitoring for response to an immunomodulatory treatment. Patients who could benefit from monitoring for response to an immunomodulatory treatment can include those who have an underlying immunodeficiency or those with an overactive immune system.

In particular embodiments, biological samples can be obtained and assessed from a subject weekly, monthly, every 2 months, every 3 months, every 4 months, every 5 months, every 6 months, every 7 months, every 8 months, every 9 months, every 10 months, or every 11 months, yearly, or at longer spaced periods, to monitor the subject's response to an immunomodulatory treatment.

In particular embodiments, "stable" measures are measures evaluated in relation to a previous comparison in the same patient and denote a stable biomarker level that has not changed significantly (as determined by a statistical measure known in the art such as a t-test or p-value, e.g., p value >0.05) since the last measurement. In particular embodiments, "stable" measures are measures evaluated in relation to a previous comparison in the same patient and denote a biomarker level that has not changed significantly (as determined by a statistical measure known in the art such as a t-test or p-value, e.g., p value >0.05) since an aggregated or averaged group of previous measurements (e.g., the last 3, 4, or 5 measurements).

"Unchanged" measures are measures evaluated in relation to a previous comparison in the same patient and denote a failure to achieve a statistically significant change (e.g., as determined by a statistical measure known in the art such as a t-test or p-value, e.g., p value >0.05) in a score towards or away from a reference level in the particular subject. In particular embodiments, "unchanged" measures are measures that have not changed in relation to a previous measurement in the same patient or since an aggregated or averaged group of previous measurements in the patient (e.g., the last 3, 4, or 5 measurements).

In particular embodiments, a subject is undergoing or has undergone immunotherapy to treat cancer. "Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx), digestive system (e.g., esophagus, stomach, small intestine, colon, rectum, liver, bile duct, gall bladder, pancreas), respiratory system (e.g., larynx, lung, bronchus), bones, joints, skin (e.g., basal cell, squamous cell, meningioma), breast, genital system, (e.g., uterus, ovary, prostate, testis), urinary system (e.g., bladder, kidney, ureter), eye, nervous system (e.g., brain, spinal cord), endocrine system (e.g., thyroid), and hematopoietic system (e.g., lymphoma, myeloma, leukemia, acute lymphocytic leukemia, chronic lymphocytic leukemia, acute myeloid leukemia, chronic myeloid leukemia, etc.). In particular embodiments, the cancer is pediatric acute lymphoblastic leukemia (ALL).

In particular embodiments, a subject is undergoing or has undergone immunotherapy to treat an infectious disease. Infectious diseases refer to diseases that are caused by infectious agents including bacteria, fungi, protozoa, and viruses. Viral diseases that can be treated include those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, coronavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases that can be treated include mycobacteria *rickettsia, mycoplasma, neisseria, S. pneumonia, Borrelia burgdorferi* (Lyme disease), *Bacillus antracis* (anthrax), tetanus, *streptococcus, staphylococcus, mycobacterium*, pertussis, cholera, plague, diptheria, *chlamydia, S. aureus* and *legionella.*

Protozoan diseases caused by protozoa that can be treated include *leishmania*, kokzidioa, *trypanosoma schistosoma* or malaria. Parasitic diseases caused by parasites that can be treated, protected against, and/or managed in accordance with the methods described herein include, but are not limited to, *chlamydia* and *rickettsia.*

In particular embodiments, a subject is undergoing or has undergone immunotherapy to treat an autoimmune disease. Autoimmune diseases include alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, dermatitis herpetiformis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia fibromyositis, Graves' disease, Guillain-Barre, Hashimoto's thyroiditis, hypothyroidism, idiopathic pulmonary fibrosis, idiopathic thrombocytopenia purpura (ITP), IgA nephropathy, insulin dependent diabetes, irritable bowel disease (IBD), juvenile arthritis, lichen planus, lupus, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-person syndrome, Takayasu arteritis, temporal arteritis/giant cell arteritis, ulcerative colitis, uveitis, vasculitis, vitiligo, Wegener's granulomatosis, and myasthenia gravis.

Methods disclosed herein include treating subjects (e.g., humans, veterinary animals (dogs, cats, reptiles, birds) livestock (e.g., horses, cattle, goats, pigs, chickens) and research animals (e.g., monkeys, rats, mice, fish) with compositions disclosed herein. In particular embodiments, a subject includes a child. Treating subjects includes delivering therapeutically effective amounts. Therapeutically effective amounts include those that provide effective amounts, prophylactic treatments and/or therapeutic treatments.

An "effective amount" is the amount of a therapeutic agent necessary to result in a desired physiological change in the subject. Effective amounts are often administered for research purposes. Effective amounts disclosed herein can cause a statistically-significant effect in an animal model or in vitro assay relevant to the assessment of the effectiveness of the therapeutic agent in promoting response to an immunotherapy or in suppressing a toxic response to an immunotherapy.

A "prophylactic treatment" includes a treatment administered to a subject who does not display signs or symptoms of an aberrant immune response to immunotherapy or displays only early signs or symptoms of an aberrant immune response such that treatment is administered for the purpose of diminishing or decreasing the risk of developing an aberrant immune response to immunotherapy. Thus, a prophylactic treatment functions as a preventative treatment against an aberrant immune response to immunotherapy. In particular embodiments, prophylactic treatments reduce, delay, or prevent the worsening of an aberrant immune response to immunotherapy. In particular embodiments, an aberrant immune response to immunotherapy includes a toxic response and/or nonresponse.

A "therapeutic treatment" includes a treatment administered to a subject who displays symptoms or signs of an aberrant immune response to immunotherapy and is administered to the subject for the purpose of diminishing or eliminating those signs or symptoms of an aberrant immune response to immunotherapy. The therapeutic treatment can reduce, control, or eliminate aberrant immune response to immunotherapy and/or reduce control or eliminate side effects of the aberrant immune response to immunotherapy. In particular embodiments, an aberrant immune response to immunotherapy includes a toxic response and/or nonresponse.

Function as an effective amount, prophylactic treatment or therapeutic treatment are not mutually exclusive, and in particular embodiments, administered dosages may accomplish more than one treatment type.

In particular embodiments, therapeutically effective amounts promote a response to an immunotherapy. In particular embodiments, therapeutically effective amounts suppress a toxic response to an immunotherapy.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of response to immunotherapy, previous or concurrent immunotherapy, idiopathy of the subject and route of administration.

Useful doses can range from 0.1 to 5 μg/kg or from 0.5 to 1 μg/kg. In other non-limiting examples, a dose can include 1 μg/kg, 15 μg/kg, 30 μg/kg, 50 μg/kg, 55 μg/kg, 70 μg/kg, 90 μg/kg, 150 μg/kg, 350 μg/kg, 500 μg/kg, 750 μg/kg, 1000 μg/kg, 0.1 to 5 mg/kg or from 0.5 to 1 mg/kg. In other non-limiting examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

(VII) Kits. The systems and methods disclosed herein include kits. Disclosed kits include material(s) and reagent(s) necessary to assay a sample obtained from a subject for the level of one or more biomarkers disclosed herein. The materials and reagents can include those necessary to assay the biomarkers disclosed herein according to any method described herein and/or known to one of ordinary skill in the art. The biomarkers to assay for include: interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; Interferon gamma (IFNγ); Granulocyte Macrophage Colony Stimulating Factor (GM-CSF); serum amyloid A (SAA); C-reactive protein (CRP); CD161+ cells; CD56+ dim cells; CD161+ CD3+ T cells; CD161+ CD4+ T cells; CD161+ CD4+ CD45RA-T cells; CD161+ CD8+ T cells; CD161+CD8+ CD45RA+ T cells; CD161+ CD56+ NK cells; CD161+ MAIT cells; CD161+ GM-CSF+ NK cells; CD161+ GM-CSF+ MAIT cells; CD161+ GM-CSF+ T cells; CD161+ IFNγ+ NK cells; CD161+ IFNγ+ MAIT cells; CD161+ IFNγ+ T cells; CD161+ IFNγ+ NKT cells; or a combination thereof.

Particular embodiments include materials and reagents necessary to assay for up- or down-regulation of a biomarker protein in a sample. In particular embodiments, the kits include antibodies, aptamers, epitopes, or mimotopes to bind biomarker proteins. Other embodiments additionally or alternatively include oligonucleotides that specifically assay for one or more biomarker nucleic acids based on homology and/or complementarity with biomarker nucleic acids. The oligonucleotide sequences may correspond to fragments of the biomarker nucleic acids. For example, the oligonucleotides can be more than 200, 175, 150, 100, 50, 25, 10, or fewer than 10 nucleotides in length. Collectively, any molecule (e.g., antibody, aptamer, epitope, mimotope, oligonucleotide) that forms a complex with a biomarker is referred to as a biomarker binding agent herein. In particular embodiments, the kits include biomarker binding agents that bind the following: IL-18; IL-18BP; IL-18R1; IL-18RAP; CD161; CD56; IL-2; sIL-2RA; IL-5; IL-6; IL-9; IL-10; IL-22; IFNγ; GM-CSF; SAA; and CRP.

Embodiments of kits can contain in separate containers biomarker binding agents either bound to a matrix or packaged separately with reagents for binding to a solid phase. In particular embodiments, the solid phase is, for example, a porous strip, array, or microtiter plate. In particular embodiments, measurement or detection regions of the solid phase can include a plurality of sites containing biomarker binding agents. In particular embodiments, the solid phase can also contain sites for negative and/or positive controls. Alternatively, control sites can be located on a separate solid phase from the solid phase including the biomarker binding agents. Optionally, the different detection sites can contain different amounts of biomarker binding agents, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable size and shape and can be, e.g., in the shape of a bar or dot spanning the width (or a portion thereof) of a solid phase.

In some embodiments the solid phase can be a "chip." See, e.g., U.S. Pat. No. 5,744,305. In some embodiments the matrix can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Additional embodiments can include control formulations (positive and/or negative), and/or one or more detectable labels including a radioactive isotope, an enzyme reporter, a colorimetric label, a chemiluminescent label, a colored particles, gold nanoparticles, colloids, magnetic beads, or biotin among others. Examples of detectable labels include fluorescein, green fluorescent protein, rhodamine, cyanine dyes, dialkylcarbocyanine dyes, Alexa dyes, luciferase, and horseradish peroxidase. Instructions for carrying out an assay to detect one or more biomarkers, including, optionally, instructions for generating a score, can be included in the kit; e.g., written, tape, VCR, or CD-ROM.

In particular embodiments, the kits include materials and reagents necessary to conduct an immunoassay (e.g., ELISA). In particular embodiments, the kits include materials and reagents necessary to conduct amplification assays (e.g., PCR). In particular embodiments, the kits include materials and reagents necessary to perform immunohistochemical staining, flow cytometry, an enzyme-based colorimetric assay, and/or a protein activity assay. In particular embodiments, materials and reagents expressly exclude equipment (e.g., plate readers). In particular embodiments, kits can exclude materials and reagents commonly found in laboratory settings (pipettes; test tubes; buffer solutions, distilled $H_2O$).

(VIII) Exemplary Embodiments

1. A method of selecting a therapeutic agent to administer to a subject, including obtaining a biological sample derived from a subject;

measuring a level of at least one biomarker selected from the group consisting of interleukin (IL)-18; IL-18 binding protein (IL-18BP), interferon gamma (IFNγ), and CD161+ cells to generate a test biomarker profile;

comparing the test biomarker profile to a reference biomarker profile including the level(s) of the same biomarker(s); and identifying the subject as having or predicting that the subject will have a toxic response and/or non-response to an immunomodulatory treatment when the test biomarker profile includes increased levels of the at least one biomarker as compared to the reference biomarker profile; and selecting a therapeutic agent to administer to the subject.

2. The method of embodiment 1, wherein the reference biomarker profile is from a subject or a population of subjects having a functional response to the immunomodulatory treatment with limited or no neurotoxicity (NTX).

3. The method of embodiment 1 or 2, wherein the biological sample includes a blood sample and/or a cell sample.

4. The method of any of embodiments 1-3, wherein the biological sample is obtained before the immunomodulatory treatment has initiated, and wherein the at least one biomarker is selected from IL-18BP and/or CD161+ cells.

5. The method of any of embodiments 1-3, wherein the biological sample is obtained 1 day, 3 days, and/or 7 days after the immunomodulatory treatment has initiated, and wherein the at least one biomarker is selected from the group consisting of IL-18, IL-18BP, and IFNγ.

6. The method of any of embodiments 1-5, wherein the immunomodulatory treatment includes administration of chimeric antigen receptor (CAR) T cell immunotherapy and the therapeutic agent includes: an anti-CD161 antibody, an anti-IL-18 antibody, an anti-IFNγ antibody, an IL-18BP, or a combination thereof.

7. The method of any of embodiments 1-6, wherein the immunomodulatory treatment includes administration of chimeric antigen receptor (CAR) T cell immunotherapy, and wherein the method further includes removing CD161+ cells from an apheresis product obtained from the subject prior to the immunomodulatory treatment to produce an apheresis product reduced in CD161+ cells.

8. The method of embodiment 7, wherein the method further includes contacting the apheresis product obtained from the subject with an anti-CD161 antibody.

9. A method for generating a test biomarker profile including:

obtaining a biological sample derived from a subject;

measuring a level of (A) at least one biomarker selected from the group consisting of interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; interferon gamma (IFNγ); granulocyte macrophage colony stimulating factor (GM-CSF); serum amyloid A (SAA); and C-reactive protein (CRP); and/or (B) at least one biomarker cell population selected from CD161+ cells, CD56+ dim cells, or a combination thereof;

thereby generating a test biomarker profile including levels of the at least one biomarker and/or the at least one biomarker cell population.

10. The method of embodiment 9, wherein the CD161+ cells further include CD161+ CD3+ T cells; CD161+ CD4+ T cells; CD161+ CD4+ CD45RA-T cells; CD161+ CD8+ T cells; CD161+CD8+ CD45RA+ T cells; CD161+ CD56+ natural killer (NK) cells; CD161+ mucosal associated invariant T (MAIT) cells; CD161+ GM-CSF+ NK cells; CD161+ GM-CSF+ MAIT cells; CD161+GM-CSF+ T cells; CD161+ IFNγ+ NK cells; CD161+ IFNγ+ MAIT cells; CD161+ IFNγ+ T cells; CD161+ IFNγ+ NKT cells; or a combination thereof.

11. The method of embodiment 9 or 10, wherein the CD56+ dim cells are circulating NK cells.

12. The method of any of embodiments 9-11, wherein the subject has not undergone an immunomodulatory treatment, is undergoing an immunomodulatory treatment, or has completed an immunomodulatory treatment.

13. The method of any of embodiments 9-12, wherein the biological sample includes a blood sample and/or a cell sample.

14. The method of embodiment 13, wherein the blood sample is serum or plasma.

15. The method of embodiment 13, wherein the cell sample is a peripheral blood mononuclear (PBMC) sample.

16. The method of any of embodiments 9-15, further including comparing the test biomarker profile to a reference biomarker profile including the level(s) of the same biomarker(s); and identifying the subject as having or predicting that the subject will have a toxic response and/or non-response to an immunomodulatory treatment when the test biomarker profile includes increased levels of the at least one biomarker of (A) and/or an increased level of the at least one biomarker cell population of (B) as compared to the reference biomarker profile.

17. The method of embodiment 16, wherein the reference biomarker profile is from a subject or a population of subjects having a functional response to the immunomodulatory treatment with limited or no neurotoxicity (NTX).

18. The method of any of embodiments 9-17, wherein the at least one biomarker cell population of (B) is CD161+ cells, and wherein the level of the CD161+ cells of the test biomarker profile is increased 2-fold to 10-fold as compared to the level of CD161+ cells of the reference biomarker profile.

19. The method of any of embodiments 9-18, wherein the at least one biomarker cell population of (B) is CD161+ cells, and wherein the level of the CD161+ cells of the test biomarker profile is 10% to 30% of total live cells in the sample.

20. The method of any of embodiments 9-19, wherein the level of the at least one biomarker of (A) is increased 1.1-fold to 10-fold as compared to the level of the same at least one biomarker of the reference biomarker profile.

21. The method of any of embodiments 9-20, wherein the subject has not undergone the immunomodulatory treatment.

22. The method of embodiment 21, further including excluding the subject from a clinical trial.

23. The method of any of embodiments 9-20, wherein the subject is undergoing the immunomodulatory treatment.

24. The method of embodiment 23, further including terminating the immunomodulatory treatment and initiating a different immunomodulatory treatment.

25. The method of any of embodiments 9-20, wherein the subject has completed the immunomodulatory treatment.

26. The method of embodiment 25, further including initiating a different immunomodulatory treatment.

27. The method of any of embodiments 9-26, wherein the immunomodulatory treatment includes administering to the subject chimeric antigen receptor (CAR) T cell immunotherapy, therapeutic agents to deplete regulatory T cells, recombinant cytokines, immune checkpoint inhibitors, monoclonal antibodies, bispecific antibodies, dual-affinity retargeting antibodies, immune-mobilizing monoclonal T cell receptors against cancer, vaccines, or a combination thereof.

28. The method of any of embodiments 9-27, wherein the at least one biomarker cell population of (B) is CD161+ cells, wherein the immunomodulatory treatment includes administration of chimeric antigen receptor (CAR) T cell immunotherapy, and wherein the method further includes removing CD161+ cells from an apheresis product obtained from the subject prior to administration of the CAR T cell immunotherapy to produce an apheresis product reduced in CD161+ cells.

29. The method of embodiment 28, wherein the method further includes contacting the apheresis product obtained from the subject with an anti-CD161 antibody.

30. The method of any of embodiments 9-29, further including administering a therapeutic agent prior to initiating the immunomodulatory treatment in the subject and/or when the subject is undergoing the immunomodulatory treatment to drive the toxic and/or non-response to a functional response.

31. The method of embodiment 30, wherein the immunomodulatory treatment includes chimeric antigen receptor (CAR) T cell immunotherapy and the therapeutic agent includes: an anti-CD161 antibody, an anti-IL-18 antibody, an anti-IFNγ antibody, an IL-18BP, or a combination thereof.

32. The method of embodiment 30 or 31, wherein the administering occurs at time points up to 7 days after initiation of the immunomodulatory treatment.

33. The method of any of embodiments 30-32, wherein the therapeutic agent includes: recombinant cytokines; epigenetic blockade regulators; nanoparticles conjugated with immunomodulatory agents; antibodies; fusion proteins; small molecules; corticosteroids; or a combination thereof.

34. The method of embodiment 33, wherein the recombinant cytokines are selected from IL-2, IFN-α, IL-15, IL-21, IL-12, IL-10, GM-CSF, or a combination thereof.

35. The method of embodiment 33, wherein the epigenetic blockade regulators are selected from azacytidine, 5-aza-2'-deoxycytidine, suberoylanilide hydroxamic acid, romidepsin, belinostat, panobinostat, chidamide, or a combination thereof.

36. The method of embodiment 33, wherein the antibodies are selected from an anti-CD154 antibody, emapalumab, alemtuzumab, tocilizumab, siltuximab, clazakizumab, anti-thymocyte globulin, adalimumab, certolizumab, golimumab, infliximab, lenzilumab, basiliximab, daclizumab, ixekizumab, secukinumab, natalizumab, vedolizumab, rituximab, ustekinumab, or a combination thereof.

37. The method of embodiment 33, wherein the fusion proteins are abatacept and/or etanercept.

38. The method of embodiment 33, wherein the small molecules are selected from aspirin, ibuprofen, cyclosporine A, tacrolimus, dasatinib, sirolimus, everolimus, mycophenolate mofetil, leflunomide, anakinra, cyclophosphamide, ruxolitinib, itacitinib, ibrutinib, or a combination thereof.

39. The method of embodiment 33, wherein the corticosteroids are selected from dexamethasone, prednisone, budesonide, prednisolone, methylprednisolone, or a combination thereof.

40. The method of any of embodiments 9-39, further including monitoring the subject for a response to the immunomodulatory treatment, wherein the monitoring includes repeating the measuring while the subject is undergoing the immunomodulatory treatment, thereby monitoring the response the subject has to the immunomodulatory treatment.

41. The method of any of embodiments 9-40, wherein the measuring is performed prior to the subject undergoing an immunomodulatory treatment, while the subject is undergoing an immunomodulatory treatment, or after the subject has undergone an immunomodulatory treatment; and includes measuring at least one biomarker selected from the group consisting of IL-18, IL-18BP, sIL-2RA, IL-10, IL-22, and IFNγ.

42. The method of any of embodiments 9-41, wherein the measuring is performed prior to the subject undergoing an immunomodulatory treatment, while the subject is undergoing an immunomodulatory treatment, or after the subject has undergone an immunomodulatory treatment; and includes measuring at least one biomarker selected from the group consisting of IL-18, IL-18BP, and IFNγ.

43. The method of any of embodiments 10-42, wherein the measuring is performed prior to the subject undergoing an immunomodulatory treatment; and includes measuring (A) at least one biomarker selected from the group consisting of IL-18, IL-18BP, IL-10, sIL-2RA, IL-22, and IFNγ; and/or (B) at least one biomarker cell population selected from the group consisting of: CD56+ dim cells; CD161+ CD3+ T cells; CD161+ CD4+ T cells; CD161+ CD4+ CD45RA-T cells; CD161+ CD8+ T cells; CD161+ CD8+ CD45RA+ T cells; CD161+ CD56+ NK cells; CD161+ MAIT cells; CD161+ GM-CSF+ NK cells; CD161+ GM-CSF+ MAIT cells; CD161+ GM-CSF+ T cells; CD161+ IFNγ+ NK cells; CD161+ IFNγ+ MAIT cells; CD161+ IFNγ+ T cells; and CD161+ IFNγ+ NKT cells.

44. The method of embodiment 43, wherein the at least one biomarker includes IL-18BP.

45. The method of any of embodiments 9-42, wherein the measuring is performed 1 day after an immunomodulatory treatment has initiated and includes measuring at least one biomarker selected from the group consisting of IL-10, IFNγ, GM-CSF, and SAA.

46. The method of any of embodiments 9-42, wherein the measuring is performed 3 days after an immunomodulatory treatment has initiated and includes measuring at least one biomarker selected from the group consisting of IL-10, IFNγ, GM-CSF, and CRP.

47. The method of any of embodiments 9-42, wherein the measuring is performed 3 days after an immunomodulatory treatment has initiated and includes measuring at least one biomarker selected from the group consisting of sIL-2RA, IL-5, IL-10, and GM-CSF.

48. The method of any of embodiments 9-42, wherein the measuring is performed 7 days after an immunomodulatory treatment has initiated and includes measuring at least one biomarker selected from the group consisting of IL-18, IL-18BP, and IFNγ.

49. The method of any of embodiments 9-42, wherein the measuring is performed 7 days after an immunomodulatory treatment has initiated and includes measuring at least one biomarker selected from the group consisting of IL-18, IL-18BP, and IL-22.

50. The method of any of embodiments 9-49, wherein the measuring includes using immunoassay or flow cytometry.

51. A method of screening a subject for exclusion from a clinical trial, including obtaining a biological sample derived from a subject;

measuring a level of (A) at least one biomarker selected from the group consisting of interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; interferon gamma (IFNγ); granulocyte macrophage colony stimulating factor (GM-CSF); serum amyloid A (SAA); and C-reactive protein (CRP); and/or (B) at least one biomarker cell population selected from CD161+ cells, CD56+ dim cells, or a combination thereof; to generate a test biomarker profile;

comparing the test biomarker profile to a reference biomarker profile including the level(s) of the same biomarker(s);

identifying the subject as having or predicting that the subject will have a toxic response and/or non-response to an immunomodulatory treatment when the test biomarker profile includes an increased level of the at least one biomarker of (A) and/or an increased level of the at least one biomarker cell population of (B) as compared to the reference biomarker profile, thereby screening a subject for exclusion from a clinical trial.

52. The method of embodiment 51, wherein the reference biomarker profile is from a subject or a population of subjects having a functional response to the immunomodulatory treatment with limited or no neurotoxicity (NTX).

53. The method of embodiment 51 or 52, wherein the CD161+ cells further include CD161+ CD3+ T cells; CD161+ CD4+ T cells; CD161+ CD4+ CD45RA-T cells; CD161+ CD8+ T cells; CD161+ CD8+ CD45RA+ T cells; CD161+ CD56+ natural killer (NK) cells; CD161+ mucosal associated invariant T (MAIT) cells; CD161+ GM-CSF+ NK cells; CD161+ GM-CSF+ MAIT cells; CD161+GM-CSF+ T cells; CD161+ IFNγ+ NK cells; CD161+ IFNγ+ MAIT cells; CD161+ IFNγ+ T cells; CD161+ IFNγ+ NKT cells; or a combination thereof.

54. The method of any of embodiments 51-53, wherein the at least one biomarker includes IL-18BP and the at least one biomarker cell population includes CD161+ cells.

55. The method of any of embodiments 51-54, wherein the CD56+ dim cells are circulating NK cells.

56. The method of any of embodiments 51-55, wherein the subject has not undergone an immunomodulatory treatment, is undergoing an immunomodulatory treatment, or has completed an immunomodulatory treatment.

57. The method of any of embodiments 51-56, wherein the biological sample includes a blood sample and/or a cell sample.

58. The method of embodiment 57, wherein the blood sample is serum or plasma.

59. The method of embodiment 57, wherein the cell sample is a peripheral blood mononuclear (PBMC) sample.

60. The method of any of embodiments 51-59, wherein the at least one biomarker cell population of (B) is CD161+ cells, and wherein the level of the CD161+ cells of the test biomarker profile is increased 2-fold to 10-fold as compared to the level of CD161+ cells of the reference biomarker profile.

61. The method of any of embodiments 51-60, wherein the at least one biomarker cell population of (B) is CD161+ cells, and wherein the level of the CD161+ cells of the test biomarker profile is 10% to 30% of total live cells in the sample.

62. The method of any of embodiments 51-61, wherein the level of the at least one biomarker of (A) is increased 1.1-fold to 10-fold as compared to the level of the same at least one biomarker of the reference biomarker profile.

63. A method of selecting a therapeutic agent to administer to a subject, including measuring a level of (A) at least one biomarker selected from the group consisting of interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; interferon gamma (IFNγ); granulocyte macrophage colony stimulating factor (GM-CSF); serum amyloid A (SAA); and C-reactive protein (CRP); and/or (B) at least one biomarker cell population selected from CD161+ cells, CD56+ dim cells, or a combination thereof; to generate a test biomarker profile;

comparing the test biomarker profile to a reference biomarker profile including the level(s) of the same biomarker(s);

identifying the subject as having or predicting that the subject will have a toxic response and/or non-response to an immunomodulatory treatment when the test biomarker profile includes an increased level of the at least one biomarker of (A) and/or an increased level of the at least one biomarker cell population of (B) as compared to the reference biomarker profile, and selecting a therapeutic agent to administer to the subject.

64. The method of embodiment 63, wherein the subject has not undergone an immunomodulatory treatment, is undergoing an immunomodulatory treatment, or has completed an immunomodulatory treatment.

65. The method of embodiment 63 or 64, wherein the biological sample includes a blood sample and/or a cell sample.

66. The method of embodiment 65, wherein the blood sample is serum or plasma.

67. The method of embodiment 65, wherein the cell sample is a peripheral blood mononuclear (PBMC) sample.

68. The method of any of embodiments 63-67, wherein the biological sample is obtained before the immunomodulatory treatment has initiated, and wherein the at least one biomarker is includes IL-18BP and the at least one biomarker cell population includes CD161+ cells.

69. The method of any of embodiments 63-67, wherein the biological sample is obtained 1 day, 3 days, and/or 7 days after the immunomodulatory treatment has initiated, and wherein the at least one biomarker is selected from the group consisting of IL-18, IL-18BP, and IFNγ.

70. The method of any of embodiments 63-68, wherein the immunomodulatory treatment includes administering to the subject chimeric antigen receptor (CAR) T cell immunotherapy, therapeutic agents to deplete regulatory T cells, recombinant cytokines, immune checkpoint inhibitors, monoclonal antibodies, bispecific antibodies, dual-affinity retargeting antibodies, immune-mobilizing monoclonal T cell receptors against cancer, vaccines, or a combination thereof.

71. The method of any of embodiments 63-70, wherein the at least one biomarker cell population of (B) is CD161+ cells, wherein the immunomodulatory treatment includes administration of chimeric antigen receptor (CAR) T cell immunotherapy, and wherein the method further includes removing CD161+ cells from an apheresis product obtained from the subject prior to administration of the CAR T cell immunotherapy to produce an apheresis product reduced in CD161+ cells.

72. The method of embodiment 71, wherein the method further includes contacting the apheresis product obtained from the subject with an anti-CD161 antibody.

73. The method of any of embodiments 63-72, wherein the immunomodulatory treatment includes chimeric antigen receptor (CAR) T cell immunotherapy and the therapeutic agent includes: an anti-CD161 antibody, an anti-IL-18 antibody, an anti-IFNγ antibody, an IL-18BP, or a combination thereof.

74. The method of any of embodiments 63-73, further including administering a therapeutic agent prior to initiating the immunomodulatory treatment in the subject and/or when the subject is undergoing the immunomodulatory treatment.

75. The method of embodiment 74, wherein the administering occurs at time points up to 7 days after initiation of the immunomodulatory treatment.

76. The method of any of embodiments 63-75, wherein the therapeutic agent includes: recombinant cytokines; epigenetic blockade regulators; nanoparticles conjugated with immunomodulatory agents; antibodies; fusion proteins; small molecules; corticosteroids; or a combination thereof.

77. The method of embodiment 76, wherein the recombinant cytokines are selected from IL-2, IFN-α, IL-15, IL-21, IL-12, IL-10, GM-CSF, or a combination thereof.

78. The method of embodiment 76, wherein the epigenetic blockade regulators are selected from azacytidine, 5-aza-2'-deoxycytidine, suberoylanilide hydroxamic acid, romidepsin, belinostat, panobinostat, chidamide, or a combination thereof.

79. The method of embodiment 76, wherein the antibodies are selected from an anti-CD154 antibody, emapalumab, alemtuzumab, tocilizumab, siltuximab, clazakizumab, anti-thymocyte globulin, adalimumab, certolizumab, golimumab, infliximab, lenzilumab, basiliximab, daclizumab, ixekizumab, secukinumab, natalizumab, vedolizumab, rituximab, ustekinumab, or a combination thereof.

80. The method of embodiment 76, wherein the fusion proteins are abatacept and/or etanercept.

81. The method of embodiment 76, wherein the small molecules are selected from aspirin, ibuprofen, cyclosporine A, tacrolimus, dasatinib, sirolimus, everolimus, mycophenolate mofetil, leflunomide, anakinra, cyclophosphamide, ruxolitinib, itacitinib, ibrutinib, or a combination thereof.

82. The method of embodiment 76, wherein the corticosteroids are selected from dexamethasone, prednisone, budesonide, prednisolone, methylprednisolone, or a combination thereof.

83. A method of identifying a subject as having or predicting that a subject will have a toxic response and/or non-response to an immunomodulatory treatment including obtaining a biological sample derived from a subject;

measuring a level of (A) at least one biomarker selected from the group consisting of interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; interferon gamma (IFNγ); granulocyte macrophage colony stimulating factor (GM-CSF); serum amyloid A (SAA); and C-reactive protein (CRP); and/or (B) at least one biomarker cell population selected from CD161+ cells, CD56+ dim cells, or a combination thereof;

comparing the test biomarker profile to a reference biomarker profile including the level(s) of the same measured biomarker(s); and identifying the subject as having or predicting that the subject will have a toxic response and/or non-response to an immunomodulatory treatment when the test biomarker profile includes an increased level of the at least one biomarker of (A) and/or an increased level of the at least one biomarker cell population of (B) as compared to a reference biomarker profile.

84. The method of embodiment 83, wherein the reference biomarker profile is from a subject or a population of subjects having a functional response to the immunomodulatory treatment with limited or no neurotoxicity (NTX).

85. The method of embodiment 83 or 84, wherein the at least one biomarker cell population of (B) is CD161+ cells, and wherein the level of the CD161+ cells of the test biomarker profile is increased 2-fold to 10-fold as compared to the level of CD161+ cells of the reference biomarker profile.

86. The method of any of embodiments 83-85, wherein the at least one biomarker cell population of (B) is CD161+ cells, and wherein the level of the CD161+ cells of the test biomarker profile is 10% to 30% of total live cells in the sample.

87. The method of any of embodiments 83-86, wherein the level of the at least one biomarker of (A) is increased 1.1-fold to 10-fold as compared to the level of the same at least one biomarker of the reference biomarker profile.

88. A kit including at least two biomarker binding agents, wherein the at least two biomarker binding agents bind biomarkers selected from the group consisting of interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; interferon gamma (IFNγ); granulocyte macrophage colony stimulating factor (GM-CSF); serum amyloid A (SAA); and C-reactive protein (CRP); C-type lectin-like receptor (CD161)+ cells; CD56+ dim cells; or a combination thereof.

89. The kit of embodiment 88, wherein the at least two biomarker binding agents bind to biomarkers selected from the group consisting of IL-18, IL-18BP, sIL-2RA, IL-10, IL-22, IFNγ, and CD161+ cells.

90. The kit of embodiment 88 or 89, wherein the biomarker binding agents are proteins, antibodies, aptamers, mimotopes, or oligonucleotides.

91. The kit of any of embodiments 88-90, further including a detectable label.

92. The kit of embodiment 91, wherein the detectable label is a radioactive isotope, enzyme reporter, colorimetric label, fluorescent label, chemiluminescent label, colored particles, gold nanoparticles, colloids, magnetic bead, or biotin.

93. The kit of any of embodiments 88-92, wherein the kit includes reagents to perform amplification of nucleic acids, an immunoassay, an immunohistochemical staining, flow cytometry, an enzyme-based colorimetric assay, and/or a protein activity assay.

94. An array including at least two biomarkers selected from the group consisting of interleukin (IL)-18; IL-18 binding protein (IL-18BP); IL-18 receptor 1 (IL-18R1); IL-18 receptor accessory protein (IL-18RAP); IL-2; soluble IL-2 receptor alpha (sIL-2RA); IL-5; IL-6; IL-9; IL-10; IL-22; interferon gamma (IFNγ); granulocyte macrophage colony stimulating factor (GM-CSF); serum amyloid A (SAA); and C-reactive protein (CRP).

95. The array of embodiment 94, wherein the at least two biomarkers include IL-18, IL-18BP, sIL-2RA, IL-10, IL-22, and IFNγ.

96. An array including at least two biomarker cell populations including CD161+ cells and/or CD56+ dim cells.

(IX) Examples

Example 1. Studies were conducted to profile how cytokine composition and kinetics of monocytes both on a transcriptional and a protein level impact the spectrum of toxicity and response to immunotherapeutics (multi-trial biomarker validation). Tools, such as in vitro assays and protein engineering, can be developed and used to predict response and toxicity and derive mechanistic causality. Notably, these studies will lead to the development of a series of assays which can predict response rates, helping to identify subjects who may fail in immunotherapy trials, and mitigate life-threatening toxicity in subjects treated with CAR T-cells. Broadly, the mechanistic interrogation of macrophage activation states will lead to an understanding of how a subject's cytokine inflammatory status drives immune response and subsequently how that response drives tumor progression and therapeutic responses.

To understand the proinflammatory cytokine transcriptional program of the patient prior to CAR T, a number of assays were carried out. An Assay for Transposase Accessible Chromatin with high-throughput sequencing (ATAC-seq; Buenrostro et al. Curr Protoc Mol Biol. 2016; 109: 21.29.1-21.29.9) was performed to identify global program or open chromatin. Chromatin immunoprecipitation with high-throughput sequencing (ChIP-seq) was performed to identify transcription factors and/or methylation/acetylation marks. qPCR was used to validate hits obtained from ATAC-seq and ChIP-seq.

A population of randomized and blinded subset of pediatric patients were studied. Cytokine and epigenetic profiling from pediatric CAR T treated patients suggested that MP activation status as measured by open chromatin can predict CAR T toxicity and efficacy.

Machine learning models in CD19 CAR T treated patients showed evidence that an interferon gamma (IFNγ) (T-cell)-interleukin (IL)-18 myeloid (Mϕ) axis mediated post-CAR toxicity and response.

In severe toxicity patients (and non-responsive patients), there was elevated sIL-2RA and slightly elevated IL-2 levels. A dysfunctional IL-12 signaling cascade was also observed. In normal physiological conditions IL-18 co-signals with IL-12 to produce a robust IFNγ T-cell response.

Patient derived epigenetic data prior to CAR T therapy demonstrated openings within MP loci that mediate IL-18 activity/secretion, which could pre-dispose these patients to cytokine release syndrome/neurotoxicity (CRS/NTX) response. IL-18 binding protein (IL-18BP) is induced by IFNγ and, consistent with the IFN signature within the monocytes, high levels of IL-18BP were observed in the serum of dysfunctional patients. IL-18BP neutralizes IL-18, acting as an important negative regulator of inflammation, and has been shown to act as a checkpoint in immunotherapy (Zhou et al. Nature 2020, 583(7817):609-614). Importantly, the difference in IL-18BP levels between patient groups was so robust that the analysis demonstrated that only 10 non-responsive patients matched with 20 responders were needed to achieve >90% power. This initial pilot data demonstrated that functional responders with toxicity have impaired IL-18/IFNγ regulation (e.g. modified IL-12 signaling and upregulated IL-2 signaling) leading to aberrant uncontrolled activation.

Prophetic Example 1. Future studies will validate whether this hemophagocytic lymphohistiocytosis (HLH) pathway predicts toxicity across multiple immunotherapy trials through biomarker cytokine and chromatin validation assays. This work will further identify predictive early biomarkers that will be used to identify mechanisms/interventional strategies (e.g. cytokine blockade).

Example 2. It is well defined in HLH disorders that IL-18 signaling plays a causative role in aberrant T-cell function and signaling; however, IL-18 does not function alone. T-cells require stimulation from additional cytokines to induce the IL-18 receptor (IL-18R1), allowing response to IL-18. IL-12 is produced by macrophages in "normal" physiological conditions to license the T-cell response (Nakahira et al. Journal of immunology 2002, 168(3):1146-1153). If IL-12 signaling is absent, IL-2 signaling will cause an aberrant Th2 phenotype with high cytokine expression, as observed in severe toxicity patients (Rex et al. J Cell Commun Signal 2020, 14(2): 257-266). This modulation may be independent of CD25 signaling, which limits use of IL-2 in humanized animal models. Studies are ongoing to test a de novo mimic of IL-2 that lacks the CD25 signaling domain (Silva et al. Nature 2019, 565(7738):186-191). In pilot studies, IL-12 induced IL-18R1 expression in CAR T cells correlating with increased IFNγ secretion upon stimulation with antigen, while IL-2 decreased IL-18R1 mRNA and IFNγ production.

Example 3. Myeloid mediated signaling characteristics pre- and early post-CD19 CAR T cell infusion associate with clinical efficacy and toxicity outcomes. This study investigated whether a series of HLH myeloid associated cytokines, along with traditional CAR activated T and endothelial cell cytokines, both pre- and 7 days post-CAR therapy could predict non-response and severe NTX in acute lymphoblastic leukemia (ALL) CD19+ CAR T treated patients, with the goal of identifying a patient proinflammatory status characterized by a series of biomarkers that could be used clinically to help inform interventional and therapeutic mechanistic strategies.

Results. HLH Cytokines Predict CAR Outcomes at Early Time Points Pre-CAR. In HLH, the dangerous interplay between T cells and the myeloid compartment is driven by IFNγ and IL-18, with IL-18 inducing high levels of IFNγ (Nakanishi. Frontiers in immunology 9, 763 (2018)). Without being bound by any one hypothesis, the IFNγ (T-cell)-IL-18 (Mϕ) axis may mediate the continuum of post-CAR response and toxicity. In HLH disorders, IL-18 signaling plays a causative role in aberrant T-cell function and signaling; however, IL-18 does not function alone. T cells require stimulation from additional cytokines such as IL-12 to induce the IL-18 receptor (IL-18R1). IL-12 is produced by myeloid (Mϕ) in "normal" physiological conditions to license the T-cell response (Nakahira et al. Journal of immunology 168, 1146-1153 (2002)). If IL-12 signaling is absent, IL-2 signaling causes an aberrant Th2 phenotype with high cytokine expression, as classically observed in severe toxicity patients (Rex et al. J Cell Commun Signal 14, 257-266 (2020)). The study assessed whether the IFNγ (T-cell)-IL-18 (Mϕ) axis could group patients into specific sub-classifications post-CAR. IFNγ and IL-18 were included, along with co-stimulatory molecules (IL-12p70, IL-2, sIL-2RA, IL-10, etc.) of the IFNγ (T-cell)-IL-18 (Mϕ) axis, regulatory molecules (GM-CSF, IL-22, IL-18BP, etc.), as well as classical CAR T and severe NTX molecules (CRP, SAA, GM-CSF, IL-5, etc.) (a total of 22 were chosen, outlined in Materials and Methods).

Traditional clinical characteristics do not define clinical outcomes. The study focused on patients in phase 1 of the Pediatric Leukemia Adaptive Therapy-02 (PLAT02, NCT02028455) clinical trial. Forty-three elapsed/refractory pediatric B-ALL patients were enrolled at SCRI from 2012-2019 under PLAT02 and underwent CD19 (murine) directed CAR-T cell therapy. Construct, safety, and efficacy were previously reported (Gardner et al. Blood 129, 3322-3331 (2017); Finney et al. The Journal of clinical investigation 130). The study of the present Example focused on a retrospective cohort of 30 patients from PLAT02, with established clinical outcomes and matched serum (days 1, 3, 7) for unbiased classification and machine learning analysis. The study of the present Example also followed up with proposed mechanistic outcomes in a small cohort of 14 patients that had defined clinical outcomes, with stored day −1, day 10 and day 14, as well as pre-apheresis PBMC samples. Four patients were defined as dysfunctional (all included in both the larger and smaller cohort) which were relapsed patients who either did not have or briefly had complete response but had return CD19+ disease while still having CAR T cells. These patients had no or mild toxicity. Eleven (all included in the larger cohort and 5 patients include in the smaller cohort) patients were defined as having severe toxicity and were treatment responsive but had severe or mild NTX defined by any grade seizure, or grade 3/4 NTX exclusive of headache with varied degrees of CRS including severe CRS, defined as the need for vasopressors or inotropes, and/or respiratory failure. The remaining 15 patients (all included in the larger cohort, and 5 included in the smaller) were defined as functional and were responsive had a mixture of CRS severity including severe CRS but in the absence of NTX. A small cohort of 16 patients from the PLAT05 clinical trial (NCT03330691) were assessed to help support the machine learning findings. Importantly, no predictive clinical factors were determined in previous publications or in the current cohort analysis (FIGS. 6A-6F).

Figure 6A:
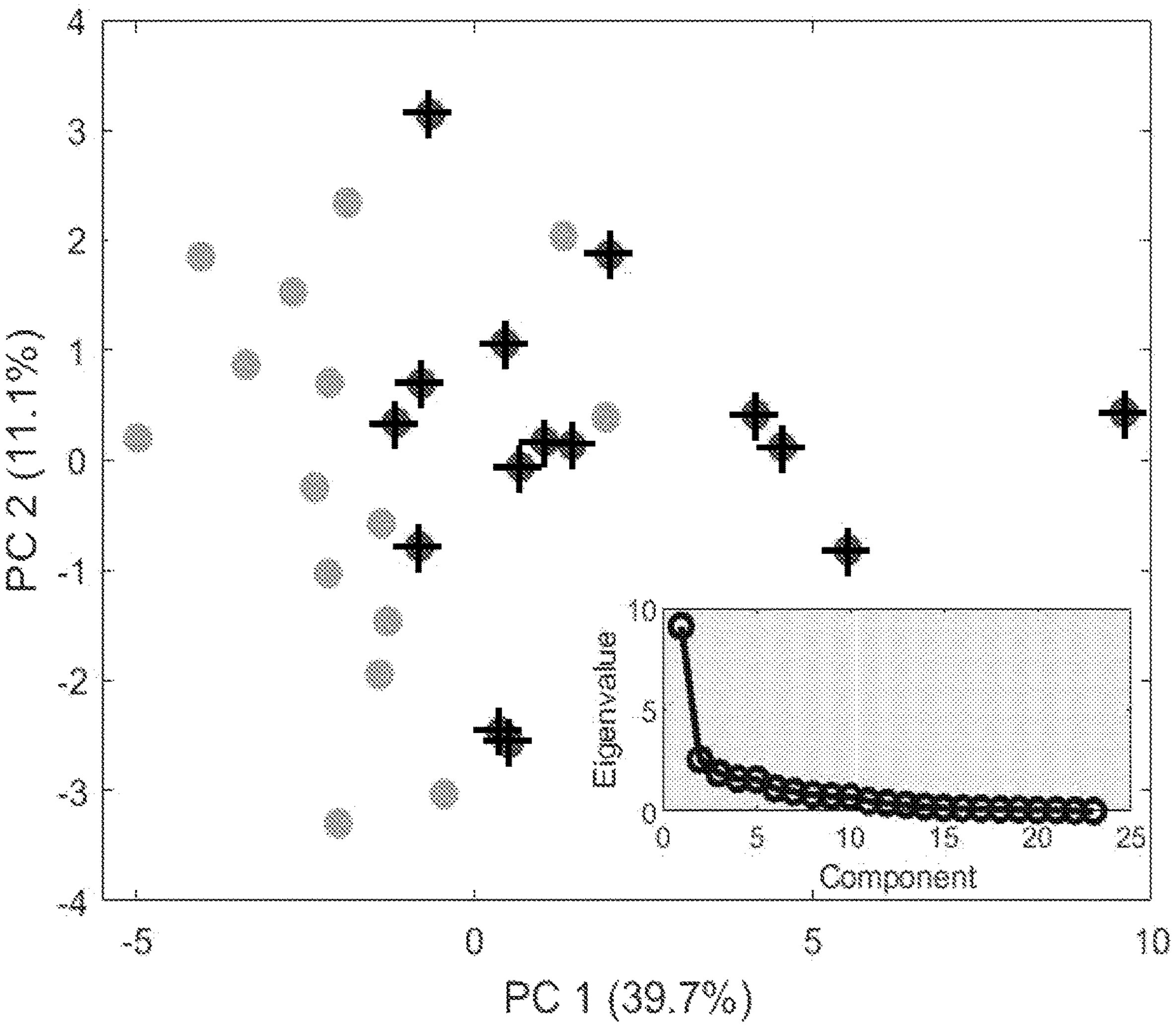
FIGS. 6A-6F. Unsupervised patient clustering based on early cytokine kinetics post-CAR T therapy drive patient groupings independent of traditional clinical outcomes.
Figure 6B:
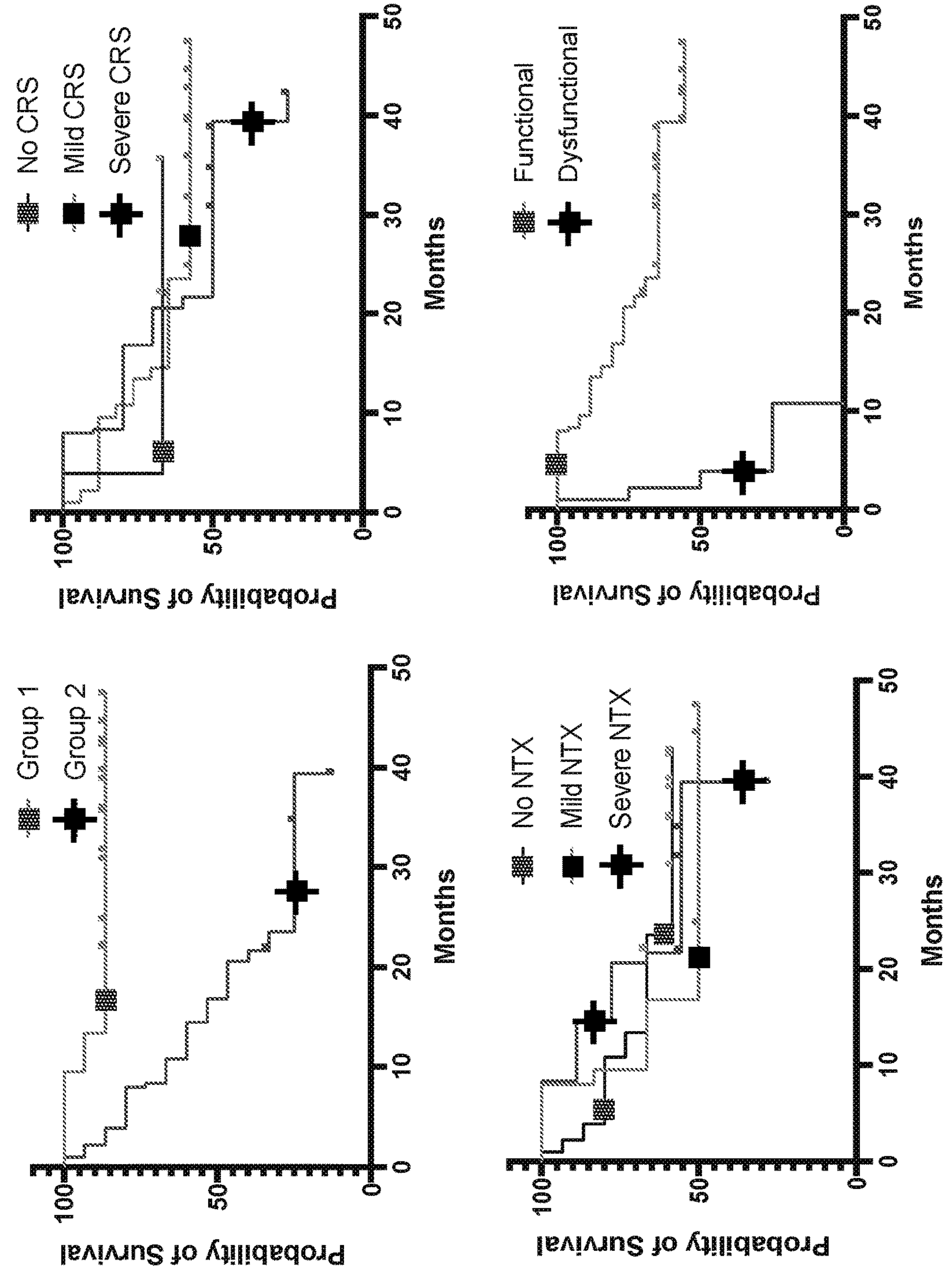
Figure 6C:
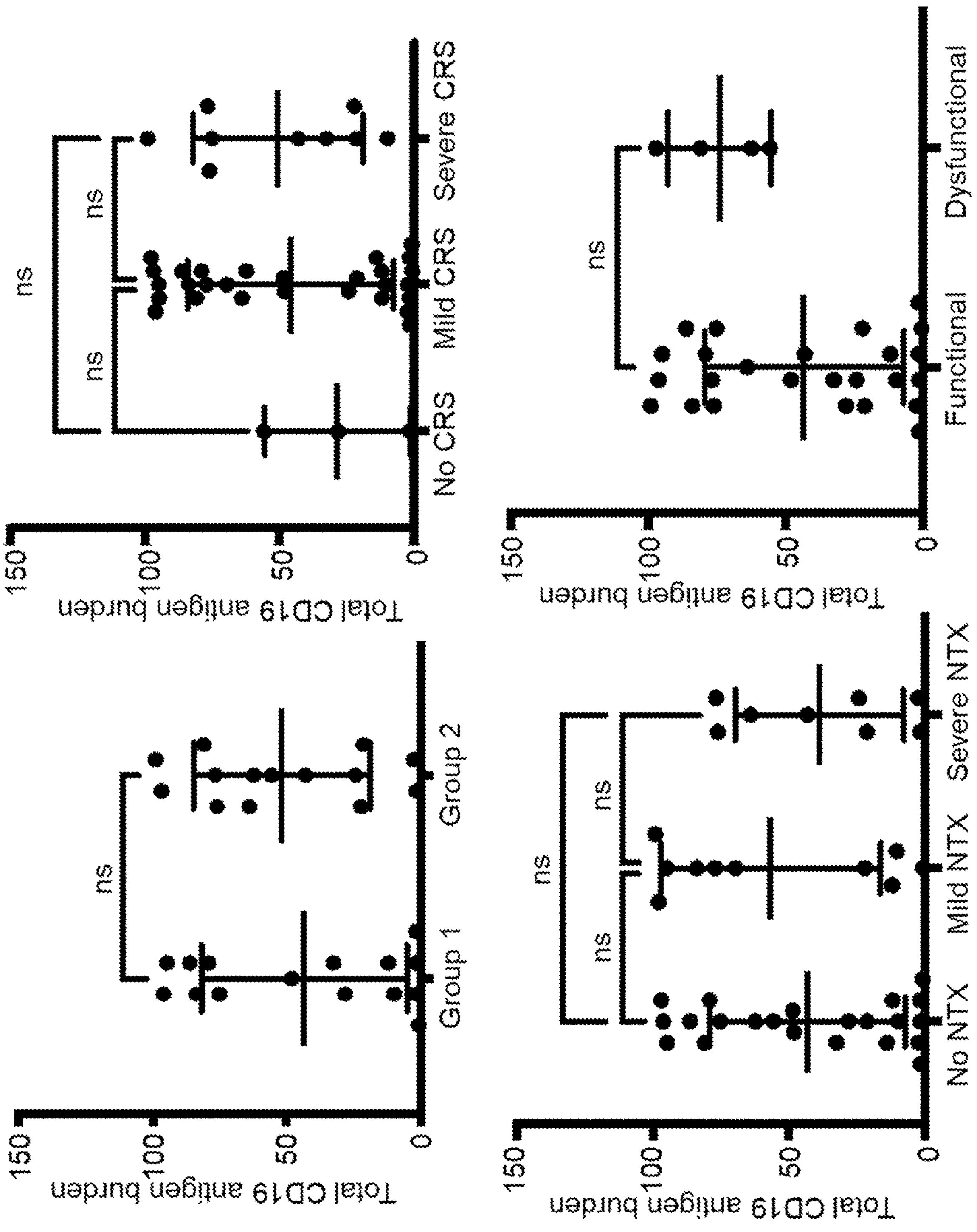
Figure 6D:
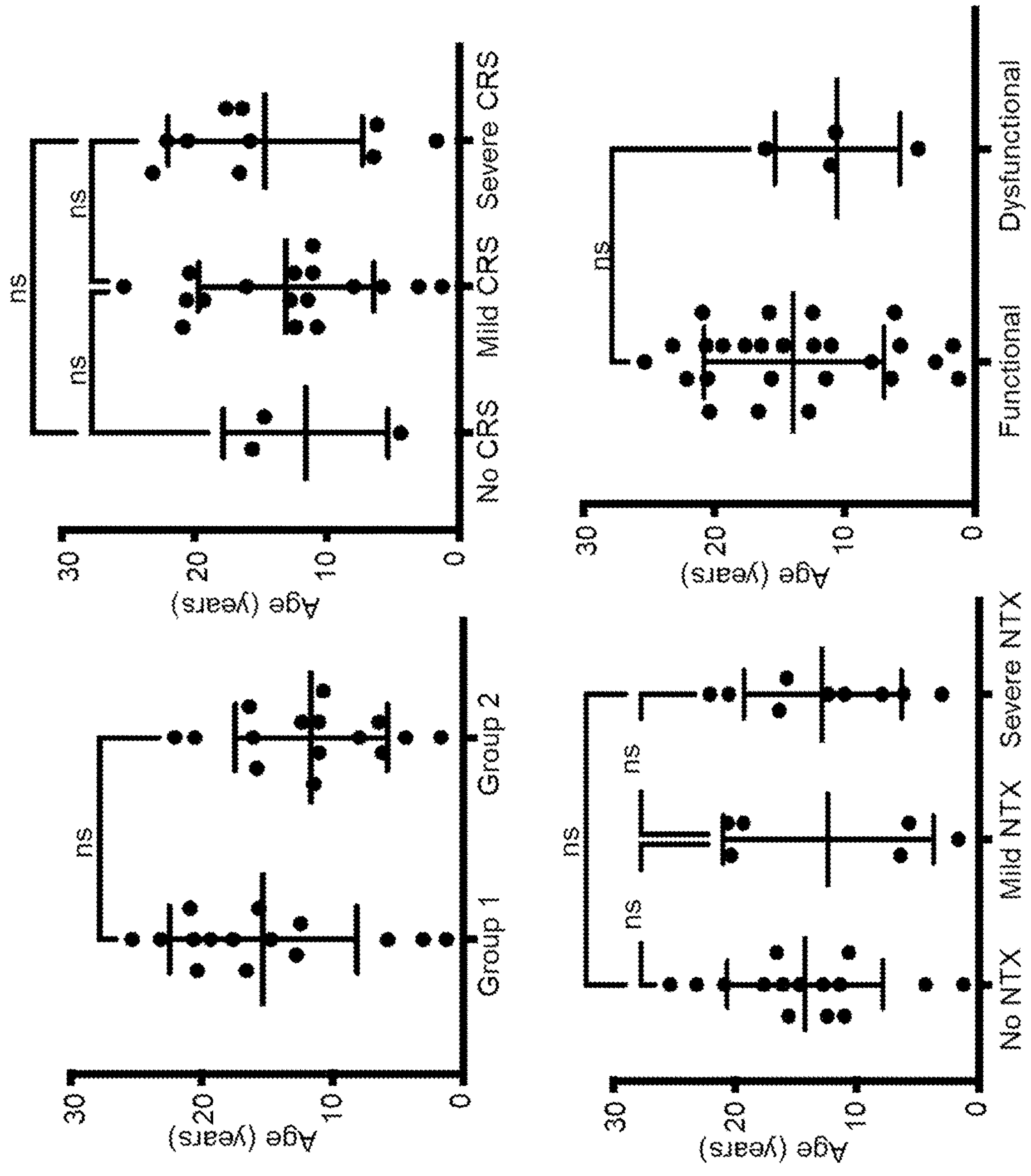
Figure 6E:
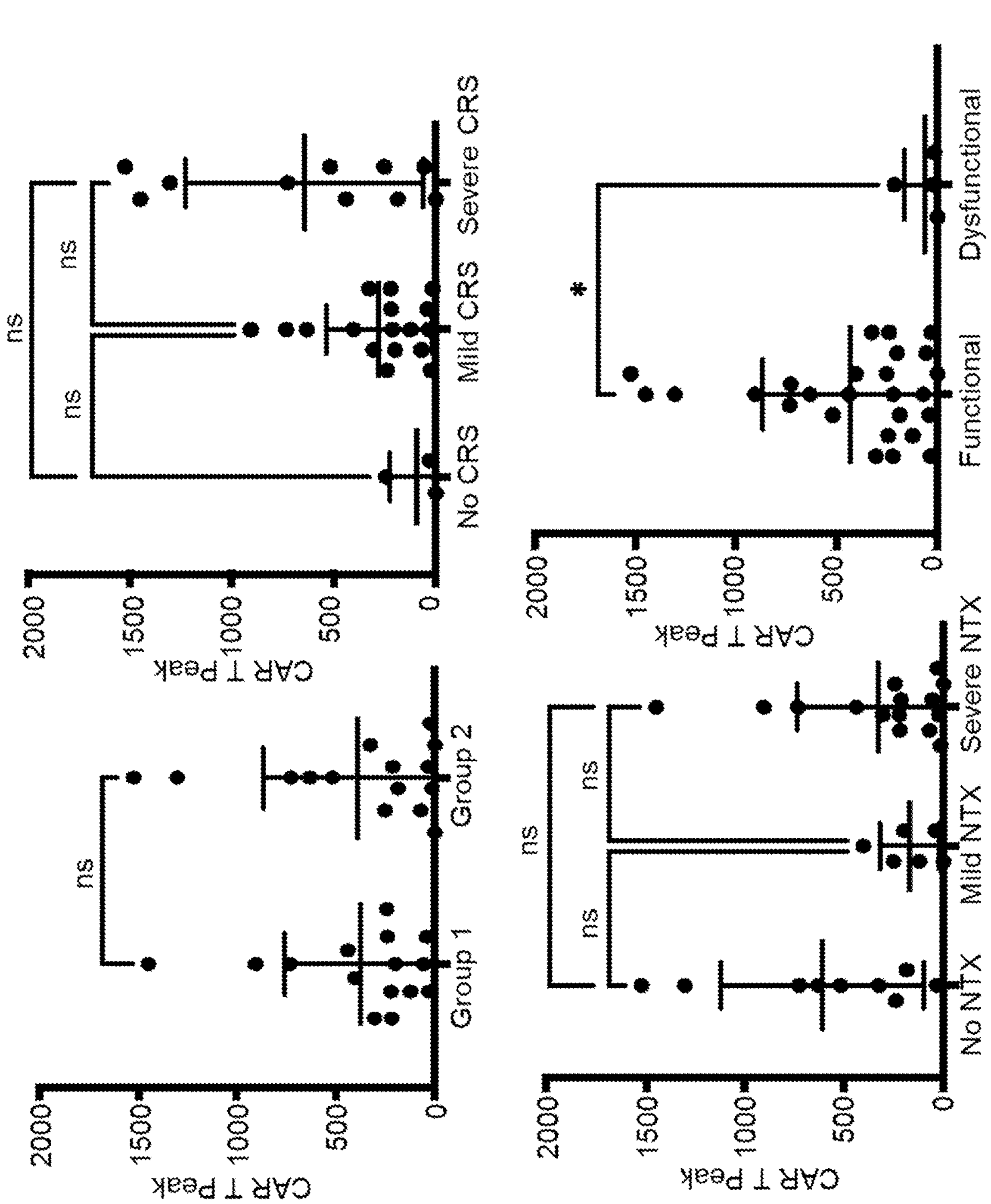
Figure 6F:
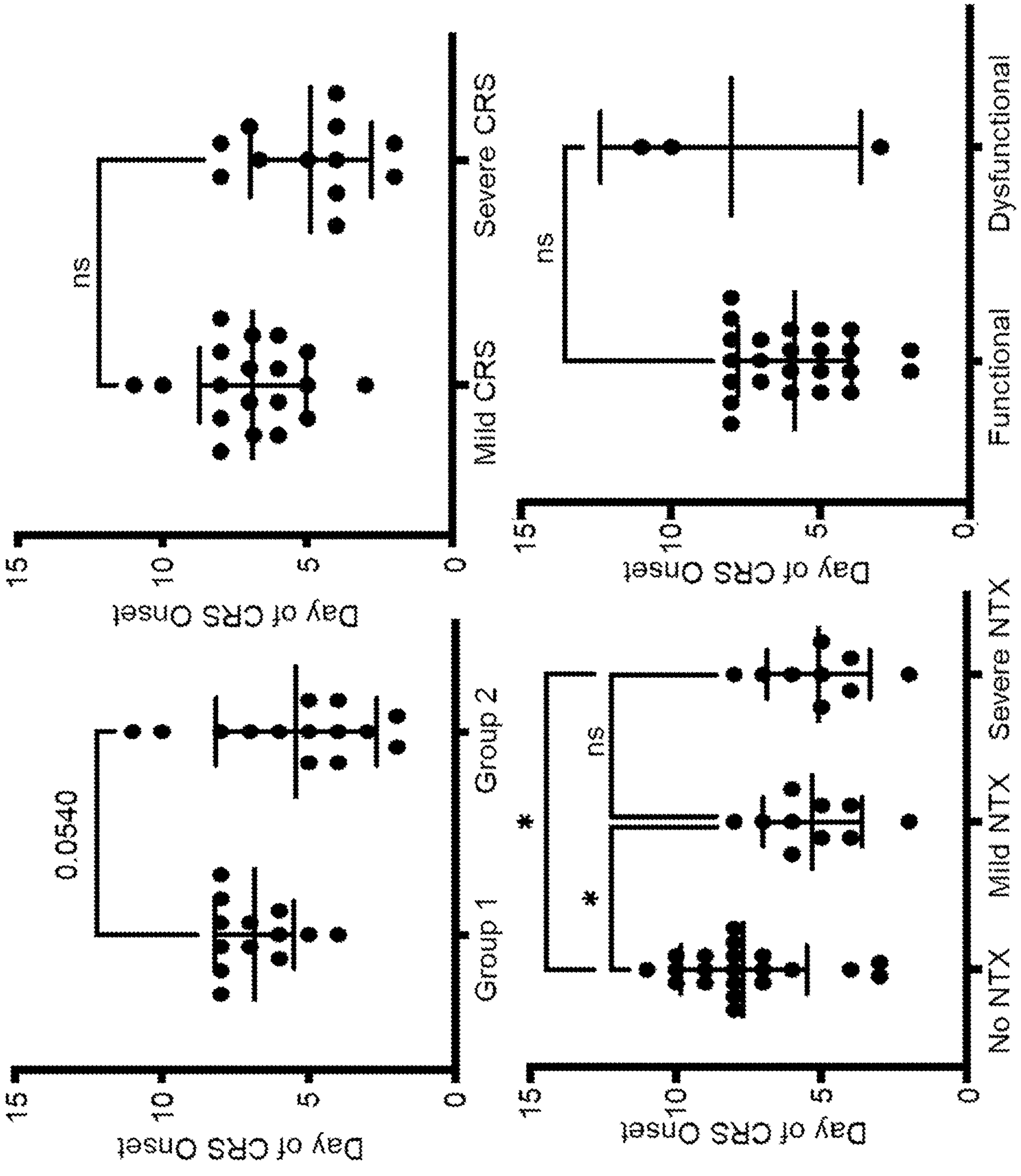

Unbiased patient classifications clustered patients into responsive and non-responsive (severe NTX and non-response) classifications with trends leading to overall survival. Patients were first binned into unbiased groups utilizing unsupervised patient clustering based on cytokine kinetics at day 1, 3 and 7 post-CAR (FIGS. 6A-6F). It was reasoned that if patients could be classified prior to mean onset of NTX, 8 days post-CAR, the assessment could provide a biomarker which physicians could use at early temporal intervention points. Unsupervised principle component analysis (PCA) identified two distinct patient clusters (FIG. 6A), Group 1 and Group 2, which differed from traditional clinical outcomes (FIGS. 6B-6F). The only clear clinical outcome that associated with the unsupervised clustering was overall survival. Group 1 (undetermined survival at 48 months post-CAR) performed significantly better than Group 2 (median overall survival of 16.84 months) (FIG. 6B). Interestingly, however, all severe NTX patients (inclusive of mild/severe NTX) and dysfunctional (non-responsive) patients clustered into Group 2. Notably, while not statistically significant, age and median time to CRS onset did have clear trends. Importantly, this data highlighted that NTX is indicative of a more severe functional CAR problem, as there appeared to be poor outcomes in terms of overall long-term CAR responses in this patient population.

Figure 7A:
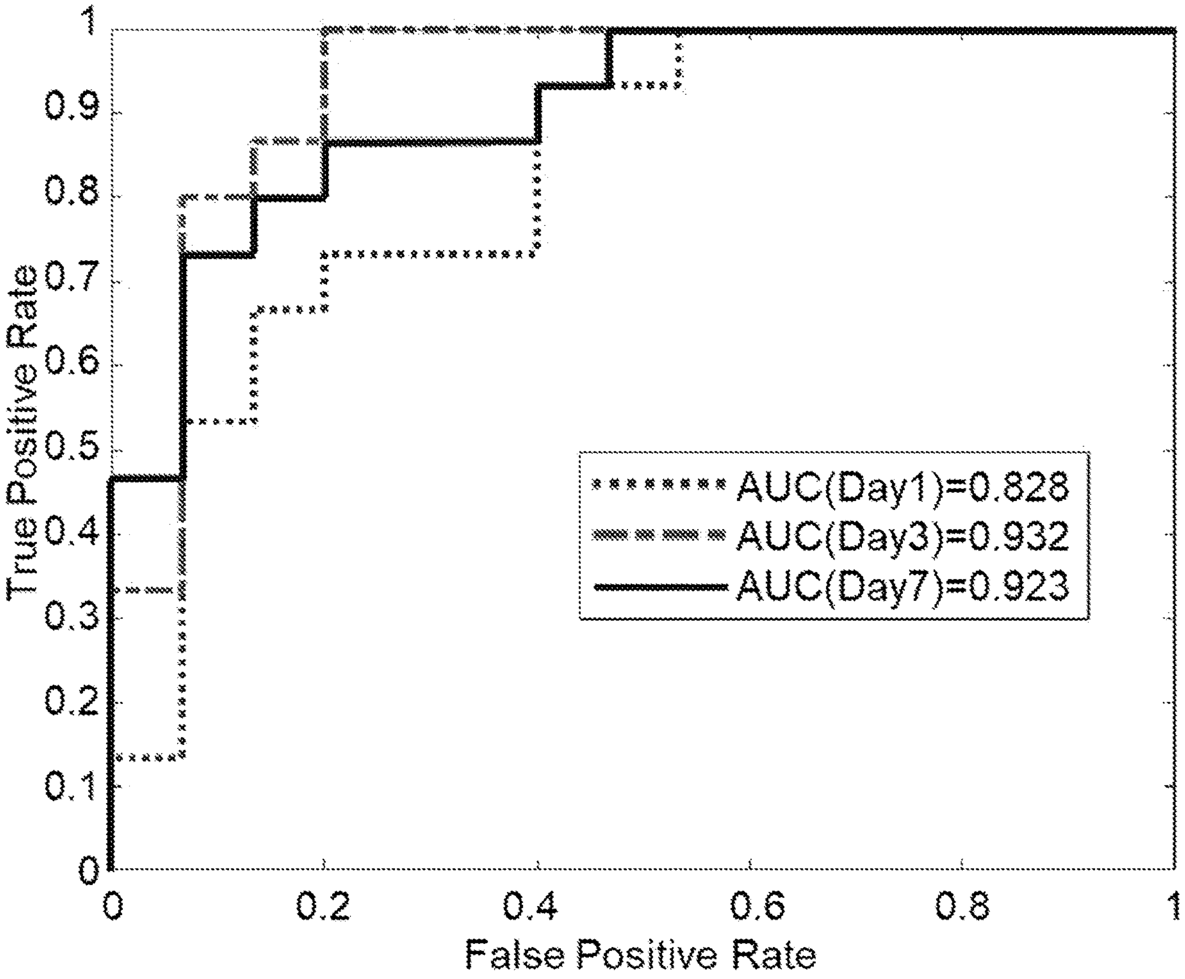
Figure 7B:
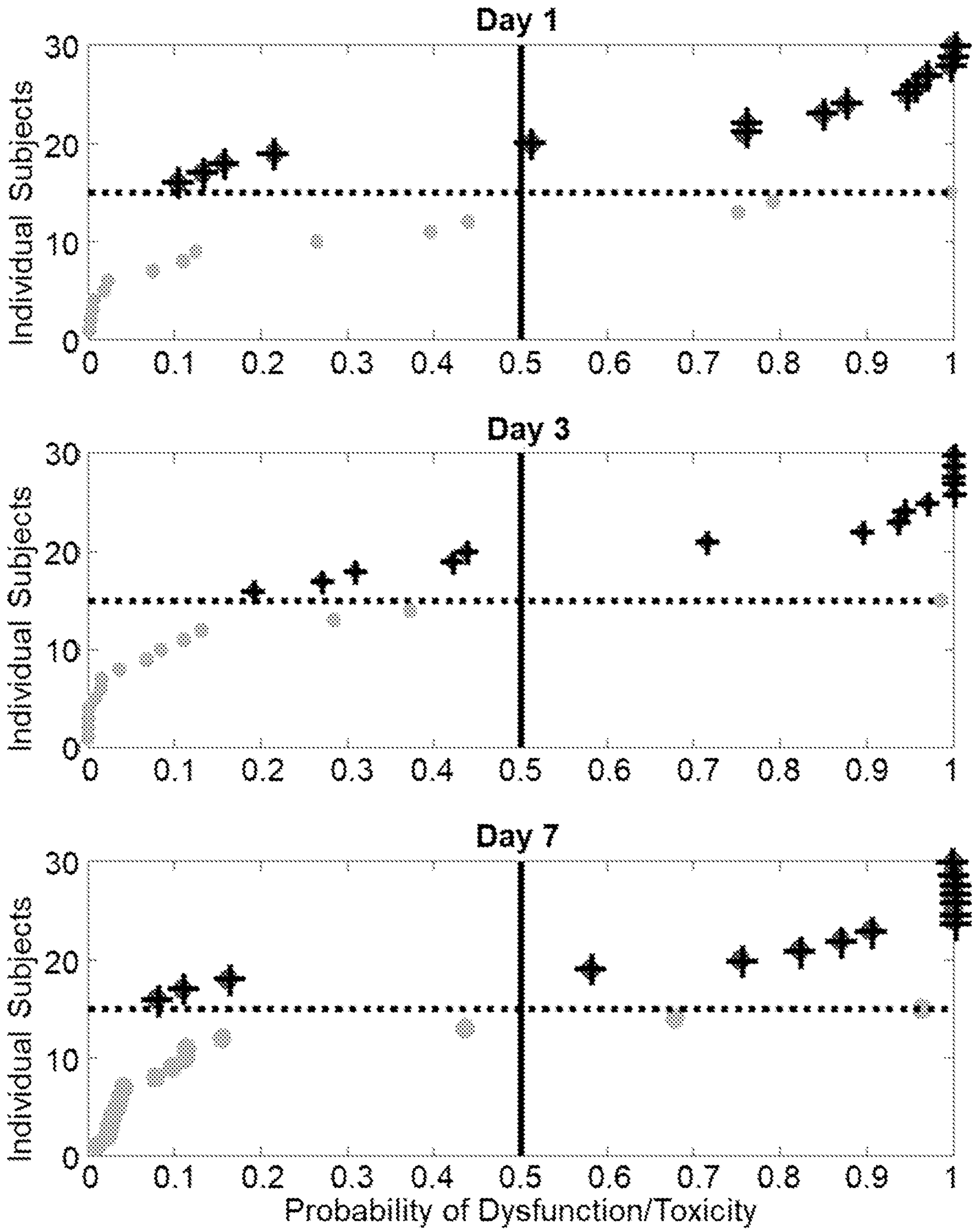
Figure 7D:
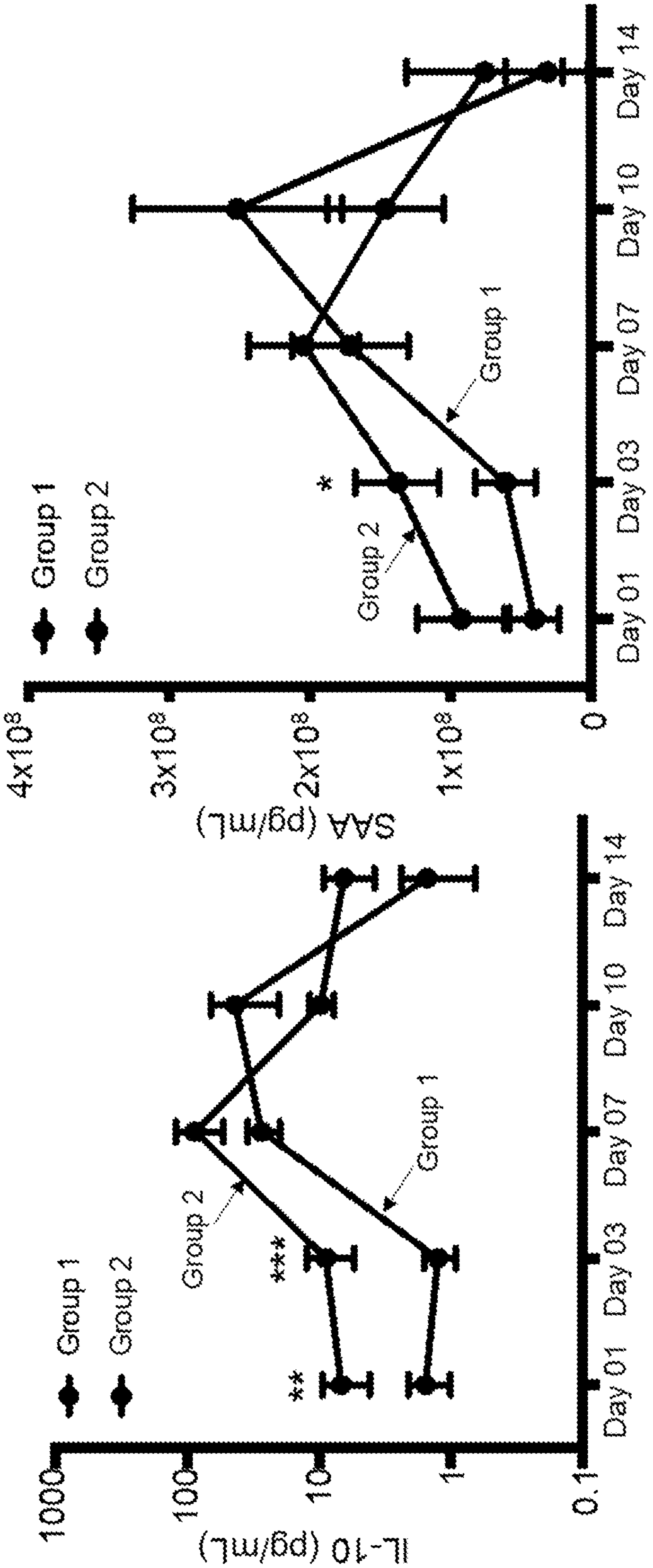
Figure 7D:
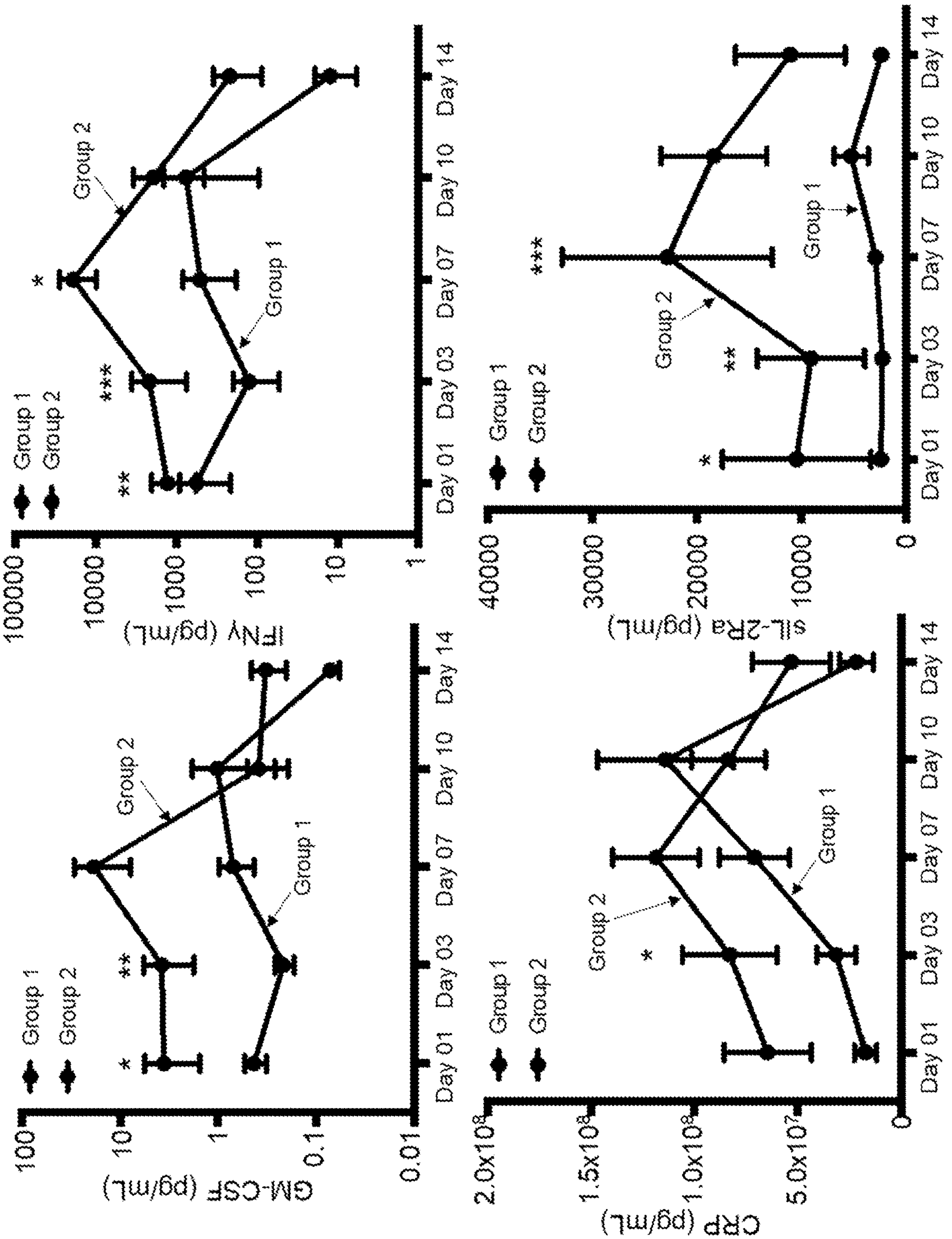
Figure 7D:
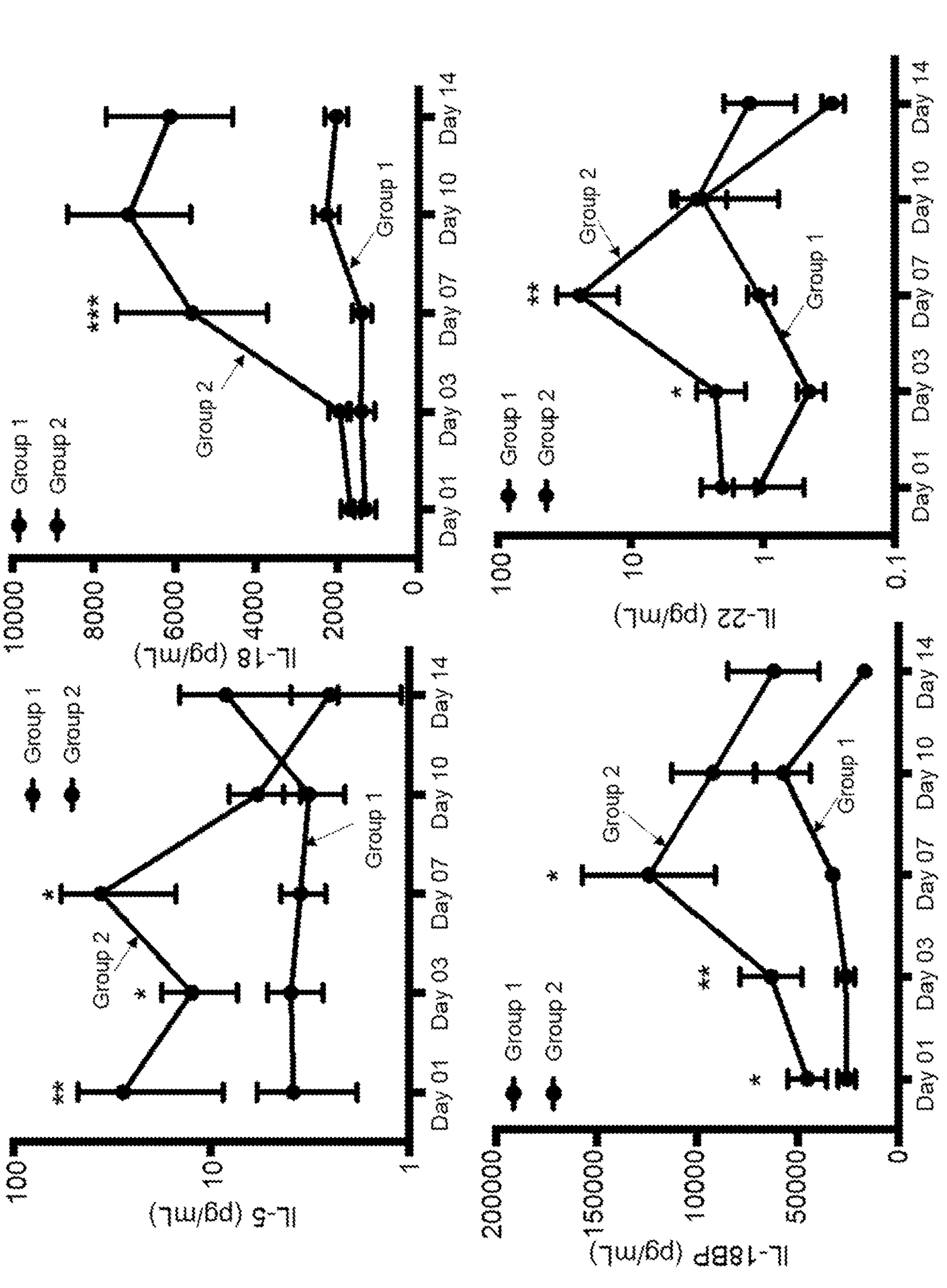

Machine learning results demonstrated that IFNγ (T cell)-IL-18 (MO) mediates outcomes at early time points post-CAR. Machine learning was utilized to identify which cytokines were driving this unsupervised clustering (FIGS. 7A-7D). Optimal models were obtained with the highest AUC following a Naïve Bayes classifier for each time point using stratified n repeated k-fold cross-validation (CV) where n=100 and k is 3 (FIG. 7A). The machine learning also gave a single probability estimate for each individual, allowing evaluation of how discriminatory on the selection criteria scale the groups were separated (FIG. 7B). One model was identified at day 1 post-CAR treatment, two models were identified at day 3 post-CAR treatment, and two models were identified at day 7 post-CAR treatment, for a total of 5 reported models (FIG. 7C). The cytokines that achieved significance in these models are outlined in FIG. 7D. Cytokines previously reported to be predictive of NTX (e.g. GM-CSF, SAA, CRP, and IL-5) achieved significance within the model, but previously unreported HLH associated cytokines, sIL-2RA, IL-18, IL-18BP, and IFNγ were also significant (FIG. 7D). Importantly, these results were indicative of chronically high interferon levels, as IFNγ achieved significance on day 1, 3 and 7 with elevated levels continuing beyond model reach to day 10 and 14 in Group 2 patients. The chronically high levels of IFNγ appeared to be driving monocytic IL-18 at day 7 post-CAR. IL-18 and its regulator IL-18BP were the hallmark predictors of Group 2 at Day 7 in both model outcomes. This suggests that the IFNγ (T cell)-IL-18 (Mϕ) axis is driving post-CAR toxicity and responses. Further, in HLH co-factors like sIL-2RA can drive aberrant T cell and myeloid activation leading to increases in GM-CSF, SAA, CRP and IL-5.

Figure 8A:
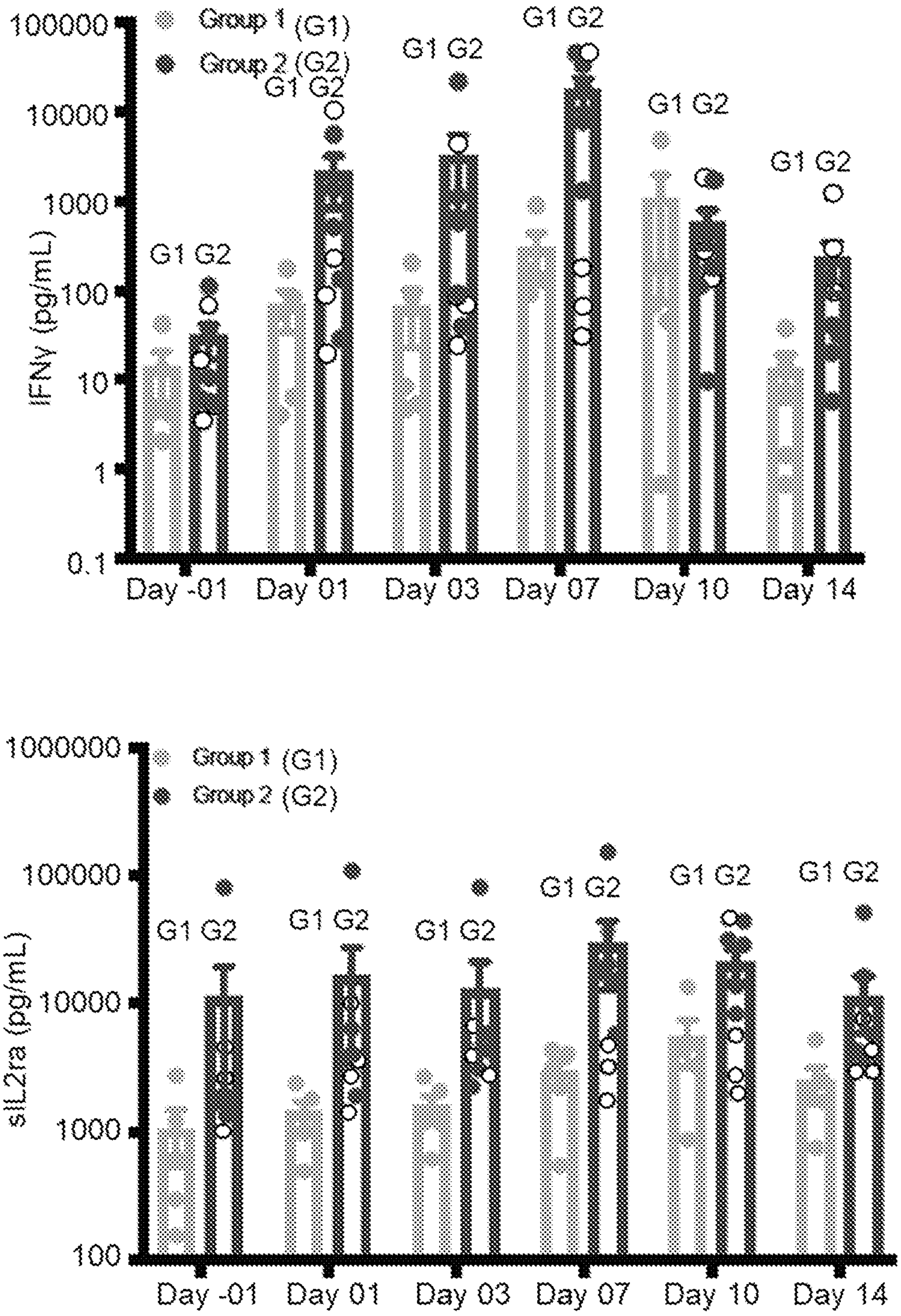
FIGS. 8A-8H. Chronic interferon signaling is present pre-CAR T driven by CD161+T and NK cells.
Figure 8A:
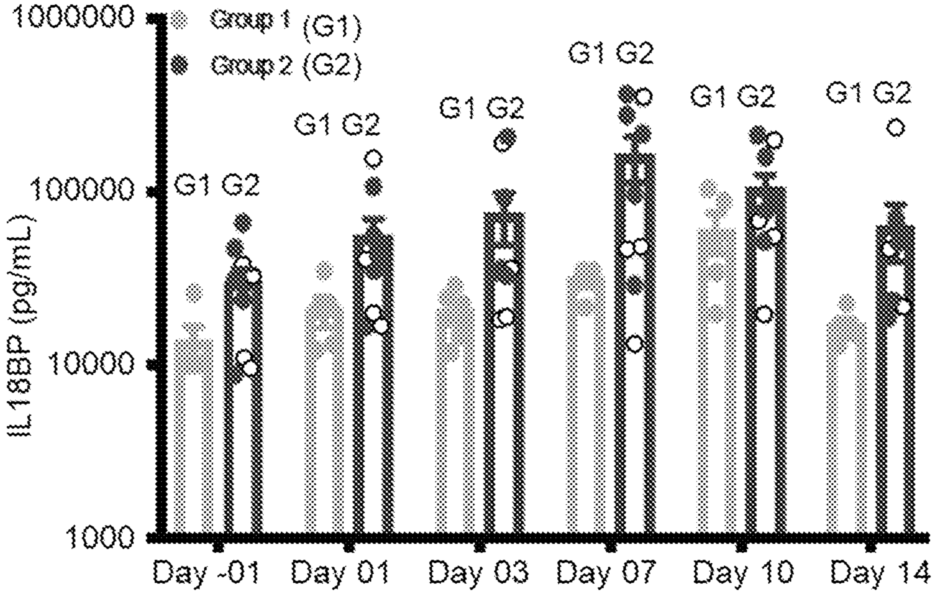
Figure 8A:
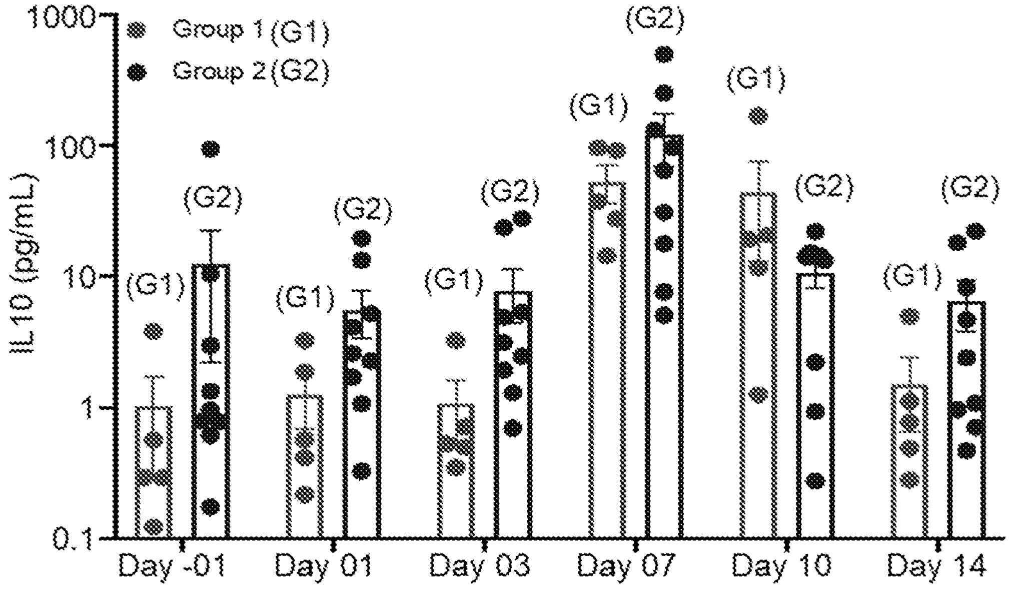
Figure 8B:
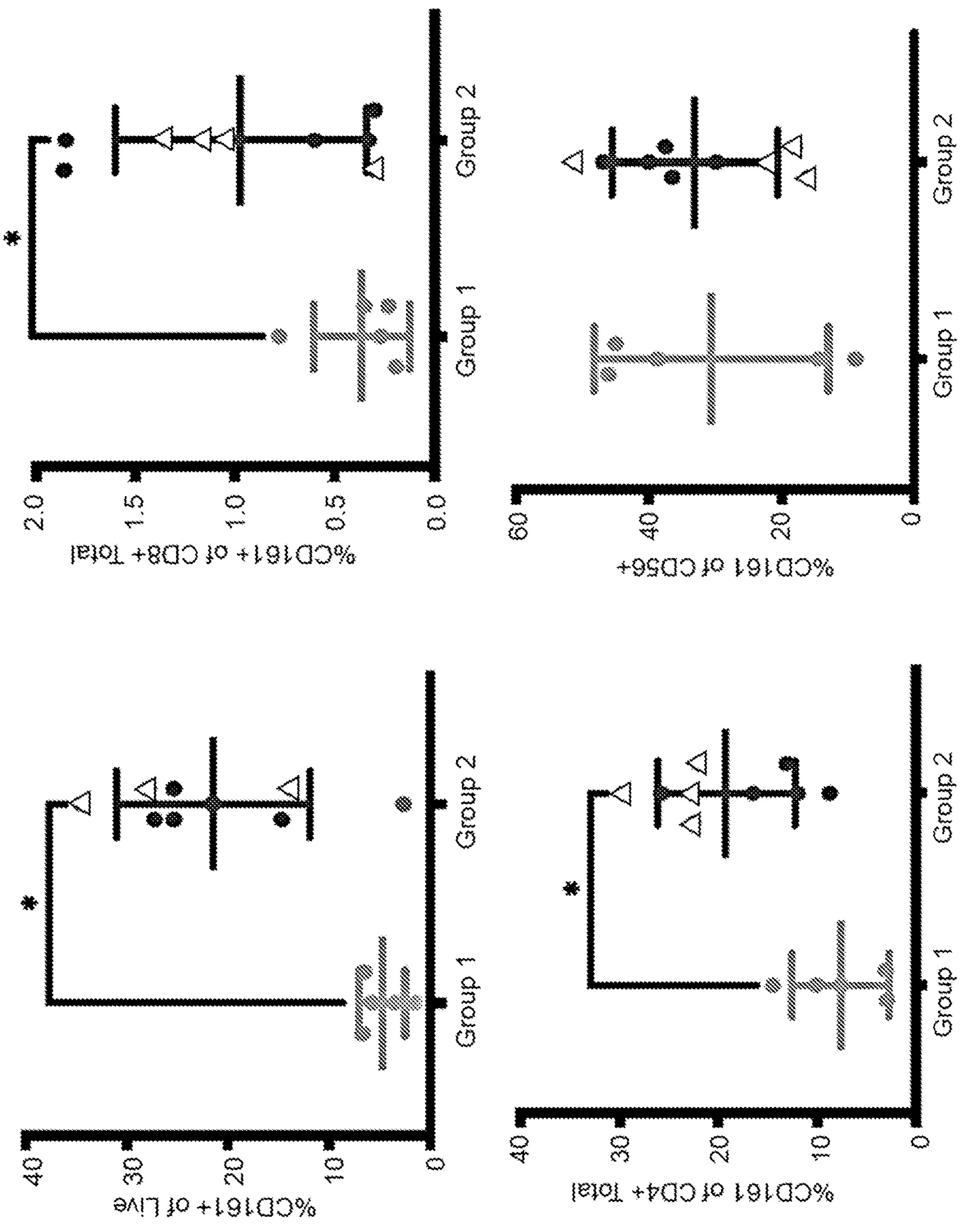
Figure 8C:
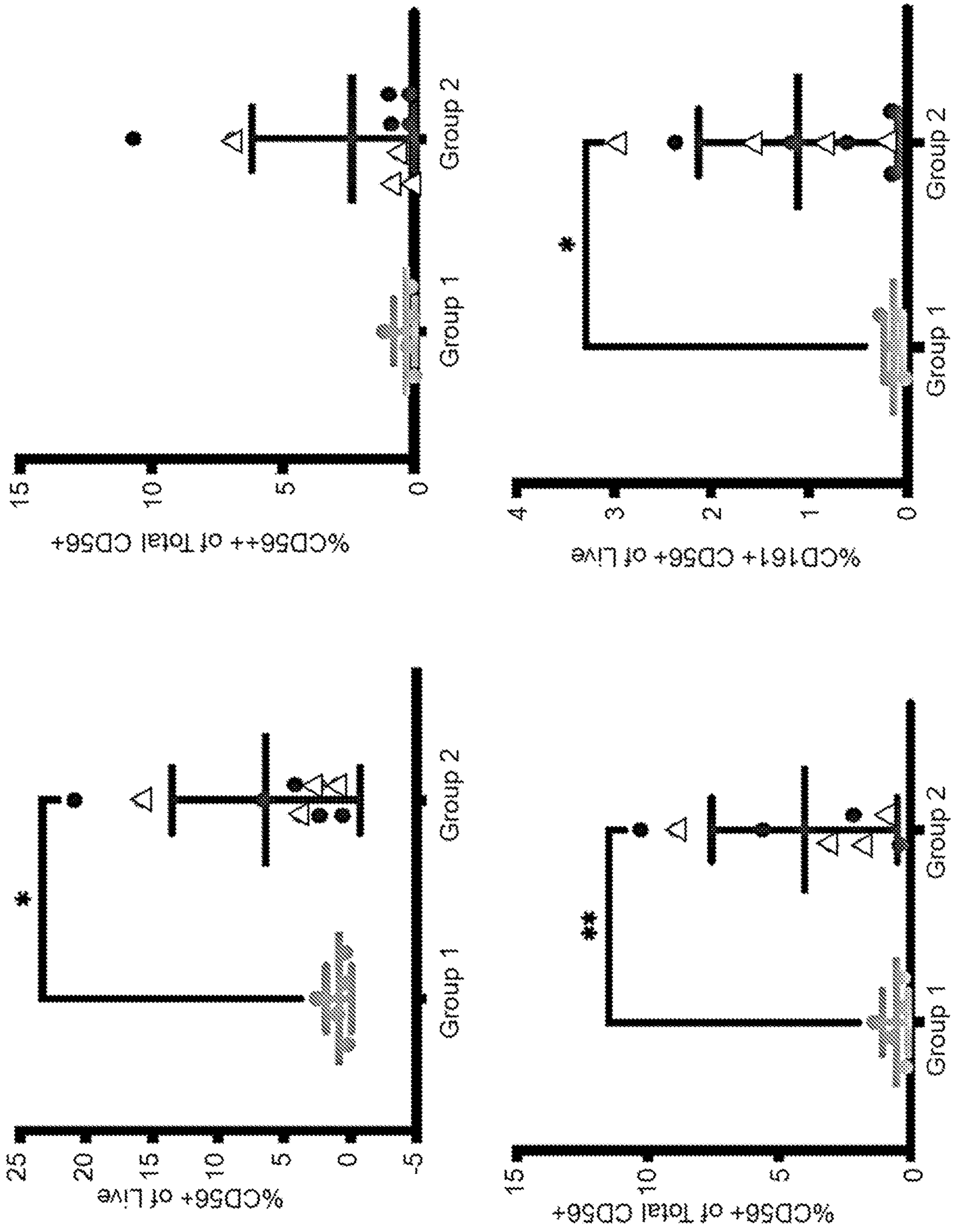
Figure 8D:
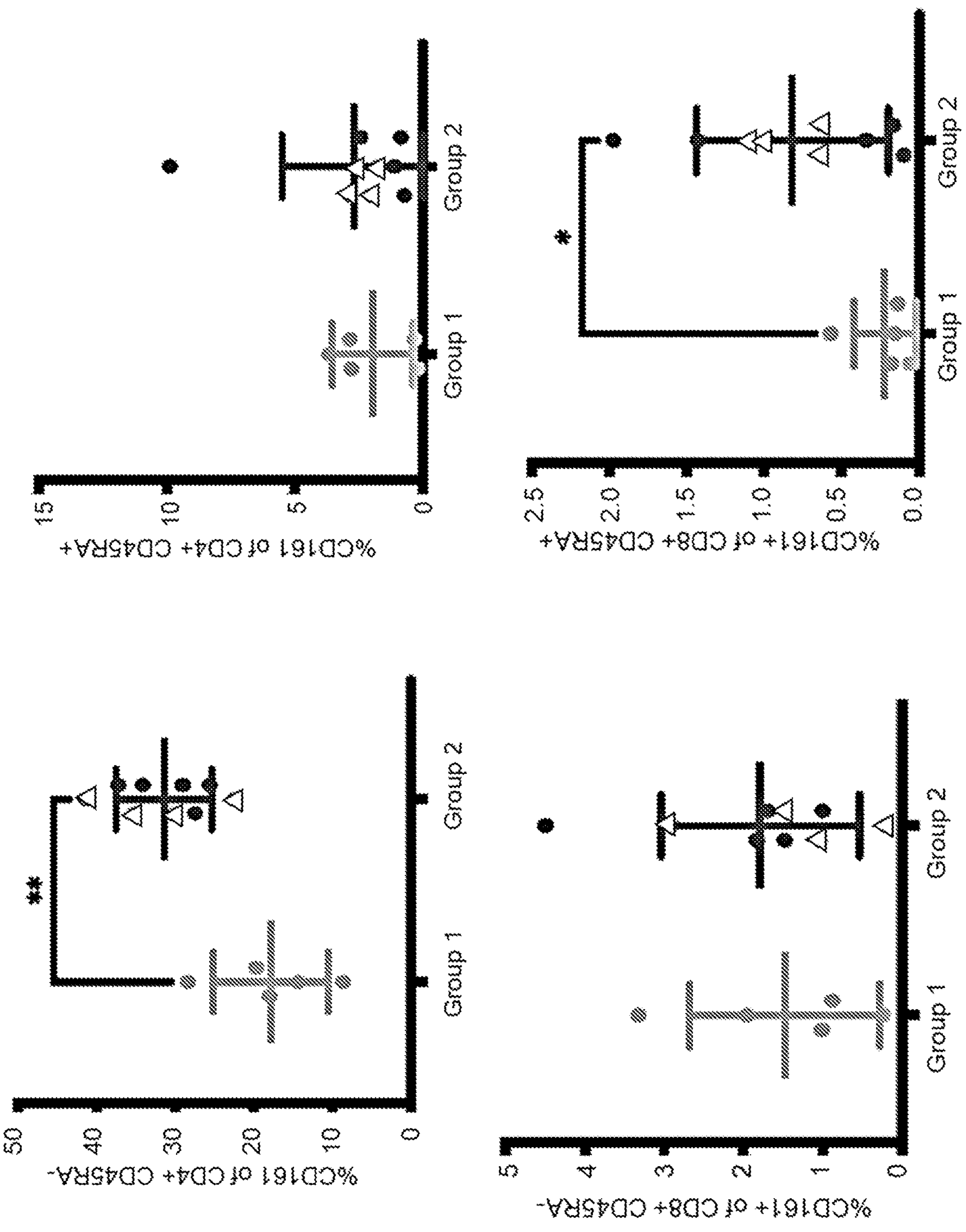

Chronic interferon signaling can be predicted pre-CAR by a previously unidentified population of lymphocytes. Pre-CAR cytokine levels are indicative of chronic interferon and classical HLH signaling. The machine learning models that predicted chronic interferon signaling post-CAR could be indicative of chronic interferon signaling pre-CAR which would prime, or drive, increased myeloid activation post-CAR. Experiments were conducted to assess whether these HLH like cytokine signatures were present pre-CAR in a small cohort of 14 patients (12 cytokines outlined in Materials and Methods). Upregulation in IFNγ was observed, as well as interferon and classical HLH regulating cytokines that could have immunosuppressive functions (IL-18BP, sIL-2RA and IL-10) leading to the poor overall survival of Group 2 (FIG. 8A).

Figure 8E:
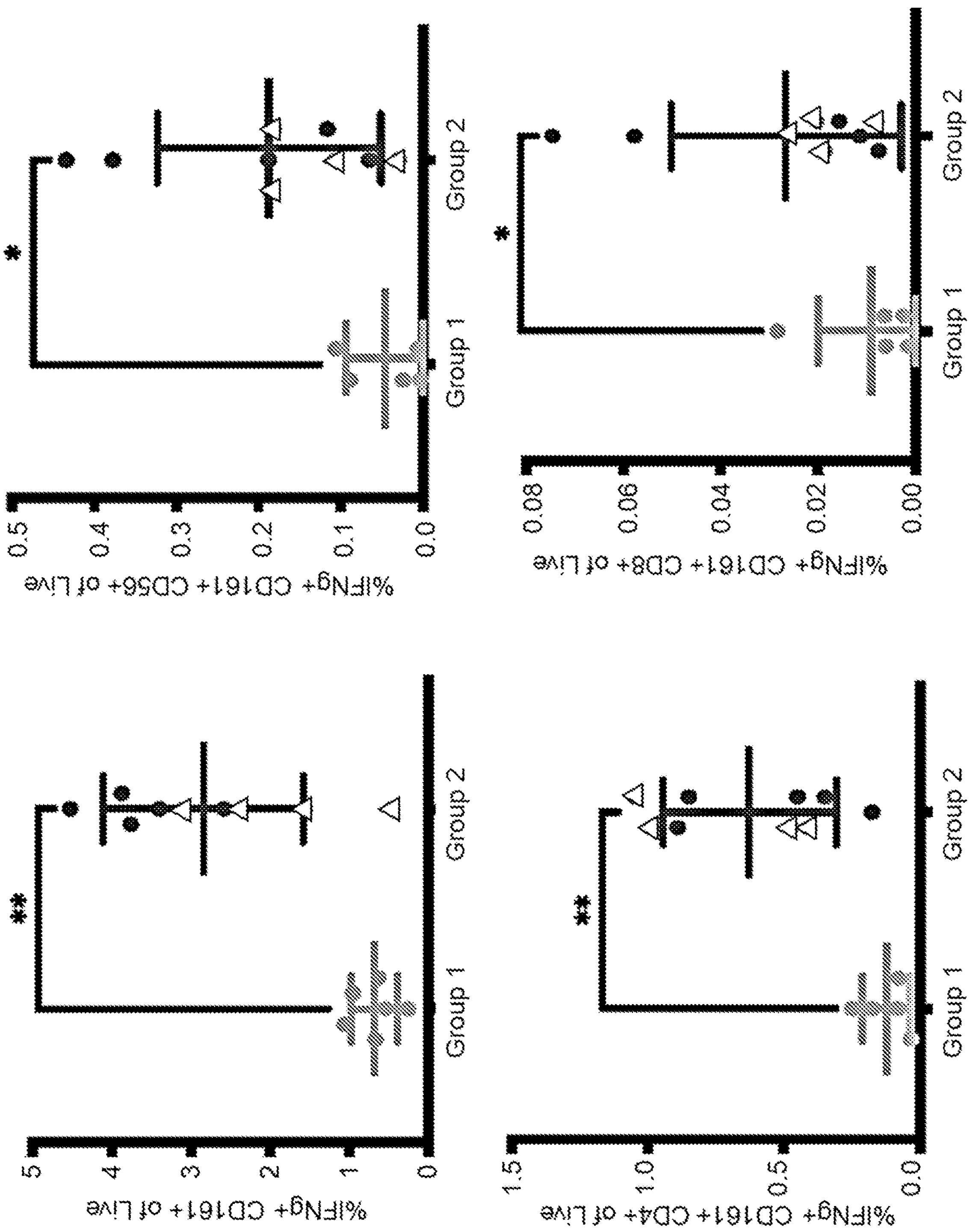
Figure 8F:
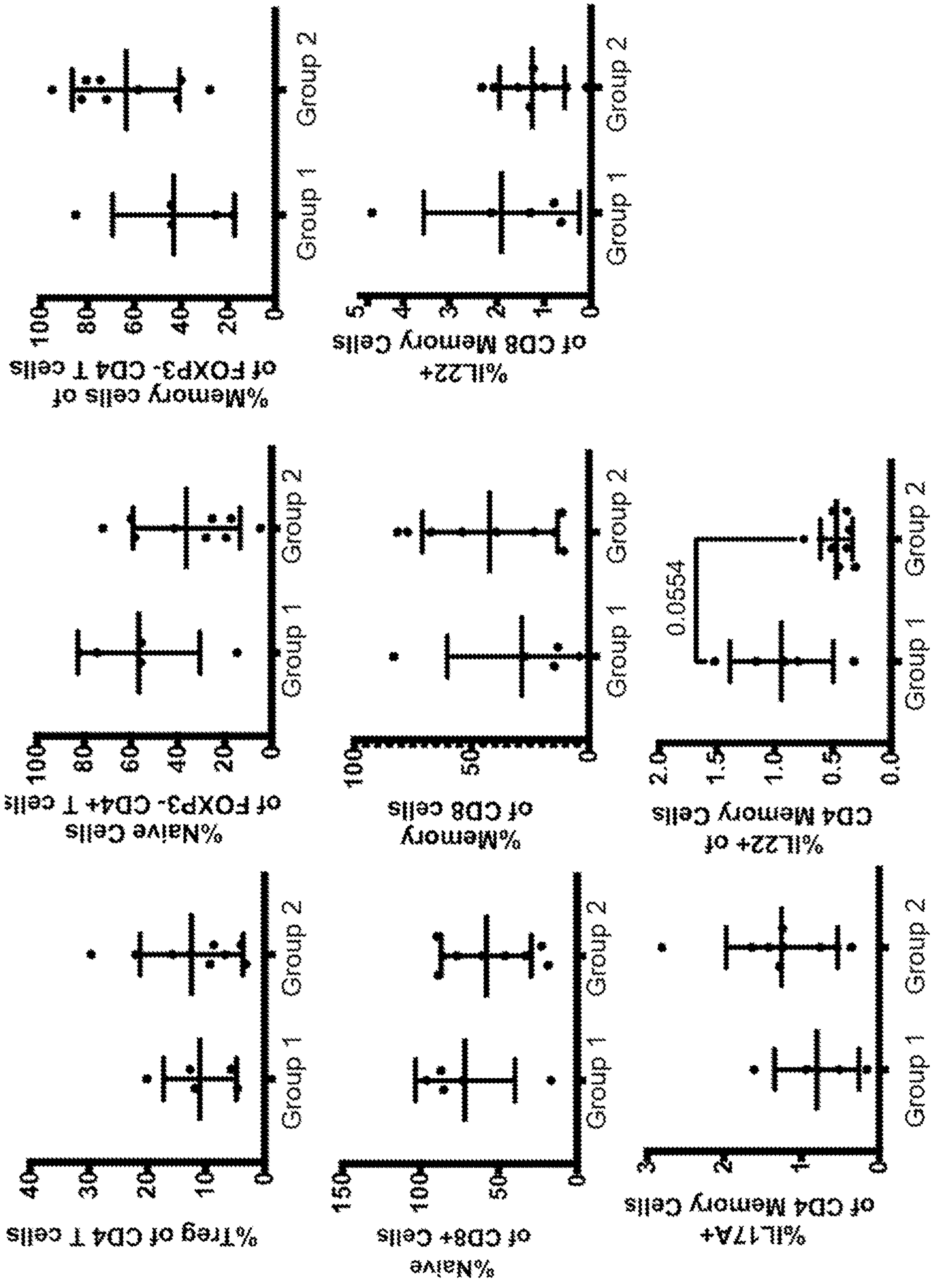
Figure 8G:
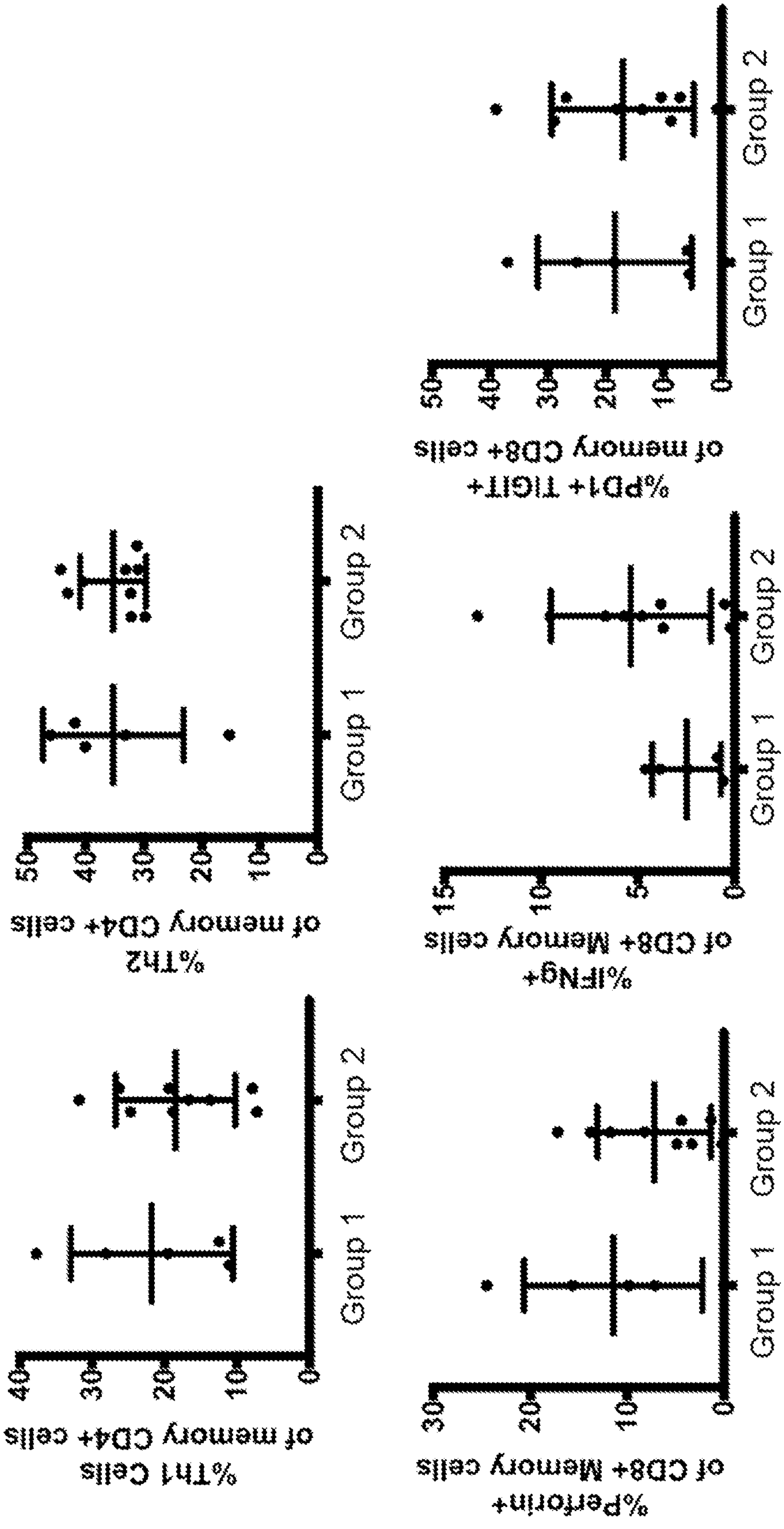
Figure 8H:
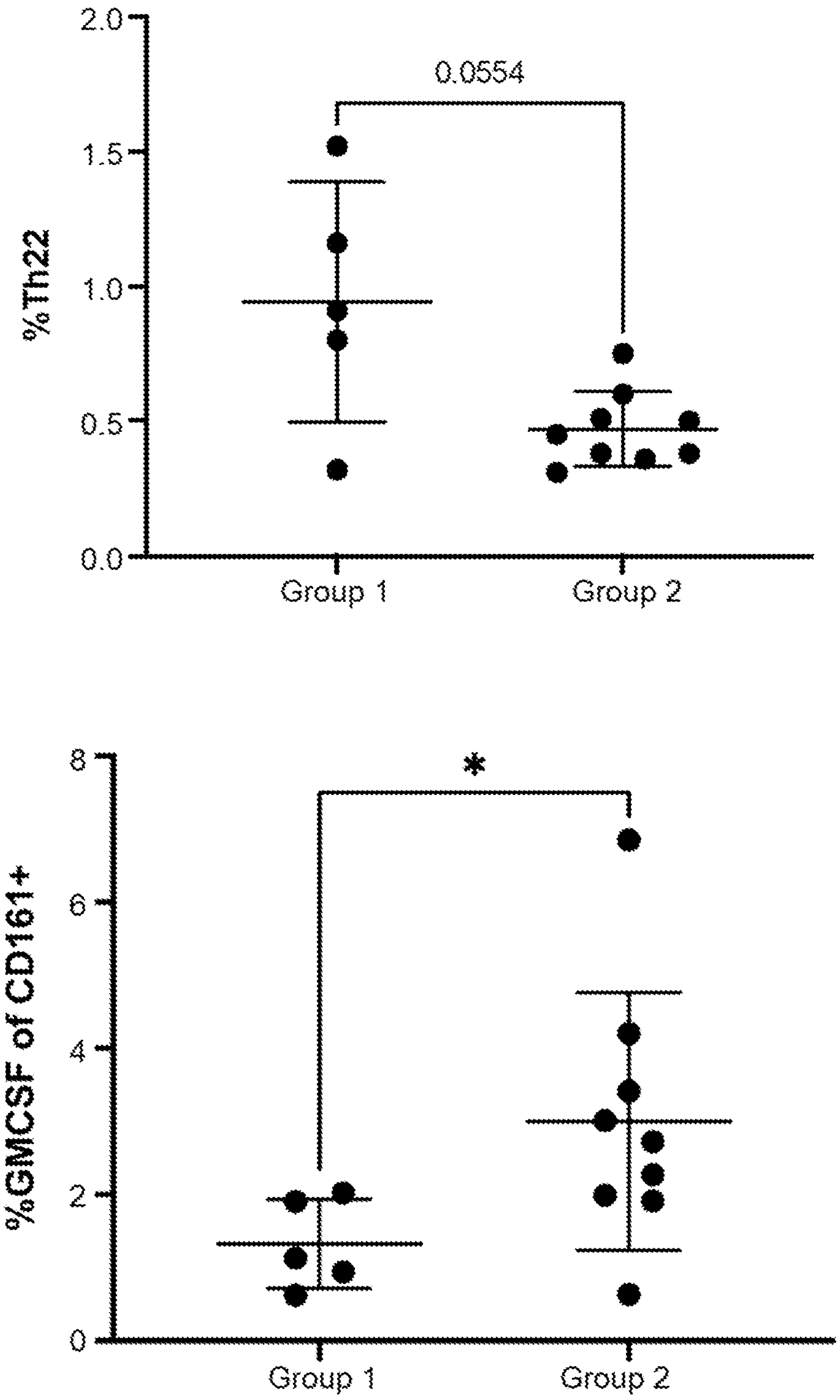

CD161+ cells are indicative of poor outcomes. Since chronic interferon and HLH-like predisposition was present in the Group 2 patient populations, flow cytometry experiments were conducted to assess whether lymphocyte populations pre-CAR indicative of chronic interferon signaling and responsive to IL-18 would be elevated. Increases in mucosal associated invariant T (MAIT) and natural killer (NK) cells that were CD161+ and in IFNγ signaling were observed (FIGS. 8B-8E). Importantly, CD161+ NK and T cells require IL-18 for survival/proliferation and increased IFNγ production (FIG. 8E). Traditional exhaustion, functional, T cell sub-setting (e.g., Th1, Th2 and Th17) markers were also evaluated within T cell (CD4 and CD8) and NK/NKT cells (CD56+ and CD3+CD56+) and no differences were observed (FIGS. 8F, 8G). However, increases were observed in Th22 cells (p value 0.0554) in Group 1 and GMCSF+ cells (p value 0.0290) in Group 2 consistent with the machine learning models (FIG. 8H, FIG. 7D). Interestingly, IL-22 can regulate IL-18 signaling and therefore may be a potential intervention point in driving better outcomes. GM-CSF has been shown to also be linked to the interferon/IL-18 axis specifically in HLH and CNS disorders. Notably, CD161+ is a robust single marker, the average of % of total live cells is 21.46% in Group 2 and 4.78% in Group 1. Within the current cohort of patients if a cutoff at 10% were set, no patients from Group 1 would be included and only 1 patient from Group 2 would be missed. Importantly, elevated CD161+ IFNγ+ subsets included NKT, CD4, and CD8 markers with CD45RA−, all of which should have T cell receptors and could be actively expanded during PLAT02 CAR manufacturing. Importantly, it is plausible that amplification of this cell type in CAR manufacturing and subsequent infusion could induce adverse elevated serum interferon and thus IL-18 outcomes in patient populations. This suggests that it may be possible to remove or reduce this cell population to improve clinical outcomes. Regardless, CD161+ is a robust marker of poor overall response (toxicity and efficacy) both during the pre-apheresis period and pre-CAR infusion or CAR manufacturing specification period. Given this information, further experiments were conducted to further inform potential clinical intervention points.

Figure 9A:
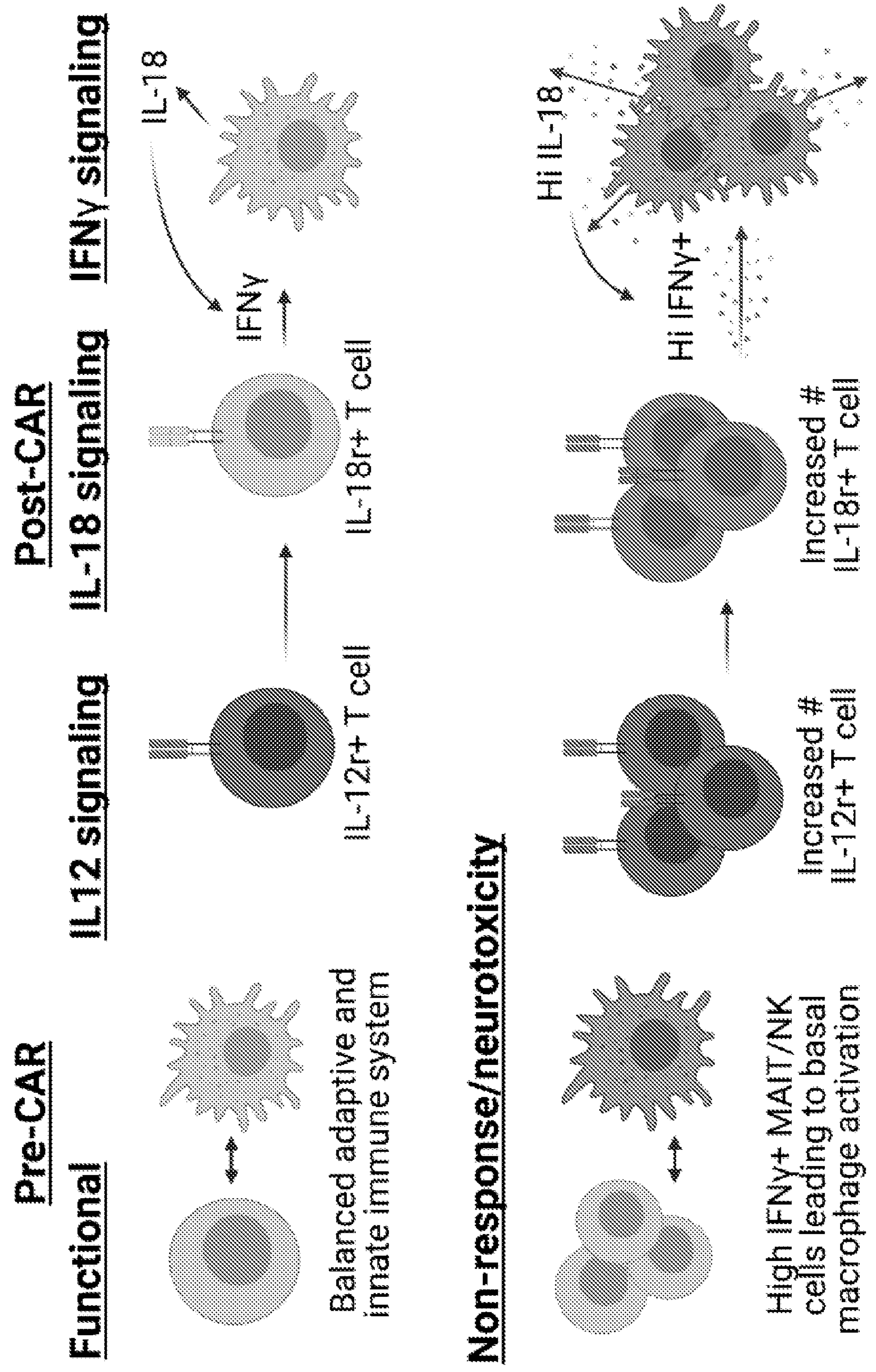
FIGS. 9A-9I. The percent of CD161+ T cells correlates with monocyte responsiveness to stimulation.
Figure 9B:
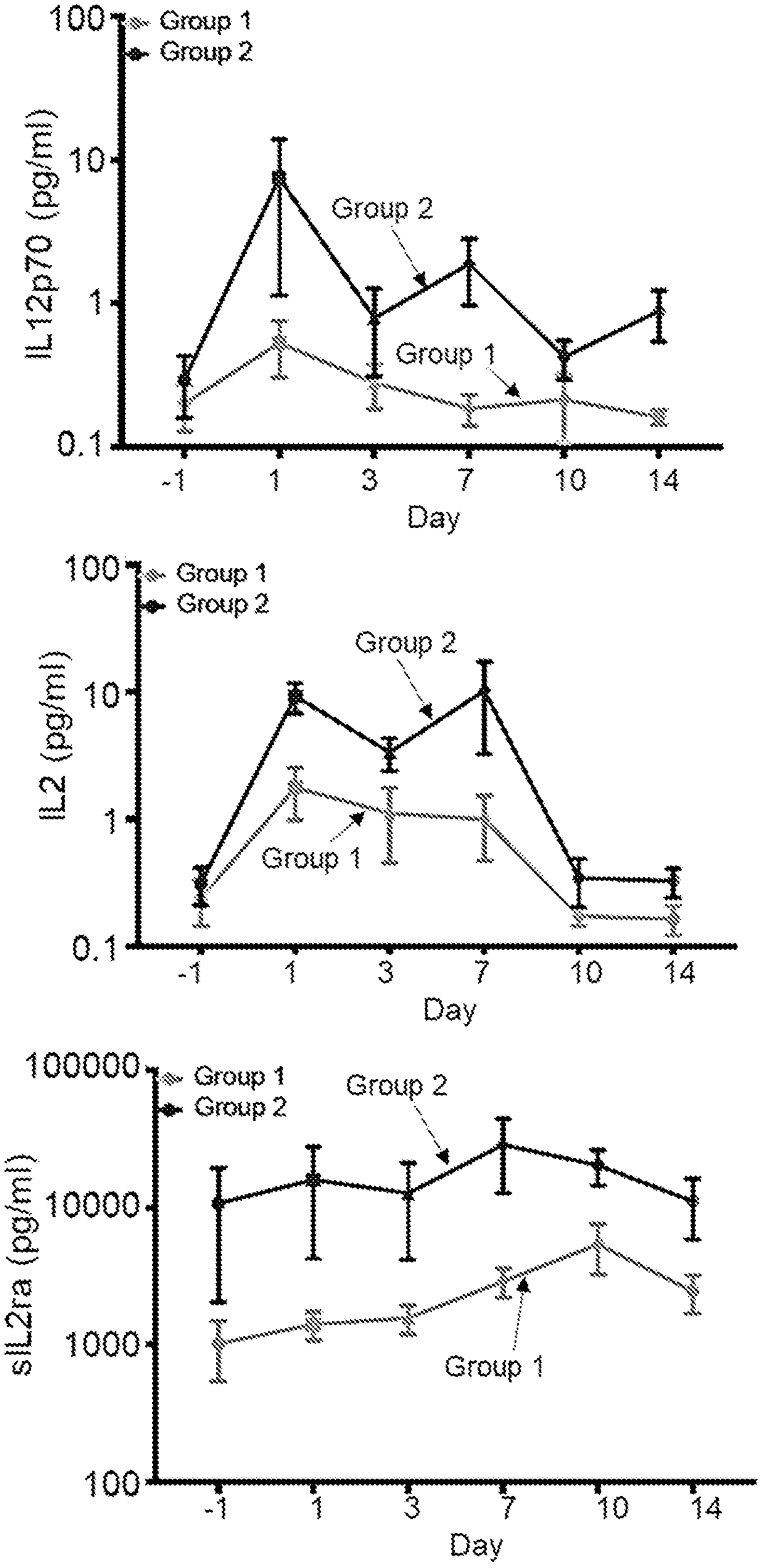
Figure 9C:
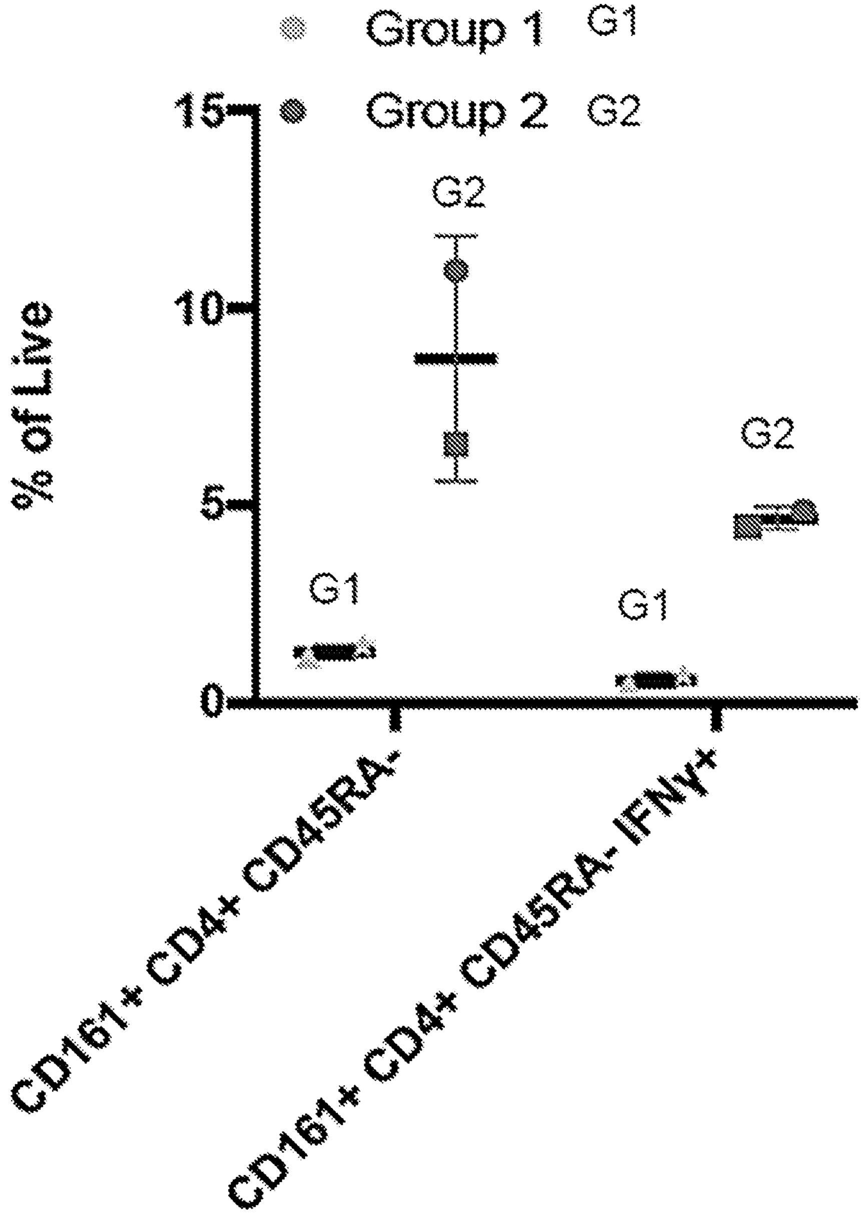
Figure 9D:
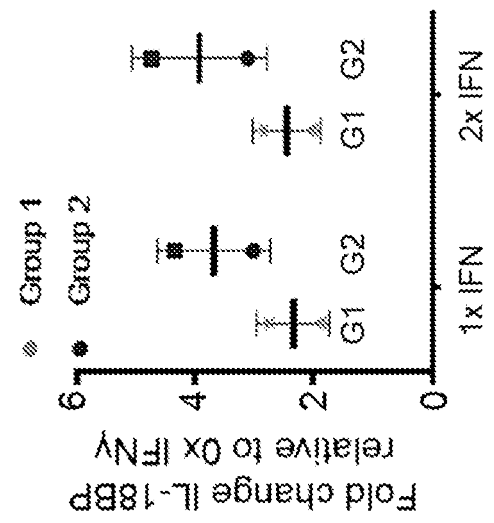
Figure 9E:
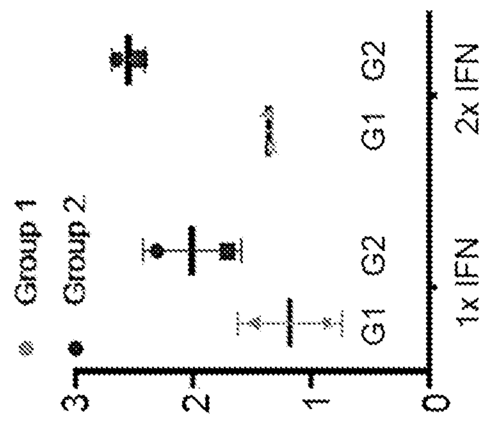
Figure 9F:
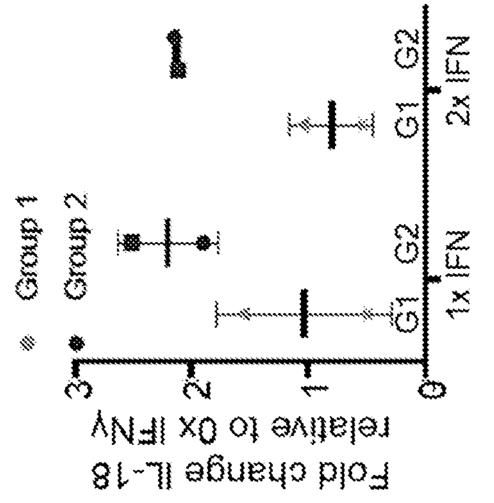
Figure 9F:
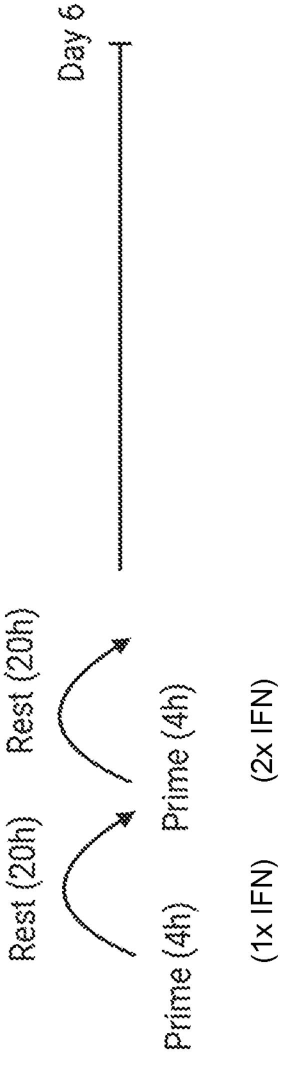
Figure 10:
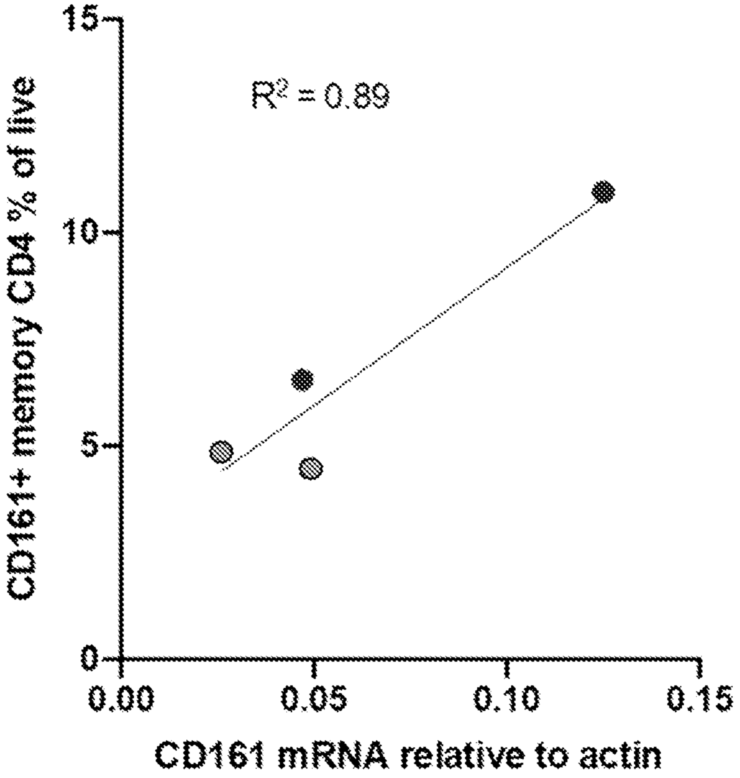
FIG. 10. CD161 mRNA expression correlates with CD161+ memory T cells. CD3+ T cells were selected from four healthy PBMC donors by positive selection and harvested for RNA processing and qPCR for CD161 expression. Represents one experiment with replicate RNA samples.
Figure 11A:
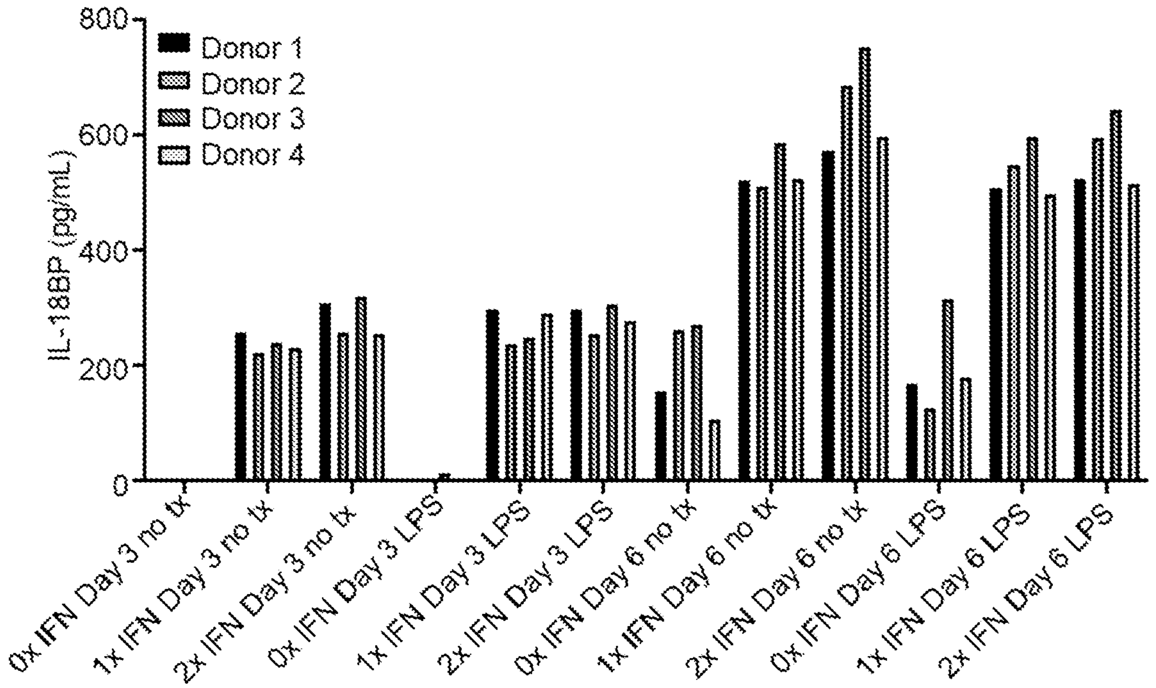
FIGS. 11A-11C. Donor variation in IFNγ primed human monocyte responses to LPS. Untransformed data from FIGS. 9A-9I, which focused on the Day 6 LPS stimulation.
Figure 11B:
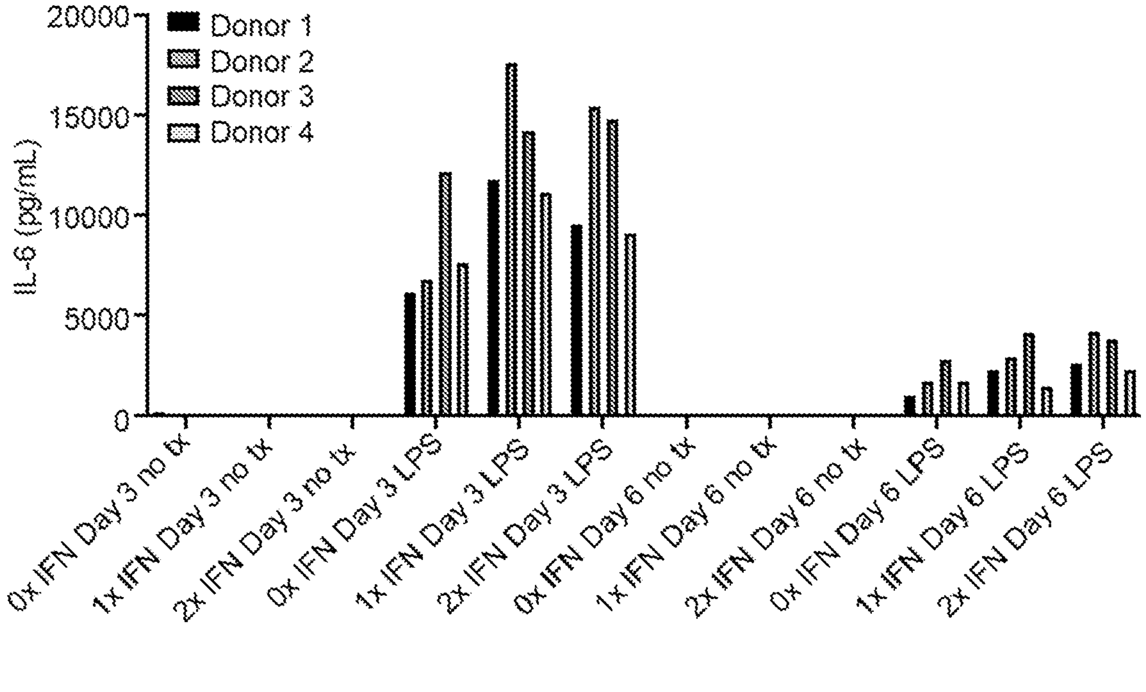
Figure 11C:
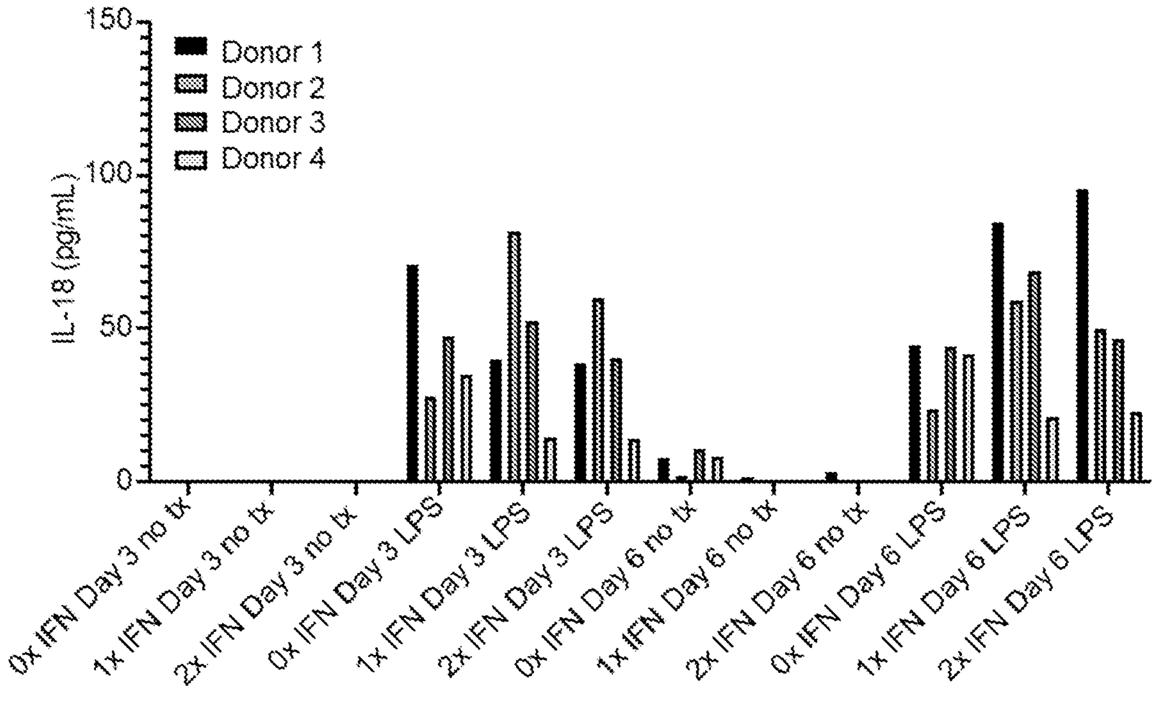

CD161+ CD4+ cells are also elevated in a subset of healthy donors, and myeloid cells from these donors can be primed to induce HLH-like IL-18 signaling. Given the poor clinical outcomes associated with high levels of CD161+ cells, it was hypothesized that high levels of CD161 may be a marker for primed pro-inflammatory myeloid activation, independent of cancer. Such that high levels of CD4+ CD45RA− CD161+ cells may increase myeloid activation in healthy human donors. Thus, it was reasoned that continued interferon signaling/priming could induce a Group 2 NTX toxicity phenotype, within healthy human donor monocytes that came from donors with high levels of CD4+ CD45RA− CD161+ cells. Two CD161+ CD4+ high donors and two CD161+ CD4+ low donors were identified and CD14+ cells were isolated from these donors (FIG. 9C, FIG. 10). The cells were primed with interferon for 4 hours on day 1 and day 2 post-isolation to mimic day 1 and day 3 CAR T patient activation. CAR T cell target lysis was then stimulated through TLR priming (e.g. LPS) on day 6. Healthy donors who had elevated CD161+ cells had increased IL-18BP, IL-6, and IL-18 expression on day 6 (FIGS. 9D-9F, FIGS. 11A-11C), consistent with Group 2 patient serum levels at day 7 post-CAR (FIG. 7D).

Figure 9G:
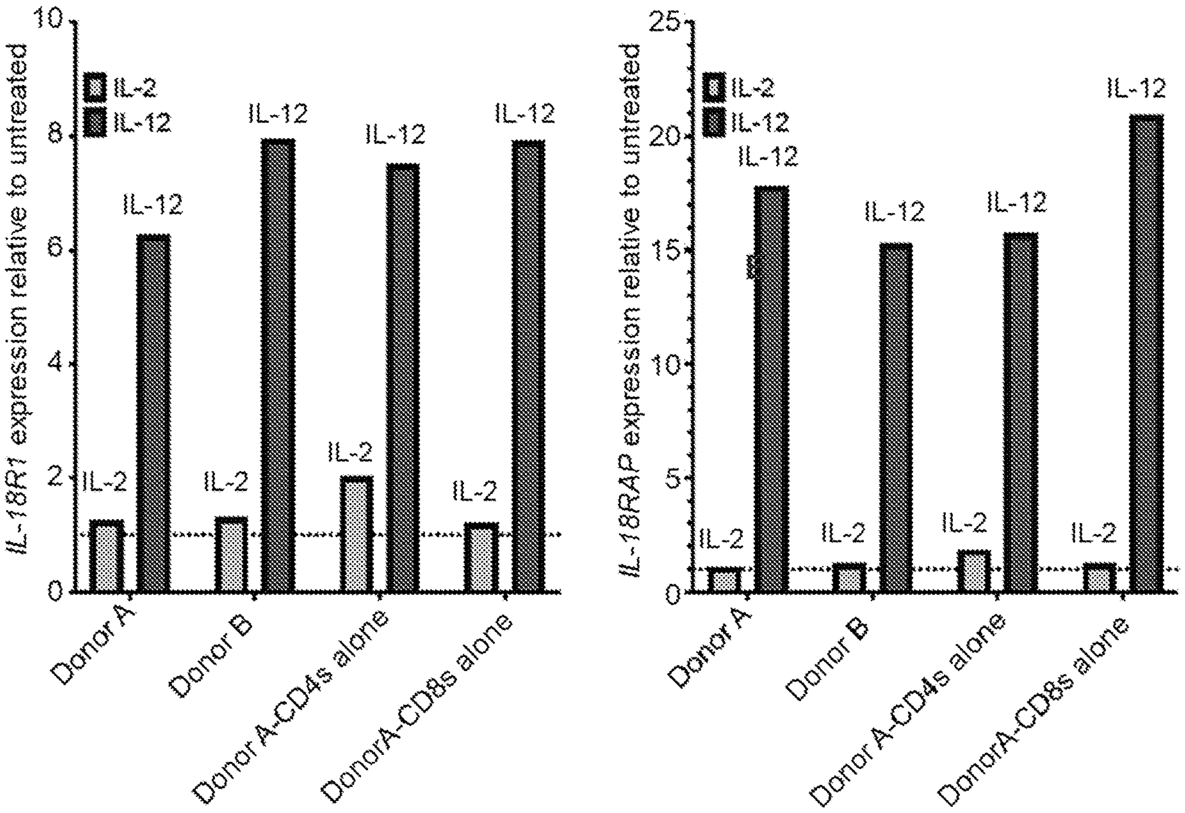
Figure 9H:
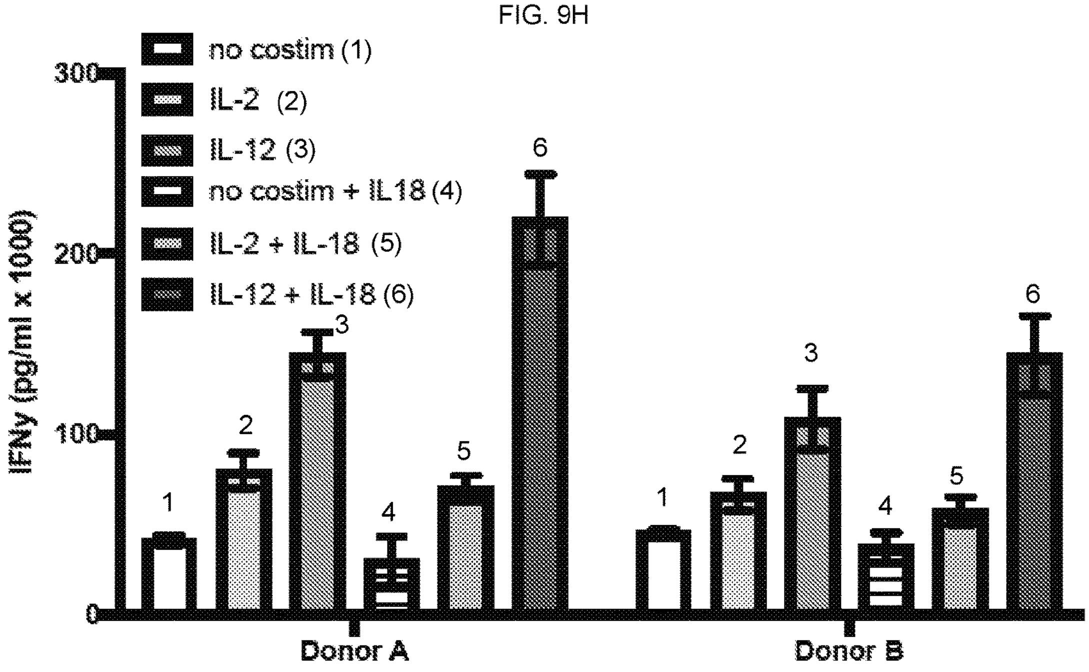
Figure 9I:
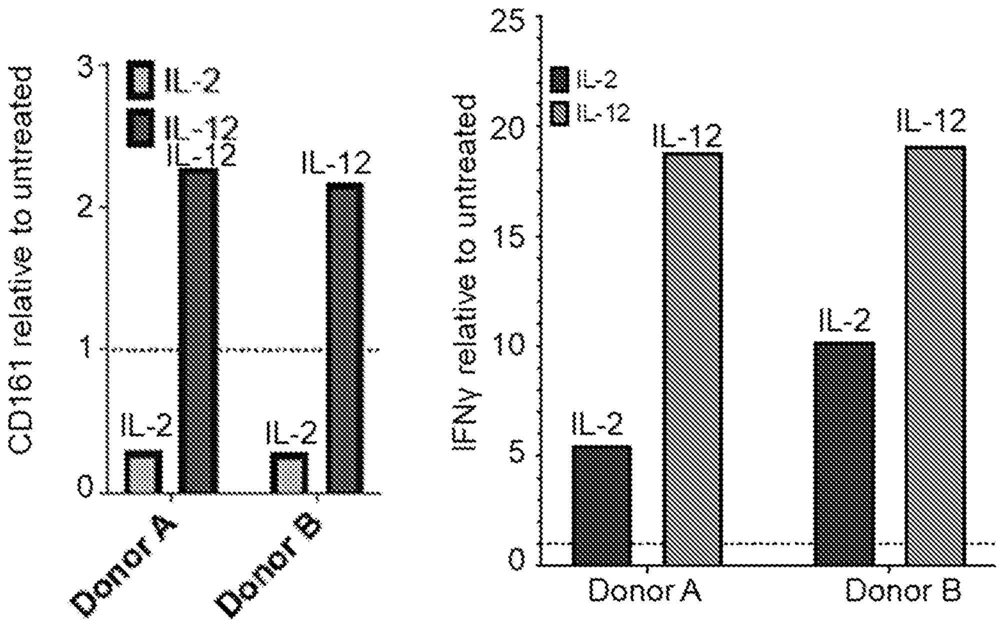
Figure 12A:
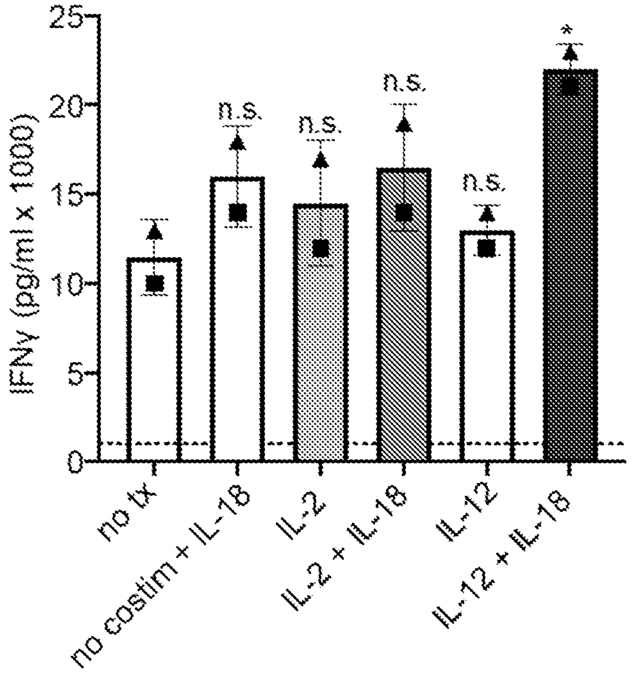
FIGS. 12A-12C. IL-12 and IL-18 promote IFNγ production but not increases in proliferation or killing. Two healthy donor CAR T products were stimulated with 1 ng/ml IL-2 or IL-12 prior to stimulation via the TCR with CD3/CD28 beads and IL-18 at 10 ng/ml. After 3 days supernatants were harvested for IFNγ assayed by ELISA (FIG. 12A), and live cells were quantified by Promega's Cell Titer Glo assay (FIG. 12B). Represents one experiment. One-way ANOVA was used to compare treated CAR T samples to untreated. Two healthy donor CAR T products were stimulated with 1 ng/ml IL-2 or IL-12 prior to incubation with EGFP+ Raji target cells at 1:1 with IL-18 at 10 ng/ml. EGFP target cells were quantified by Incucyte and EGFP counts at Days 1-5 in each well were normalized to the count at Day 0 (FIG. 12C). Represents two experiments. The dotted line in FIG. 12A represents the limit of detection of the assay.
Figure 12B:
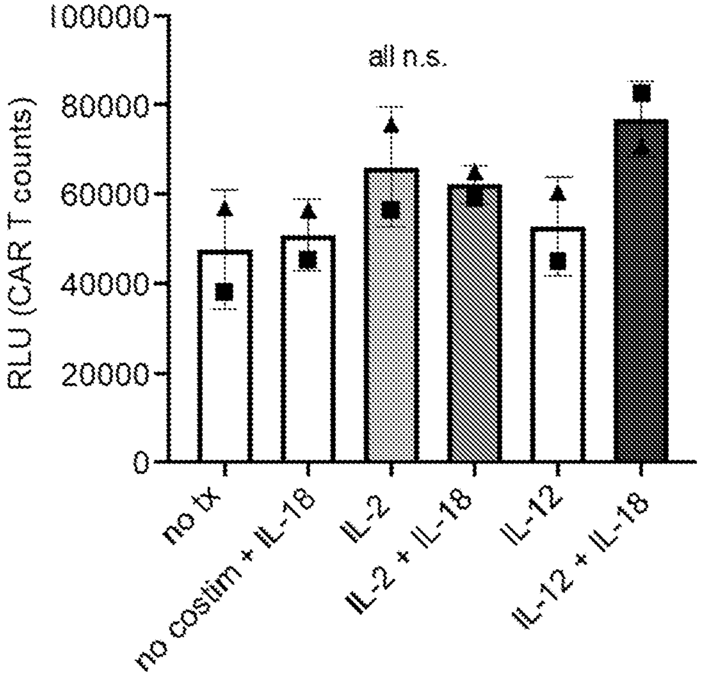
Figure 12C:
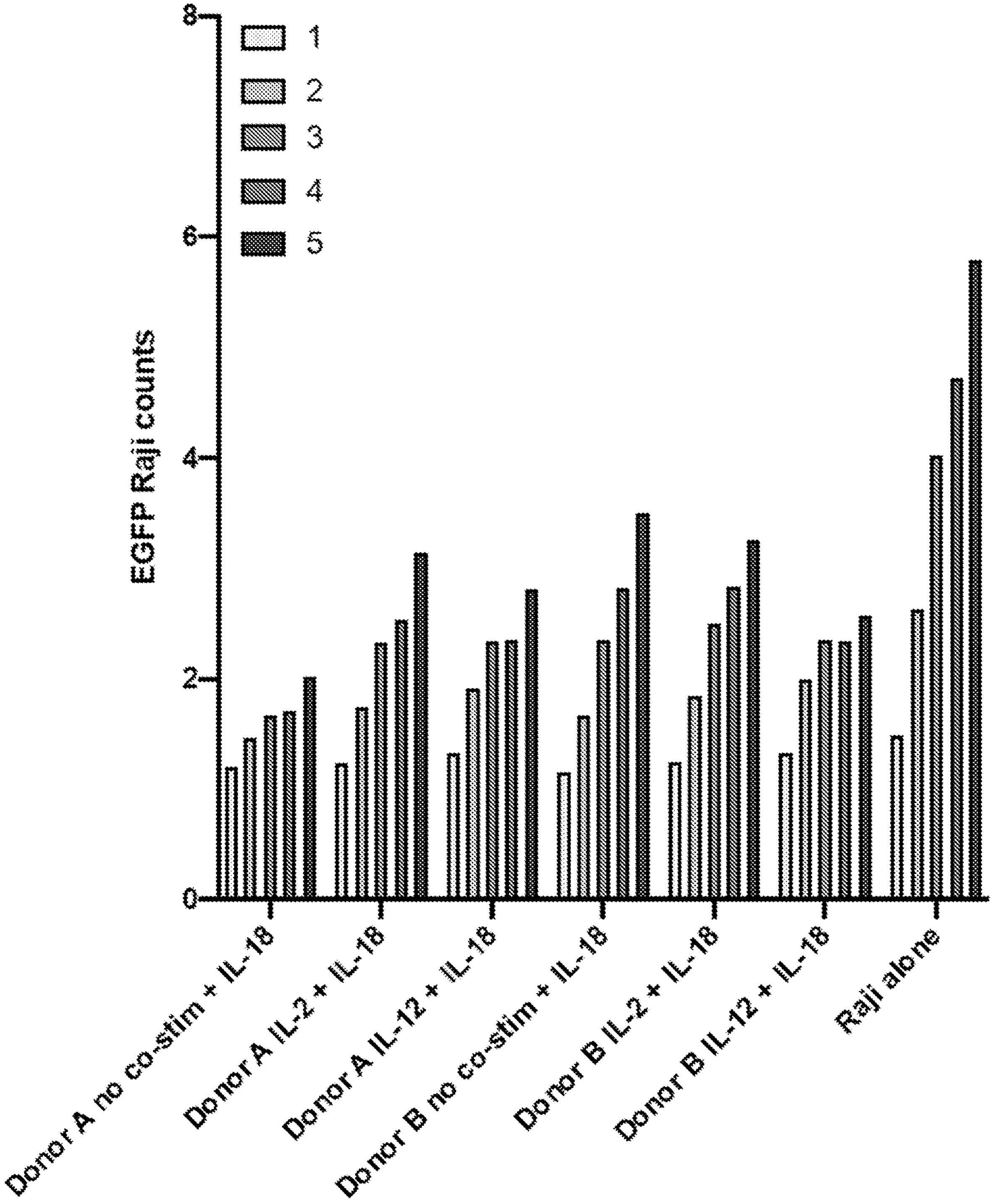
Figure 15:
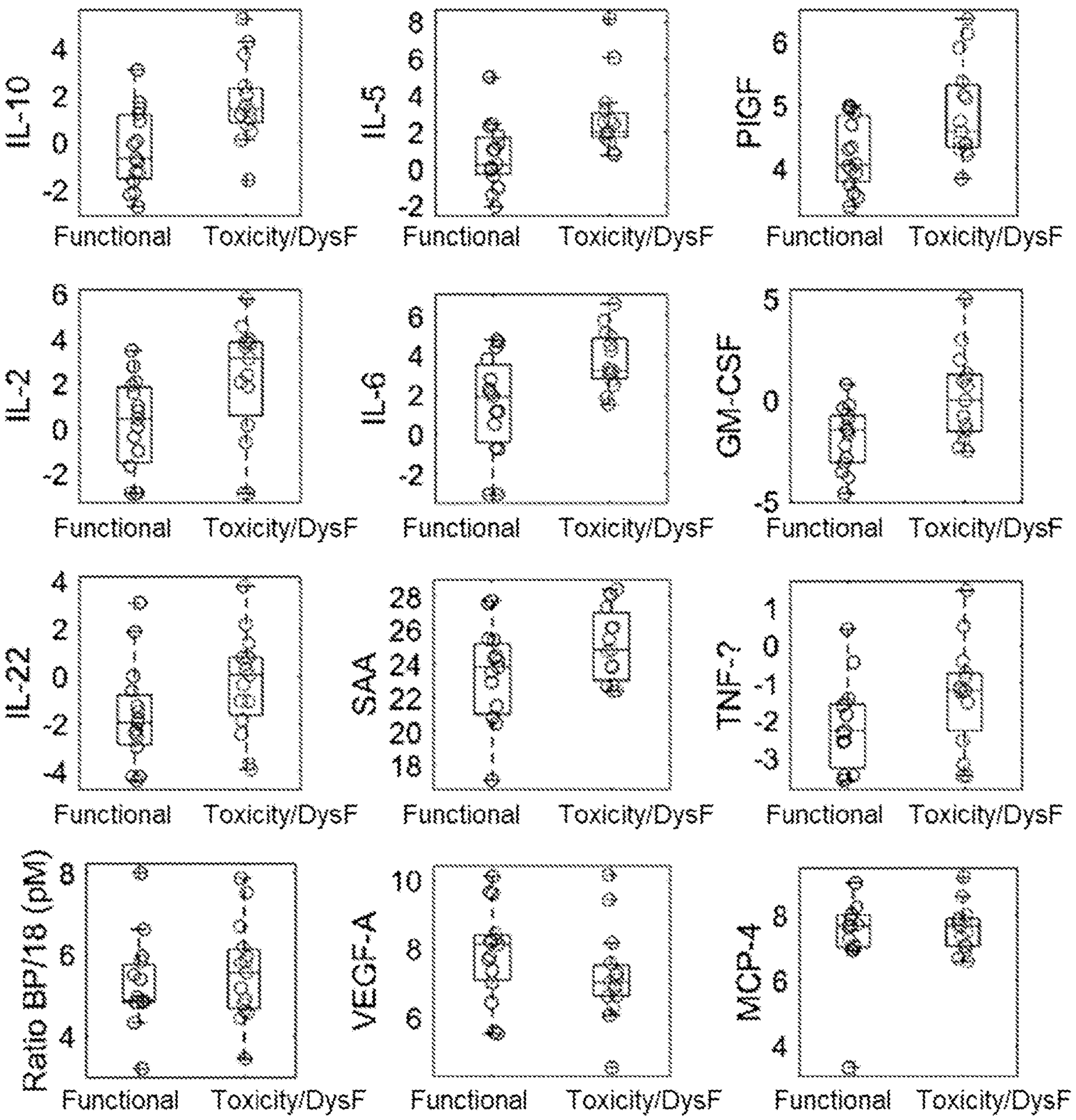
FIG. 15. Boxplots of all cytokines in order of FIGS. 13 and 14.
Figure 15:
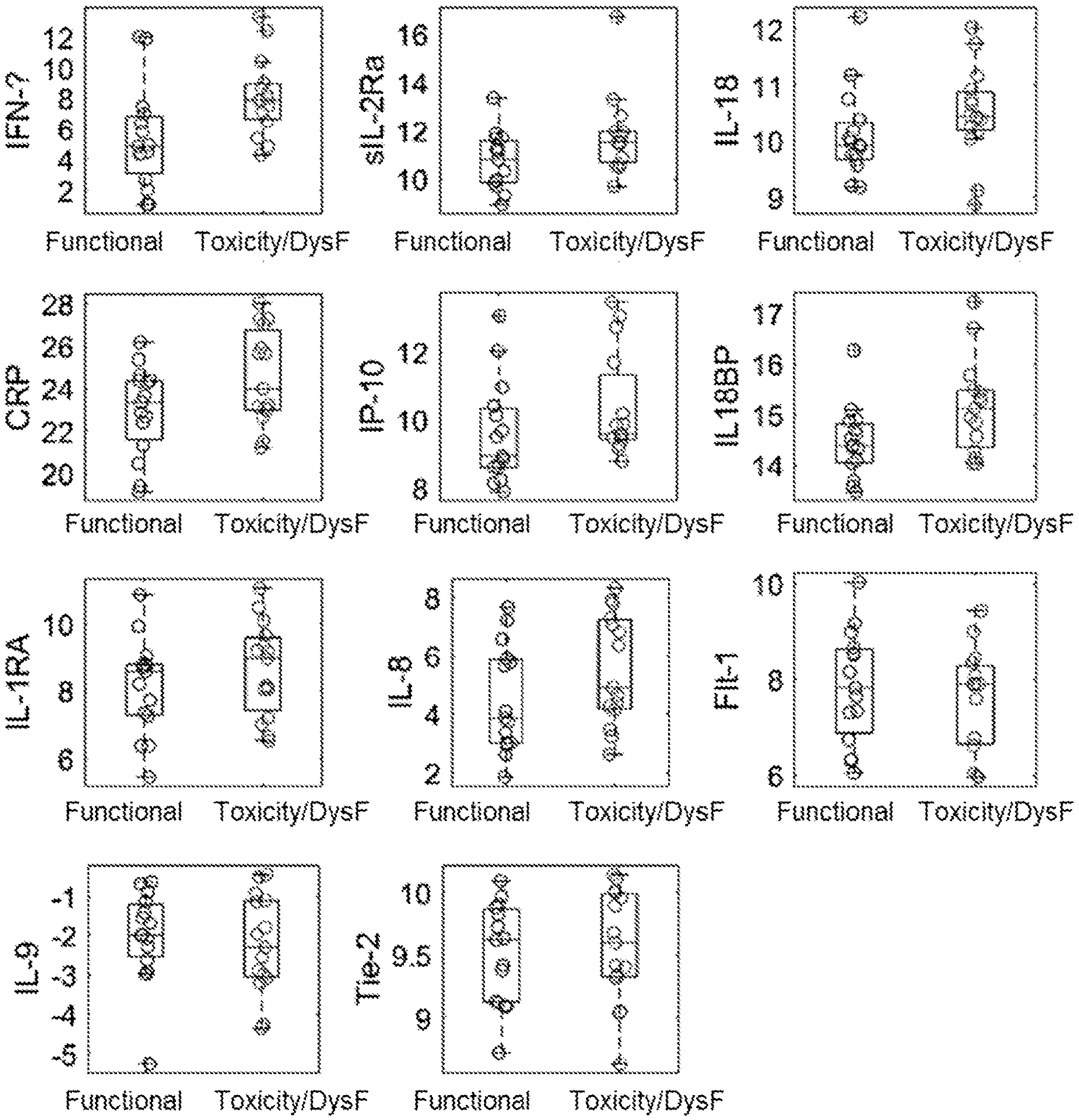
Figure 17A:
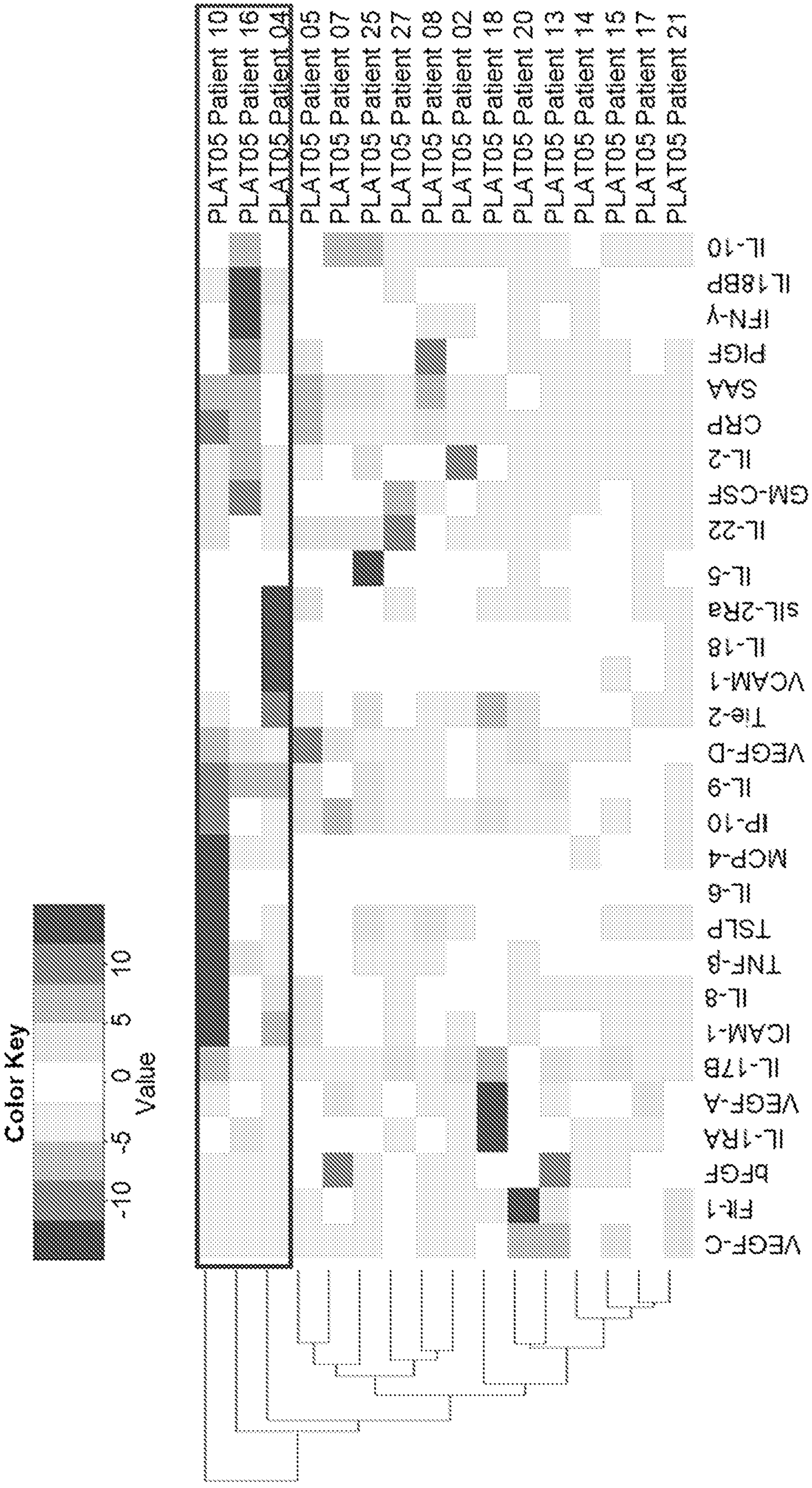
FIGS. 17A, 17B. Dysfunctional PLAT05 patients are distinguished from functional patients by their cytokine profiles at Day 3. Serum samples from PLAT05 patients were assayed across 3 timepoints by Meso Scale Discovery assay. The Day 3 data was transformed into t-scores; these are visualized by heatmap (FIG. 17A) and PCA plot (FIG. 17B). Both clearly demonstrate that the dysfunctional patients (Patient 04, 10, 16) are distinct from the functional patients. Because the clinical scoring system differed between PLAT02 and PLAT05, CRS/neurotox levels could not be compared between trials.
Figure 17B:
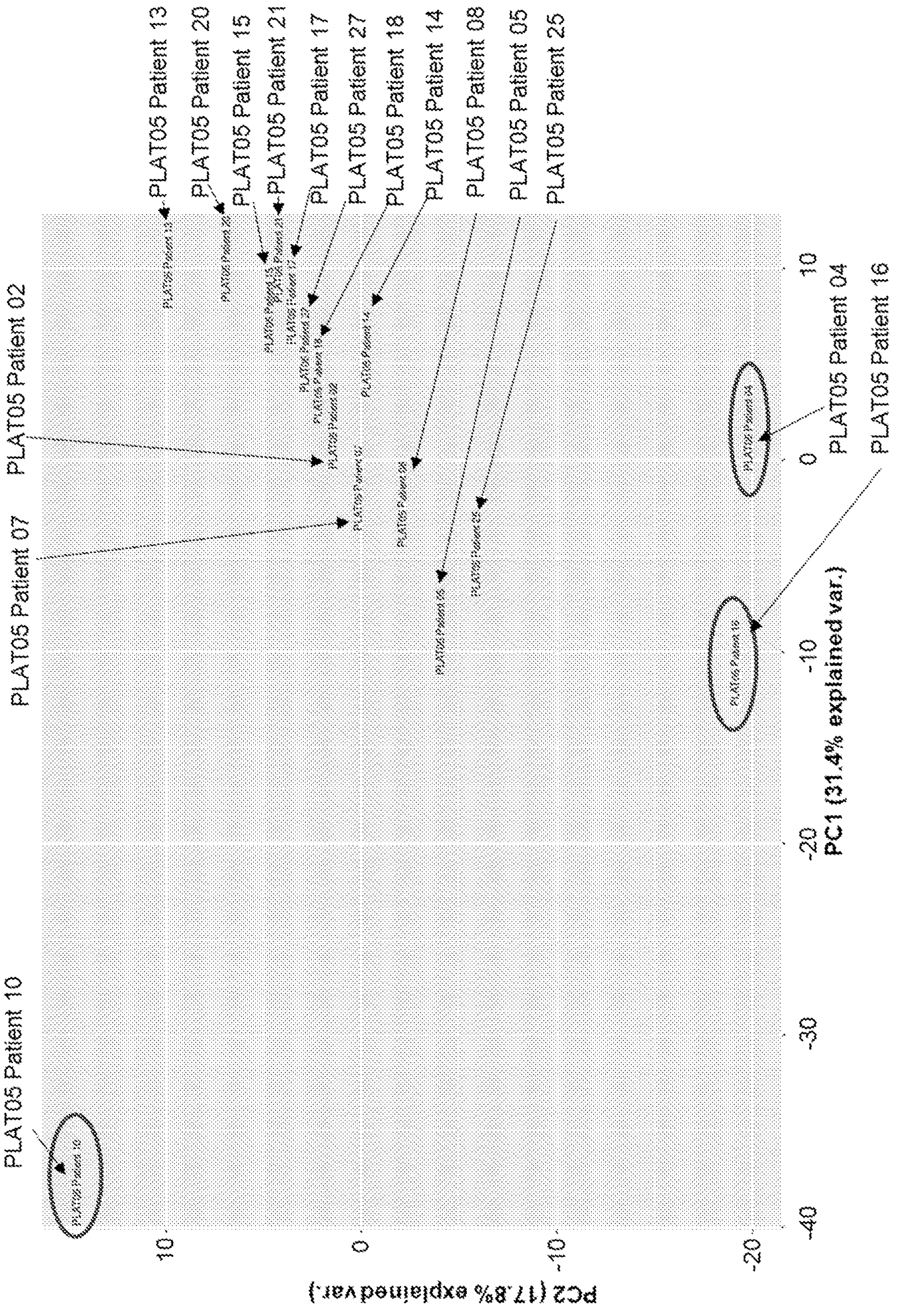
Figure 18:
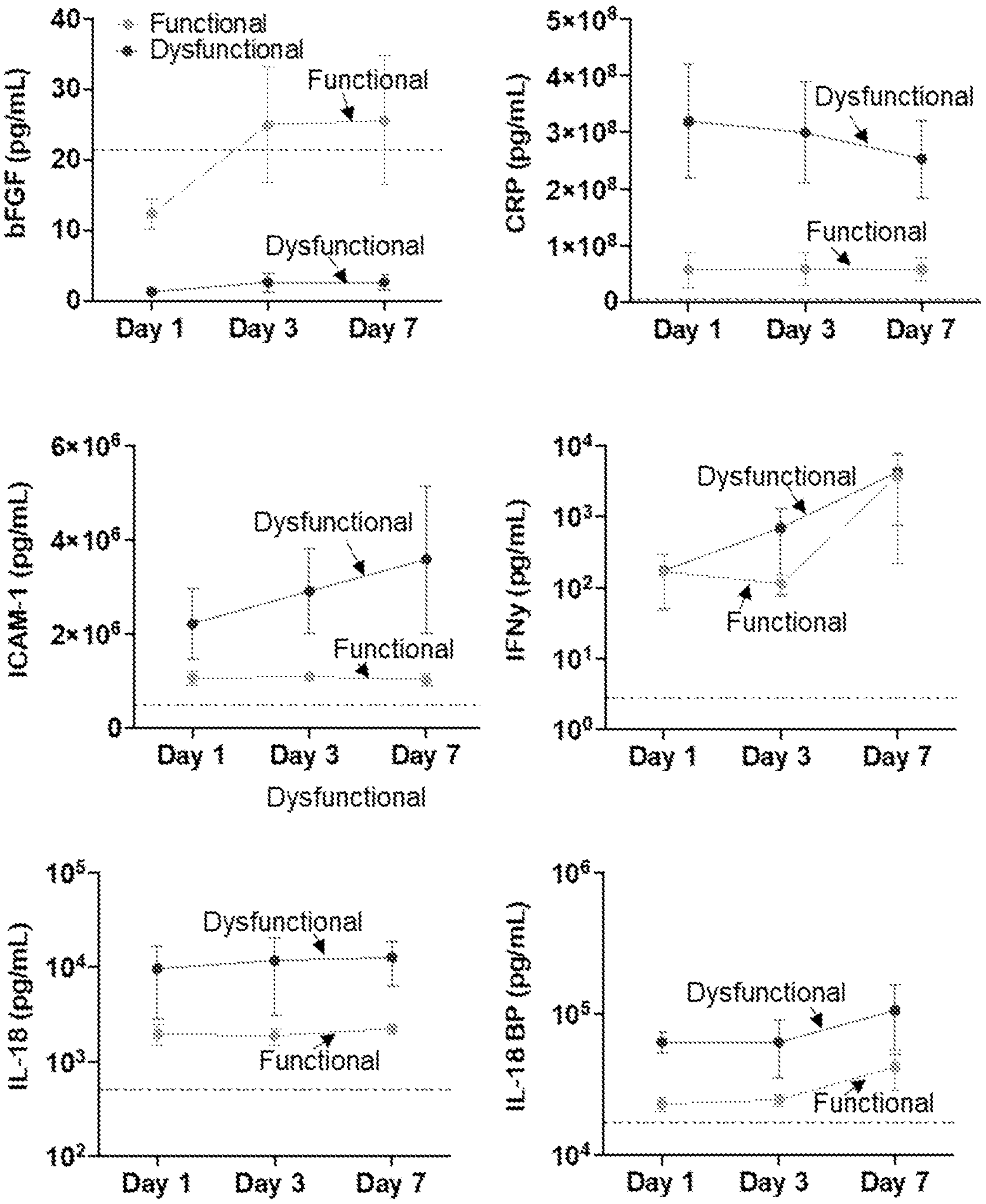
FIG. 18. Cytokine kinetics of patients on the PLAT05 CD19 CD22 CAR T trial. Serum samples from PLAT05 patients were assayed across 3 timepoints by Meso Scale Discovery assay. CRS/neurotox could not be compared between trials, so functional versus dysfunctional patients was plotted. The dotted line in each graph represents the limit of detection of each assay.
Figure 18:
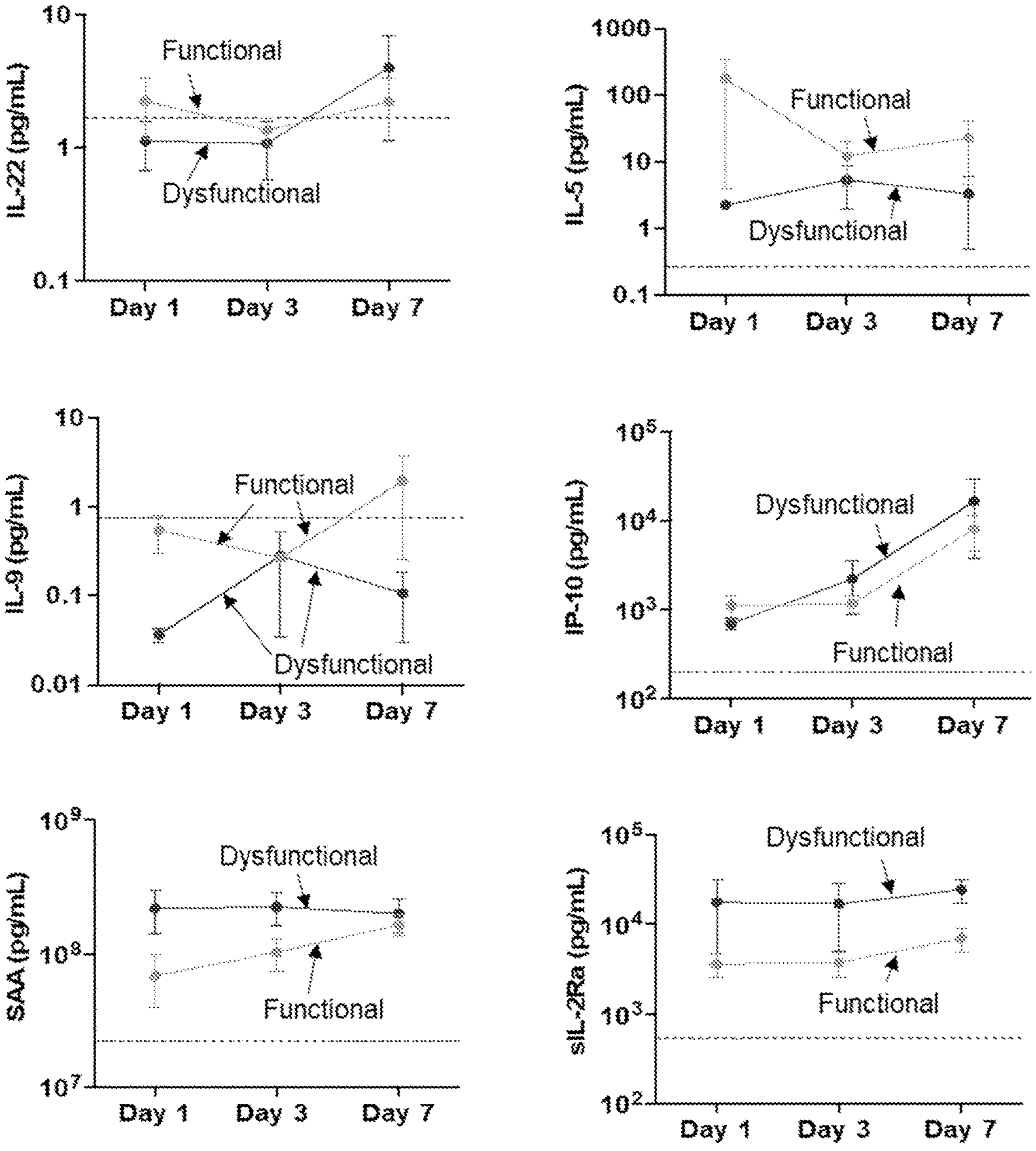
Figure 18:
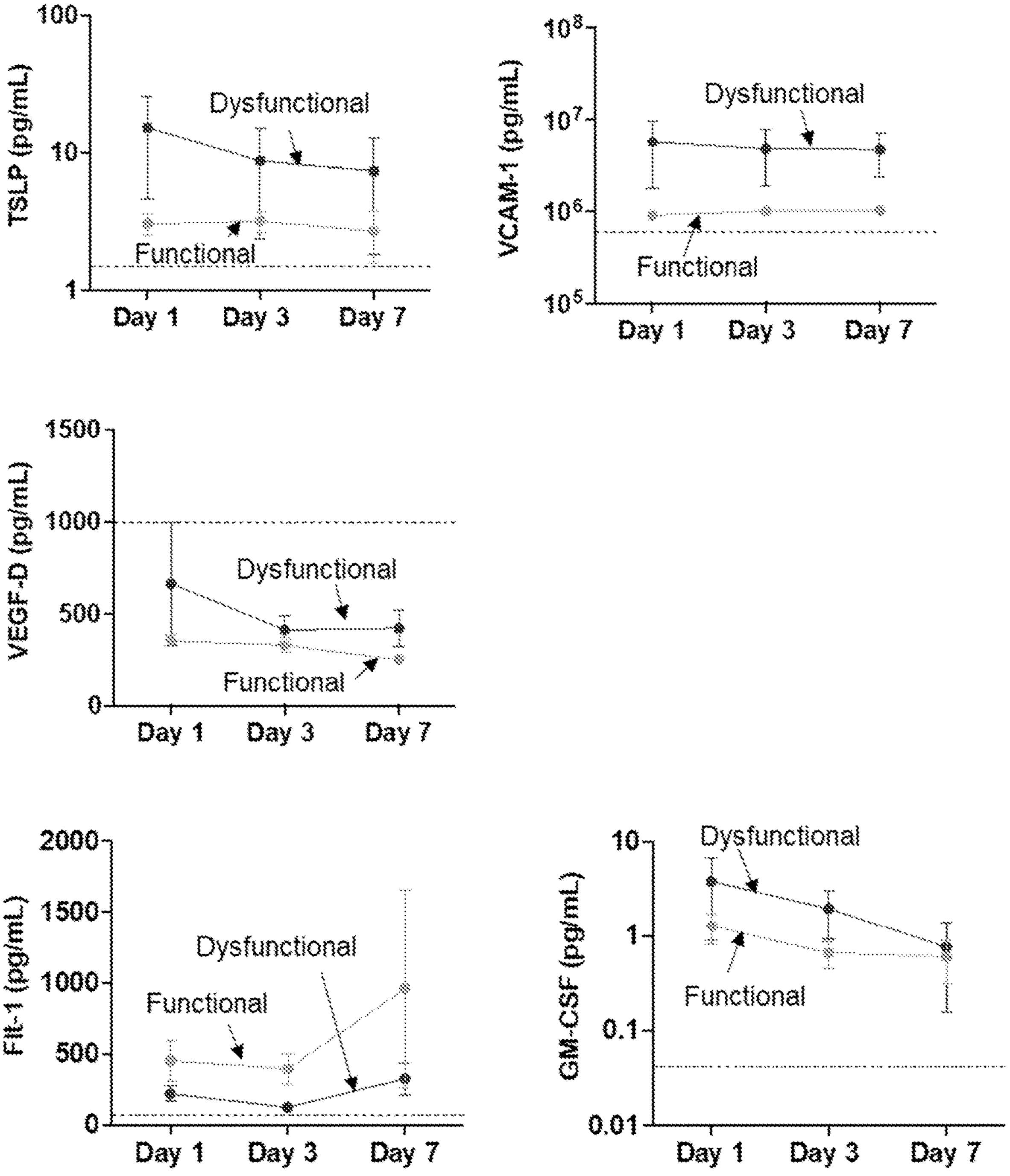
Figure 18:
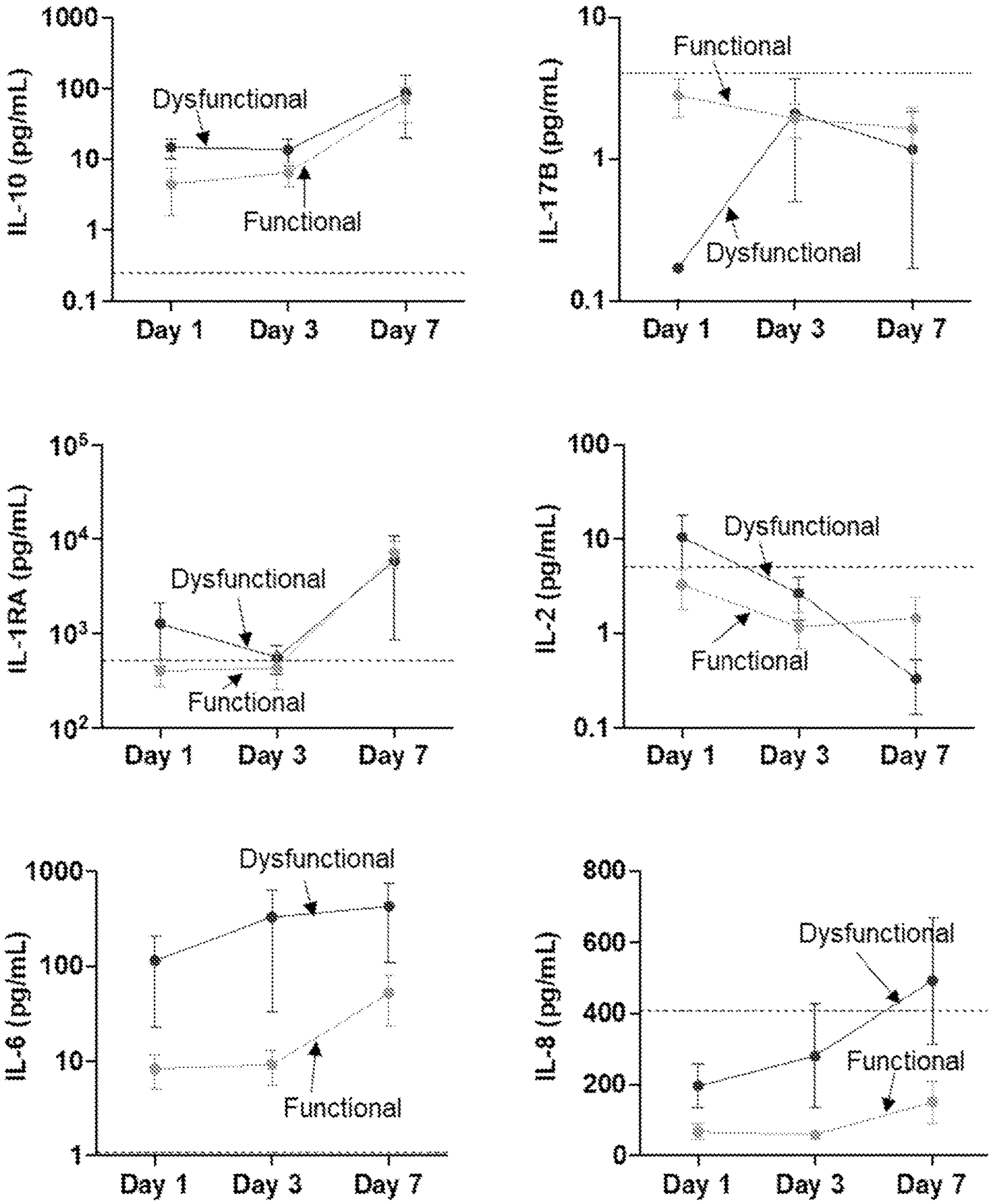
Figure 18:
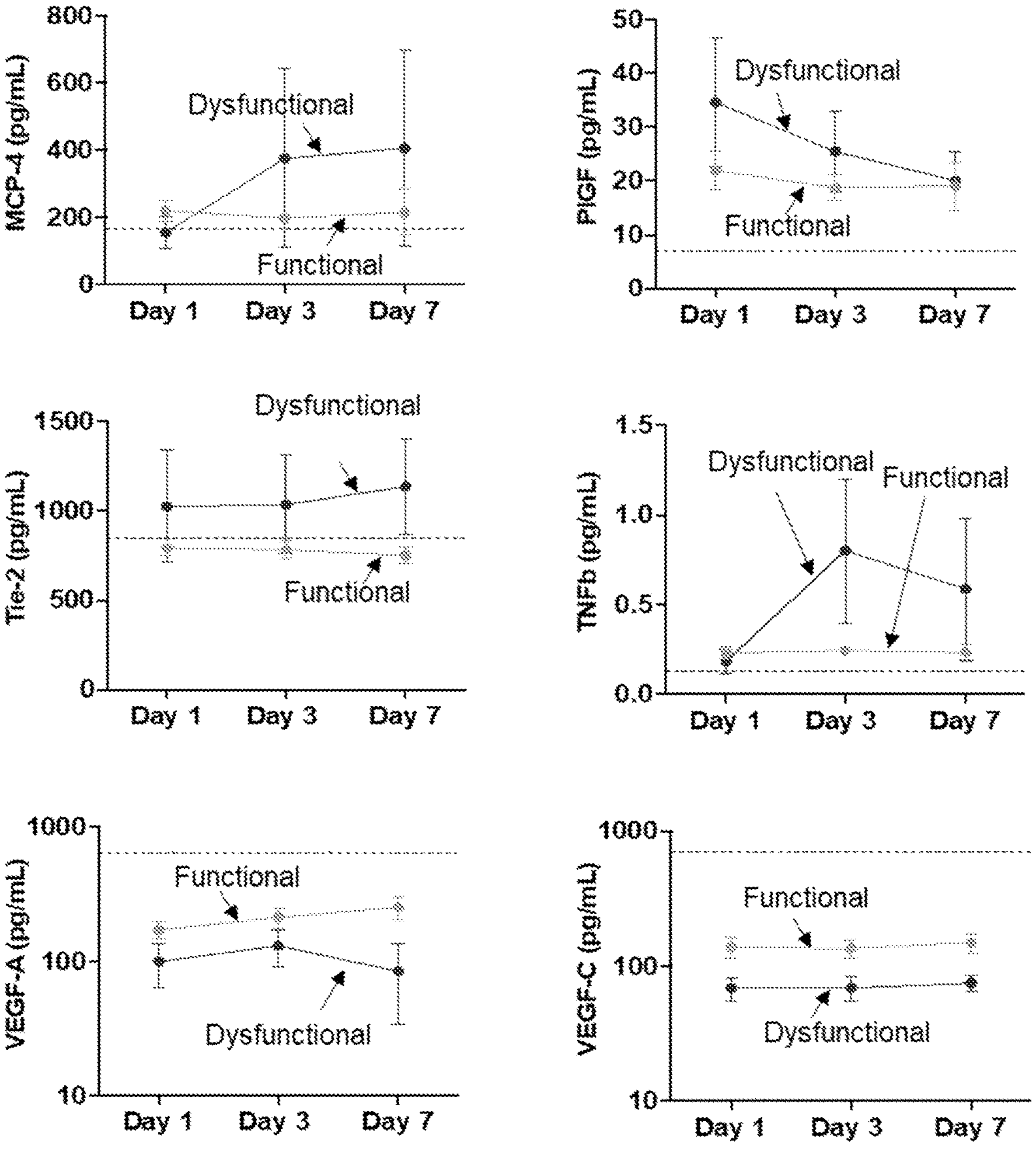
Figure 19:
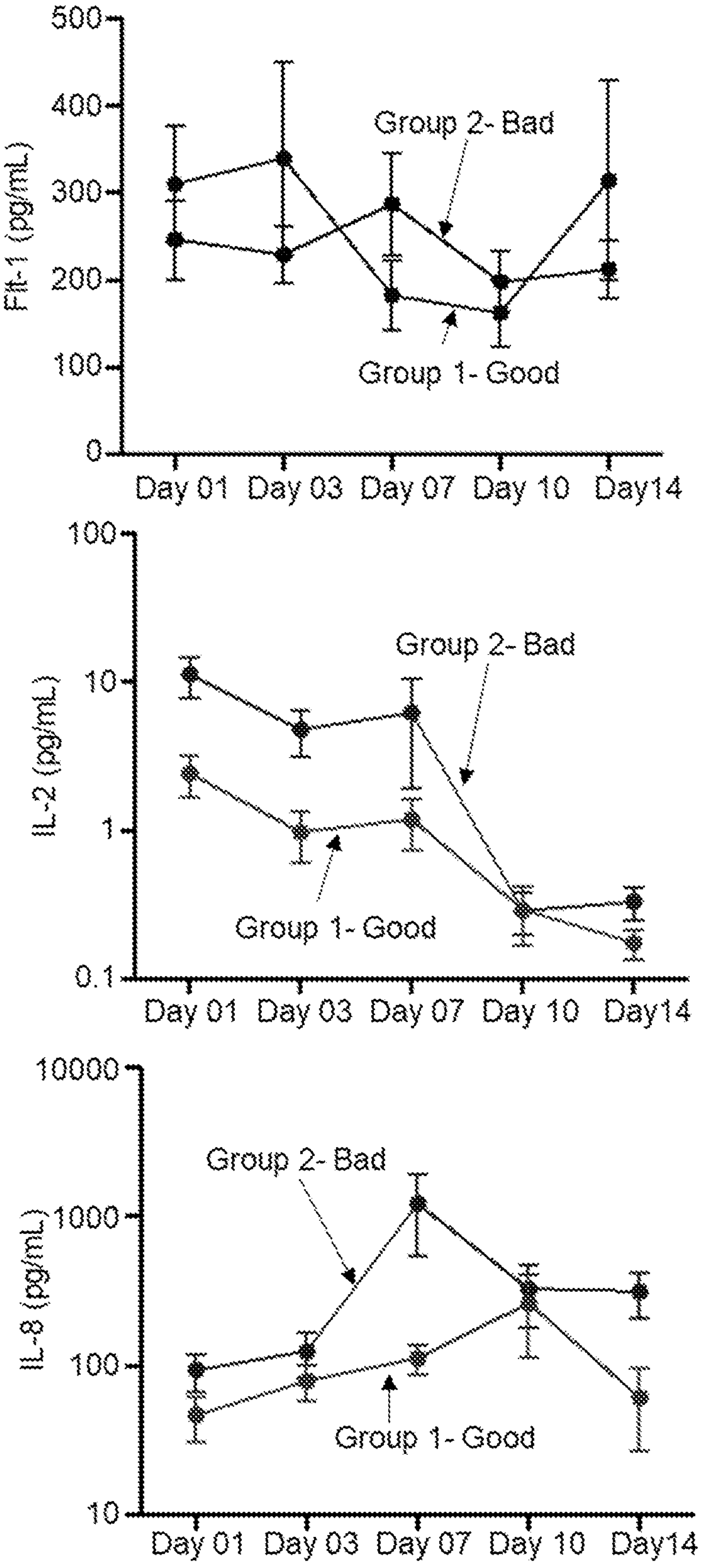
FIG. 19. 22 assayed cytokines and kinetics for machine learning PLAT02 (30 patients): Cytokine Panel: bFGF, CRP, Flt-1, GM-CSF, ICAM-1, IFNγ, IL-10, IL-17B, IL-18, IL-18BP, IL-1RA, IL-2, IL-22, IL-5, IL-6, IL-8, IL-9, IP-10, MCP-4, PIGF, SAA, sIL-2Ra, Tie-2, TNF-β, VCAM-1, and VEGF-A.
Figure 19:
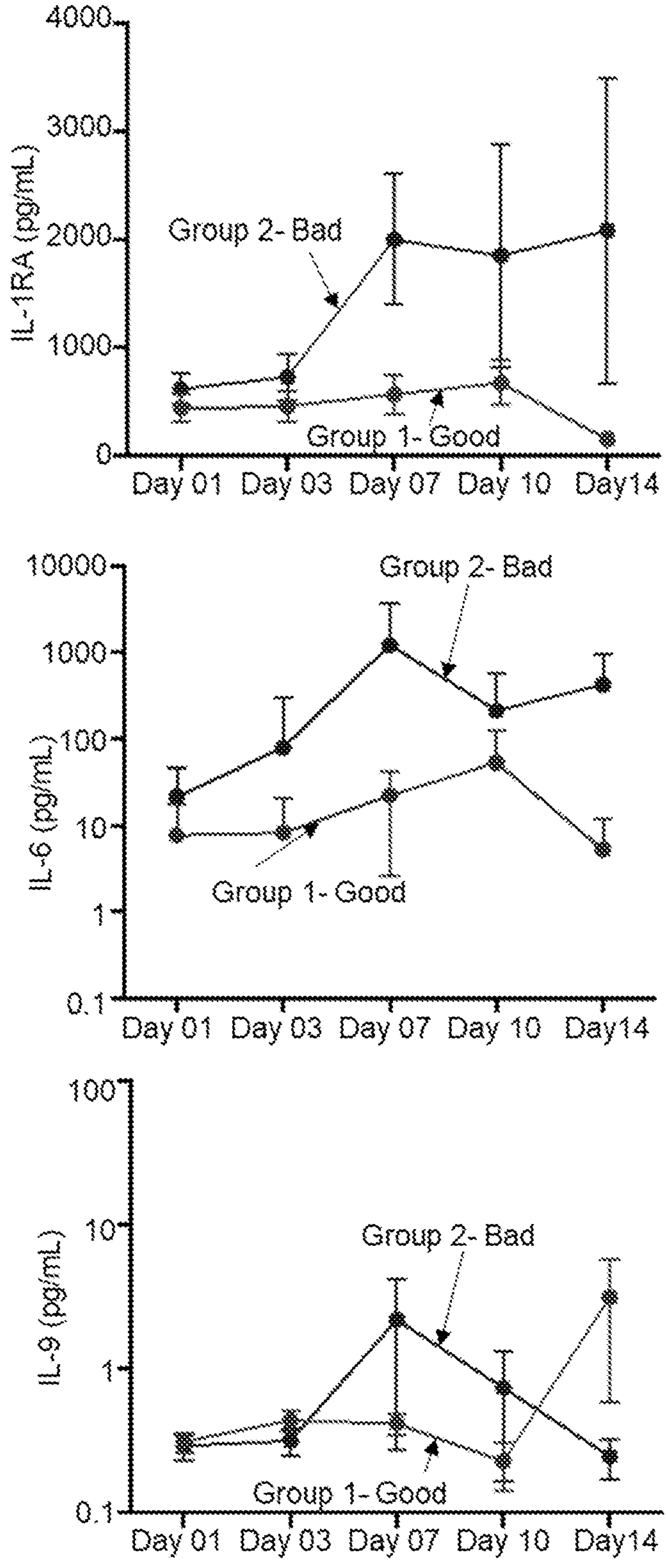
Figure 19:
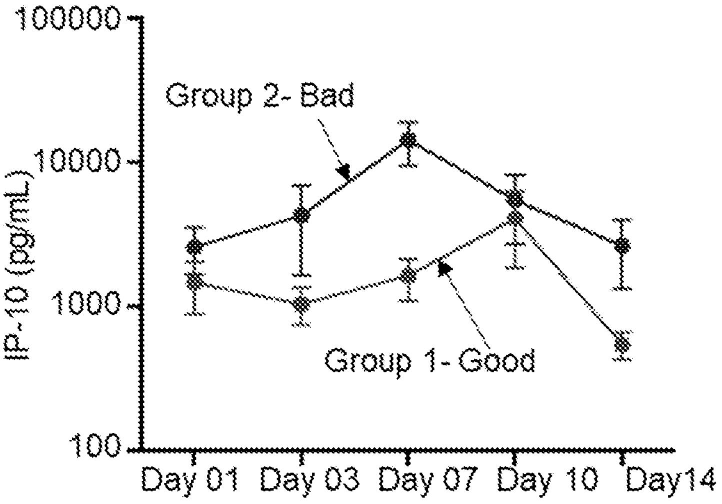
Figure 19:
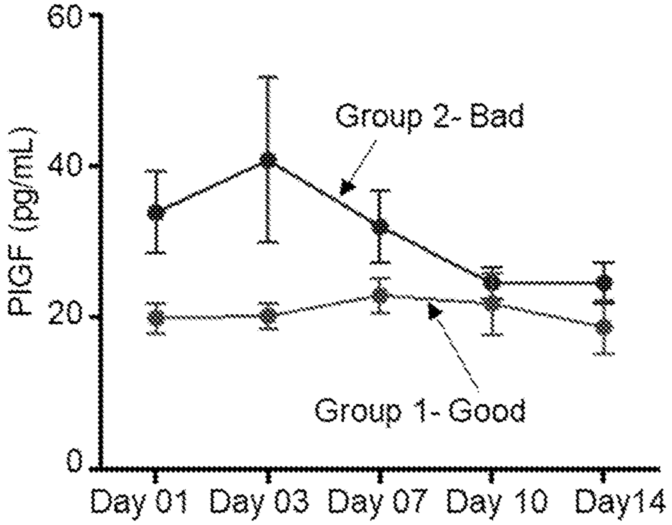
Figure 19:
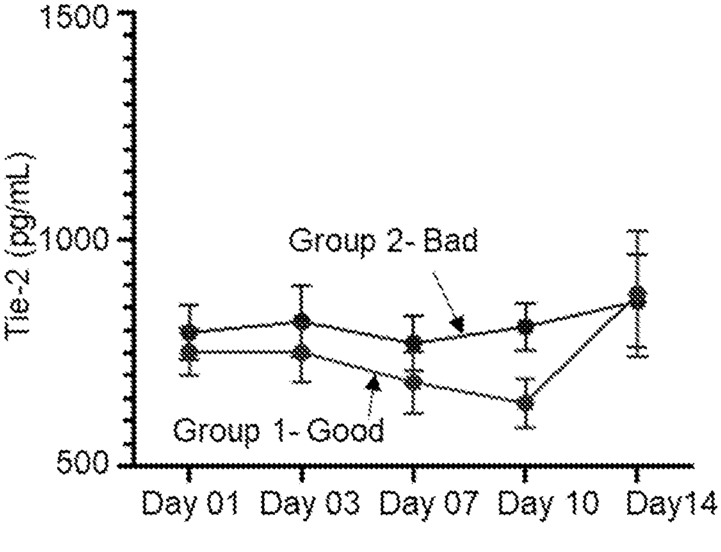
Figure 19:
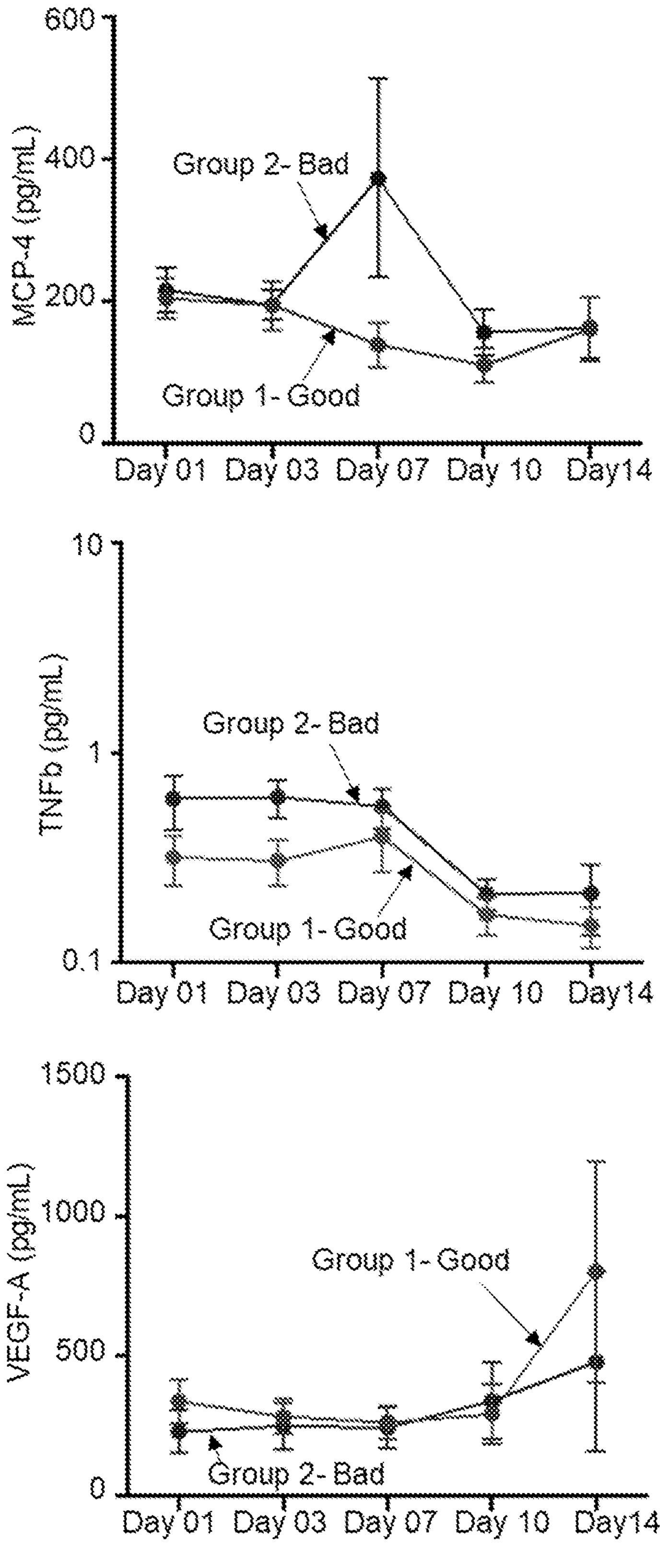
Figure 20:
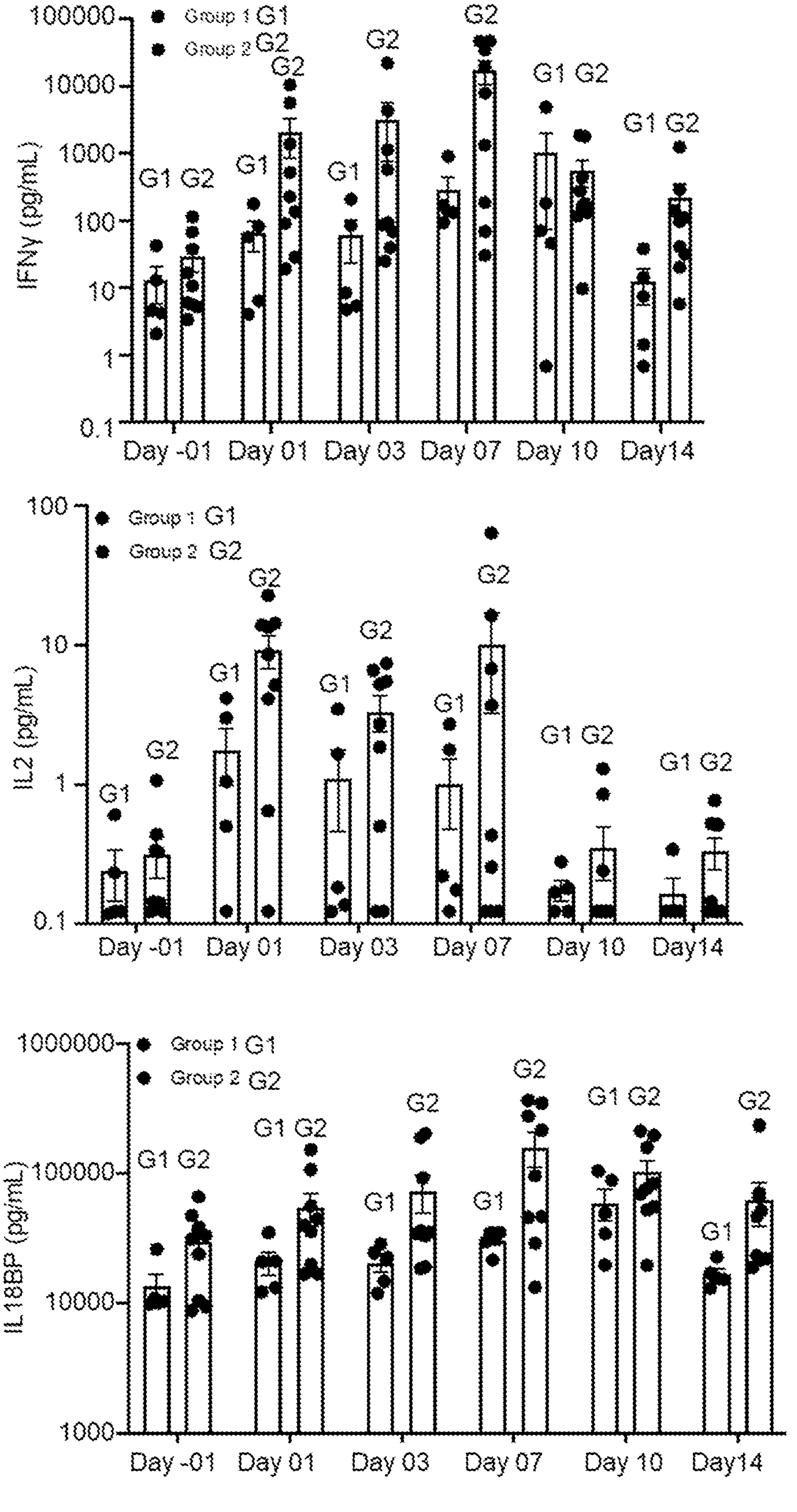
FIG. 20. 12 assayed cytokines pre-CAR for pre-interferon signaling in PLAT02 (14 patients): Cytokine: IFNγ, IL-10, IL-18, IL-18BP, sIL-2ra, IL-2, IL-5, IL-6, IL-12p70, IL-13, IL-4, and IL-15.
Figure 20:
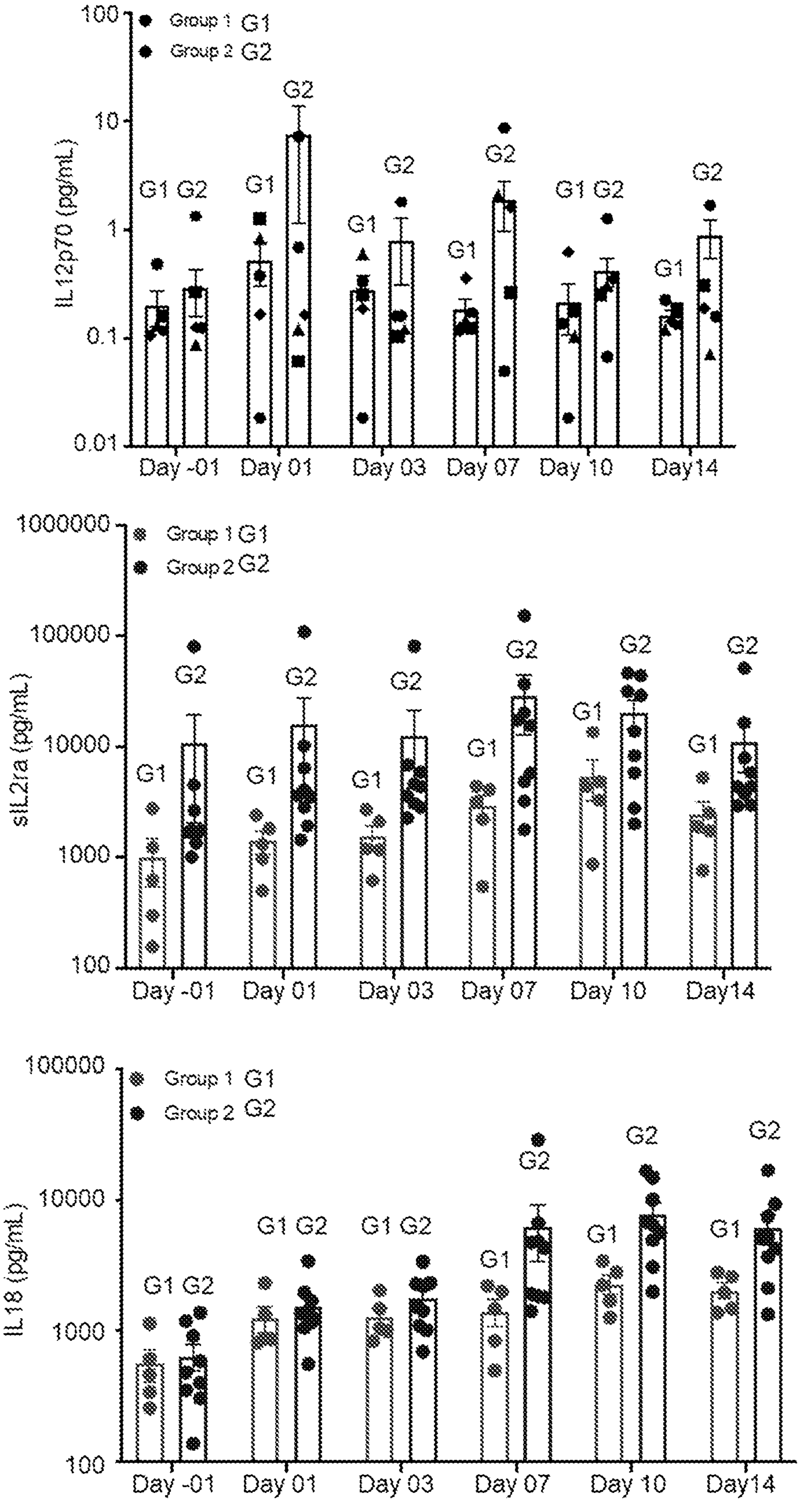
Figure 20:
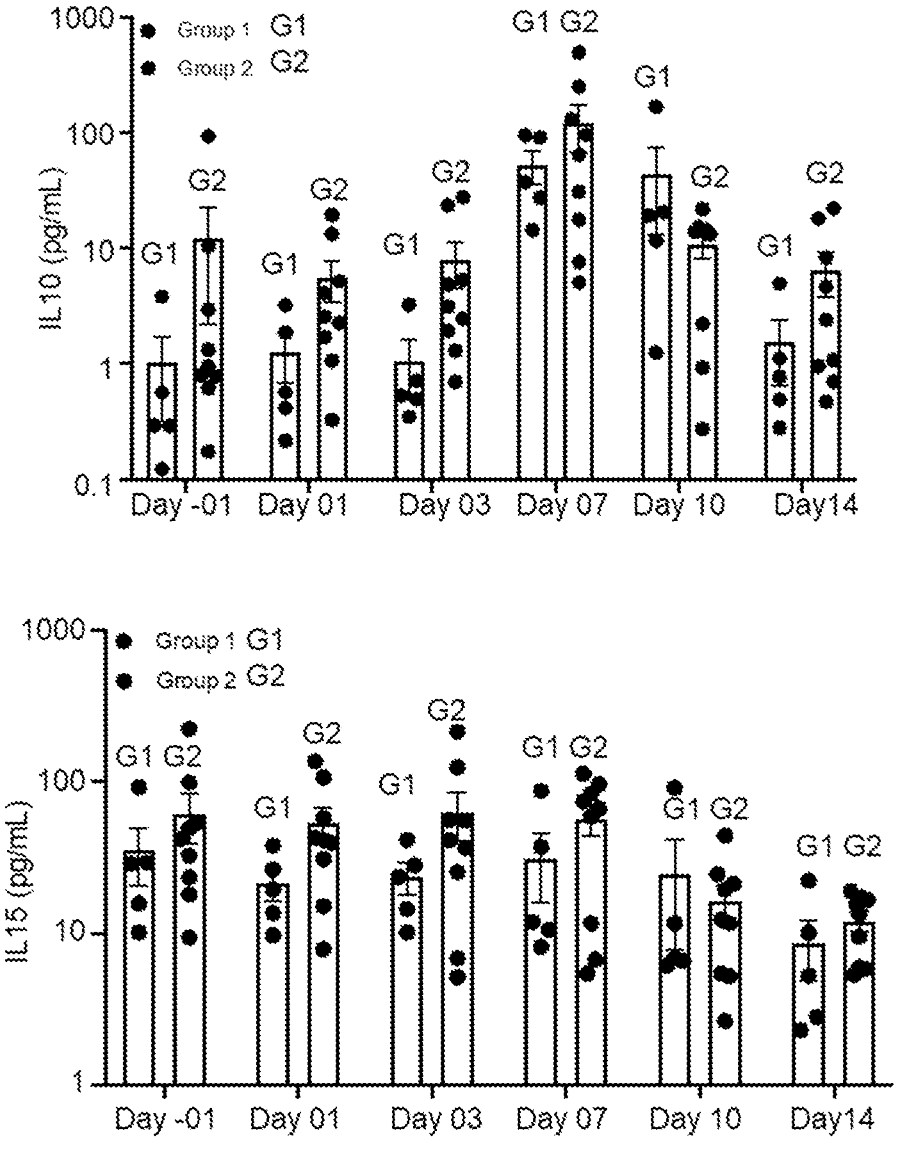
Figure 20:
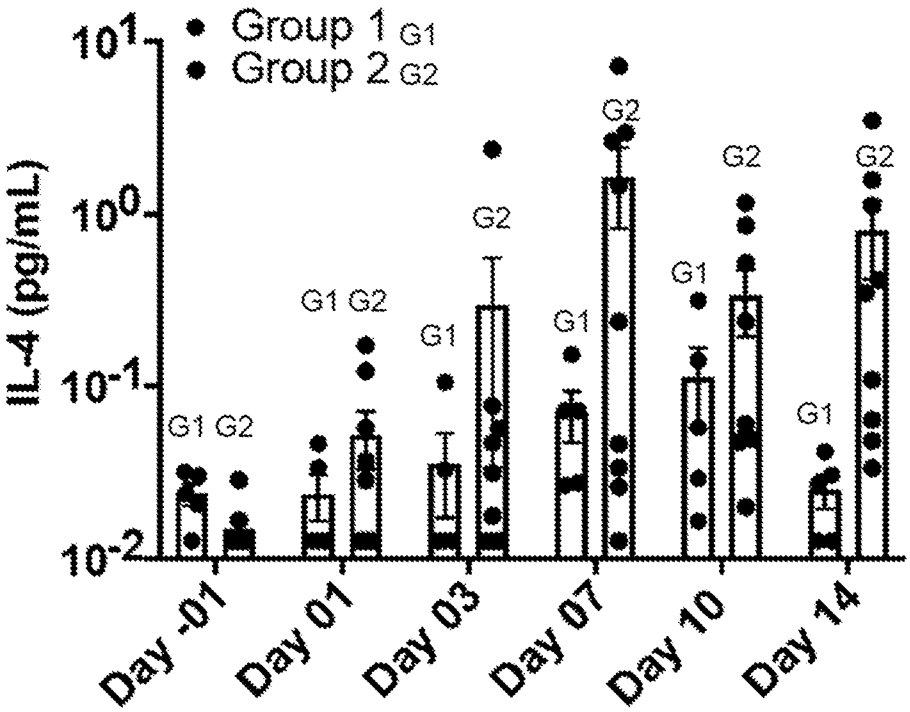
Figure 20:
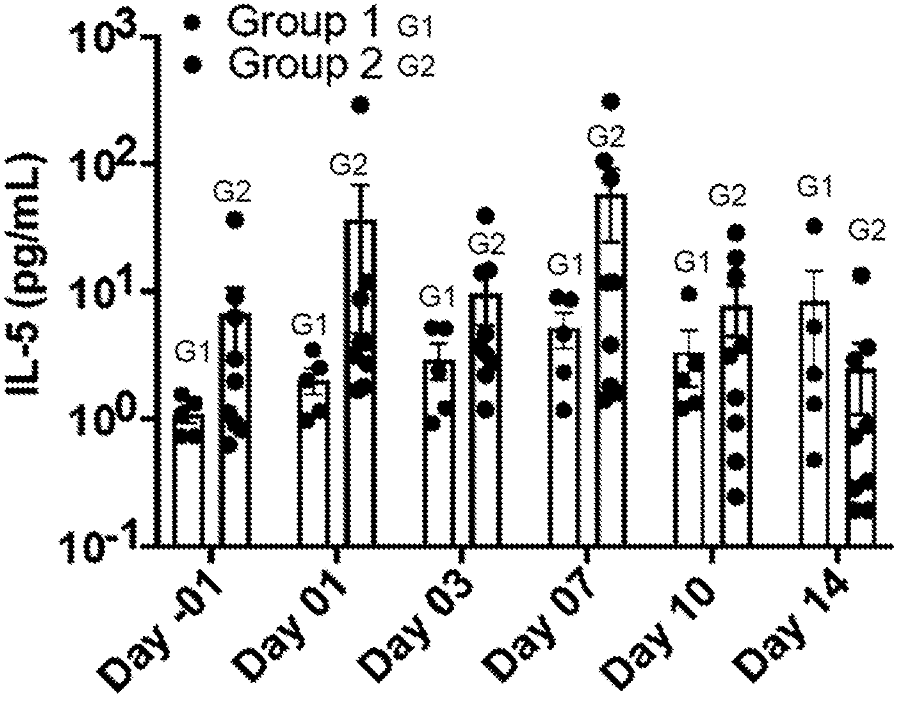
Figure 20:
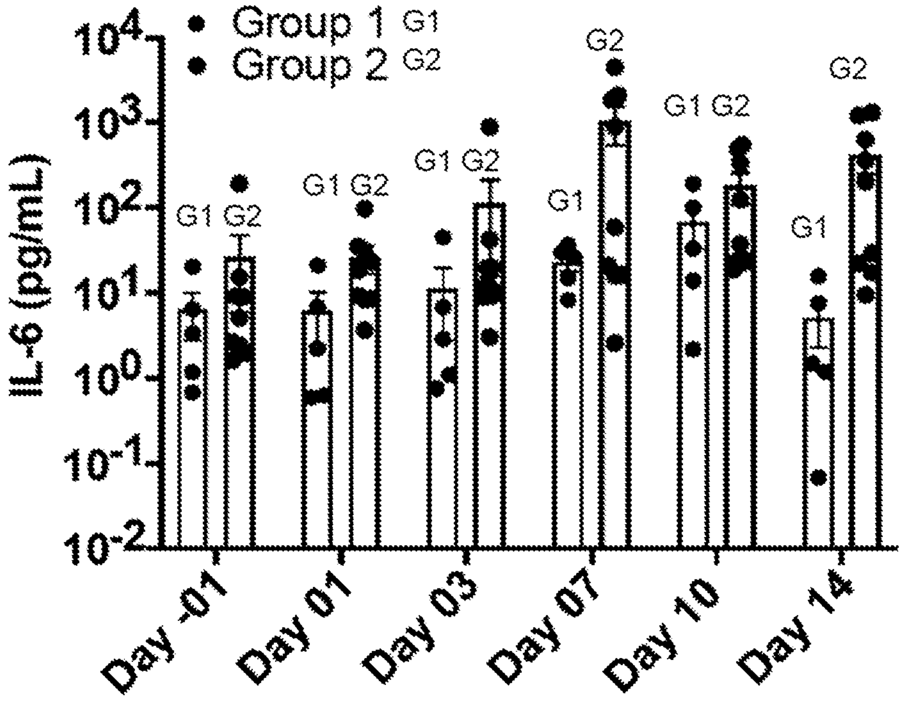
Figure 20:
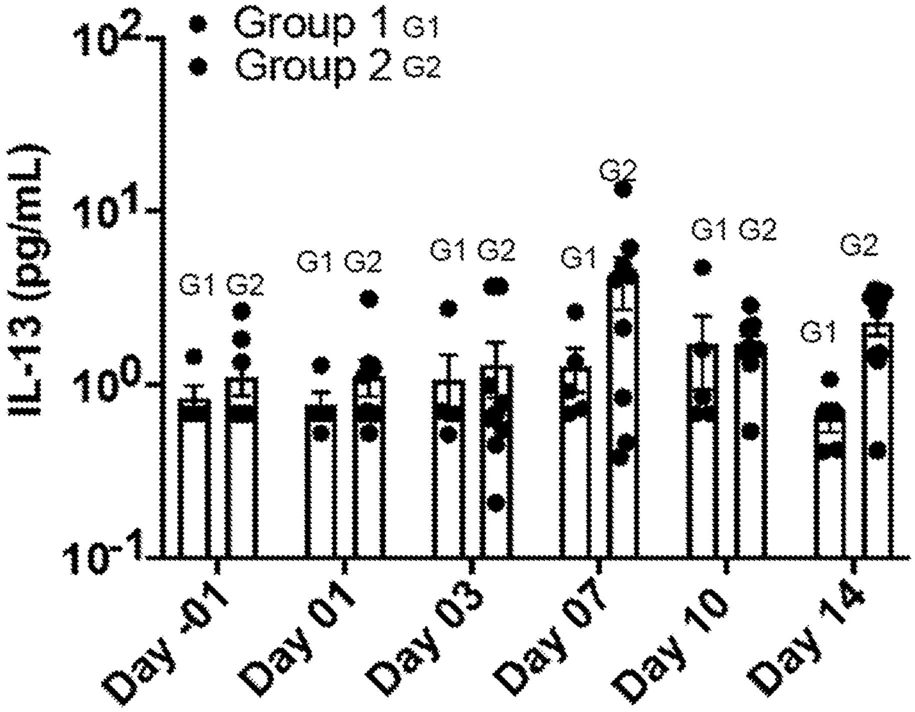
Figure 21:
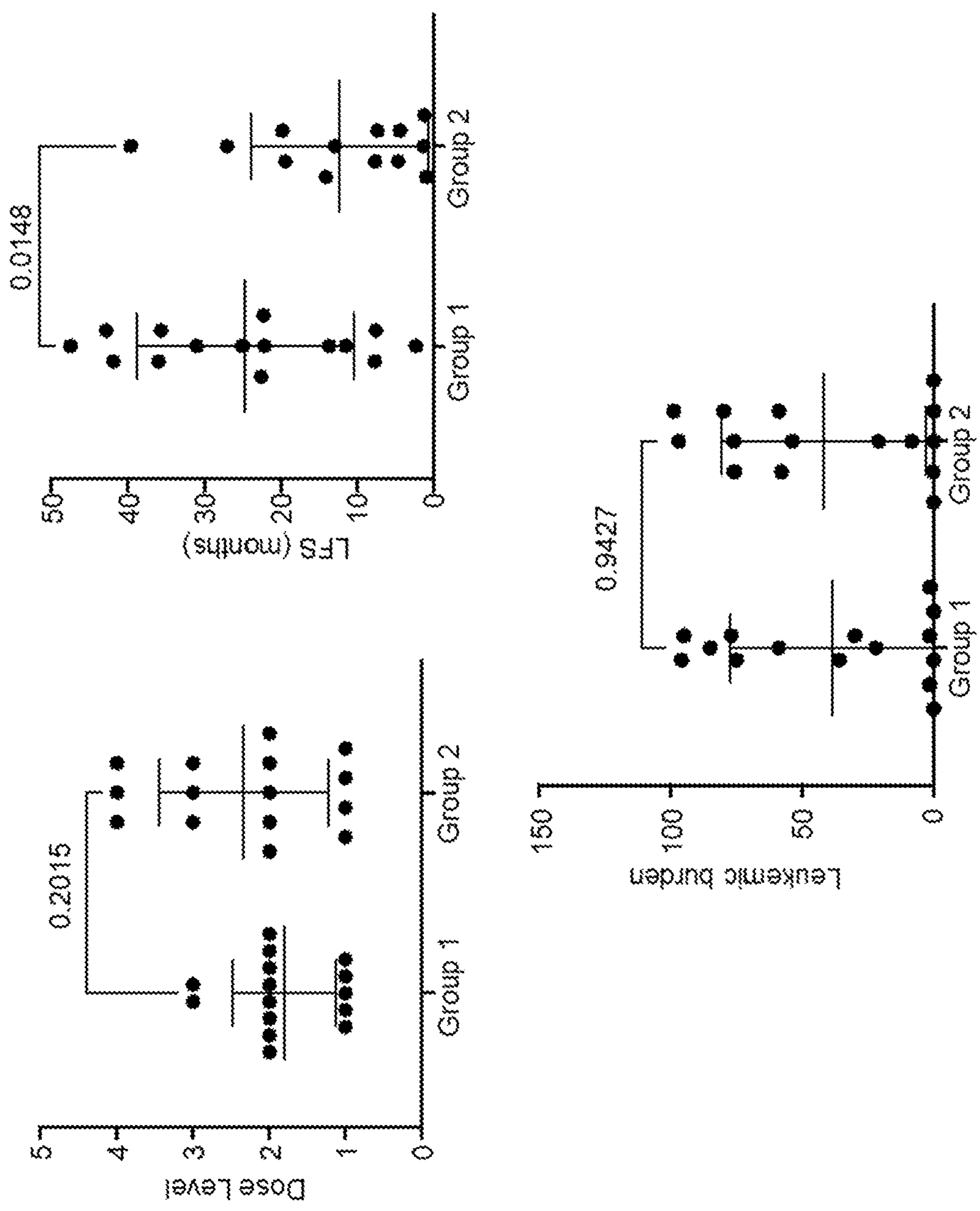
FIG. 21. Additional patient outcomes in CAR patients as a function of Group outcomes.

Healthy donor CAR T cell can be induced to increased IL-18 signaling capacity increase interferon output. CD161+ cells require not only IL-18 but IL-12 to functionally signal and produce increases in IFNγ. IL-12 increases the IL-18 heterodimeric receptor on the surface of lymphocytes triggering NF-κB, enhancing interferon output. Consistent with this, increased IFNγ in healthy donor CAR T cells (FIG. 9H) was observed following overnight incubation in IL-12 and confirmation of dramatic increases in the IL-18 heterodimeric receptor components (IL-18R1 and IL-18RAP) (FIG. 9G). Interestingly, increases in IL-18 heterodimeric receptor also correlated with increased expression of CD161 in healthy donors (FIG. 9I, FIG. 10). Importantly, IL-2 signaling can drive reductions in IL-18 heterodimeric receptors reducing IFNγ production, as observed in healthy donor CAR T cells (FIG. 9G,9H). Interestingly, Group 2 patients have increases in sIL-2RA which neutralizes IL-2 (FIG. 9B). Notably, IL-12, IL-18 and IL-2 signaling did not seem to alter CAR T target cell lysis or increase CAR T expansion, consistent with the non-significant clinical parameter changes observed between Group 1 and Group 2 (FIGS. 12A-12C). IL-12p70 signaling was only slightly elevated in Group 2 of the cohort (FIG. 9B). However, elevated levels of CD161+ cells which correlate with increased IL-12 responsiveness will enhance interferon output leading to aberrant myeloid and IL-18 activation (FIG. 9A).

CD161+ IFNγ cells prime Group 2 patients pre-CAR to drive aberrant uncontrolled monocytic IL-18 signaling post-CAR. These signaling events trigger a reduction in overall survival by a currently unknown mechanism. The current data suggests that IFNγ (T-cell) and IL-18 (myeloid) axis, and CD161+ cells can be used clinically to predict poor clinical outcomes (survival, therapeutic response and NTX). Additionally, these models lend therapeutic intervention points pre-CAR and days 1-7 post-CAR, where interferon or IL-18 neutralization and/or removal of CD161+ cells may improve clinical outcomes.

Materials and Methods

Clinical serum samples: The initial cohort of samples included 14 patients—5 of Group 1 and 9 of Group 2—at 5 timepoints post-CAR (Days 1-14) and one pre-CAR timepoint (Day −1). Cohort 2 included 16 additional patients—10 of Group 1 and 6 of Group 2—at 3 timepoints post-CAR (Days 1, 3, and 7). Seven of the 16 patients (2 of Group 1 and 5 of Group 2) were also assayed at Day 10.

Cytokine levels in clinical samples. MSD: All cytokines besides IL-18BP were assessed by Meso Scale Discovery's custom U-PLEX, Angiogenesis V-PLEX Panel 1 (K15190D-1), and Vascular Injury V-PLEX Panel 2 (K15198D-1) assays according to manufacturer's instructions. Samples were run in technical duplicate and interpolated against standards using a 4-parameter logistic curve fit. To facilitate cross-run comparison, healthy controls were run each time. Assays where the CV for these controls exceeded 30% were excluded from further analysis. Machine learning analysis does not tolerate zero values; therefore, values were included that were in detection range/above curve fit and non-detects were replaced with the value of the Lower Limit of Detection (LLOD) for the assay. Final values were reported in pg/ml.

IL-18BP ELISA: Serum IL-18BP levels were measured by ELISA (R&D, DY119) at a 1:40 dilution in reagent diluent according to manufacturer's instructions. Optical density was measured at 450 nm using a Victor3 instrument and corrected by subtraction with OD at 570 nm. Samples were run in technical duplicate and interpolated against standards using a 4-parameter logistic curve fit. Final values were reported in μg/ml. Cohort 1 and 2 inter-run CV for healthy controls=12%. Cohort 1 D1-D14 and preT inter-run CV for spike controls=42%.

22 assayed cytokines and kinetics for machine learning PLAT02 (30 patients): bFGF, CRP, Flt-1, GM-CSF, ICAM-1, IFNγ, IL-10, IL-17B, IL-18, IL-18BP, IL-1RA, IL-2, IL-22, IL-5, IL-6, IL-8, IL-9, IP-10, MCP-4, PIGF, SAA, sIL-2Ra, Tie-2, TNF-β, VCAM-1, and VEGF-A.

12 assayed cytokines pre-CAR for pre-interferon signaling in PLAT02 (14 patients): IFNγ, IL-10, IL-18, IL-18BP, sIL-2ra, IL-2, IL-5, IL-6, IL-12p70, IL-13, IL-4, and IL-15.

In vitro assays: Monocytes were isolated from healthy donor PBMCs using the Easysep CD14 positive selection kit II (StemCell Technologies, 17858) and plated at 100 k/well in a 96 well tissue-culture treated plate in 200 μL/well complete RPMI. Stimulations were carried out by removing 150 μL culture media and replacing with 150 μL supplemented RPMI. Recombinant human IFNγ (R&D 285-IF-100) was used at 10 ng/ml. Ultrapure LPS (Thermo Fisher, NC0202558) was used at 200 ng/ml. Supernatants were harvested and stored at −80° C. prior to assessing IL-18BP (R&D, DY119) and IL-6 (Biolegend, 430504) levels by ELISA. To measure total IL-18 (R&D, DY318-05), cells were treated with nigericin (Sigma, N7143-10MG) at 10 μM for 2 hours prior to harvesting supernatant.

To assess expression of the IL-18 receptor, CD4:CD8 CD19 CAR T cells from healthy donors were incubated in RPMI overnight with 1 ng/ml of IL-2 (Biolegend, 589104) or IL-12 (Biolegend, 573004) prior to harvest in Trizol for RNA processing. To assess IFNγ production, CD19 CAR T cells were seeded on a poly-I-ornithine (Sigma, P4957) treated plate, and pre-treated with 1 ng/ml of IL-2 or IL-12 for 4 hours prior to the addition of Raji target cells at 1:1 E:T as well as IL-18 at 10 ng/ml (Biolegend, 592104). Three days post incubation, supernatants were harvested for IFNγ ELISA (Biolegend, 430115) at a 1:1000 dilution.

RNA processing and qPCR. Cells were harvested in Trizol before purification via Direct-zol RNA miniprep (Zymo Research, R2061) per manufacturer's instructions with an additional dry spin after disposing of the final wash to prevent carryover. cDNA was generated using a high capacity RNA to cDNA kit (Fisher, 43-874-06). qPCR was performed using Applied Biosystems Power SYBR Green master mix (Fisher, 43-676-59) on the Bio-Rad CFX96 Real-Time system.

The following primers were used: Actin fwd: 5' GAGAAAATCTGGCACCACACC 3' (SEQ ID NO: 1); Actin rev: 5' GGATAGCACAGCCTGGATAGCAA 3' (SEQ ID NO: 2); IL-18R1 fwd: 5' GTGGAAGATCGCAGTAATATAGTTCCGG 3' (SEQ ID NO: 3); IL-18R1 rev: 5' CATTCAGCAAAGCAGAGCAGTTGA 3' (SEQ ID NO: 4); IL-18RAP fwd: 5' GATTCTGTAGATTCTCCCAGCG 3' (SEQ ID NO: 5); IL-18RAP rev: 5' CCTGAGTATCCCCTTCATTTCTGG 3' (SEQ ID NO: 6); CD161 fwd: 5' AAATGCAGTGTGGACATTCAA 3' (SEQ ID NO: 7); CD161 rev: 5' CTCGGAGTTGCTGCCAATA 3' (SEQ ID NO: 8); IL18RAP and actin primers from: World Wide Web at frontiersin.org/articles/10.3389/fgene0.2020.00645/full#supplementary-material. IL18R1 designed in Benchling. CD161: World Wide Web at ncbi.nlm.nih.gov/pmc/articles/PMC4760235/.

Flow phenotyping. Cryopreserved peripheral blood mononuclear cells (PBMCs) were thawed and counted: $1\times10^6$ cells per stain. For the intracellular cytokine panel, PBMC were stimulated with phorbol myristate acetate (PMA) (500 ng/mL) and ionomycin (500 ng/mL) in the presence of Brefeldin A (2.5 μg/mL) and Monensin (1 μM) for 2 hours before surface staining, fix and permeabilization, and intracellular staining. For the IL-18RAP phenotyping panel, PBMC were stimulated with plate bound αCD3 (1 μg/mL) and soluble αCD28 (2 μg/mL) in the presence of Brefeldin A (2.5 μg/mL) and Monensin (1 μM) for 3 hours at 37° C. Following stimulation, cells were incubated with viability dye (LIVE/DEAD blue fixable stain kit, ThermoFisher) and Human TruStain FcX blocking solution (Biolegend) prior to staining with surface monoclonal antibodies, fix and permeabilization with a 1:1 ratio of FOXP3 Transcription Factor Fixation/Permeabilization Buffer (eBioscience) and IC Fixation Buffer (eBioscience), and then staining with intracellular antibodies. Instrument standardization was performed using 8 peak rainbow calibration beads (Spherotech, Lake Forest, IL) adjusting PMT voltages for consistent 7th peak mean fluorescent intensities. A technical control from one individual was run concomitantly on each acquisition day to control for reagents. All samples from each panel were thawed, stained, and assayed on the LSRFortessa on the same day to mediate any batch effects. Criteria for analysis exclusion were <25 events for frequency and <50 events for MFI reporting. An average of 200,000 live lymphocyte events were collected per sample on a BD Fortessa using Diva software and data were analysed using FlowJo software version 10.5.3 (Tree Star, Ashland, OR).

Panel 1—Intracellular staining panel.

| | Vendor | Catalog # | Fluor | Target | Clone |
|---|---|---|---|---|---|
| 1 | BL | 366711 | FITC | IL-22* | 2G12A41 |
| 2 | BL | 300430 | PerCP-Cy5.5 | CD3 | UCHT1 |
| 3 | BD | 564755 | BV421 | IL-21* | 3A3-N2.1 |
| 4 | BL | 339922 | BV510 | CD161 | HP-3G10 |
| 5 | BL | 304323 | BV605 | VLA-4α | 9F10 |
| 6 | BL | 318344 | BV650 | CD56 | HCD56 |
| 7 | BL | 301837 | BV711 | CD14 | M5E2 |
| 8 | BD | 563877 | BV786 | CD4 | SK3 |
| 9 | BL | 501907 | APC | IL-13* | JES10-5A2 |
| 10 | BL | 506516 | AF700 | IFNγ* | B27 |
| 11 | BL | 512319 | APC-Cy7 | IL-17A* | B2168 |
| 12 | BL | 502305 | PE | GM-CSF* | BVD2-21C11 |
| 13 | BD | 562421 | PE-CF594 | FOXP3* | 259D/C7 |
| 14 | BL | 363417 | PE-Cy7 | LFA-1 | M24 |
| 15 | BD | 563795 | BUV395 | CD8 | RPA-T8 |
| 16 | Invitrogen | L34962 | BUV496 | Live/Dead Blue | — |
| 17 | BD | 564442 | BUV737 | CD45RA | HI100 |

*Indicates antibody omitted for FMM control

Panel 2—Exhaustion and functional panel

| | Vendor | Catalog # | Fluor | Target | Clone |
|---|---|---|---|---|---|
| 1 | BL | 313810 | FITC | IL-18RA* | H44 |
| 2 (Dump) | BL | 302230 | PerCP-Cy5.5 | CD19 | HIB19 |
| | BL | 302028 | PerCP-Cy5.5 | CD16 | 3G8 |
| | BD | 564157 | PerCP-Cy5.5 | TCRgd | B1 |
| 3 | BL | 329920 | BV421 | PD-1* | EH12.2H7 |
| 4 | BL | 308120 | BV510 | Perforin* | dG9 |
| 5 | BL | 359417 | BV605 | CCR4 | L291H4 |
| 6 | BD | 564057 | BV650 | CD56 | NCAM 16.2 |
| 7 | BL | 351328 | BV711 | CD127 | A019D5 |
| 8 | BD | 563877 | BV786 | CD4 | SK3 |
| 9 | R&D | FAB118R-100 | AF647 | IL-18RAP* | FAB118R |
| 10 | BL | 506516 | AF700 | IFNg | B27 |
| 11 | BL | 3000426 | APC-H7 | CD3 | UCHT1 |
| 12 | BL | 353705 | PE | CXCR3 | G025H7 |
| 13 | BD | 562403 | PE-CF594 | CD25 | M-A251 |

-continued

| | Vendor | Catalog # | Fluor | Target | Clone |
|---|---|---|---|---|---|
| 14 | BD | 372714 | PE-Cy7 | TIGIT | A15153G |
| 15 | BD | 563795 | BUV395 | CD8 | RPA-T8 |
| 16 | Invitrogen | L34962 | BUV496 | Live/Dead Blue | — |
| 17 | BD | 564442 | BUV737 | CD45RA | HI100 |

*Indicates antibody omitted for FMM control

Unbiased principal component analysis: A Principal Component Analysis (PCA) was performed on the 30 subjects at time point Day 3; data was log 2 transformed and z-score transformed. This showed that two distinct classes could be observed as segregated on the first component and there were no obvious separations on the second component. The scree plot demonstrated that the majority of the variance in the samples were described in the first component, which largely separated based on those that were functional (n=15) versus those that were either dysfunctional or demonstrated toxicity (n=15). The Functional Group consisted of 7 males and 8 females and the Dysfunction/Toxicity group consisted of 8 males and 7 females. The average age of the two groups were 15.9 (1.3 to 25.4) and 11.1 (1.7 to 22.1), respectively. Both age distributions were normally distributed based on a Kolmogorov Smirnoff test (p-values >0.95 in both cases) and had equal variance based on a tow-sample F-test for equal variances (p-value of ~0.88). A paired t-test comparing the ages showed some evidence that the age of the Dysfunction/Toxicity were less than that of the Functional group. This could be a component that could be factored into a predictive model.

Cytokine statistics: A Kolmogorov-Smirnoff test was run, this time on the data of the individual cytokines, to determine if the log 2 transformed data was normally distributed. All 23 of the cytokines failed to reject the null hypothesis at all three time points (p-values ranging from 0.08 to 0.99); thus, the cytokine data was analyzed using a parametric test.

A linear mixed effects model was used to analyze the data with fixed effects for Group (Functional versus Dysfunction/Toxicity), as well as an interaction between Group, adjusting for sex and age, and a random effect for subject. Given the discrete increments of day, it was treated as a categorical variable. A linear mixed effects model was also run at each time point (Day 1, Day 3, and Day 7) with a fixed effect for Group, sex and age. FIG. 13 gives the p-values for the main effect of Group, as well as the initial evaluation of the interaction between Group and Day. There were very few significant markers for sex or age when include as a main effect and none of these remained significant after a Benjamini-Hochberg multiple test correction. The comparison of interest is given in FIG. 13. The log 2 fold-changes associated with each of these comparisons are provided in FIG. 14.

Machine-learning: A Naïve Bayes classifier was run for each time point using stratified n repeated k-fold cross-validation (CV) where n=100 and k is 3. As seen in FIG. 7A, the models have a high Area Under the Curve (AUC) as described by the "optimal model". The optimal model was defined based on a forward feature selection. First finding first the best single marker based on average AUC and then evaluating each of the remaining 22 cytokines for inclusion of the model with the first feature. The cytokine again with the maximum AUC was selected and if yielded a significant higher AUC than the prior model where it was not included based on a paired t-test of the 100 repetitions of CV it was included. This process was continued until there was no longer a significant increase in the AUC. Cases were also then evaluated where there were multiple cytokines at an iteration that yielded AUC values that were not statistically different from one another and evaluated if there were alternative models that yield the same overall prediction accuracy. For Day 1 only a single model was found, and for Days 3 and 7 two models were found, highlighted in FIG. 7C. Machine learning also gave a single probability estimate for each individual, which allowed evaluation of how discriminatory on the selection criteria scale the groups are separated, as seen in FIG. 7B.

(X) Variants. Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (lie), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, lie, Phe, Met, and Trp; Group 11 (aliphatic): Gly, Ala, Val, Leu, and lie; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically significant degree.

Variants of the protein, nucleic acid, and gene sequences also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

(XI) Closing Paragraphs. Each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability of a biomarker profile disclosed herein to predict whether a subject undergoing an immunomodulatory treatment will be responsive, or will have a toxic response and/or nonresponse from the immunomodulatory treatment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; 17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

The invention claimed is:

1. A method of treating a subject undergoing therapy for cancer, an infectious disease, or an autoimmune disease, the method comprising:

identifying or predicting a toxic and/or dysfunctional response to an immunomodulatory treatment by:

obtaining a biological sample derived from the subject;

measuring a level of at least one biomarker selected from the group consisting of interleukin (IL)-18; IL-18 binding protein (IL-18BP), interferon gamma (IFNγ), and CD161+ cells to generate a test biomarker profile; and comparing the test biomarker profile to a reference biomarker profile comprising the level(s) of the same at least one biomarker; and identifying the subject as having or predicting that the subject will have a toxic response and/or dysfunctional response to the immunomodulatory treatment when the test biomarker profile comprises increased levels of the at least one biomarker of the group of biomarkers as compared to the reference biomarker profile;

removing CD161+ cells from an apheresis product obtained from the subject prior to the immunomodulatory treatment to produce an apheresis product reduced in CD161+ cells;

administering to the subject a selected therapeutic agent, wherein the selected therapeutic agent comprises an anti-CD161 antibody, an anti-IL-18 antibody, an anti-IFNγ antibody, an IL-18BP, or a combination thereof.

2. The method of claim 1, wherein the reference biomarker profile is from a subject or a population of subjects having a functional response to the immunomodulatory treatment with limited or no neurotoxicity (NTX).

3. The method of claim 1, wherein the biological sample comprises a blood sample and/or a cell sample.

4. The method of claim 1, wherein the biological sample is obtained before the immunomodulatory treatment has initiated, and wherein the at least one biomarker is selected from IL-18BP and/or CD161+ cells.

5. The method of claim 1, wherein the biological sample is obtained 1 day, 3 days, and/or 7 days after the immunomodulatory treatment has initiated, and wherein the at least one biomarker is selected from the group consisting of IL-18, IL-18BP, and IFNγ.

6. The method of claim 1, wherein the immunomodulatory treatment comprises administration of chimeric antigen receptor (CAR) T cell immunotherapy.

7. The method of claim 1, wherein the method further comprises contacting the apheresis product obtained from the subject with an anti-CD161 antibody.

8. The method of claim 1, wherein identifying the subject as having or predicting that the subject will have a toxic response comprises determining that the levels of the at least one biomarker are increased 1.1-fold to 10-fold as compared to the level of the same at least one biomarker of the reference biomarker profile.

9. The method of claim 1, wherein the at least one biomarker comprises CD161+ cells, and wherein comparing the test biomarker profile to the reference biomarker profile comprises determining that the level of the CD161+ cells of the test biomarker profile is increased 2-fold to 10-fold as compared to the level of CD161+ cells of the reference biomarker profile.

10. The method of claim 1, wherein the at least one biomarker comprises CD161+ cells, the method further comprising determining that the level of the CD161+ cells of the test biomarker profile is 10% to 30% of total live cells in the sample.

11. A method of treating a subject undergoing therapy for cancer, an infectious disease, or an autoimmune disease, the method comprising:

identifying or predicting a toxic and/or dysfunctional response to an immunomodulatory treatment by:

obtaining a biological sample derived from the subject;

measuring a level of at least one biomarker selected from the group consisting of IL-18 binding protein (IL-18BP) and CD161+ cells to generate a test biomarker profile;

and comparing the test biomarker profile to a reference biomarker profile comprising the level(s) of the same at least one biomarker;

identifying the subject as having or predicting that the subject will have a toxic response and/or dysfunctional response to an immunomodulatory treatment when the test biomarker profile comprises increased levels of the at least one biomarker of the group of biomarkers as compared to the reference biomarker profile; and administering to the subject a selected therapeutic agent based upon whether the subject is identified or predicted as having a toxic or dysfunctional response to the immunomodulatory treatment, wherein the selected therapeutic agent comprises an anti-CD161 antibody, an IL-18BP, or a combination thereof.

* * * * *